US012649921B2

(12) United States Patent
Rajeev et al.

(10) Patent No.: US 12,649,921 B2
(45) Date of Patent: Jun. 9, 2026

(54) CHEMICALLY MODIFIED GUIDE RNAs FOR GENOME EDITING WITH Cas12b

(71) Applicant: Verve Therapeutics, Inc., Boston, MA (US)

(72) Inventors: Kallanthottathil G. Rajeev, Wayland, MA (US); Alexandra Chadwick, Somerville, MA (US); Caroline Reiss, Somerville, MA (US)

(73) Assignee: Verve Therapeutics, Inc., Boston, MA (US)

( * ) Notice: Subject to any disclaimer, the term of this patent is extended or adjusted under 35 U.S.C. 154(b) by 789 days.

(21) Appl. No.: 17/918,090

(22) PCT Filed: Apr. 9, 2021

(86) PCT No.: PCT/US2021/026655

§ 371 (c)(1),
(2) Date: Oct. 10, 2022

(87) PCT Pub. No.: WO2021/207651

PCT Pub. Date: Oct. 14, 2021

(65) Prior Publication Data

US 2023/0134582 A1      May 4, 2023

Related U.S. Application Data

(60) Provisional application No. 63/007,814, filed on Apr. 9, 2020.

(51) Int. Cl.
*C12N 15/11*      (2006.01)
*C12N 9/22*      (2006.01)
*C12N 15/90*      (2006.01)

(52) U.S. Cl.
CPC ............... *C12N 15/11* (2013.01); *C12N 9/22* (2013.01); *C12N 15/907* (2013.01); *C12N 2310/20* (2017.05); *C12N 2310/315* (2013.01); *C12N 2310/321* (2013.01); *C12N 2310/331* (2013.01); *C12N 2800/80* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan, Jr. et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 5,082,830 A | 1/1992 | Brakel et al. |
| 5,109,124 A | 4/1992 | Ramachandran et al. |
| 5,112,963 A | 5/1992 | Pieles et al. |
| 5,118,802 A | 6/1992 | Smith et al. |
| 5,138,045 A | 8/1992 | Cook et al. |
| 5,149,782 A | 9/1992 | Chang et al. |
| 5,214,136 A | 5/1993 | Lin et al. |
| 5,218,105 A | 6/1993 | Cook et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,272,250 A | 12/1993 | Spielvogel et al. |
| 5,292,873 A | 3/1994 | Rokita et al. |
| 5,317,098 A | 5/1994 | Shizuya et al. |
| 5,371,241 A | 12/1994 | Brush |
| 5,391,723 A | 2/1995 | Priest |
| 5,414,077 A | 5/1995 | Lin et al. |
| 5,416,203 A | 5/1995 | Letsinger |
| 5,451,463 A | 9/1995 | Nelson et al. |
| 5,486,603 A | 1/1996 | Buhr |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van et al. |
| 5,525,465 A | 6/1996 | Haralambidis et al. |

(Continued)

FOREIGN PATENT DOCUMENTS

| | | |
|---|---|---|
| EP | 1067182 A2 | 1/2001 |
| EP | 1440981 A2 | 7/2004 |

(Continued)

OTHER PUBLICATIONS

Strecker et al. Engineering of CRISPR-Cas12b for human genome editing. Nat Commun. Jan. 22, 2019. (Year: 2019).*
Teng et al. Repurposing CRISPR-Cas12b for mammalian genome engineering. Cell Discov 4, 63 (2018) (Year: 2018).*
Tian et al. A novel thermal Cas12b from a hot spring bacterium with high target mismatch tolerance and robust DNA cleavage efficiency. Int J Biol Macromol. Mar. 15, 2020;147:376-384 (Year: 2020).*
Liu et al. C2c1-sgRNA Complex Structure Reveals RNA-Guided DNA Cleavage Mechanism. Mol Cell. Jan. 19, 2017;65(2):310-322 (Year: 2017).*
Yin et al. Structure-guided chemical modification of guide RNA enables potent non-viral in vivo genome editing. Nat Biotechnol 35, 1179-1187 (2017) (Year: 2017).*

(Continued)

*Primary Examiner* — Christopher M Babic
(74) *Attorney, Agent, or Firm* — Wilson Sonsini Goodrich & Rosati

(57)      ABSTRACT

Provided herein are compositions related to Cas12b guide RNAs. Also provided herein are methods for modifying target polynucleotide sequences and methods of treating or preventing a condition in a subject in need thereof, such as conditions resultant from the expression of ANGPTL3 or mutations thereto.

27 Claims, 11 Drawing Sheets

Specification includes a Sequence Listing.

(56)  References Cited

U.S. PATENT DOCUMENTS

| | | |
|---|---|---|
| 5,541,313 A | 7/1996 | Ruth |
| 5,545,730 A | 8/1996 | Urdea et al. |
| 5,552,538 A | 9/1996 | Urdea et al. |
| 5,565,552 A | 10/1996 | Magda et al. |
| 5,567,810 A | 10/1996 | Weis et al. |
| 5,574,142 A | 11/1996 | Meyer, Jr. et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,371 A | 12/1996 | Sessler et al. |
| 5,591,584 A | 1/1997 | Chang et al. |
| 5,595,726 A | 1/1997 | Magda et al. |
| 5,597,696 A | 1/1997 | Linn et al. |
| 5,599,923 A | 2/1997 | Sessler et al. |
| 5,599,928 A | 2/1997 | Hemmi et al. |
| 5,608,046 A | 3/1997 | Cook et al. |
| 5,672,662 A | 9/1997 | Harris et al. |
| 5,688,941 A | 11/1997 | Cook et al. |
| 5,714,166 A | 2/1998 | Tomalia et al. |
| 5,885,613 A | 3/1999 | Holland et al. |
| 6,153,737 A | 11/2000 | Manoharan et al. |
| 6,172,208 B1 | 1/2001 | Cook |
| 6,214,345 B1 | 4/2001 | Firestone et al. |
| 6,300,319 B1 | 10/2001 | Manoharan |
| 6,335,434 B1 | 1/2002 | Guzaev et al. |
| 6,335,437 B1 | 1/2002 | Manoharan |
| 6,395,437 B1 | 5/2002 | Wollesen |
| 6,444,806 B1 | 9/2002 | Veerapanani et al. |
| 6,486,308 B2 | 11/2002 | Kutyavin et al. |
| 6,525,031 B2 | 2/2003 | Manoharan |
| 6,528,631 B1 | 3/2003 | Cook et al. |
| 6,559,279 B1 | 5/2003 | Manoharan et al. |
| 7,745,651 B2 | 6/2010 | Heyes et al. |
| 7,799,565 B2 | 9/2010 | MacLachlan et al. |
| 8,017,804 B2 | 9/2011 | Keil et al. |
| 8,106,022 B2 | 1/2012 | Manoharan et al. |
| 8,192,753 B2 | 6/2012 | Essler et al. |
| 8,193,246 B2 | 6/2012 | Panzner et al. |
| 8,202,983 B2 | 6/2012 | Dellinger et al. |
| 8,357,722 B2 | 1/2013 | Keil et al. |
| 8,877,901 B2 | 11/2014 | Govindan |
| 9,365,610 B2 | 6/2016 | Payne et al. |
| 9,549,983 B2 | 1/2017 | Brown et al. |
| 9,879,265 B2 | 1/2018 | Albæk et al. |
| 10,011,849 B1 | 7/2018 | Gill et al. |
| 10,358,643 B2 | 7/2019 | Albaek et al. |
| 11,207,416 B2 | 12/2021 | Rajeev et al. |
| 11,801,306 B2 | 10/2023 | Rajeev et al. |
| 12,274,753 B2 | 4/2025 | Rajeev |
| 2003/0119038 A1 | 6/2003 | Bingham et al. |
| 2004/0009553 A1 | 1/2004 | Glucksmann et al. |
| 2012/0082680 A1 | 4/2012 | Sitlani et al. |
| 2012/0101148 A1 | 4/2012 | Aking et al. |
| 2012/0114696 A1 | 5/2012 | Pang et al. |
| 2012/0183602 A1 | 7/2012 | Chen et al. |
| 2013/0202652 A1 | 8/2013 | Manoharan et al. |
| 2014/0287024 A1 | 9/2014 | Wang et al. |
| 2015/0126718 A1 | 5/2015 | Prakash et al. |
| 2015/0273068 A1 | 10/2015 | Maier et al. |
| 2015/0291958 A1 | 10/2015 | Albaek et al. |
| 2016/0060354 A1 | 3/2016 | Avila et al. |
| 2017/0143631 A1 | 5/2017 | Chen et al. |
| 2018/0237770 A1 | 8/2018 | May et al. |
| 2018/0290965 A1 | 10/2018 | Brito et al. |
| 2018/0312846 A1 | 11/2018 | Albaek et al. |
| 2019/0032087 A1 | 1/2019 | Cullis et al. |
| 2019/0316127 A1 | 10/2019 | Schlegel et al. |
| 2021/0207146 A1 | 7/2021 | Prakash et al. |
| 2024/0131166 A1 | 4/2024 | Rajeev et al. |
| 2024/0316212 A1 | 9/2024 | Rajeev et al. |

FOREIGN PATENT DOCUMENTS

| | | | |
|---|---|---|---|
| EP | 1471152 A1 | 10/2004 | |
| EP | 4114360 A1 | 1/2023 | |
| GB | 2213818 A | 8/1989 | |
| GB | 2613225 B | 1/2024 | |
| JP | 2015518463 A | 7/2015 | |
| JP | 2019511491 A | 4/2019 | |
| WO | WO-9819705 A1 | 5/1998 | |
| WO | WO-0131007 A2 | 5/2001 | |
| WO | WO-0134768 A2 | 5/2001 | |
| WO | WO-0157081 A2 | 8/2001 | |
| WO | WO-0177137 A1 | 10/2001 | |
| WO | WO-0198468 A2 | 12/2001 | |
| WO | WO-0214358 A2 | 2/2002 | |
| WO | WO-0246383 A2 | 6/2002 | |
| WO | WO-02090526 A2 | 11/2002 | |
| WO | WO-02102993 A2 | 12/2002 | |
| WO | WO-02102994 A2 | 12/2002 | |
| WO | WO-2006007712 A1 | 1/2006 | |
| WO | WO-2008103276 A2 | 8/2008 | |
| WO | WO-2009120878 A2 | 10/2009 | |
| WO | WO-2009134487 A2 | 11/2009 | |
| WO | WO-2010006282 A2 | 1/2010 | |
| WO | WO-2010088537 A2 | 8/2010 | |
| WO | WO-2010093395 A1 | 8/2010 | |
| WO | WO-2012016188 A2 | 2/2012 | |
| WO | WO-2013076844 A1 | 5/2013 | |
| WO | WO-2013176844 A1 | 11/2013 | |
| WO | WO-2014118272 A1 | 8/2014 | |
| WO | WO-2015089354 A1 | 6/2015 | |
| WO | WO-2015095340 A1 | 6/2015 | |
| WO | WO-2016168286 A1 | 10/2016 | |
| WO | WO-2016205749 A1 * | 12/2016 | ............... C12N 9/22 |
| WO | WO-2017070632 A2 | 4/2017 | |
| WO | WO-2017134529 A1 | 8/2017 | |
| WO | WO-2017173054 A1 | 10/2017 | |
| WO | WO-2018027078 A1 | 2/2018 | |
| WO | WO-2018136620 A2 | 7/2018 | |
| WO | WO-2018216785 A1 | 11/2018 | |
| WO | WO-2019126709 A1 | 6/2019 | |
| WO | WO-2019126774 A1 | 6/2019 | |
| WO | WO-2019145543 A1 | 8/2019 | |
| WO | WO-2020033601 A1 * | 2/2020 | ........... C12N 15/113 |
| WO | WO-2020097540 A1 | 5/2020 | |
| WO | WO-2020160397 A1 | 8/2020 | |
| WO | WO-2020219276 A1 | 10/2020 | |
| WO | WO-2021178725 A1 | 9/2021 | |
| WO | WO-2021207651 A2 | 10/2021 | |
| WO | WO-2022060871 A1 | 3/2022 | |
| WO | WO-2022271806 A1 | 12/2022 | |
| WO | WO-2023015223 A2 | 2/2023 | |

OTHER PUBLICATIONS

Xu et al. Role of angiopoietin-like 3 (ANGPTL3)in regulating plasma level of low-density lipoprotein cholesterol. Atherosclerosis. Jan. 2018; Epub Sep. 21, 2017) (Year: 2017).*

Teng et al. Repurposing CRISPR-Cas12b for mammalian genome engineering. Cell Discov 4, 63 (2018).*

Tian et al. A novel thermal Cas12b from a hot spring bacterium with high target mismatch tolerance and robust DNA cleavage efficiency. Int J Biol Macromol. Mar. 15, 2020;147:376-384).*

Liu et al. C2c1-sgRNA Complex Structure Reveals RNA-Guided DNA Cleavage Mechanism. Mol Cell. Jan. 19, 2017;65(2):310-322).*

Yin et al. Structure-guided chemical modification of guide RNA enables potent non-viral in vivo genome editing. Nat Biotechnol 35, 1179-1187 (2017).*

EP21783880.4 Extended European Patent Search Report dated May 12, 2025.

Abifadel; M. et al.: Identification and characterization of new gain-of-function mutations in the PCSK9 gene responsible for autosomal dominant hypercholesterolemia, Atherosclerosis 223(2):394-400 (2012).

(56)                    References Cited

OTHER PUBLICATIONS

Abifadel, Marianne et al.: Mutations in PCSK9 Cause Autosomal Dominant Hypercholesterolemia. Nature Genetics 34(2):154-156 (2003).

Sander, J. D. et al.: CRISPR-Cas systems for editing, regulating and targeting genomes. Nature Biotechnology 32:347-355 (2014).

Bae, Sangsu et al.: Cas-OFFinder: a fast and versatile algorithm that searches for potential off-target sites of Cas9 RNA-guided endonucleases, Bioinformatics 30(10):1473-1475 (2014). https://doi.org/10.1093/bioinformatics/btu048.

Baker, Kristian et al.: Nonsense-mediated mRNA decay: terminating erroneous gene expression. Current Opinion in Cell Biology 16(3):293-299 (2004).

Batzer et al. Enhanced evolutionary PCR using oligonucleotides with inosine at the 3'-terminus. Nucleic Acids Res. 19(18):5081 (1991).

Behm-Ansmant, Isabelle et al.: Quality Control of Gene Expression: a Stepwise Assembly Pathway for the Surveillance Complex That Triggers Nonsense-mediated Mrna Decay. Genes & Development 20(4):391-398 (2006).

Benjannet et al.: Loss- and Gain-of-function PCSK9 Variants. J. Biol. Chem. 287(40):33745-55 (2012).

Benjannet et al.: NARC-1/PCSK9 and its natural mutants: zymogen cleavage and effects on the low density lipoprotein (LDL) receptor and LDL cholesterol. J. Biol. Chem. 279(47):48865-48875 (2004).

Bonnefond; Amélie et al.: Molecular Diagnosis of Neonatal Diabetes Mellitus Using Next-Generation Sequencing of the Whole Exome. PLoS ONE 5(10): e13630 (2010). doi:10.1371/journal.pone. 0013630.

Cameron; J. et al.: Effect of mutations in the PCSK9 gene on the cell surface LDL receptors. Hum. Mol. Genet. 15(9):1551-1558 (2006).

Chang. et al.: The Nonsense-mediated Decay Rna Surveillance Pathway. Annual Review of Biochemistry vol. 76: 51-74 (2007).

Chu, V. T. et al.: Increasing the efficiency of homology-directed repair for CRISPR-Cas9-induced precise gene editing in mammalian cells, Nature Biotechnology 33:543-548 (2015).

Cohen; J.C. et al.: Sequence Variations in PCSK9, Low LDL, and Protection against Coronary Heart Disease. N. Engl. J. Med. 354:1264-1272 (2006).

Cong, Le. et al.: Multiplex Genome Engineering using CRISPR/Cas systems. Science 339(6121):819-823 (2013).

Deltcheva, E. et al.: CRISPR RNA maturation by trans-encoded small RNA and host factor RNase III. Nature 471(7340) 602-607 (2011).

Dubuc, G. et al.: Statins upregulate PCSK9, the gene encoding the proprotein convertase neural apoptosis-regulated convertase-1 implicated in familial hypercholesterolemia. Thromb. Vase. Biol. 24(8):1454-1459 (2004).

Seidah, N. G.: PCSK9 as a therapeutic target of dyslipidemia. Expert Opin Ther Targets 13(1):19-28 (2009).

Ferretti; J. J et al.: Complete genome sequence of an MI strain of *Streptococcus pyogenes*. Natl. Acad. Sci. 98(8):4658-4663 (2001).

Fu, Y. et al.: High-frequency off-target mutagenesis induced by CRISPR-Cas nucleases in human cells. Nature Biotechnology 31(9):822-826 (2013).

Garneau, et al.: The CRISPR/Cas bacterial immune system cleaves bacteriophage and plasmid DNA. Nature 468(7320):67-71 (2010).

Gasiunas, Giedrius et al. Cas9-crRNA Ribonucleoprotein complex Mediates specific DNA cleavage for Adaptive Immunity in Bacteria. Proceedings of the National Academy of Sciences of the United States of America 109(39):E2579-E2586 (2012).

Hampton; Eric N. et al.: The self-inhibited structure of full-length PCSK9 at 1.9 Å reveals structural homology with resistin within the C-terminal domain. PNAS 104(37)14604-14609 (2007).

Hedrick; Joseph A.: Targeting PCSK9 for the treatment of hypercholesterolemia. Curr. Opin. Investig. Drugs 10(9):938-46 (2009) Abstract.

Shmakov, S. et al.: Discovery and functional characterization of diverse class 2 CRISPR-Cas systems. Molecular Cell 60(3)1-13 (2015).

Hooper, A. J. et al.: Anti-PCSK9 therapies for the treatment of hypercholesterolemia. Expert Opin Biol Ther 13(3):429-35 (2013).

Hsu; P.D. et al.: Development and Applications of CRISPR-Cas9 for Genome Engineering. Cell 157(6):1262-1278 (2014).

Huang; Chiang-Ching et al.: Longitudinal Association of PCSK9 Sequence Variations With Low-Density Lipoprotein Cholesterol Levels The Coronary Artery Risk Development in Young Adults Study. Circ Cardiovasc Genet. 2:354-361 (2009).

Jinek, M. et al.: A programmable Dual-RNA-Guided DNA endonuclease in adaptive bacterial immunity, Science 337(6096): 816-821 (2012).

Kotowski; Ingrid K. et al.: A Spectrum of PCSK9 Alleles Contributes to Plasma Levels of Low-Density Lipoprotein Cholesterol. Am. J. Hum. Genet. 78:410-422 (2006).

Leren, T. P.: Mutations in the PCSK9 gene in Norwegian subjects with autosomal dominant hypercholesterolemia, Clin. Genet. 65:419-422 (2004).

Lewis et al.: Building the Class 2 CRISPR-Cas Arsenal. Molecular Cell 65(3):377-379 (2017).

Liang; Liu et al.: C2c1-sgRNA complex structure reveals RNA-guided DNA cleavage mechanism. Molecular Cell 65(2):310-322 (2017).

Makarova, K. S. et al.: An updated evolutionary classification of CRISPR-Cas systems. Nature Reviews Microbiology 13(11):722-736 (2015).

Maxwell, K. N. et al.: Overexpression of PCSK9 accelerates the degradation of the LDLR in a post-endoplasmic reticulum compartment. PNAS 102(6):2069-2074.

Maxwell; K.N. et al.: Adenoviral-mediated expression of Pcsk9 in mice results in a low-density lipoprotein receptor knockout phenotype. Proc. Nat. Acad. Sci. 101(18):7100-7105 (2004).

Micklefield; J.: Backbone Modification of Nucleic Acids: Synthesis, Structure and Therapeutic Applications. Current Medicinal Chemistry 8(10):1157-1179 (2001). doi: https://doi.org/10.2174/0929867013372391.

Ohtsuka, Eiko et al.: An Alternative Approach to Deoxyoligonucleotides as Hybridization Probes by Insertion of Deoxyinosine at Ambiguous Codon Positions. Journal of Biological Chemistry 260(5):2605-2608 (1985).

Park, S. W. et al.: Post-transcriptional regulation of low density lipoprotein receptor protein by proprotein convertase subtilisin/kexin type 9a in mouse liver. J. Biol. Chem. 279(48):50630-50638 (2004).

PCT/US2021/026655 International Search Report and Written Opinion dated Sep. 28, 2021.

Peterson, A. S. et al.: PCSK9 function and physiology. J Lipid Res. 49(6):1152-1156 (2008).

Rashid, S. et al.: Decreased plasma cholesterol and hypersensitivity to statins in mice lacking Pcsk9. PNAS 102(15):5374-5379 (2005).

Rossolini, Gian Maria. et al.: Use of Deoxyinosine-containing Primers Vs Degenerate Primers For Polymerase Chain Reaction Based On Ambiguous Sequence Information. Molecular and Cellular Probes 8(2):91-98 (1994).

Saavedra; Yascara Grisel Luna et al.: PCSK9 R46L, Lower LDL, and Cardiovascular Disease Risk in Familial Hypercholesterolemia. Arteriosclerosis, Thrombosis, and Vascular Biology 34:2700-2705 (2014).

Seidah et al.: The secretory proprotein convertase neural apoptosis-regulated convertase 1 (NARC-1): Liver regeneration and neuronal differentiation. PNAS 100:928-933 (2003). www.pnas.org/cgi/doi/10.0335507100.

Strecker et al.: Engineering of CRISPR-Cas12b for human genome editing. Nature Communications 10(1):212 (2019).

Strom; Thea Bismo et al.: Loss-of-function mutation R46L in the PCSK9 gene has little impact on the levels of total serum cholesterol in familial hypercholesterolemia heterozygotes. Clinica Chimica Acta 411(3-4, 2):229-233 (2010). https://doi.org/10.1016/j.cca.2009.11.008.

Timms, K. M. et al.: A mutation in PCSK9 causing autosomal-dominant hypercholesterolemia in a Utah pedigree, Hum. Genet. 114(4):349-353 (2004).

(56)                  References Cited

OTHER PUBLICATIONS

Sun, X. M. et al.: Evidence for effect of mutant PCSK9 on apolipoprotein B secretion as the cause of unusually severe dominant hypercholesterolaemia. Hum. Mol. Genet 14(9):1161-1169 (2005).

Wu et al.: Structural basis of stringent PAM recognition by CRISPR-C2c1 in complex with sgRNA. Cell Research 27(5):705 (2017).

Zhao; Zhenze et al.: Molecular Characterization of Loss-of-Function Mutations in PCSK9 and Identification of a Compound Heterozygote. Am. J. Hum. Genet. 79:514-523 (2006).

Extended European Search Report dated May 12, 2025 issued in European Patent Application No. 21783880.4.

Akinc, Akin et al.: Targeted Delivery of RNAi Therapeutics With Endogenous and Exogenous Ligand-Based Mechanisms. Molecular Therapy: the Journal of the American Society of Gene Therapy 18(7):1357-1364 (2010).

Akinc, et al.: A combinatorial library of lipid-like materials for delivery of RNAi therapeutics. Nat. Biotechnol. 26, 561-569 (2008).

Betz, Karin et al.: Klentaq Polymerase Replicates Unnatural Base Pairs by Inducing a Watson-crick Geometry. Nature Chemical Biology 8(7):612-614(2012).

Brown, EA et al.: Secondary Structure of the 5' Nontranslated Regions of Hepatitis C Virus and Pestivirus Genomic RNAs. Nucleic Acids Research vol. 20,19: 5041-5045 (1992).

Brown, Jonathan et al.: Ligand Conjugated Multimeric siRNAs Enable Enhanced Uptake and Multiplexed Gene Silencing. Nucleic Acid Therapeutics 29:5 (2019), Mary Ann Liebert, Inc., DOI: 10.1089/nat.2019.0782.

Catalog # 880151P, Avanti Polar Lipids Inc, https://avantilipids.com/product/880151.

Catalog # PG1-CLS-2k, Nanocos, http://www.nanocs.com/PEG/LPEG.htm.

Chadwick, Alexandra C. et al.: In Vivo Base Editing of PCSK9 (Proprotein Convertase Subtilisin/Kexin Type 9) as a Therapeutic Alternative to Genome Editing. Arteriosclerosis, Thrombosis, and Vascular Biology 37(9):1741-1747 (2017).

Chari , Raj et al.: Unraveling CRISPR-Cas9 genome engineering parameters via a library-on-library approach. Nature Methods vol. 12,9: 823-826 (2015). doi:10.1038/nmeth.3473.

Clement, Kendell et al.: CRISPResso2 Provides Accurate and Rapid Genome Editing Sequence Analysis. Nature Biotechnology 37:224-226 (2019).

Crooke, Stanley T. et al.: Pharmacokinetic properties of several novel oligonucleotide analogs in mice. The Journal of Pharmacology and Experimental Therapeutics 277(2):923-937 (1996).

Delcheva, Elitza et al.: CRISPR RNA maturation by trans-encoded small RNA and host factor RNase III. Nature vol. 471,7340: 602-607. doi: 10.1038/nature09886.

Dellinger, Douglas J et al.: Solid-phase chemical synthesis of phosphonoacetate and thiophosphonoacetate oligodeoxynucleotides. Journal of the American Chemical Society 125,4: 940-950 (2003). Epub Jan. 3, 2003. DOI: 10.1021/ja027983f.

Dellinger; Douglas J.: Streamlined process for the chemical synthesis of RNA using 2'-O-thionocarbamate-protected nucleoside phosphoramidites in the solid phase. J. Am. Chem. Soc. 133(30):11540-11556 (2011). doi: 10.1021/ja201561z. Epub Jul. 11, 2011 (Abstract).

Diebold, Sandra: Recognition of Viral Single-stranded RNA by Toll-like Receptors. Advanced Drug Delivery Reviews 60(7):813-823 (2008).

Ding, Qiurong et al.: Permanent Alteration of PCSK9 With In Vivo CRISPR-Cas9 Genome Editing. Circulation Research 115,5: 488-492 (2014).

Doench, John G. et al.: Rational design of highly active sgRNAs for CRISPR-Cas9-mediated gene inactivation. Nature Biotechnology32:1262-1267 (2014).

Englisch et al.: Chemically Modified Oligonucleotides as Probes and Inhibitors. Angewandte Chemie International Edition in English vol. 30,6: 613-629 (1991) (abstract).

Farboud, Behnom et al.: Dramatic Enhancement of Genome Editing by CRISPR/Cas9 Through Improved Guide RNA Design. Genetics 199(4):959-971 (2015). https://doi.org/10.1534/genetics.115.175166.

Finn, Jonathan D. et al.: A Single Administration of CRISPR/Cas9 Lipid Nanoparticles Achieves Robust and Persistent In Vivo Genome Editing. Cell Reports vol. 22(9):2227-2235 (2018).

Flajolet, Marc et al.: Woodchuck Hepatitis Virus Enhancer I and Enhancer II Are Both Involved in N-myc2 Activation in Woodchuck Liver Tumors. Journal of Virology 72(7):6175-6180 (1998).

Fusi et al.: In Silico Predictive Modeling of CRISPR/Cas9 guide efficiency. bioRxiv 021568 (2015). doi: https://doi.org/10.1101/021568.

Gaudelli, Nicole M. et al.: Programmable Base Editing Of A•T to G•C In Genomic DNA Without DNA Cleavage. Nature 551(7681):464-471 (2017).

Gehrke, Jason M. et al.: An APOBEC3A-Cas9 base Editor with Minimized Bystander and off-target Activities. Nature Biotechnology 36(10):977-982 (2018).

Guo, Jian, et al.: Protecting groups in carbohydrate chemistry: influence on stereoselectivity of glycosylations. Molecules 15(10):7235-7265 (2010).

Haeusslet et al.: Evaluation of off-target and on-target scoring algorithms and integration into the guide RNA selection tool CRISPOR. Genome Biology 17:148 (2016). DOI 10.1186/s13059-016-1012-2.

Housden, Benjamin E. et al.: Identification of potential drug targets for tuberous sclerosis complex by synthetic screens combining CRISPR-based knockouts with RNAi. Science Signaling 8(393):rs9-rs9 (2015).

Hsu, et al.: DNA Targeting Specificity of RNA-guided Cas9 Nucleases. Nature Biotechnology 31(9):827-832 (2013).

Hu, Johnny H. et al.: Evolved Cas9 Variants with Broad PAM Compatibility and High DNA Specificity. Nature 556(7699):57-63 (2018).

Jacobs, Frank et al.: The Role of Liver Sinusoidal Cells in Hepatocyte-directed Gene Transfer. The American Journal of Pathology 176(1):14-21 (2010).

Jayaraman, et al.: Maximizing the Potency of siRNA Lipid Nanoparticles for Hepatic Gene Silencing In Vivo. Angew. Chem. Int. Ed. 51:8529-8533 (2012).

Kabanov, Alexander V. et al.: A New Class of Antivirals: Antisense Oligonucleotides Combined With a Hydrophobic Substituent Effectively Inhibit Influenza Virus Reproduction and Synthesis of Virus-specific Proteins in Mdck Cells. FEBS Letters 259(2):327-330 (1990).

Katzmann, Julius L. et al.: Targeting RNA With Antisense Oligonucleotides and Small Interfering RNA: JACC State-of-the-Art Review. Journal of the American College of Cardiology 76(5):563-579 (2020).

Komor, Alexis C. et al.: Improved Base Excision Repair Inhibition and Bacteriophage Mu Gam Protein Yields C:g-to-t:a Base Editors With Higher Efficiency and Product Purity. Science Advances 3(8):eaao4774, pp. 1-9 (2017).

Komor, Alexis C. et al.: Programmable Editing of a Target Base in Genomic DNA without Double-stranded DNA Cleavage. Nature 533(7603):420-424 (2016).

Kramer, M Gabriela et al.: In vitro and in vivo comparative study of chimeric liver-specific promoters. Molecular Therapy 7(3):375-385 (2003).

Krutzfeldt, Jan et al.: Silencing of microRNAs in vivo with antagomirs. Nature vol. 438,7068: pp. 685-689 (2005).

Kumar, Ravindra et al.: Template-directed Oligonucleotide Strand Ligation, Covalent Intramolecular DNA Circularization and Catenation Using Click Chemistry. Journal of the American Chemical Society 129(21):6859-6864 (2007).

Letsinger, Robert L. et al.: Cholesteryl-conjugated Oligonucleotides: Synthesis, Properties, and Activity as Inhibitors of Replication of Human Immunodeficiency Virus in Cell Culture. PNAS 86(17):6553-6556 (1989).

Loakes, David et al.: Survey and Summary: The applications of universal DNA base analogues. Nucleic Acids Research 29(12):2437-2447 (2001).

(56)            References Cited

OTHER PUBLICATIONS

Manoharan, M. et al.: Chemical Modifications to Improve Uptake and Bioavailability of Antisense Oligonucleotides. Annals of the New York Academy of Sciences 660:306-309 (1992).

Manoharan, Muthiah et al.: Cholic acid-oligonucleotide conjugates for antisense applications. Bioorganic & Medicinal Chemistry Letters 4(8):1053-1060 (1994).

Manoharan, Muthiah et al.: Introduction of a Lipophilic Thioether in the Minor Groove of Nucleic Acids for Antisense Applications. Bioorganic & Medicinal Chemistry Letters 3(12):2765-2770 (1993).

Manoharan, Muthiah et al.: Lipidic Nucleic Acids. Tetrahedron Letters 36(21):3651-3654 (1995).

Manoharan, Muthiah et al.: Oligonucleotide Conjugates: Alteration of the Pharmacokinetic Properties of Antisense Agents. Nucleosides & Nucleotides 14(3-5):969-973 (1995).

Matsuda et al.: siRNA Conjugates Carrying Sequentially Assembled Trivalent N-Aceytlgalactosamine Linked Through Nucleosides Elicit Robust Gene Silencing In Vivo in Hepatocytes, ACS Chem Biol. 10(5): 7 pages (2015).

Miller, Jason B. et al.: Non-Viral CRISPR/Cas Gene Editing In Vitro and In Vivo Enabled by Synthetic Nanoparticle Co-Delivery of Cas9 mRNA and sgRNA. Angewandte Chemie (International Ed. In English) 56(4):1059-1063 (2017).

Mishra, Rakesh Kumar et al.: Improved Leishmanicidal Effect of Phosphorotioate Antisense Oligonucleotides by Ldl-mediated Delivery. Biochimica Et Biophysica Acta (BBA)—Gene Structure and Expression 1264(2):229-237 (1995).

Moreno-Mateos, Miguel A et al.: CRISPRscan: designing highly efficient sgRNAs for CRISPR-Cas9 targeting in vivo. Nature Methods vol. 12,10: 982-988 (2015).

Nair et al.: Multivalent N-Acetylgalactosamine-Conjugated siRNA Localizes in Hepatocytes and Elicits Robust RNAi-Mediated Gene Silencing, Journal of the American Chemical Society, 136:16958-16961 (2014).

Nishida, Keiji et al.: Targeted nucleotide editing using hybrid prokaryotic and vertebrate adaptive immune systems. Science 353,6305: aaf8729 (2016 ). DOI: 10.1126/science.aaf8729.

Onopchechko, Anatoli et al.: The Reaction of Phthalic Anhydride with Diethylenetriamine and Triethylenetetramine. A Literature Correction. Bulletin of the Chemical Society of Japan 71(3):717-721 (1998). https://doi.org/10.1246/bcsj.71.717.

Onopchenko, A.: The Reaction of Phthalic Anhydride with Diethylenetriamine and Triethylenetetramine. A Literature Correction. Bull. Chem. Soc. Japan 71(3):717-721 (1998).

PCT International Search Report and Written Opinion dated Jul. 1, 20214, 2021 issued in PCT application PCT/US2021/020955.

PCT/US2022/074493 International Search Report and Written Opinion dated Jul. 28, 2023 (Pub. No. WO2023015223).

Prakash, Thazha P. et al.: Lipid nanoparticles improve activity of single-stranded siRNA and gapmer antisense oligonucleotides in animals. ACS Chemical Biology 8(7):1402-1406 (2013). Abstract.

Pratesi, Alessandro et al.: Biotin Derivatives Carrying Two Chelating DOTA Units. Synthesis, in Vitro Evaluation of Biotinidases Resistance, Avidin Binding, and Radiolabeling Tests. Journal of Medicinal Chemistry vol. 53: 432-440 (2010). DOI: 10.1021/jm9014372.

PUBCHEM, SID 233374427, Available Date: Feb. 12, 2015 [retrieved on Apr. 21, 2021]. Retrieved from the internet: URL: https://pubchem.ncbi.nim.nih.gov/substance/233374427 entire document.

Qu, Shuai, et al.: Non-viral Nucleic Acid Therapeutics: Revolutionizing the Landscape of Atherosclerotic Treatment. Nano Today 45(101514):1-14 (2022).

Ramzy, Ibrahim: Clinical Cytopathology And Aspiration Biopsy: Fundamental Principles And Practice, 2nd Edition. McGraw Hill Companies (2001).

Ran, Ann et al.: In Vivo Genome Editing Using *Staphylococcus aureus* Cas9. Nature 520(7546):186-191 (2015).

Rejman, Joanna et al.: Characterization And Transfection Properties Of Lipoplexes Stabilized With Novel Exchangeable Polyethylene Glycol-lipid Conjugates. Biochimica et Biophysica Acta 1660(1-2):41-52 (2004).

Roberts, Thomas C. et al.: Advances in Oligonucleotide Drug Delivery. Nature Reviews Drug Discovery 19(10):673-694 (2020).

Romberg, Birgit et al.: Sheddable Coatings for Long-Circulating Nanoparticles. Pharmaceutical Research vol. 25, 1: 55-71 (2008).

Rossidis Avery Cet al.: In utero CRISPR-mediated therapeutic editing of metabolic genes. Nature Medicine vol. 24(10): 1513-1518 (2018).

Sabnis, Staci et al.: A Novel Amino Lipid Series for mRNA Delivery: Improved Endosomal Escape and Sustained Pharmacology and Safety in Non-human Primates. Molecular Therapy 26(6):1509-1519 (2018).

Saison-Behmoaras, T. et al.: Short Modified Antisense Oligonucleotides Directed Against Ha-ras Point Mutation Induce Selective Cleavage of the Mrna and Inhibit T24 Cells Proliferation. The EMBO Journal 10(5):1111-1118 (1991).

Sato, Yusuke et al., Highly specific delivery of siRNA to hepatocytes circumvents endothelial cell-mediated lipid nanoparticle-associated toxicity leading to the safe and efficacious decrease in the hepatitis B virus. Journal of Controlled Release vol. 266: 216-225 (2017).

Sharma et al.: Novel Cluster and Monomer-Based GaINAc Structures Induce Effective Uptake of siRNAs in Vitro and in Vivo. Bioconjugate Chem. 29(7): 2478-2488 (2018).

Shea, G. Regan et al.: Synthesis, hybridization properties and antiviral activity of lipid-oligodeoxynucleotide conjugates. Nucleic Acids Research 18(13):3777-3783 (1990).

Shmakov, Sergey et al.: Discovery and Functional Characterization of Diverse Class 2 CRISPR-Cas Systems. Molecular Cell 60:385-397 (2015).

Singh, Mohan et al.: Primary cilia are present on human blood and bone marrow cells and mediate Hedgehog signaling. Experimental Hematology vol. 44, 12: 1181-1187.e2 (2016).

Singleton, Paul and Diana Sainsbury. Dictionary of Microbiology and Molecular Biology, 3rd Edition. John Wiley & Sons (2001).

Sorrentino, S.: Human extracellular ribonucleases: multiplicity, molecular diversity and catalytic properties of the major RNase types. Cellular and Molecular Life Sciences CMLS 54(8):785-794 (1998).

Springer et al.: GaINAc-siRNA Conjugates: Leading the Way for Delivery of TNAi Therapeutics. Nucleic Acid Therapeutics, vol. 28, No. 3 (2018).

Srinivasarao et al.: Ligand-Targeted Drug Delivery. Chem. Rev. 17(19): 12133-12164 (2017).

Stepney, Keeley et al.: Multivariate Analysis of API Particle Size Distribution Variation in a Manufacturing Environment. Computer Aided Chemical Engineering 31:1140-1144 (2012)—abstract and introduction, https://doi.org/10.1016/B978-0-444-59506-5.50059-6.

Svinarchuk, F.B. et al.: Inhibition of HIV Proliferation in Mt-4 Cells by Antisense Oligonucleotide Conjugated to Lipophilic Groups. Biochimie 75(1-2):49-54 (1993).

U.S. Appl. No. 18/420,112 Notice of Allowance dated Nov. 25, 2025.

U.S. Appl. No. 18/470,280 Office Action dated Apr. 3, 2024.

Wang, Tim et al.: Genetic screens in human cells using the CRISPR-Cas9 system. Science 343(6166):80-84 (2014).

Wang, Xinmei et al.: Enhanced hepatic delivery of siRNA and microRNA using oleic acid based lipid nanoparticle formulations. Journal of Controlled Release: Official Journal of the Controlled Release Society vol. 172,3: 690-698 (2013). doi:10.1016/j.jconrel.2013.09.027.

Willoughby, Jennifer L.S. et al.: Evaluation of GaINAc-siRNA Conjugate Activity in Pre-clinical Animal Models with Reduced Asialoglycoprotein Receptor Expression. Molecular therapy : the journal of the American Society of Gene Therapy vol. 26,1: 105-114 (2018).

Yin, Hao et al.: Therapeutic Genome Editing by Combined Viral and Non-viral Delivery of CRISPR System Components in Vivo. Nature Biotechnology 34(3):328-333 (2016).

(56)                 References Cited

OTHER PUBLICATIONS

Zetsche, Bernd et al.: A Split-cas9 Architecture for Inducible Genome Editing and Transcription Modulation. Nature Biotechnology. 33(2): 139-142 (2015).

Zhang, Mengzi et al.: Lactosylated gramicidin-based lipid nanoparticles (Lac-GLN) for targeted delivery of anti-miR-155 to hepatocellular carcinoma. Journal of Controlled Release : Official Journal of the Controlled Release Society vol. 168,3: 251-261 (2013). doi:10.1016/j.jconrel.2013.03.020.

Zufferey, R. et al.: Woodchuck hepatitis virus posttranscriptional regulatory element enhances expression of transgenes delivered by retroviral vectors. Journal of Virology 73(4):2886-2892 (1999).

* cited by examiner hANG_Cas12b_3:

hANG_Cas12b_5:

hANG_Cas12b_7:

hANG_Cas12b_14:

hANG_Cas12b_33:

hANG_Cas12b_34:

hANG_Cas12b_42:

hANG_Cas12b_64:

hANG_Cas12b_82:

hANG_Cas12b_84:

hANG_Cas12b_87:

hANG_Cas12b_88:

hANG_Cas12b_95:

hANG_Cas12b_117:

1= hANG_Cas12b_1
2= hANG_Cas12b_2
3= hANG_Cas12b_3
4= hANG_Cas12b_4
5= hANG_Cas12b_5
6= negative control
7= hANG_Cas12b_7
8= hANG_Cas12b_8

| Lane # | Plasmid ID |
|--------|------------|
| 1 | Size marker |
| 2 | hANG_Cas12b_10 |
| 3 | hANG_Cas12b_11 |
| 4 | hANG_Cas12b_12 |
| 5 | hANG_Cas12b_13 |
| 6 | hANG_Cas12b_14 |
| 7 | hANG_Cas12b_15 |
| 8 | hANG_Cas12b_16 |
| 9 | hANG_Cas12b_17 |

| Lane # | Plasmid ID |
|--------|------------|
| 1 | hANG_Cas12b_24 |
| 2 | hANG_Cas12b_25 |
| 3 | hANG_Cas12b_26 |
| 4 | hANG_Cas12b_27 |
| 5 | hANG_Cas12b_28 |
| 6 | hANG_Cas12b_29 |
| 7 | Blank Lane |
| 8 | Size marker |

Nucleotide Position 1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0 1 2 3 4 5 6 7 8 9 0

10   20   30   40   50   60   70   80   90   100   110   120

SEQ ID No. 1  G U U CUGUCCUUUUGGUCUCAGGACAACCGUCUAGCUAUUAGUGCUGCAGGCAUUAGCCUAUUGCUGACCAAUGCCAUUAGCCACAACCAACAGCAUUAGUCUCAAAU A A A UUUU

GB0002  gsususCugUCUUUUGGUcAGgACaACCgUCuaGCUAUUAGUGCUGcagGgUgAGAAACUCCuaUUgcugGACCAAUGcCauUagCaGGCAUUAGCCACAACCAACAGCAUUAGUCUCAAAUsasasa GB0003  gsususCugUCUUUUGGUcAGgACaACCgUCuaGCUAUUAGUGCUGcagGgUgAGAAACUCCuaUUgcugGACCAAUGcCauUagCaGGCAUUAGCCACAACCAACAGCAUUAGUCUCAAAUsasasa GB0007  gsususcugaCUUnUGGUcaggaCAACCguCucuAGCUAUUAGUGCuGcagGgUgUGAGAAACUCCgacgauguCUcUuacgagCAUUAGCCACAACCAACAGCAUUAGUCUCAAAUsasasa GB0008  gsususcugaCUUnUGGUcaggaCAACCguCucuAGCUAUUAGUGCUGCagggUgUGAGAAACUCCgacgauguCUcUuacgagCAUUAGCCACAACCAACAGCAUUAGUCUCAAAUsasasa Underlined: ANGPTL3 Spacer (Positions 98 to 120)

FIG. 20

SEQUENCE LISTING

<160> NUMBER OF SEQ ID NOS: 196

<210> SEQ ID NO 1
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 1
guucugucuu uggucagga caaccgucua gcuauaagug cugcagggug ugagaaacuc        60
cuauugcugg acgaugucuc uuacgaggca uuagcacaac caacagcaua gucaaauaaa      120
uuuu                                                                   124

<210> SEQ ID NO 2
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 2
guucugucuu uggucagga caaccgucua gcuauaagug cugcagggug ugagaaacuc        60
cuauugcugg acgaugucuc uuacgaggca uuagcacaac caacagcaua gucaaauaaa      120

<210> SEQ ID NO 3
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 3
guucugucuu uggucagga caaccgucua gcuauaagug cugcagggug ugagaaacuc        60
cuauugcugg acgaugucuc uuacgaggca uuagcacaac caacagcaua gucaaauaaa      120
uuuu                                                                   124

<210> SEQ ID NO 4
<211> LENGTH: 123
<212> TYPE: RNA
<213> ORGANISM: Artificial Sequence
<220> FEATURE:
<223> OTHER INFORMATION: Description of Artificial Sequence: Synthetic -continued

```
        polynucleotide

<400> SEQUENCE: 4
guucugucuu uuggucagga caaccgucua gcuauaagug cugcaggggug ugagaaacuc        60 cuauugcugg acgaugucuc uuacgaggca uuagcacaac caacagcaug ucaaauaaau       120
uuu                                                                     123

<210> SEQ ID NO 5
<211> LENGTH: 120
<212> TYPE: RNA
<213> ORGANISM: Artificial Sequence
<220> FEATURE:
<223> OTHER INFORMATION: Description of Artificial Sequence: Synthetic
        polynucleotide

<400> SEQUENCE: 5
guucugucuu uuggucagga caaccgucua gcuauaagug cugcaggggug ugagaaacuc        60 cuauugcugg acgaugucuc uuacgaggca uuagcacagg uaguccaugg acauuaauuc       120

<210> SEQ ID NO 6
<211> LENGTH: 123
<212> TYPE: RNA
<213> ORGANISM: Artificial Sequence
<220> FEATURE:
<223> OTHER INFORMATION: Description of Artificial Sequence: Synthetic
        polynucleotide

<400> SEQUENCE: 6
guucugucuu uuggucagga caaccgucua gcuauaaguc ugcagggugu gagaaacucc        60
uauugcugga cgaugucucu uacgaggcau uagcacaggu aguccaugga cauuaauucu       120
uuu                                                                     123

<210> SEQ ID NO 7
<211> LENGTH: 124
<212> TYPE: RNA
<213> ORGANISM: Artificial Sequence
<220> FEATURE:
<223> OTHER INFORMATION: Description of Artificial Sequence: Synthetic
        polynucleotide

<400> SEQUENCE: 7
guucugucuu uuggucagga caaccgucua gcuauaagug cugcaggggug ugagaaacuc        60 cuauugcugg acgaugucuc uuacgaggca uuagcacagg uaguccaugg acauuaauuc       120
uuuu                                                                    124

<210> SEQ ID NO 8
<211> LENGTH: 124
<212> TYPE: RNA
<213> ORGANISM: Artificial Sequence
<220> FEATURE:
<223> OTHER INFORMATION: Description of Artificial Sequence: Synthetic
        polynucleotide

<400> SEQUENCE: 8
guucugucuu uuggucagga caaccgucua gcuauaagug cugcaggggug ugagaaacuc        60 cuauugcugg acgaugucuc uuacgaggca uuagcaccaa aaacucaaca uauuugauca       120
uuuu                                                                    124

<210> SEQ ID NO 9
<211> LENGTH: 124
```

-continued

<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 9
guucugucuu uuggucagga caaccgucua gcuauaagug cugcaggggug ugagaaacuc      60 cuauugcugg acgaugucuc uuacgaggca uuagcacuac uucaacaaaa agugaaauau      120
uuuu                                                                    124

<210> SEQ ID NO 10
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 10
guucugucuu uuggucagga caaccgucua gcuauaagug cugcaggggug ugagaaacuc      60 cuauugcugg acgaugucuc uuacgaggca uuagcacaga agagcaacua acuaacuuaa      120
uuuu                                                                    124

<210> SEQ ID NO 11
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 11
guucugucuu uuggucagga caaccgucua gcuauaagug cugcaggggug ugagaaacuc      60 cuauugcugg acgaugucuc uuacgaggca uuagcacugg aggaaauaac uagaggaaca      120
uuuu                                                                    124

<210> SEQ ID NO 12
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 12
guucugucuu uuggucagga caaccgucua gcuauaagug cugcaggggug ugagaaacuc      60 cuauugcugg acgaugucuc uuacgaggca uuagcacaag aacccacaga aauuucucua      120
uuuu                                                                    124

<210> SEQ ID NO 13
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 13
guucugucuu uuggucagga caaccgucua gcuauaagug cugcaggggug ugagaaacuc      60 cuauugcugg acgaugucuc uuacgaggca uuagcacaac caacagcaua gucaaauaaa      120

-continued uuuu                                                                                      124

<210> SEQ ID NO 14
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 14
guucugucuu uuggucagga caaccgucua gcuauaagug cugcagggug ugagaaacuc      60
cuauugcugg acgaugucuc uuacgaggca uuagcacagg uaguccaugg acauuaauuc     120
uuuu                                                                 124

<210> SEQ ID NO 15
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 15
guucugucuu uuggucagga caaccgucua gcuauaagug cugcagggug ugagaaacuc      60
cuauugcugg acgaugucuc uuacgaggca uuagcaccug gcaauguccc caaugcaauc     120
uuuu                                                                 124

<210> SEQ ID NO 16
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 16
guucugucuu uuggucagga caaccgucua gcuauaagug cugcagggug ugagaaacuc      60
cuauugcugg acgaugucuc uuacgaggca uuagcaccau uggggacauu gccaguaauc     120
uuuu                                                                 124

<210> SEQ ID NO 17
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 17
guucugucuu uuggucagga caaccgucua gcuauaagug cugcagggug ugagaaacuc      60
cuauugcugg acgaugucuc uuacgaggca uuagcacccc aaguaaaaag aauauucaau     120
uuuu                                                                 124

<210> SEQ ID NO 18
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide -continued

<400> SEQUENCE: 18
guucugucuu uuggucagga caaccgucua gcuauaagug cugcagggug ugagaaacuc      60
cuauugcugg acgaugucuc uuacgaggca uuagcacaau auaauguuug uugucuuucc     120
uuuu                                                                124

<210> SEQ ID NO 19
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 19
guucugucuu uuggucagga caaccgucua gcuauaagug cugcagggug ugagaaacuc      60
cuauugcugg acgaugucuc uuacgaggca uuagcacgaa gagcaacuaa cuaacuuaau     120
uuuu                                                                124

<210> SEQ ID NO 20
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 20
guucugucuu uuggucagga caaccgucua gcuauaagug cugcagggug ugagaaacuc      60
cuauugcugg acgaugucuc uuacgaggca uuagcacaac caacagcaua gucaaauaaa     120

<210> SEQ ID NO 21
<211> LENGTH: 123
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 21
guucugucuu uuggucagga caaccgucua gcuauaagug cugcagggug ugagaaacuc      60
cuauugcugg acgaugucuc uuacgaggca uuagcacaac caacagcaug ucaaauaaau     120
uuu                                                                 123

<210> SEQ ID NO 22
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 22
guucugucuu uuggucagga caaccgucua gcuauaagug cugcagggug ugagaaacuc      60
cuauugcugg acgaugucuc uuacgaggca uuagcacagg uaguccaugg acauuaauuc     120

<210> SEQ ID NO 23
<211> LENGTH: 123
<212> TYPE: RNA
<213> ORGANISM: Artificial Sequence
<220> FEATURE:

```
<223> OTHER INFORMATION: Description of Artificial Sequence: Synthetic
      polynucleotide

<400> SEQUENCE: 23
guucugucuu uuggucagga caaccgucua gcuauaaguc ugcagggugu gagaaacucc    60
uauugcugga cgaugucucu uacgaggcau uagcacaggu aguccaugga cauuaauucu   120
uuu                                                                 123

<210> SEQ ID NO 24
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 24
guucugucuu uuggucagga caaccgucua gcuauaagug cugcagggug ugagaaacuc    60
cuauugcugg acgaugucuc uuacgaggca uuagcacaac caacagcaua gucaaauaaa   120

<210> SEQ ID NO 25
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 25
guucugucuu uuggucagga caaccgucua gcuauaagug cugcagggug ugagaaacuc    60
cuauugcugg acgaugucuc uuacgaggca uuagcacaac caacagcaua gucaaauaaa   120
uuuu                                                                124

<210> SEQ ID NO 26
<211> LENGTH: 123
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 26
guucugucuu uuggucagga caaccgucua gcuauaagug cugcagggug ugagaaacuc    60
cuauugcugg acgaugucuc uuacgaggca uuagcacaac caacagcaug ucaaauaaau   120
uuu                                                                 123

<210> SEQ ID NO 27
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 27
guucugucuu uuggucagga caaccgucua gcuauaagug cugcagggug ugagaaacuc    60
cuauugcugg acgaugucuc uuacgaggca uuagcacagg uaguccaugg acauuaauuc   120

<210> SEQ ID NO 28
<211> LENGTH: 123
<212> TYPE: RNA
```

<213> ORGANISM: Artificial Sequence
<220> FEATURE:
<223> OTHER INFORMATION: Description of Artificial Sequence: Synthetic
      polynucleotide

<400> SEQUENCE: 28
guucugucuu uuggucagga caaccgucua gcuauaaguc ugcagggugu gagaaacucc        60
uauugcugga cgaugucucu uacgaggcau uagcacaggu aguccaugga cauuaauucu       120
uuu                                                                    123

<210> SEQ ID NO 29
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 29
guucugucuu uuggucagga caaccgucua gcuauaagug cugcagggug ugagaaacuc        60
cuauugcugg acgaugucuc uuacgaggca uuagcacagg uaguccaugg acauuaauuc       120
uuuu                                                                   124

<210> SEQ ID NO 30
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 30
guucugucuu uuggucagga caaccgucua gcuauaagug cugcagggug ugagaaacuc        60
cuauugcugg acgaugucuc uuacgaggca uuagcaccaa aaacucaaca uauuugauca       120
uuuu                                                                   124

<210> SEQ ID NO 31
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 31
guucugucuu uuggucagga caaccgucua gcuauaagug cugcagggug ugagaaacuc        60
cuauugcugg acgaugucuc uuacgaggca uuagcacuac uucaacaaaa agugaaauau       120
uuuu                                                                   124

<210> SEQ ID NO 32
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 32
guucugucuu uuggucagga caaccgucua gcuauaagug cugcagggug ugagaaacuc        60
cuauugcugg acgaugucuc uuacgaggca uuagcacaga agagcaacua acuaacuuaa       120

-continued uuuu                                                                                                         124

<210> SEQ ID NO 33
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 33
guucugucuu uuggucagga caaccgucua gcuauaagug cugcaggggug ugagaaacuc       60 cuauugcugg acgaugucuc uuacgaggca uuagcacugg aggaaauaac uagaggaaca      120
uuuu                                                                                                         124

<210> SEQ ID NO 34
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 34
guucugucuu uuggucagga caaccgucua gcuauaagug cugcaggggug ugagaaacuc       60 cuauugcugg acgaugucuc uuacgaggca uuagcacaag aacccacaga aauuucucua      120
uuuu                                                                                                         124

<210> SEQ ID NO 35
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 35
guucugucuu uuggucagga caaccgucua gcuauaagug cugcaggggug ugagaaacuc       60 cuauugcugg acgaugucuc uuacgaggca uuagcacaac caacagcaua gucaaauaaa      120
uuuu                                                                                                         124

<210> SEQ ID NO 36
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 36
guucugucuu uuggucagga caaccgucua gcuauaagug cugcaggggug ugagaaacuc       60 cuauugcugg acgaugucuc uuacgaggca uuagcacagg uaguccaugg acauuaauuc      120
uuuu                                                                                                         124

<210> SEQ ID NO 37
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide -continued

<400> SEQUENCE: 37
guucugucuu uuggucagga caaccgucua gcuauaagug cugcaggggug ugagaaacuc      60 cuauugcugg acgaugucuc uuacgaggca uuagcaccug gcaaugucccc caaugcaauc     120 uuuu                                                                   124

<210> SEQ ID NO 38
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 38
guucugucuu uuggucagga caaccgucua gcuauaagug cugcaggggug ugagaaacuc      60 cuauugcugg acgaugucuc uuacgaggca uuagcaccau ugggggacauu gccaguaauc     120 uuuu                                                                   124

<210> SEQ ID NO 39
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 39
guucugucuu uuggucagga caaccgucua gcuauaagug cugcaggggug ugagaaacuc      60 cuauugcugg acgaugucuc uuacgaggca uuagcacccc aaguaaaaag aauauucaau     120
uuuu                                                                   124

<210> SEQ ID NO 40
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 40
guucugucuu uuggucagga caaccgucua gcuauaagug cugcaggggug ugagaaacuc      60 cuauugcugg acgaugucuc uuacgaggca uuagcacaau auaauguuug uugucuuucc     120
uuuu                                                                   124

<210> SEQ ID NO 41
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 41
guucugucuu uuggucagga caaccgucua gcuauaagug cugcaggggug ugagaaacuc      60 cuauugcugg acgaugucuc uuacgaggca uuagcacgaa gagcaacuaa cuaacuuaau     120
uuuu                                                                   124

<210> SEQ ID NO 42
<211> LENGTH: 120

```
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 42
guucugucuu uuggucagga caaccgucua gcuauaagug cugcagggug ugagaaacuc        60
cuauugcugg acgaugucuc uuacgaggca uuagcacaac caacagcaua gucaaauaaa       120

<210> SEQ ID NO 43
<211> LENGTH: 123
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 43
guucugucuu uuggucagga caaccgucua gcuauaagug cugcagggug ugagaaacuc        60
cuauugcugg acgaugucuc uuacgaggca uuagcacaac caacagcaug ucaaauaaau       120
uuu                                                                     123

<210> SEQ ID NO 44
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 44
guucugucuu uuggucagga caaccgucua gcuauaagug cugcagggug ugagaaacuc        60
cuauugcugg acgaugucuc uuacgaggca uuagcacagg uaguccaugg acauuaauuc       120

<210> SEQ ID NO 45
<211> LENGTH: 123
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 45
guucugucuu uuggucagga caaccgucua gcuauaaguc ugcagggugu gagaaacucc        60
uauugcugga cgaugucucu uacgaggcau uagcacaggu aguccaugga cauuaauucu       120
uuu                                                                     123

<210> SEQ ID NO 46
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (22)..(22)
<223> OTHER INFORMATION: Nebularine

<400> SEQUENCE: 46
guucugucuu uuggucagga cnaccgucua gcuauaagug cugcagggug ugagaaacuc        60
cuauugcugg acgaugucuc uuacgaggca uuagcacaac caacagcaua gucaaauaaa       120
```

-continued

```
<210> SEQ ID NO 47
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (23)..(23)
<223> OTHER INFORMATION: Nebularine

<400> SEQUENCE: 47
guucugucuu uuggucagga canccgucua gcuauaagug cugcagggug ugagaaacuc      60
cuauugcugg acgaugucuc uuacgaggca uuagcacaac caacagcaua gucaaauaaa     120

<210> SEQ ID NO 48
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (34)..(34)
<223> OTHER INFORMATION: Nebularine

<400> SEQUENCE: 48
guucugucuu uuggucagga caaccgucua gcunuaagug cugcagggug ugagaaacuc      60
cuauugcugg acgaugucuc uuacgaggca uuagcacaac caacagcaua gucaaauaaa     120

<210> SEQ ID NO 49
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (36)..(36)
<223> OTHER INFORMATION: Nebularine

<400> SEQUENCE: 49
guucugucuu uuggucagga caaccgucua gcuaunagug cugcagggug ugagaaacuc      60
cuauugcugg acgaugucuc uuacgaggca uuagcacaac caacagcaua gucaaauaaa     120

<210> SEQ ID NO 50
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(37)
<223> OTHER INFORMATION: Nebularine

<400> SEQUENCE: 50
guucugucuu uuggucagga caaccgucua gcuauangug cugcagggug ugagaaacuc      60
cuauugcugg acgaugucuc uuacgaggca uuagcacaac caacagcaua gucaaauaaa     120

<210> SEQ ID NO 51
```

```
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (53)..(53)
<223> OTHER INFORMATION: Nebularine

<400> SEQUENCE: 51
guucugucuu uuggucagga caaccgucua gcuauaagug cugcagggug ugngaaacuc      60
cuauugcugg acgaugucuc uuacgaggca uuagcacaac caacagcaua gucaaauaaa     120

<210> SEQ ID NO 52
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (55)..(55)
<223> OTHER INFORMATION: Nebularine

<400> SEQUENCE: 52
guucugucuu uuggucagga caaccgucua gcuauaagug cugcagggug ugagnaacuc      60
cuauugcugg acgaugucuc uuacgaggca uuagcacaac caacagcaua gucaaauaaa     120

<210> SEQ ID NO 53
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (56)..(56)
<223> OTHER INFORMATION: Nebularine

<400> SEQUENCE: 53
guucugucuu uuggucagga caaccgucua gcuauaagug cugcagggug ugaganacuc      60
cuauugcugg acgaugucuc uuacgaggca uuagcacaac caacagcaua gucaaauaaa     120

<210> SEQ ID NO 54
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (57)..(57)
<223> OTHER INFORMATION: Nebularine

<400> SEQUENCE: 54
guucugucuu uuggucagga caaccgucua gcuauaagug cugcagggug ugagaancuc      60
cuauugcugg acgaugucuc uuacgaggca uuagcacaac caacagcaua gucaaauaaa     120

<210> SEQ ID NO 55
<211> LENGTH: 120
<212> TYPE: RNA
<213> ORGANISM: Artificial Sequence
```

```
<220> FEATURE:
<223> OTHER INFORMATION: Description of Artificial Sequence: Synthetic
      polynucleotide
<220> FEATURE:
<221> NAME/KEY: modified_base
<222> LOCATION: (71)..(71)
<223> OTHER INFORMATION: Nebularine

<400> SEQUENCE: 55
guucugucuu uuggucagga caaccgucua gcuauaagug cugcagggug ugagaaacuc      60
cuauugcugg ncgaugucuc uuacgaggca uuagcacaac caacagcaua gucaaauaaa     120

<210> SEQ ID NO 56
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (74)..(74)
<223> OTHER INFORMATION: Nebularine

<400> SEQUENCE: 56
guucugucuu uuggucagga caaccgucua gcuauaagug cugcagggug ugagaaacuc      60
cuauugcugg acgnugucuc uuacgaggca uuagcacaac caacagcaua gucaaauaaa     120

<210> SEQ ID NO 57
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (30)..(30)
<223> OTHER INFORMATION: Nebularine

<400> SEQUENCE: 57
guucugucuu uuggucagga caaccgucun gcuauaagug cugcagggug ugagaaacuc      60
cuauugcugg acgaugucuc uuacgaggca uuagcacaac caacagcaua gucaaauaaa     120

<210> SEQ ID NO 58
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (45)..(45)
<223> OTHER INFORMATION: Nebularine

<400> SEQUENCE: 58
guucugucuu uuggucagga caaccgucua gcuauaagug cugcnggggu ugagaaacuc      60
cuauugcugg acgaugucuc uuacgaggca uuagcacaac caacagcaua gucaaauaaa     120

<210> SEQ ID NO 59
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
```

<220> FEATURE:
<221> NAME/KEY: modified_base
<222> LOCATION: (63)..(63)
<223> OTHER INFORMATION: Nebularine

<400> SEQUENCE: 59
guucugucuu uuggucagga caaccgucua gcuauaagug cugcagggug ugagaaacuc      60
cunuugcugg acgaugucuc uuacgaggca uuagcacaac caacagcaua gucaaauaaa     120

<210> SEQ ID NO 60
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (22)..(22)
<223> OTHER INFORMATION: Nebularine
<220> FEATURE:
<221> NAME/KEY: modified_base
<222> LOCATION: (56)..(56)
<223> OTHER INFORMATION: Nebularine

<400> SEQUENCE: 60
guucugucuu uuggucagga cnaccgucua gcuauaagug cugcagggug ugaganacuc      60
cuauugcugg acgaugucuc uuacgaggca uuagcacaac caacagcaua gucaaauaaa     120

<210> SEQ ID NO 61
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (23)..(23)
<223> OTHER INFORMATION: Nebularine
<220> FEATURE:
<221> NAME/KEY: modified_base
<222> LOCATION: (30)..(30)
<223> OTHER INFORMATION: Nebularine
<220> FEATURE:
<221> NAME/KEY: modified_base
<222> LOCATION: (45)..(45)
<223> OTHER INFORMATION: Nebularine

<400> SEQUENCE: 61
guucugucuu uuggucagga canccgucun gcuauaagug cugcnggguc ugagaaacuc      60
cuauugcugg acgaugucuc uuacgaggca uuagcacaac caacagcaua gucaaauaaa     120

<210> SEQ ID NO 62
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (34)..(34)
<223> OTHER INFORMATION: Nebularine
<220> FEATURE:
<221> NAME/KEY: modified_base
<222> LOCATION: (63)..(63)
<223> OTHER INFORMATION: Nebularine

<400> SEQUENCE: 62

-continued

```
guucugucuu uuggucagga caaccgucua gcunuaagug cugcaggggug ugagaaacuc      60 cunuugcugg acgaugucuc uuacgaggca uuagcacaac caacagcaua gucaaauaaa     120

<210> SEQ ID NO 63
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(37)
<223> OTHER INFORMATION: Nebularine
<220> FEATURE:
<221> NAME/KEY: modified_base
<222> LOCATION: (71)..(71)
<223> OTHER INFORMATION: Nebularine

<400> SEQUENCE: 63
guucugucuu uuggucagga caaccgucua gcuauangug cugcaggggug ugagaaacuc      60 cuauugcugg ncgaugucuc uuacgaggca uuagcacaac caacagcaua gucaaauaaa     120

<210> SEQ ID NO 64
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (30)..(30)
<223> OTHER INFORMATION: Nebularine
<220> FEATURE:
<221> NAME/KEY: modified_base
<222> LOCATION: (55)..(55)
<223> OTHER INFORMATION: Nebularine

<400> SEQUENCE: 64
guucugucuu uuggucagga caaccgucun gcuauaagug cugcaggggug ugagnaacuc      60 cuauugcugg acgaugucuc uuacgaggca uuagcacaac caacagcaua gucaaauaaa     120

<210> SEQ ID NO 65
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (30)..(30)
<223> OTHER INFORMATION: Nebularine
<220> FEATURE:
<221> NAME/KEY: modified_base
<222> LOCATION: (45)..(45)
<223> OTHER INFORMATION: Nebularine
<220> FEATURE:
<221> NAME/KEY: modified_base
<222> LOCATION: (56)..(56)
<223> OTHER INFORMATION: Nebularine

<400> SEQUENCE: 65
guucugucuu uuggucagga caaccgucun gcuauaagug cugcnggggug ugaganacuc      60 cuauugcugg acgaugucuc uuacgaggca uuagcacaac caacagcaua gucaaauaaa     120
```

```
<210> SEQ ID NO 66
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (23)..(23)
<223> OTHER INFORMATION: Nebularine
<220> FEATURE:
<221> NAME/KEY: modified_base
<222> LOCATION: (57)..(57)
<223> OTHER INFORMATION: Nebularine

<400> SEQUENCE: 66
guucugucuu uuggucagga canccgucua gcuauaagug cugcaggggug ugagaancuc      60 cuauugcugg acgaugucuc uuacgaggca uuagcacaac caacagcaua gucaaauaaa      120

<210> SEQ ID NO 67
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (71)..(71)
<223> OTHER INFORMATION: Nebularine
<220> FEATURE:
<221> NAME/KEY: modified_base
<222> LOCATION: (83)..(83)
<223> OTHER INFORMATION: Nebularine

<400> SEQUENCE: 67
guucugucuu uuggucagga caaccgucua gcuauaagug cugcaggggug ugagaaacuc      60 cuauugcugg ncgaugucuc uuncgaggca uuagcacaac caacagcaua gucaaauaaa      120

<210> SEQ ID NO 68
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (30)..(30)
<223> OTHER INFORMATION: Nebularine
<220> FEATURE:
<221> NAME/KEY: modified_base
<222> LOCATION: (45)..(45)
<223> OTHER INFORMATION: Nebularine
<220> FEATURE:
<221> NAME/KEY: modified_base
<222> LOCATION: (63)..(63)
<223> OTHER INFORMATION: Nebularine
<220> FEATURE:
<221> NAME/KEY: modified_base
<222> LOCATION: (83)..(83)
<223> OTHER INFORMATION: Nebularine

<400> SEQUENCE: 68
guucugucuu uuggucagga caaccgucun gcuauaagug cugcnggggug ugagaaacuc      60 cunuugcugg acgaugucuc uuncgaggca uuagcacaac caacagcaua gucaaauaaa      120

<210> SEQ ID NO 69
<211> LENGTH: 120
```

<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (83)..(83)
<223> OTHER INFORMATION: Nebularine

<400> SEQUENCE: 69
guucugucuu uuggucagga caaccgucua gcuauaagug cugcagggug ugagaaacuc      60
cuauugcugg acgaugucuc uuncgaggca uuagcacaac caacagcaua gucaaauaaa     120

<210> SEQ ID NO 70
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (86)..(86)
<223> OTHER INFORMATION: Nebularine

<400> SEQUENCE: 70
guucugucuu uuggucagga caaccgucua gcuauaagug cugcagggug ugagaaacuc      60
cuauugcugg acgaugucuc uuacgnggca uuagcacaac caacagcaua gucaaauaaa     120

<210> SEQ ID NO 71
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (22)..(22)
<223> OTHER INFORMATION: Nebularine
<220> FEATURE:
<221> NAME/KEY: modified_base
<222> LOCATION: (56)..(56)
<223> OTHER INFORMATION: Nebularine

<400> SEQUENCE: 71
guucugucuu uuggucagga cnaccgucua gcuauaagug cugcagggug ugaganacuc      60
cuauugcugg acgaugucuc uuacgaggca uuagcacaac caacagcaua gucaaauaaa     120

<210> SEQ ID NO 72
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (23)..(23)
<223> OTHER INFORMATION: Nebularine
<220> FEATURE:
<221> NAME/KEY: modified_base
<222> LOCATION: (30)..(30)
<223> OTHER INFORMATION: Nebularine
<220> FEATURE:
<221> NAME/KEY: modified_base
<222> LOCATION: (45)..(45)
<223> OTHER INFORMATION: Nebularine -continued

<400> SEQUENCE: 72
guucugucuu uuggucagga canccgucun gcuauaagug cugcngggug ugagaaacuc      60
cuauugcugg acgaugucuc uuacgaggca uuagcacaac caacagcaua gucaaauaaa     120

<210> SEQ ID NO 73
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (34)..(34)
<223> OTHER INFORMATION: Nebularine
<220> FEATURE:
<221> NAME/KEY: modified_base
<222> LOCATION: (63)..(63)
<223> OTHER INFORMATION: Nebularine

<400> SEQUENCE: 73
guucugucuu uuggucagga caaccgucua gcunuaagug cugcagggug ugagaaacuc      60
cunuugcugg acgaugucuc uuacgaggca uuagcacaac caacagcaua gucaaauaaa     120

<210> SEQ ID NO 74
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (36)..(36)
<223> OTHER INFORMATION: Nebularine

<400> SEQUENCE: 74
guucugucuu uuggucagga caaccgucua gcuaunagug cugcagggug ugagaaacuc      60
cuauugcugg acgaugucuc uuacgaggca uuagcacaac caacagcaua gucaaauaaa     120

<210> SEQ ID NO 75
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(37)
<223> OTHER INFORMATION: Nebularine
<220> FEATURE:
<221> NAME/KEY: modified_base
<222> LOCATION: (71)..(71)
<223> OTHER INFORMATION: Nebularine

<400> SEQUENCE: 75
guucugucuu uuggucagga caaccgucua gcuauangug cugcagggug ugagaaacuc      60
cuauugcugg ncgaugucuc uuacgaggca uuagcacaac caacagcaua gucaaauaaa     120

<210> SEQ ID NO 76
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide -continued

```
<220> FEATURE:
<221> NAME/KEY: modified_base
<222> LOCATION: (53)..(53)
<223> OTHER INFORMATION: Nebularine

<400> SEQUENCE: 76
guucugucuu uuggucagga caaccgucua gcuauaagug cugcagggug ugngaaacuc        60
cuauugcugg acgaugucuc uuacgaggca uuagcacaac caacagcaua gucaaauaaa       120

<210> SEQ ID NO 77
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (30)..(30)
<223> OTHER INFORMATION: Nebularine
<220> FEATURE:
<221> NAME/KEY: modified_base
<222> LOCATION: (55)..(55)
<223> OTHER INFORMATION: Nebularine

<400> SEQUENCE: 77
guucugucuu uuggucagga caaccgucun gcuauaagug cugcagggug ugagnaacuc        60
cuauugcugg acgaugucuc uuacgaggca uuagcacaac caacagcaua gucaaauaaa       120

<210> SEQ ID NO 78
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (30)..(30)
<223> OTHER INFORMATION: Nebularine
<220> FEATURE:
<221> NAME/KEY: modified_base
<222> LOCATION: (45)..(45)
<223> OTHER INFORMATION: Nebularine
<220> FEATURE:
<221> NAME/KEY: modified_base
<222> LOCATION: (56)..(56)
<223> OTHER INFORMATION: Nebularine

<400> SEQUENCE: 78
guucugucuu uuggucagga caaccgucun gcuauaagug cugcngggug ugaganacuc        60
cuauugcugg acgaugucuc uuacgaggca uuagcacaac caacagcaua gucaaauaaa       120

<210> SEQ ID NO 79
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (23)..(23)
<223> OTHER INFORMATION: Nebularine
<220> FEATURE:
<221> NAME/KEY: modified_base
<222> LOCATION: (57)..(57)
<223> OTHER INFORMATION: Nebularine

<400> SEQUENCE: 79
```
guucugucuu uuggucagga canccgucua gcuauaagug cugcaggggug ugagaancuc          60 cuauugcugg acgaugucuc uuacgaggca uuagcacaac caacagcaua gucaaauaaa          120

<210> SEQ ID NO 80
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (71)..(71)
<223> OTHER INFORMATION: Nebularine
<220> FEATURE:
<221> NAME/KEY: modified_base
<222> LOCATION: (83)..(83)
<223> OTHER INFORMATION: Nebularine

<400> SEQUENCE: 80
guucugucuu uuggucagga caaccgucua gcuauaagug cugcagggug ugagaaacuc          60
cuauugcugg ncgaugucuc uuncgaggca uuagcacaac caacagcaua gucaaauaaa          120

<210> SEQ ID NO 81
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (30)..(30)
<223> OTHER INFORMATION: Nebularine
<220> FEATURE:
<221> NAME/KEY: modified_base
<222> LOCATION: (45)..(45)
<223> OTHER INFORMATION: Nebularine
<220> FEATURE:
<221> NAME/KEY: modified_base
<222> LOCATION: (63)..(63)
<223> OTHER INFORMATION: Nebularine
<220> FEATURE:
<221> NAME/KEY: modified_base
<222> LOCATION: (83)..(83)
<223> OTHER INFORMATION: Nebularine

<400> SEQUENCE: 81
guucugucuu uuggucagga caaccgucun gcuauaagug cugcngggug ugagaaacuc          60
cunuugcugg acgaugucuc uuncgaggca uuagcacaac caacagcaua gucaaauaaa          120

<210> SEQ ID NO 82
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (83)..(83)
<223> OTHER INFORMATION: Nebularine

<400> SEQUENCE: 82
guucugucuu uuggucagga caaccgucua gcuauaagug cugcagggug ugagaaacuc          60
cuauugcugg acgaugucuc uuncgaggca uuagcacaac caacagcaua gucaaauaaa          120

-continued

```
<210> SEQ ID NO 83
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (86)..(86)
<223> OTHER INFORMATION: Nebularine

<400> SEQUENCE: 83
guucugucuu uuggucagga caaccgucua gcuauaagug cugcagggug ugagaaacuc        60
cuauugcugg acgaugucuc uuacgnggca uuagcacaac caacagcaua gucaaauaaa       120

<210> SEQ ID NO 84
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (22)..(23)
<223> OTHER INFORMATION: Nebularine
<220> FEATURE:
<221> NAME/KEY: modified_base
<222> LOCATION: (30)..(30)
<223> OTHER INFORMATION: Nebularine
<220> FEATURE:
<221> NAME/KEY: modified_base
<222> LOCATION: (34)..(34)
<223> OTHER INFORMATION: Nebularine
<220> FEATURE:
<221> NAME/KEY: modified_base
<222> LOCATION: (36)..(37)
<223> OTHER INFORMATION: Nebularine
<220> FEATURE:
<221> NAME/KEY: modified_base
<222> LOCATION: (45)..(45)
<223> OTHER INFORMATION: Nebularine
<220> FEATURE:
<221> NAME/KEY: modified_base
<222> LOCATION: (53)..(53)
<223> OTHER INFORMATION: Nebularine
<220> FEATURE:
<221> NAME/KEY: modified_base
<222> LOCATION: (55)..(57)
<223> OTHER INFORMATION: Nebularine
<220> FEATURE:
<221> NAME/KEY: modified_base
<222> LOCATION: (63)..(63)
<223> OTHER INFORMATION: Nebularine
<220> FEATURE:
<221> NAME/KEY: modified_base
<222> LOCATION: (71)..(71)
<223> OTHER INFORMATION: Nebularine
<220> FEATURE:
<221> NAME/KEY: modified_base
<222> LOCATION: (74)..(74)
<223> OTHER INFORMATION: Nebularine
<220> FEATURE:
<221> NAME/KEY: modified_base
<222> LOCATION: (83)..(83)
<223> OTHER INFORMATION: Nebularine
<220> FEATURE:
<221> NAME/KEY: modified_base
<222> LOCATION: (86)..(86)
<223> OTHER INFORMATION: Nebularine
<220> FEATURE:
<221> NAME/KEY: modified_base
<222> LOCATION: (90)..(90)
<223> OTHER INFORMATION: Nebularine
<220> FEATURE:
```

```
<221> NAME/KEY: modified_base
<222> LOCATION: (93)..(93)
<223> OTHER INFORMATION: Nebularine
<220> FEATURE:
<221> NAME/KEY: modified_base
<222> LOCATION: (96)..(96)
<223> OTHER INFORMATION: Nebularine
<220> FEATURE:
<221> NAME/KEY: modified_base
<222> LOCATION: (98)..(99)
<223> OTHER INFORMATION: Nebularine
<220> FEATURE:
<221> NAME/KEY: modified_base
<222> LOCATION: (102)..(103)
<223> OTHER INFORMATION: Nebularine
<220> FEATURE:
<221> NAME/KEY: modified_base
<222> LOCATION: (105)..(105)
<223> OTHER INFORMATION: Nebularine
<220> FEATURE:
<221> NAME/KEY: modified_base
<222> LOCATION: (108)..(108)
<223> OTHER INFORMATION: Nebularine
<220> FEATURE:
<221> NAME/KEY: modified_base
<222> LOCATION: (110)..(110)
<223> OTHER INFORMATION: Nebularine
<220> FEATURE:
<221> NAME/KEY: modified_base
<222> LOCATION: (114)..(116)
<223> OTHER INFORMATION: Nebularine
<220> FEATURE:
<221> NAME/KEY: modified_base
<222> LOCATION: (118)..(120)
<223> OTHER INFORMATION: Nebularine

<400> SEQUENCE: 84
guucugucuu uuggucagga cnnccgucun gcununngug cugcngggug ugngnnncuc      60
cunuugcugg ncgnugucuc uuncgnggcn uungcncnnc cnncngcnun gucnnnunnn     120

<210> SEQ ID NO 85
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (22)..(23)
<223> OTHER INFORMATION: Nebularine
<220> FEATURE:
<221> NAME/KEY: modified_base
<222> LOCATION: (36)..(37)
<223> OTHER INFORMATION: Nebularine
<220> FEATURE:
<221> NAME/KEY: modified_base
<222> LOCATION: (53)..(53)
<223> OTHER INFORMATION: Nebularine
<220> FEATURE:
<221> NAME/KEY: modified_base
<222> LOCATION: (55)..(56)
<223> OTHER INFORMATION: Nebularine
<220> FEATURE:
<221> NAME/KEY: modified_base
<222> LOCATION: (83)..(83)
<223> OTHER INFORMATION: Nebularine

<400> SEQUENCE: 85
guucugucuu uuggucagga cnnccgucua gcuaunngug cugcagggug ugngnnacuc      60
cuauugcugg acgaugucuc uuncgaggca uuagcacaac caacagcaua gucaaauaaa     120

<210> SEQ ID NO 86
```

```
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (17)..(17)
<223> OTHER INFORMATION: Nebularine
<220> FEATURE:
<221> NAME/KEY: modified_base
<222> LOCATION: (20)..(20)
<223> OTHER INFORMATION: Nebularine
<220> FEATURE:
<221> NAME/KEY: modified_base
<222> LOCATION: (22)..(23)
<223> OTHER INFORMATION: Nebularine
<220> FEATURE:
<221> NAME/KEY: modified_base
<222> LOCATION: (30)..(30)
<223> OTHER INFORMATION: Nebularine
<220> FEATURE:
<221> NAME/KEY: modified_base
<222> LOCATION: (34)..(34)
<223> OTHER INFORMATION: Nebularine
<220> FEATURE:
<221> NAME/KEY: modified_base
<222> LOCATION: (36)..(37)
<223> OTHER INFORMATION: Nebularine
<220> FEATURE:
<221> NAME/KEY: modified_base
<222> LOCATION: (45)..(45)
<223> OTHER INFORMATION: Nebularine
<220> FEATURE:
<221> NAME/KEY: modified_base
<222> LOCATION: (53)..(53)
<223> OTHER INFORMATION: Nebularine
<220> FEATURE:
<221> NAME/KEY: modified_base
<222> LOCATION: (55)..(57)
<223> OTHER INFORMATION: Nebularine
<220> FEATURE:
<221> NAME/KEY: modified_base
<222> LOCATION: (63)..(63)
<223> OTHER INFORMATION: Nebularine
<220> FEATURE:
<221> NAME/KEY: modified_base
<222> LOCATION: (71)..(71)
<223> OTHER INFORMATION: Nebularine
<220> FEATURE:
<221> NAME/KEY: modified_base
<222> LOCATION: (74)..(74)
<223> OTHER INFORMATION: Nebularine
<220> FEATURE:
<221> NAME/KEY: modified_base
<222> LOCATION: (83)..(83)
<223> OTHER INFORMATION: Nebularine
<220> FEATURE:
<221> NAME/KEY: modified_base
<222> LOCATION: (86)..(86)
<223> OTHER INFORMATION: Nebularine
<220> FEATURE:
<221> NAME/KEY: modified_base
<222> LOCATION: (90)..(90)
<223> OTHER INFORMATION: Nebularine
<220> FEATURE:
<221> NAME/KEY: modified_base
<222> LOCATION: (93)..(93)
<223> OTHER INFORMATION: Nebularine
<220> FEATURE:
<221> NAME/KEY: modified_base
<222> LOCATION: (96)..(96)
<223> OTHER INFORMATION: Nebularine
<220> FEATURE:
<221> NAME/KEY: modified_base
<222> LOCATION: (98)..(99)
<223> OTHER INFORMATION: Nebularine
<220> FEATURE:
```

-continued

```
<221> NAME/KEY: modified_base
<222> LOCATION: (102)..(103)
<223> OTHER INFORMATION: Nebularine
<220> FEATURE:
<221> NAME/KEY: modified_base
<222> LOCATION: (105)..(105)
<223> OTHER INFORMATION: Nebularine
<220> FEATURE:
<221> NAME/KEY: modified_base
<222> LOCATION: (108)..(108)
<223> OTHER INFORMATION: Nebularine
<220> FEATURE:
<221> NAME/KEY: modified_base
<222> LOCATION: (110)..(110)
<223> OTHER INFORMATION: Nebularine
<220> FEATURE:
<221> NAME/KEY: modified_base
<222> LOCATION: (114)..(116)
<223> OTHER INFORMATION: Nebularine
<220> FEATURE:
<221> NAME/KEY: modified_base
<222> LOCATION: (118)..(120)
<223> OTHER INFORMATION: Nebularine

<400> SEQUENCE: 86
guucugucuu uuggucnggn cnnccgucun gcununngug cugcngggug ugngnnncuc        60
cunuugcugg ncgnugucuc uuncgnggcn uungcncnnc cnncngcnun gucnnnunnn       120

<210> SEQ ID NO 87
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (30)..(30)
<223> OTHER INFORMATION: Nebularine
<220> FEATURE:
<221> NAME/KEY: modified_base
<222> LOCATION: (45)..(45)
<223> OTHER INFORMATION: Nebularine
<220> FEATURE:
<221> NAME/KEY: modified_base
<222> LOCATION: (63)..(63)
<223> OTHER INFORMATION: Nebularine
<220> FEATURE:
<221> NAME/KEY: modified_base
<222> LOCATION: (83)..(83)
<223> OTHER INFORMATION: Nebularine
<220> FEATURE:
<221> NAME/KEY: modified_base
<222> LOCATION: (118)..(120)
<223> OTHER INFORMATION: Nebularine

<400> SEQUENCE: 87
guucugucuu uuggucagga caaccgucun gcuauaagug cugcngggug ugagaaacuc        60
cunuugcugg acgaugucuc uuncgaggca uuagcacaac caacagcaua gucaaaunnn       120

<210> SEQ ID NO 88
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (17)..(17)
<223> OTHER INFORMATION: Nebularine
<220> FEATURE:
<221> NAME/KEY: modified_base
```

```
<222> LOCATION: (45)..(45)
<223> OTHER INFORMATION: Nebularine
<220> FEATURE:
<221> NAME/KEY: modified_base
<222> LOCATION: (118)..(120)
<223> OTHER INFORMATION: Nebularine

<400> SEQUENCE: 88
guucugucuu uggucngga caaccgucua gcuauaagug cugcngggug ugagaaacuc        60
cuauugcugg acgaugucuc uuacgaggca uuagcacaac caacagcaua gucaaaunnn      120

<210> SEQ ID NO 89
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (118)..(120)
<223> OTHER INFORMATION: Nebularine

<400> SEQUENCE: 89
guucugucuu uggucagga caaccgucua gcuauaagug cugcagggug ugagaaacuc        60
cuauugcugg acgaugucuc uuacgaggca uuagcacaac caacagcaua gucaaaunnn      120

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
aaccaacagc atagtcaaat aaa                                               23

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
aggtagtcca tggacattaa ttc                                               23

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
caaaaactca acatatttga tca                                               23

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 93
tacttcaaca aaaagtgaaa tat                                            23

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
agaagagcaa ctaactaact taa                                            23

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
tggaggaaat aactagagga aca                                            23

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
aagaacccac agaaatttct cta                                            23

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ctggcaatgt ccccaatgca atc                                            23

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
cattggggac attgccagta atc                                            23

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 99
cccaagtaaa aagaatattc aat                                                23

<210> SEQ ID NO 100
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
aatataatgt ttgttgtctt tcc                                                23

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gaagagcaac taactaactt aat                                                23

<210> SEQ ID NO 102
<211> LENGTH: 1108
<212> TYPE: PRT
<213> ORGANISM: Bacillus sp.

<400> SEQUENCE: 102

Met Ala Thr Arg Ser Phe Ile Leu Lys Ile Glu Pro Asn Glu Glu Val
1               5                   10                  15

Lys Lys Gly Leu Trp Lys Thr His Glu Val Leu Asn His Gly Ile Ala
            20                  25                  30

Tyr Tyr Met Asn Ile Leu Lys Leu Ile Arg Gln Glu Ala Ile Tyr Glu
        35                  40                  45

His His Glu Gln Asp Pro Lys Asn Pro Lys Lys Val Ser Lys Ala Glu
    50                  55                  60

Ile Gln Ala Glu Leu Trp Asp Phe Val Leu Lys Met Gln Lys Cys Asn
65                  70                  75                  80

Ser Phe Thr His Glu Val Asp Lys Asp Glu Val Phe Asn Ile Leu Arg
                85                  90                  95

Glu Leu Tyr Glu Glu Leu Val Pro Ser Ser Val Glu Lys Lys Gly Glu
            100                 105                 110

Ala Asn Gln Leu Ser Asn Lys Phe Leu Tyr Pro Leu Val Asp Pro Asn
        115                 120                 125

Ser Gln Ser Gly Lys Gly Thr Ala Ser Ser Gly Arg Lys Pro Arg Trp
    130                 135                 140

Tyr Asn Leu Lys Ile Ala Gly Asp Pro Ser Trp Glu Glu Glu Lys Lys
145                 150                 155                 160

Lys Trp Glu Glu Asp Lys Lys Lys Asp Pro Leu Ala Lys Ile Leu Gly
                165                 170                 175

Lys Leu Ala Glu Tyr Gly Leu Ile Pro Leu Phe Ile Pro Tyr Thr Asp
            180                 185                 190

Ser Asn Glu Pro Ile Val Lys Glu Ile Lys Trp Met Glu Lys Ser Arg
        195                 200                 205

Asn Gln Ser Val Arg Arg Leu Asp Lys Asp Met Phe Ile Gln Ala Leu
    210                 215                 220
```

Glu Arg Phe Leu Ser Trp Glu Ser Trp Asn Leu Lys Val Lys Glu Glu
225                 230                 235                 240

Tyr Glu Lys Val Glu Lys Glu Tyr Lys Thr Leu Glu Glu Arg Ile Lys
                    245                 250                 255

Glu Asp Ile Gln Ala Leu Lys Ala Leu Glu Gln Tyr Glu Lys Glu Arg
                260                 265                 270

Gln Glu Gln Leu Leu Arg Asp Thr Leu Asn Thr Asn Glu Tyr Arg Leu
            275                 280                 285

Ser Lys Arg Gly Leu Arg Gly Trp Arg Glu Ile Ile Gln Lys Trp Leu
        290                 295                 300

Lys Met Asp Glu Asn Glu Pro Ser Glu Lys Tyr Leu Glu Val Phe Lys
305                 310                 315                 320

Asp Tyr Gln Arg Lys His Pro Arg Glu Ala Gly Asp Tyr Ser Val Tyr
                325                 330                 335

Glu Phe Leu Ser Lys Lys Glu Asn His Phe Ile Trp Arg Asn His Pro
            340                 345                 350

Glu Tyr Pro Tyr Leu Tyr Ala Thr Phe Cys Glu Ile Asp Lys Lys Lys
        355                 360                 365

Lys Asp Ala Lys Gln Gln Ala Thr Phe Thr Leu Ala Asp Pro Ile Asn
    370                 375                 380

His Pro Leu Trp Val Arg Phe Glu Glu Arg Ser Gly Ser Asn Leu Asn
385                 390                 395                 400

Lys Tyr Arg Ile Leu Thr Glu Gln Leu His Thr Glu Lys Leu Lys Lys
                405                 410                 415

Lys Leu Thr Val Gln Leu Asp Arg Leu Ile Tyr Pro Thr Glu Ser Gly
                420                 425                 430

Gly Trp Glu Glu Lys Gly Lys Val Asp Ile Val Leu Leu Pro Ser Arg
            435                 440                 445

Gln Phe Tyr Asn Gln Ile Phe Leu Asp Ile Glu Glu Lys Gly Lys His
        450                 455                 460

Ala Phe Thr Tyr Lys Asp Glu Ser Ile Lys Phe Pro Leu Lys Gly Thr
465                 470                 475                 480

Leu Gly Gly Ala Arg Val Gln Phe Asp Arg Asp His Leu Arg Arg Tyr
                485                 490                 495

Pro His Lys Val Glu Ser Gly Asn Val Gly Arg Ile Tyr Phe Asn Met
            500                 505                 510

Thr Val Asn Ile Glu Pro Thr Glu Ser Pro Val Ser Lys Ser Leu Lys
            515                 520                 525

Ile His Arg Asp Asp Phe Pro Lys Val Val Asn Phe Lys Pro Lys Glu
        530                 535                 540

Leu Thr Glu Trp Ile Lys Asp Ser Lys Gly Lys Lys Leu Lys Ser Gly
545                 550                 555                 560

Ile Glu Ser Leu Glu Ile Gly Leu Arg Val Met Ser Ile Asp Leu Gly
            565                 570                 575

Gln Arg Gln Ala Ala Ala Ser Ile Phe Glu Val Val Asp Gln Lys
            580                 585                 590

Pro Asp Ile Glu Gly Lys Leu Phe Phe Pro Ile Lys Gly Thr Glu Leu
        595                 600                 605

Tyr Ala Val His Arg Ala Ser Phe Asn Ile Lys Leu Pro Gly Glu Thr
    610                 615                 620

Leu Val Lys Ser Arg Glu Val Leu Arg Lys Ala Arg Glu Asp Asn Leu
625                 630                 635                 640

-continued

```
Lys Leu Met Asn Gln Lys Leu Asn Phe Leu Arg Asn Val Leu His Phe
              645                 650                 655

Gln Gln Phe Glu Asp Ile Thr Glu Arg Glu Lys Arg Val Thr Lys Trp
              660                 665                 670

Ile Ser Arg Gln Glu Asn Ser Asp Val Pro Leu Val Tyr Gln Asp Glu
              675                 680                 685

Leu Ile Gln Ile Arg Glu Leu Met Tyr Lys Pro Tyr Lys Asp Trp Val
    690                 695                 700

Ala Phe Leu Lys Gln Leu His Lys Arg Leu Glu Val Glu Ile Gly Lys
705                 710                 715                 720

Glu Val Lys His Trp Arg Lys Ser Leu Ser Asp Gly Arg Lys Gly Leu
              725                 730                 735

Tyr Gly Ile Ser Leu Lys Asn Ile Asp Glu Ile Asp Arg Thr Arg Lys
              740                 745                 750

Phe Leu Leu Arg Trp Ser Leu Arg Pro Thr Glu Pro Gly Glu Val Arg
              755                 760                 765

Arg Leu Glu Pro Gly Gln Arg Phe Ala Ile Asp Gln Leu Asn His Leu
    770                 775                 780

Asn Ala Leu Lys Glu Asp Arg Leu Lys Lys Met Ala Asn Thr Ile Ile
785                 790                 795                 800

Met His Ala Leu Gly Tyr Cys Tyr Asp Val Arg Lys Lys Lys Trp Gln
              805                 810                 815

Ala Lys Asn Pro Ala Cys Gln Ile Ile Leu Phe Glu Asp Leu Ser Asn
              820                 825                 830

Tyr Asn Pro Tyr Glu Glu Arg Ser Arg Phe Glu Asn Ser Lys Leu Met
              835                 840                 845

Lys Trp Ser Arg Arg Glu Ile Pro Arg Gln Val Ala Leu Gln Gly Glu
    850                 855                 860

Ile Tyr Gly Leu Gln Val Gly Glu Val Gly Ala Gln Phe Ser Ser Arg
865                 870                 875                 880

Phe His Ala Lys Thr Gly Ser Pro Gly Ile Arg Cys Ser Val Val Thr
              885                 890                 895

Lys Glu Lys Leu Gln Asp Asn Arg Phe Phe Lys Asn Leu Gln Arg Glu
              900                 905                 910

Gly Arg Leu Thr Leu Asp Lys Ile Ala Val Leu Lys Glu Gly Asp Leu
              915                 920                 925

Tyr Pro Asp Lys Gly Gly Glu Lys Phe Ile Ser Leu Ser Lys Asp Arg
    930                 935                 940

Lys Cys Val Thr Thr His Ala Asp Ile Asn Ala Ala Gln Asn Leu Gln
945                 950                 955                 960

Lys Arg Phe Trp Thr Arg Thr His Gly Phe Tyr Lys Val Tyr Cys Lys
              965                 970                 975

Ala Tyr Gln Val Asp Gly Gln Thr Val Tyr Ile Pro Glu Ser Lys Asp
              980                 985                 990

Gln Lys Gln Lys Ile Ile Glu Glu  Phe Gly Glu Gly Tyr  Phe Ile Leu
              995                 1000                1005

Lys Asp  Gly Val Tyr Glu Trp  Val Asn Ala Gly Lys  Leu Lys Ile
    1010                1015                1020

Lys Lys  Gly Ser Ser Lys Gln  Ser Ser Ser Glu Leu  Val Asp Ser
    1025                1030                1035

Asp Ile  Leu Lys Asp Ser Phe  Asp Leu Ala Ser Glu  Leu Lys Gly
    1040                1045                1050

Glu Lys  Leu Met Leu Tyr Arg  Asp Pro Ser Gly Asn  Val Phe Pro
```

```
        1055              1060              1065

Ser Asp Lys Trp Met Ala Ala  Gly Val Phe Phe Gly  Lys Leu Glu
        1070              1075              1080

Arg Ile  Leu Ile Ser Lys Leu  Thr Asn Gln Tyr Ser  Ile Ser Thr
        1085              1090              1095

Ile Glu  Asp Asp Ser Ser Lys  Gln Ser Met
        1100              1105
```

<210> SEQ ID NO 103
<211> LENGTH: 9
<212> TYPE: PRT
<213> ORGANISM: Unknown
<220> FEATURE:
<223> OTHER INFORMATION: Description of Unknown:
      PCSK9 cleavage site sequence

<400> SEQUENCE: 103

```
Ser Ser Val Phe Ala Gln Ser Ile Pro
1               5
```

<210> SEQ ID NO 104
<211> LENGTH: 25377
<212> TYPE: DNA
<213> ORGANISM: Homo sapiens

<400> SEQUENCE: 104

```
gtccgatggg gctctggtgg cgtgatctgc gcgccccagg cgtcaagcac ccacacccta      60
gaaggtttcc gcagcgacgt cgaggcgctc atggttgcag gcgggcgccg ccgttcagtt     120
cagggtctga gcctggagga gtgagccagg cagtgagact ggctcgggcg ggccgggacg     180
cgtcgttgca gcagcggctc ccagctccca gccaggattc cgcgcgcccc ttcacgcgcc     240
ctgctcctga acttcagctc ctgcacagtc ctccccaccg caaggctcaa ggcgccgccg     300
gcgtggaccg cgcacggcct ctaggtctcc tcgccaggac agcaacctct ccctggccc      360 tcatgggcac cgtcagctcc aggcggtcct ggtggccgct gccactgctg ctgctgctgc     420
tgctgctcct gggtcccgcg ggcgcccgtg cgcaggagga cgaggacggc gactacgagg     480
agctggtgct agccttgcgt tccgaggagg acggcctggc cgaagcaccc gagcacggaa     540
ccacagccac cttccaccgc tgcgccaagg tgcgggtgta gggatgggag ccggggcga      600 acccgcagcc gggacggtgc ggtgctgttt cctctcgggc ctcagtttcc ccccatgtaa     660
gagaggaagt ggagtgcagg tcgccgaggg ctcttcgctt ggcacgatct tggggactgc     720
aggcaaggcg gcgggggagg acgggtagtg gggagcacgg tggagagcgg ggacggccgg     780
ctctttgggg acttgctggg gcgtgcggct gcgctattca gtgggaaggt tcgcggggtt     840
gggagacccg gaggccgagg aagggcgagc agagcactgc caggatatcc tgcccagatt     900
tcccagtttc tgcctcgccg cggcacaggt gggtgaagga gtgaatgcct ggaacgtact     960
gggaactgca ccaggcacag agaaagcggg cttgccatta tagtgggttc cgatttggtt    1020
tggaaaacat gggcagcgga gggtggaggg cctggagaga aggccctacc cgagacaggg    1080
gcggggtggg aaggacggca gatgctggga gcacgaggca atttctttat gacacagaac    1140
tcatgctcta gtattccatc tgtttcagcc gaagaaaaga accagctgaa ggggcagggg    1200 agaagggcg gaggtattct cgaggcccat tggcgtcctt taggactcag gcagggaagg    1260
gcccttggtg ctctggagcc ggaggtggtg cgcctggtac tgggaccccg gagctgagcc    1320
cggcgcctca gcccacctgg ctgtctgccg accgtgtgcg gggcgagttt gctcaacaac    1380
```

-continued

```
tctgccagct tctggccctc aggctgtggg aagcttcttc ccggggcgag accactagct   1440
ttttctaagt attaccagcc caggacttgg ctgaggttct gtgtccccca gcttggagtc   1500
agatgtgggg ttgaatcttg gcttcctctc actagctgtg gtgcttgaca agtcacttat   1560
ccttgagcct ccattgccta atctttaaaa gggaggtgac aatcgtccct acggctcagt   1620
ggcagcagat ggggagatga agggaaagtt ctgttgacca tgagtgaact tacaatgcaa   1680
gccccggggg gatcacttgc agttttgtcc ctgtctgcag tgtgacctgt tggtgacatt   1740
gtctttgctc caaaccacag ctcctggggc agaggggaaa attctgccac tcacagctgc   1800
ctgcccacgc ttctgtctga gtgtgctggg tggcaggatg gcaagtcctt actcagctca   1860
gtatagccct cttccttgtt ccctgagcct ttgactttct cgagggatgt tgtgggggttg   1920 tggccaggat aagaaagggc atttcaagtt accactgctc caaaacaact gttctggaaa   1980
tagtgagtac cccatcctga gaggtgagta agcagaggct gtatgaccac ctgaaccaag   2040
cccttgagga tgtttcttct ctggtggaag tttggaacag gagcctcctc aagttcattt   2100
attcattcat tcaatggtta ttttgtggga atcgaattta gaatgaaaat attttttggc   2160
aagcagaaaa taattttttag accaatcctt ttcttttagt catgagaaac tgaggcccag   2220
agagaggagg tcaccccagg tgcattagaa ctgggtttcc agaactgaca ctccactgca   2280
cagagtactc tcccaattca ttcaattttt atttagcgga aggcattttc agatgggtct   2340
ttgaagcatt agtaggagtt cagcgatgat ggtgtcatga gaattttatt ctaggattag   2400
gaggtaccat gaacaaagat acagagctgg gaaaaccaga ggtggaagat aaggagcaca   2460
tgtccacagt tcttttttctt ttttttttga gatggagttt cgctcttgtt gcccaggctg   2520
gagtgcaatg gtgcagtctc agctcactgc aacatctgtc tcccgggttc aagtggttct   2580
cctgcctcag cctcccaaga agctgggatt acaggtacct gccaccacgc ccggctaatt   2640
tttgtatttt tagtagagaa ggggtttcac cacgttggcc aggctagtcg caaactcctg   2700
acctcctcag tggatccgag gaggtgatcc tcccgcctca gcctcccaaa gtgctcgaat   2760
tacaggtgtg agccaccacg cctggcctcc acagttcttt atccaccgtc tgaaatgtaa   2820
aatgttacga aaaccaaaag tttttttttgt gatttatttg atggtagcac ctgacgtgaa   2880
ctgacatgag attattttta atttagttgt gtgaatatgc atattcatat attttgctgc   2940
atagattaca gtatgcagct ccagattctt ccaagcagac tctgattgcc cattactgcc   3000
tttctaaaat ccaaacaagt tctgaggttc aaaaccgttt tggccctaag gctttgggta   3060
aagggggtgg actctgttct actctgactg gagtccaaga tgcatatata cagagatatg   3120
ggtgatgggg ctgcaaggta ggttgaggta ggggccaagg aggagcatgg agtttggact   3180
tgattcatga ggctgtgggg agccagtgaa ggttcttaag caggtatgtc tgcctgagag   3240
cagttggagc agacaagagc taaaaaccaa acaaatcacc atagatagtg gctgctataa   3300
tttgtttgtc ccctccaaat ctcatgtgga aatttggtcc tcagtgttgg aagtggggcc   3360
taatgggagg tgtttgggtc atgggggagg aacccctgtg aaaggcttgg tgccgtcctt   3420
gtgataatga gtaagttctc ccgctatgat ttcccttgaa ggctgattat taaaaagagc   3480
ttggcacctc cctctcttct ctcttgcttc ttctcttgcc atgtgattga tctctgcaca   3540
tgtaggctcc ccttcacctt ctgccatcag tgaaagcagc ttaaggccct caccagaagc   3600
agatgctggt gccatgcttc ctggagagct tgcagaatca tgagctgaat aaatcccttt   3660
tccttgtaaa ttactcacct tcaggtattc ctttatatag caacacaaaa ggactaagac   3720
agtggccttg acttttctct ctctttaaga agtgttgcct ttgctcactt agtcatccct   3780
```

```
tctgcctgca tttgtagagc atctggatgg gagatttata taaccgtcac tcttgacttt    3840
cccagcaggc ctatgtcata ggtactgtgg tctctacaat acagcagagg tatctgaggc    3900
tccgagaggt tgagtgactt gctcatggct gcacaaccag taaatattgg agctggaatt    3960
caggtccacg gtttcctggc tccaaagccc atgatttttt ccctcaattt attctgactg    4020
gggcatgggg gagggggtgg cctttgggca gggccaccag gagcgaccag gcccgtagag    4080
agctgggtgc aggtacagag gaaaacctgt tgtcgagtgt ggcccgtagt tcccattttt    4140
gcctgaatgg cacatttgaa agtgttatat aaccatgtga ataataatag ttggcctata    4200
tgagttcttt aatttgcttt ttggtccgca tttggtaact tctttatcat ctactatact    4260
ctgttgtgtc tcttttgttg taatttgtaa gtaggggtga dataaagtac acctagggtt    4320
tgctgggttt cttccatgtc atcatgttcc tccttgcatg gggccaggat ccgtggaggt    4380
tgcctggcac ctacgtggtg gtgctgaagg aggagaccca cctctcgcag tcagagcgca    4440
ctgcccgccg cctgcaggcc caggctgccc gccggggata cctcaccaag atcctgcatg    4500
tcttccatgg ccttcttcct ggcttcctgg tgaagatgag tggcgacctg ctggagctgg    4560
tgagccaccc tttttgggaa tggcacttcc tgatagggct gggccactgc atatacactg    4620
gggactgtgc ttagtaggcc cattgctgaa aatcagaagg ggacagcaag tatgtattga    4680
gcacttatcg ggtaccaagc acagtaacta ctggctttct gtatagaatt ccctttaagc    4740
ctggccatgc cccagtggta cgtctatctt catttgaaag acgaggagac tgaagttcag    4800
aggggaccac acagacagct aggggtagag cctggatcaa acccattggt ctgcctgcca    4860
gccattcttg tgccaatgca tctgctgcct acggaaacct gtagggacaa ggccctggga    4920
tgttcagtgg agcctgagtc attttataaa aaagcatgac tctagggtcc aaaattcctt    4980
tgaagctgtt gctatccaga gtgaagtccc ttctttagga cagggtggcc ctcctccctc    5040
ctggatgtca catcttcggt ggagggggcag aaaggggact gggtattctc ctcaccctgg    5100
ccctagtgct tcaaatctta aaaaaacgtt tttatttgtg cttctgcacc accttctagc    5160
ccacctcgtt tcctggcctc taacttgatg agagcgtgtg tcattttcac actgattctc    5220
cacatggcag gcggtgcttc ttagcctcct gcagacagtg aggccccacg gtcttgtcca    5280
aggtcacaca gcgtgtaatg ggcagggtca gagtctggag tctggacctg ggtctcctag    5340
ctgcactgca ctgctgcccc atgggttaat cagctcagca taccgtggct gaacagctac    5400
ctcataccaa ggcctgtggc gccatgacag ggattgacag ggtccctgcc ttggaaaccc    5460
gtagtctaag tagaggagac tgacaagtca atgccttcca tcagtctgct caacacacgt    5520
ttaccaagtg cctactgtgt gctgcagagg cgaagatgac acagctcagg cctttccctt    5580
gagcttacag ttcaggagga gagactgacc agtgactgcc agtacagttg actatgggac    5640
aatgtgctca gccttgggga gagacgaaga aggtacccgt atagcaccag atgacaggca    5700
cgagccccac aggccagggc agctgctcag aggagagtag gccaagcaga aggcaaacag    5760
aaggctgcag gcatttgcca tcgagagctg gacttcaaac tgggcatcat accagcctgg    5820
gttcgagtcc tgcccagccc cttattggct gtctaaccct gagcaaatcc cttcacctct    5880
ctgagcctca ttcctctatc tgtaaaccag ttataataat tggaacattc atttaaggac    5940
taaatgaggt cgtgaagcat tcagcagatg ctaggtacgg aaactcgctg aagtgggggc    6000
aggttaagaa gcctctgggg atacgaaggc atccaggac tagttgtggc aggaggctgt    6060
taccacttag gtctgaaggg taaggagagg gaatagcttt ccctctgccc agttggagcc    6120
```

-continued

```
ggtggcatgg aggagaggct gcctgtgggg aatcacccga gggttcaccg ctgccatgcg      6180
cagggagtca ggaggtaggg agggagtggg gcagatgcac accatttttt ttttttttg       6240 agactctgtt gcccagactg gagtgcagtg gtgccatatc tgcacctctg cctcccgggt      6300
tcaagctcac tgcaacctct gcctcccggg ttcaagcgat tctcctgcct cagcctcccg      6360
agtagctggg actacaggtg tgtgccacca tgcctggcta attttttgtat ttttaataga     6420 gatgggcttt caccatgttg gccaggctgg tctcgaactc tcgacctcag gtgatccccc      6480
acctcggcct cccaaagtgc tgggattaca ggcgtgagtc accgctccca gctgctgatg      6540
cactcttgtc cttctaactc ctgctagtgc ctcccattgg ctgagcccaa ctggaagctt      6600
tgcaagggag ctggtgctgc agtttgcact gagcaggctg gagaaggctg gagaatagac      6660
taggggacaa accgaattgc cagtgctgtt atgtcatgat ttaggcatgg agtccagggc      6720
ctgagcttca ctccatgtcc atcctgccca gagccttggc acagcctggc tcccagacaa      6780
gatgtcaagt tcagaatcct tcctaaaagg aatcctctat gccagaccgt gttgcaggga      6840
tatgggagtg ctgggctccc agcctgatca aggagcgaga aaactcaggc tcctagtctg      6900
tcctccgggg cactagcagg gacaaggtgg gaggctgctg ggctgggatg tggggacagg      6960
tttgatcagg taaggccagg ctgtggctgt gtttgctgct gtccaaatgg cttaagcaga      7020
gtcccccggc ctctctggct tctgcaggcc ttgaagttgc cccatgtcga ctacatcgag      7080
gaggactcct ctgtctttgc ccagagcatc ccgtggaacc tggagcggat tacccctcca      7140
cggtaccggg cggatgaata ccagcccccc ggtaagaccc ccatctgtgc cctgccccac      7200
cccatctgag ctgaatccat ttgctctgcc ctggcctggc ctccctgctg gtggtttcca      7260
cttctcgggg ggctttggga ctcagcacct ccactgaccc cttttttttct gtcccatccc    7320 catcccctgc agcccccact gcctgccttc ctgttgcccc acaaatgcaa aagtcttgcc      7380
ttaaatgatc ctctttttcct tctttttctct tgttttcctt ttctcaccat ttggaatggc    7440
ccagcaggct gcacttacct tggaaggagg gttcatctga tggtgactct acctagggcc      7500
cccaggcctc tataactccc agtgccctgc agactggacc agatcctttta atgggataga    7560 cacaaccctg tctgggatgc ctctgcctac cttcctgttt tgctgctcca cctgcctcca     7620
gctccgtttg gcttcctggg gctccctgcc tgggccactt tgtgtcttcc ctctaggcct     7680
ttctttccac tgttccctct gcctggtgtg gcctggctat ggaagggagg gaggaggagc      7740
ggccatggaa aacggtctgc attctagcag ggacttgcag gtggcaattc agtcggggaa     7800
gactctagat gcacctggcc tgaggagaga atgaagggtt ctagttggac tgtgttaagt      7860
ttgaggtgcc catggtgtga ggtctggagc tcagcgcaga gatgatgcaa tgtggtgggt      7920
ccatgcaaca tggtgccagg acgcagagct tggggtgaac tcagctttca ccccttaccg      7980
gttctcgtgg gatcttggga agccactttc ttctatgagc tttgtcgttc ttgtctgtaa      8040
aatgggcaca taaccctgtc cctgtccttc tcacaggttg ctgtgagact ccaatgagtt      8100
gaaggatgtg cagatgcttt tggaagtgaa aagttggggg gctactgtgt gactttgcat      8160
acacccaaac tgtgtgacct tgcatatgtc tgagttgctg ccattgcaac agatcagagc      8220
tggtgggctg ggtgtggaga aagggtttgt gtggggaca tcctctggca agggtggcag      8280
cagcagaagt gaggggcctg gtcggtcatg tgtgctgacc cggcctgggc agcctgtggc     8340
cagggagagg acagctcctc tgtaggaaga gcctgttcct ttccaaccag gtgagacctc     8400
ttcagtggag ccctgagccc ccctgtactc cacatcagtg cctcagggac ctcccggagc     8460
aggctaatat cagagaccaa gagggacact ggcagaggat cacagagacc ccagtccagg     8520
```

-continued

```
cagggactga gaagatcttg ccccctaagt tagtttccta gcactgctgt gacaaattac   8580 cacccccctcg gttggaacaa gttgattctc tgcagtcctg gaggccagaa gcctgaatca   8640
gtgtcggcag gaccactttc tcccgggggg ctccagggag aagcttctct tgcctcttcc   8700
gtgtcccaac agcggcagca caccaatccc agcctctgtc ttcacacagc cttctctgtg   8760
tctctctcct cttcattgtc tcataaggac acttgtcatt ggatttaggg cccactggat   8820
cctccaggat gatctcatgt ggggaacctt aaccacatct gcaaggaccc tttttccaaa   8880
taaggtcaca gccacaggtt gtgggggtta ggatgtgagt gtatctcttt ggcagccact   8940
gttccctcct ctcccttggg ccagaagcag acgtgggggcc ctttcttccc cataggatgc   9000
ccatggattg cccccccttcc cgcttccccc gagtgtctgt gggaggtggc aggaatggca   9060
ggcaggggtg tggaacccct tctggagtca tatcaagggc ttggctggag gaagtcctcc   9120
tggagctgtt gggctggcat ggggcaggct ggctgggccc agcagcagct tcttcattca   9180
tggggaggcc acaagcatgg gccctagagc tggctgccgc cctcaaaccc agaccctgca   9240
ctcttaactg tgtgaccttg catacgtcac tcaccctctc tgatcttcag gttcctctgc   9300
aaaagggagg taatgataac cctcactctg ggggctgtt tggagggtta aatcagttat   9360
tgctgtagca tgcatttctc tgtcaggtat tgagtgaggt gctgtgattt tagccctgca   9420
tttttctttt cttaccattc aataataacg ttttgagcac ccactgtgcg ccaggcacca   9480
tattaggtgc tggggataca aatgtgaatg aaatgaatgt ggtctcttcc cccaacagtg   9540
tatccagaag attaatccat tccttaaaca aatgctactt gacacagatt agttctggat   9600
aggctgagag ctctgaagga gtgcaggcag ctgcgagcct gtgtatccag cagaaggatc   9660
aggaaaggat tcctggagga agcgctgttc tagccaagac ctacgggggc attattaacc   9720
aggcaaaggg gacggtgtcc aagcagtgga atgaacgtgg attgaagctg tgaggcagga   9780
gggagtgtgg cctgtgcaga agggaccgag gctggtgaga ccaggagggc ctgggtggcc   9840
tccaggtcag atgtgaaagg aagaacttgg ccacagtctg agcttctcag gcgtatggca   9900
gggctgcctg gtgagaggga atgagctccc tgctctggag gtatgcaagc aggactgggc   9960
tctcacctgc cagaggccac agagctttcc agaggctgga agaggccact ccaaggcctc   10020
tttgcccctg agagtggtgg ctcttcttga ggccaccttg ccacgctgtc acagggaact   10080
agcagcccct gcctcacccg ggggtttgga agatagaggg aggcctagga agggccctgt   10140
gtctcatccg agctgggccc ctttccagcc tctcactgga aggaagccca aggatgttcc   10200
tgtgggggct tttaccaggc ccacctgccc tctgctggcc atgcttgcag cctcctgacc   10260
ctgtcccagc aggacagtgg gctggtgtga gcgggcagga accgcctgca cttagaaggt   10320
gtggggctgc ctccccgagc ttccatctgc cgctggggcc acaccccagg cccagggatg   10380
ggaccccaca gtggtcacat catcttgcag cagaacccag gtacagctcc tggagcagat   10440
ggtggtccca agcacgggtg ggaccagaaa ggactctcac ctgggctaac tcagctgcag   10500
cctcagttcc ctcctcacac acgacgagga acatggactg gaagcctgcc cagcaggcct   10560
tctgctcgat gtgcgttgtg tggcttacgt ccagggaggg aagcagcctc tgtgctgtct   10620
tctagataag cctgtattcc ccgggctgtc tgccaatgta tccagttgtc ccgtcagcct   10680
ggaagctctg agggaaaacc ttgggctgct tcctgagcac ctgtatcccc tgcagccagc   10740
ccggggcctc tgctaggagc agactgagca tggcttatgg gcctggcacc atctggcctc   10800
tgcccacctt gctggccttg tcttgtgtct gcccccttcga cattccatag cccagctcaa   10860
```

-continued

```
tatctagtgg ttcctctagg gtggcgagca ctgtttggtc tccagatgtc ttcaggtcgg   10920
agctcacagc gctctcagcc accccttccc agtgtagcac cgggcacatg gtagatgcct   10980
attgatgagt gaaagctcct aacacactca gagagcaagg actccgcctc atcccacagc   11040
ctgggaggag aggcagactg ccaaggacct gctcagcatg ctacagaaga aaccaaagtg   11100
cccacgggac tgatcagtgg agcttcctgc cgagactgga ggccttaggg cagggtagac   11160
agtgtgtgtg caggctgggg actcacagtt cggactgtgc ccagacctac tagcatagtg   11220
ggtgggtggg aggatgcggg actgggggcc gaccttgcct gaaattcatg tgggatctca   11280
gagcagccac tgaattgctc tgtaggggc taaatagtgg cccccacaga tacacacacc   11340
cagacagagc ctgtgagcca gaccttattt ggagaaaagg tctttgtaga tgtaattaag   11400
catctcaaga tggcatcatc tggattatgc ggtgggctgt aagtcctgtg atgtgtcttt   11460
atgagagaaa ggcagaggga gatttgacac acacaggagg ggccacgtgg agacagaggt   11520
ggagattgga gaaatgtggc cacaagccag ggaacaccag cagccaccag aagccggaag   11580
acgtgaggca gggttcttcc cagagccttc gctgctgagt ctgggaattt gtgaccgaag   11640
ccataagaag tgggtacacg ccctgagcct cccacacttg ctcacctgtc ctgagatgag   11700
aatctctact ctgcagcata tttgaggat cactgcgggg gccacagagg tgctgttcag   11760
atggcacttc agaagactca ggagaccctg gggcaggagc agtttgactg acagcccaga   11820
gggctgccct ctgattccac ctgaggccct gcttttcctg gctgcagggg ttccagggcc   11880
aggccatttc cgctggcgca ggactctgct agcagcaacc tgcctgaagt cttcctttgg   11940
cctggctgag agtttctgag acctgcgctg gagcggaggt gcttccttcc ttgcttcctt   12000
tcttcctctc tcccttctcc atccagcagg ctggacctgc ctggcatctg tgagctctcc   12060
ctactttctc ctataccctaa accttgtcc tgcatgggcg actcccccag tgagtctctt   12120
gcagctttta ccccagtgcc tgcttcttgg agaatccaaa ctgatccagt tagggatgat   12180
aaagtgtagg gtaggcgctc ggtgactgtt ttctctgagg ttgtgactcg tgtgaggcag   12240
aagcagtccc cgtgagccct cctggtatct tgtggagtgg agaacgcttg gacctggagc   12300
caggaggccc agacatacat cctgtccgag ctgcagcttc ctgtctctaa aatgagccgg   12360
ccagcgcagg tggccagaca tcactgttat tctcctttga gtctttaaat cttgttgtct   12420
ttcttgcaga ctcggtgagc tgtgaaaggc tataataggg gctttatttt acactttgat   12480 actattttt gaacattcat attattgtta gatattgata ttcatatgaa ggagcaggat   12540
gacttgggtc cttcttggca gtagcattgc cagctgatgg ccttggacag ttacctgccc   12600
tctctaggcc tcccttttcct tgtctatgaa atacattata gaataggatg tagtgtgtga   12660 ggatttttttg gaggttaaac gagtgaatat atttaaggcg ctttcaccag tgcctgggat   12720
gtgctctgta gtttctgtgt gttaactata aggttgactt tatgctcatt ccctcctctc   12780
ccacaaatgt cgccttggaa agacggaggc agcctggtgg aggtgtatct cctagacacc   12840
agcatacaga gtgaccaccg ggaaatcgag ggcagggtca tggtcaccga cttcgagaat   12900
gtgcccgagg aggacgggac ccgcttccac agacaggtaa gcacggccgt ctgatgggag   12960
ggctgcctct gccatatcc ccatcctgga ggtgggtggg gactgccacc ccagagcgtt   13020
gcagctgtac tcctgggttg cacccccccc agctgtcact gtccctccc tgccatcagt   13080 tgtgggaagg gcgttcatcc atccagccac ctgctgattt gttataggt ggagggggggg   13140 tctttctcat gtggtccttg tgttcgtcga gcaggccagc aagtgtgaca gtcatggcac   13200
ccacctggca ggggtggtca gcggccggga tgccggccgtg gccaagggtg ccagcatgcg   13260
```

```
cagcctgcgc gtgctcaact gccaagggaa gggcacggtt agcggcaccc tcataggtaa    13320
gtgatggccc cagacgctgg tctctctcca tctggacctg gcctgggagg tggcttgggc    13380
tgggcccagg gagagctaat gtctcctaac caagaatgct gtggcagcct ctgccgcaga    13440
gccagagaac cagagtgcca aggctggcag ggttcccagt ggccacgagt gcagatgaag    13500
aaacccaggc cccaagaggg tcatgcaggt agcccaggga gttcagcctt gaccctgggt    13560
caatgacctt tccacagttc cacactgctc cccttttaaa atccggtgat gtctttatgt    13620
cttttgttat gttatcttca atgtggaggg actcgaggtg atctaagcaa acttttttcta   13680 tcttctgctt gcatacctct gagaccaggg gactcactca cttgcatgac tgggccctgc    13740
aggtcacact ggccaggcag atgtggtgga ggaactggca gaggactttt tctagactgt    13800
gactacattt agtccaccca gcggcccccc tatgaagtcc agttgagaac taggactctg    13860
ggggccggtg gacagagaag agggaggggtt ctctcccttta ctgacttcct tctgtggcca   13920
gacattgagc aaggcctctg tacagcatgt cctggggctg gccttgccgt agctgctaaa    13980
tagttgacga aaccagtcca gagaggggag gtgactgcca gggtcgcaca gctcaagctg    14040
gggaactcgc tgggaaaact gtcagctctg ggcagcagct tgacttccac tgtaagcccc    14100
agcccccagg gtcaaacact ggctctggtg ctggcagagg cagcccacta gcctgtttca    14160
aaggctgaga aggcccagga gtctgccctg tgctccacca gttctgcccg agactttcct    14220
acagagtaca ggttttgatg ttcagtttta aaggcaagaa tcaataacct tctgccccat    14280
caggtgaccc cttgtgcctg tcccacccct ttattgactg acctcggctc agtcaggtca    14340
gttcctgaag gtcagtgtgt ggaggggagg ctgttctttc ccagaaaggc cttccccagg    14400
cctggtgctc tggcctctgg aggacttcct ggagaagtcc cttctttggg gtcccagtca    14460
gtgtatggga agcccttatt gcatgacctg gcacggggca ggggctcaac agtcactatt    14520
gccttccttg ccactgccat ttcctcctct gtaagcaggt gattgtgtgt ccagtctgag    14580
cacagagata agcacacagc aggtgcttaa taactagcag ctgtaggctg ggcgcggtgg    14640
ctcatgcctg taatcccagc actttgggag gccgaggtgg gcagatcacc tgaggtcagg    14700
agttcgagac cagcctgttc aacatggtga aaccccgtct ctactaaaaa tacaaaaatt    14760
agccaggcat ggtggtgggt gtctgtatcc cagctacttg ggaggctaag gcaggagaat    14820
cgcttgaacc caggaggtgg aggttgcagt gagctgagat cgtgccactg caatccagcc    14880
tgagtgatag agcgagattc catctcaaaa ataaataagt aaataactag cagctgtaaa    14940
tgtggctgtt gttcttcacc tccacactca gtgccactcc actccctccc tccgtggtgt    15000
gaggggcctc actagctgtc tcctaggagg agcatggctg tgagattcca gctccatcct    15060
tggccacggc tcctggagac atcttagagg ccaggatcca gaaggctccc acacctcatt    15120
tgacagggga gaagctgtca gttccaggtc cccttgcaca tcagggccag agctgcgtta    15180
ggcctccagt ctccaggcca ctgggccaga gctcacaggc tggcagaggg ttagaactgt    15240
tactggtggc tgggtgcagt ggctcacgcc tgtaatctta gcactttggg agggcaaggc    15300
gggaggatca tgaggtcagg acatcgagac catccttgct aacacggtga agccccgtct    15360
ctactaaaac tacaaaaaat tagccggggcg tggtggcagg cgcctgtagt cccagctact    15420
caggaggctg aggcaggaga atggcgtgaa cccgggaggc ggagcttgca gtgagccgag    15480
attgcgccac tgcactccag cctgggcaat agagcgagac tccgtctgga aagaaaaaaa    15540
aaaaaaagag ctgttactgt tgacagtagc atgaggtaga ccatggcctg caccaaaatg    15600
```

```
ggggagtgga gtgccactga ggccagaagg aaccacaccc tcaagggtgg ggagttatgg   15660
tatggggggt cctaggcatg gagtcttta  attctttaga caatcctggg agcaactgtc   15720
cctgtttcac agagggcggg gccacacagc tggtgagtgg gcagccaaga ctctgttcaa   15780
gtttgtgtgg gtccaacact tgcggccacg gtggaggggc atctgagcca ggcctcagag   15840
agtggcgggg gaagttgggt ggggaagtgt gcccttctca ttcctctgag gctcatcctc   15900
ttggtgcctc tctttcatgg aaagggataa taaggttatt gtgaggatcc cctgagttcg   15960
tatattcaga cgcttagaca gagccaggca cagagaaggg cccgggttg  gctagtttga   16020 ttgctggtgt aattgctaat atcttccagt ttgtattggt caaggttctg cagagaagca   16080
gaaccagtag gatgtatata ttaagagttt caagctcatg tgaccgtgcg ggctggcaag   16140
tctgaaatcc gcagggcagg ccaggcaggc tggcaattcc tgcagaattt gatgttgcaa   16200
tactgagtcc taaggcagtc ctggggcaga attccttctt ccctgggagg cctcagtctg   16260
ttctcttaag gccttcaact gattaaatga ggcctgccca agttatagag agtaacctgc   16320
cttactccgt cttctgattt aaatgttagt cacatctaaa aaatattttc gcagcagcat   16380
ttccactggc ttttgaccaa acatcaggcc acaaagttga tccccaaaat taaccatcac   16440
tctgtgcctg taagggaggg gctgggaaag gggagcaggc ctccccaagg ggtgaccttg   16500
gctttgttcc tcccaggcct ggagtttatt cggaaaagcc agctggtcca gcctgtgggg   16560
ccactggtgg tgctgctgcc cctggcgggt gggtacagcc gcgtcctcaa cgccgcctgc   16620
cagcgcctgg cgagggctgg ggtcgtgctg gtcaccgctg ccggcaactt ccgggacgat   16680
gcctgcctct actccccagc ctcagctccc gaggtaggtg ctggggctgc tgccccaagg   16740
cgcgggtagg gggcggaggg cggagggcgg agggagggcg ggcgggcagg cgggcttctt   16800
gtggcacgtg ggcttcttgt ggcacgttcc tggaggccga accttctggg ctttggaagg   16860
agtcgtcaga gaccccgcc  atgcgggagg ctggggagga aggggctcga aacctccatc   16920
atcgcagagt ctgaatagca gtggccccgc catgcgccca cgtagcggcg cctacgtagc   16980
cacgccccca cacccgtcc  tggccactct ccctcctgaa ggtcttctgg tacccgcccc   17040
ctccccatct ccatccccag gccctgcgtc ctctgcccaa tactctttgg gcctccctgt   17100
tgtccagctc tctccgcggc tccatgactg acaacttgag caaggctaat gtgaatggga   17160
gcggttgagg gctcagacct ctcacccgag gaacatccac agagtgtgcc gcatgcccgg   17220
tgcagtgtgg ctgcggggac acagacacgg agcctcggcc ctgaggagct gggggggcagt   17280 gaccgtccct cctctgaccc accactcctc cagtgtcagg acactgcggg tatctagggg   17340
aaggaatctt gttccacttc aagtctggaa cttcaagtct gtgtgtgtgc gtgcgcgcgc   17400
gcgcgttggg ggtggggggtt gcagagcaga tgcgtacctg acagcggtaa cctaggtccc   17460
ccctggccta tcaaggcttc cctggcggcc gaatttaaag gcatcaagca aacaaagccc   17520
aacacatctc tgccttgtcc tctcagtttc ccccgtggc  acttagaacc acttgataca   17580
ccgaatagtt tcctatctcc cccactagga tgtaaactcc acaggggcat tgggaatgct   17640
gcctggctat ggtagggaca gaggggagca ccagggcggg gcaggggtgc cagagttctg   17700
cctgggcagt cagattttcc ttaggagggg acatttgagt gggacccaaa caggtgtata   17760
gcagttgtcc agcccagctg gcaaggcctg agtctgcctc tgcaacccct ctcttgggct   17820
cctttctctg ccacccacct cctcacctttt ccaggtcatc acagttgggg ccaccaatgc   17880
ccaagaccag ccggtgaccc tggggacttt ggggaccaac tttggccgct gtgtggacct   17940
ctttgcccca ggggaggaca tcattggtgc ctccagcgac tgcagcacct gctttgtgtc   18000
```

-continued

```
acagagtggg acatcacagg ctgctgccca cgtggctggt aagtcaccac cccactgcct   18060
cggccaccgt gatgctaaca gcccctttgg cagtcagggg ctgtgccggg acctccagtg   18120
ccaggctctg tgcagggga ccagagatga agtaggcctg atggtgcctt caaggacact   18180
cagtctgatg agggaggcga gtgcacagag gaaacacgag gtcagggctg tattagaggg   18240
agcccagagg aggcacctgc ccagcccgag ggtcagagaa ggcatcttgg aggagggaca   18300
tttgatcggg agcttgatgg atgaatagga gttcacctgg ccgataagac agcaactacc   18360
aaggcttaga ggtgtgagag gaggctgtct tacctcactg agtaaggact gcaggcggct   18420
taccttcgag aagagagctt agtgtctgtg tgcacgtgtg tttgtgtgta tgtgtgtgcg   18480
tgtgtgcact ggcaggagtc ccctgctggg gcaggagggc cgggccatca ccatctttca   18540
ccattcaccc ctgcaccagg cattgcagcc atgatgctgt ctgccgagcc ggagctcacc   18600
ctggccgagt tgaggcagag actgatccac ttctctgcca aagatgtcat caatgaggcc   18660
tggttccctg aggaccagcg ggtactgacc cccaacctgg tggccgccct gcccccagc   18720 acccatgggg caggtaagca ggatggcagg gtgggcaagt ccaggctggg gcttgggagg   18780
tctgtgtgac cttgacagtc tctcccttct cccttgtctg tgtaaggagg atgacgccac   18840
cttaaatagg attaaatgag aatggggctc tgaaagggct gtgcaatatt ttcataacgt   18900
gtttttatag agacagttga gtatgttctt taagccctcc tctctcctac catgaactaa   18960
agatttctgt ggaggtcccc tcactcccag cacccctcc tcatcccagg ccctttttgc   19020
aggttggcag ctgttttgca ggactgtatg gtcagcacac tcggggccta cacggatggc   19080
cacagccgtc gcccgctgcg ccccagatga ggagctgctg agctgctcca gtttctccag   19140
gagtgggaag cggcggggcg agcgcatgga ggtgactgta ccctccttc gtgtgtgtgt   19200 gtgtgtgtgt gtgtgtgtgt gtgtgtgtgt gtgtgtgtgt gtcagtgctg ggccctcagg   19260 gaccccagc aagcccctcc atcctccaga ctccagctct tctgtaagct tacagggctg   19320
gccagaccag gagtgggggca ctcctcactt cacgcggctg ggggctgctg gagagagcca   19380
cagcgggaag ggtttcctag aggctgcagg acagtgctgg atggattttc aatgctcacc   19440
tgggtgtgag cgtgcggcag ggccgcgtga gggtcagcga tctgctactc tggactcagc   19500
catctctagg cccctctcac tcaggtgctc catggttctg ggagctgaga aatctcaaac   19560
cagcaaaaaa gtggaattga tgttgatgct acaggatagt gcacagatgc catctggttg   19620
cagcattttg gtggaagggc agtgcccagc taggagagtg aggaggggca ggcatttctg   19680
gcttgaggag atggggtctt aatgctcgtg tgagaggcag agtgggtgga gtggagctgg   19740
ctggatcctt gctttggcct cctggatttc tctctatctc cattttgaaa ccactctgtg   19800
tttggaagaa cttttgagta ttcagagctg cccactggca gaacagtctt ccttgggcag   19860
gagtgagctc cttgtcccca gaaggctggg tctggctggc ccctggcagg gacactgatg   19920
agggtgcttg agttgatcct gtctagtccc tttctgtgtt ttcaaagccc attctaaagc   19980
agattcccat ttccgtcttt gactctaagg cccaagggg caagctggtc tgccgggccc   20040
acaacgcttt tgggggtgag ggtgtctacg ccattgccag gtgctgcctg ctaccccagg   20100
ccaactgcag cgtccacaca gctccaccag ctgaggccaa catggggacc cgtgtccact   20160
gccaccaaca gggccacgtc ctcacaggta ggaggctggg cttgccctgg ggtgaggagg   20220
ggtctctttc tccttatgca cccactgccc gcgaggcttg gtcctcacaa gtgtgatcca   20280
tgagactcaa gcctgacttg cagttccata ctctggttct gccacttcca tgccctttga   20340
```

-continued

```
gcctgggcag gtgaccttac ttctcctcat ctcagcttcc tcctccataa gagggaaaaa   20400
ggtattacct gcctcattgt gttgcaagga gatgggcagc atctagggca ctggcctgga   20460
gtatcgcagg tgctttgcct aaggtggtgc agtccaggag aggcagctcc agagagaggc   20520
ccccggctgg ggctgaaagg agggcagacc tcggtttgaa tttcaccctg ccgctctata   20580
gctgtgtgac ttgggcaaat tacttaacat ctctgtatga ggaaatgatg agtgctaagc   20640
acttagctta gtgccgggac aatataaatt ctagctatcg ttactattgt tttcatcacc   20700
cgttgcttta aaatccagcc tctggtatag gcaactattg acgggctacc ctgtgtcgaa   20760
aacatgccca ggcaggtagc aggaagtcac agatggggac ctcttggggc atcaagggat   20820
ggtgccctga ggctgagctg ttctggttgg gtggagcatg agaggtctgg gaagacagtg   20880
ggactccagc ctggaataag aggctcagag ttgattctcg tctgagcacg tccaggggaa   20940
ccactgaggg tttgggaaca ggagagtgag ggtgagaacc tggttctggg cacagcaggc   21000
tggcatgtag gatggatgtt caggaaagat gagcatagtc aggtggctgg tgcccttgtc   21060
caggggagag gctccgtcag gttcaggggt cctggcttgg agggaagtcc gccatgctct   21120
aatcacgctc ccctttggaa gtgctcagcc gatgagctca caggcacatg tcagtttgaa   21180
gtcatggaat ctgactccat gaagcgcacc tcaaagagca ccattttgca gctaagggaa   21240
ctgcaggctg gacatgctga gtggctgccc cgagcccttg cagctaggac atagagaatg   21300
ctagtaacca caaccctacc atgttcagag cacatgccag gctccatgct ggggcttcgc   21360
acgtgtcatc ttcacagtgt ccctgtgagt aggtgtggtt tctctttcca tcttacaaat   21420
gagtaaacag agcctcagtg tagctaagta accactattt taggtttctt agccaatggg   21480
tgtgtctgac tcctaagccc atggagggca ttctgaggtg gttcagacag accccggctt   21540
acccttgaac ttctgcctgc tggctgcata gggaggggct gggggggagtt tgagcatctc   21600 aggccataga gccctgcct cactgtctcc atctctgggt ggaaagatgg tgttttccct   21660
gagaaactaa ggctcagaga ggttgaatgg ctctcccaag gtcacacagc tggtcagctg   21720
cagagttgag aacacaggag tcctggtgct caggccagca tctctttttt tctttgagtt   21780
gtttctaggt ttcctagctc ttgcctcaga ccttaaagag agaggtctg atggggatgg   21840 gcactggaga cggagcatcc cagcatttca catctgagct ggctttcctc tgccccaggc   21900
tgcagctccc actgggaggt ggaggacctt ggcacccaca agccgcctgt gctgaggcca   21960
cgaggtcagc ccaaccagtg cgtgggccac agggaggcca gcatccacgc ttcctgctgc   22020
catgccccag gtctggaatg caaagtcaag gagcatggaa tcccggcccc tcaggagcag   22080
gtgaagaggc ccgtgaggcc gggtgggtgg ggtgctgcgt gtctctcctg cacagctttt   22140
ctgtgtcagt ttgtgccacc accataccgc catgcatcag ggtggcggtt tgccaggtag   22200
atgctgtggg cagcttccgc cattgtgtgg acagcatgta tatgtgtctc tgtgtggctg   22260
ggtctgtttt tgcttttgtc cagatcagta aggtttgcta cctgggtacc ccactccact   22320
tggagtagaa tgtgcataaa tatggcataa agaaatgcaa tatgcatgca tttattgatt   22380
gatctatttt tttctgagat ggggtcttgc tgtgttgccc aggctggtct caaattcctg   22440
ggctcaagca atcctctggt ctcagcctcc ccaagtgttg ggattatagg catgagccgc   22500
tgcacctggc ctctctgatc tatttaacaa acctgctggg agggtctcag ggtcaggagc   22560
agcactgggc tctgaggaca cagagctcac tcagccgtga cccagagggg gtgcctgagc   22620
tgcatgctga aggttgttag catgaccagc aaggcaagaa aaggccctgc cgagattagc   22680
aaggcatgtg ccaagccctg gaatgtgaca gccgggcctt ctagaaacct gagtgtataa   22740
```

-continued

```
ctctccttaa aagccagtag gagctcctca aaaggcagcc ctaaggagtc cactcttaaa  22800
tgaactcaga gtcagtttta aaatgcaagt ctgtgttgat tctggtctgg atggtgcatt  22860
cctcgagagc aaaagacagt cttggtcttg gatccacttg ccctgggtac actgagggct  22920
gctaggttcc aggtgctctt cctggcactg ggggaggata caggcccaag agacatgctg  22980
ttctccctcc tggagcatct attttagtgg aggaagacag aaaacaaacc attaatatag  23040
agtactgaaa agatgcgatg gagaaaacta tagcaaggaa gggaatgggg tgggagagag  23100
gtcaggagag gtctcgctga caaggtggac gaaacaggcc atgaggcaga gaacatgttc  23160
caggcaaagc aaaggccccc aggtggggat gtgcaggag taccaggaaa ccagagaggt  23220
gggaatagtt atgagatggg gggtgcctca gaggggacag ggccaagtca ggtgagacct  23280
gagggtcaca gtcagcagtg agctgggggcc atgcaggggc ctggcctcag aggagtgtgg  23340
tctggcctgg atctgaacct ctcactgtgg cctagctgct gagctgagaa gagatgacaa  23400
ggaccttggg cagaagcagg gagactggag ggaggcggtg gagggtccag gcgttggggc  23460
ggggctcagg ctggagtctg aagggagcct gcaggcctgg tgggtggatg tgggtgggag  23520 aggggggagga tggcaccaag gctcgggccc ctggacagat ggagttgcca ttaagtggga  23580
tggggcaggc tatggggcca tcagtttcag agggatgagt ttggcactgg catggtaggc  23640
atctgtctat ctccacggcc ctcaaaccag gcatgaagca ggagctcacg tgtttggtca  23700
gccatggtgc agaaccgcct gggtgggagg tgcggggtgg gagatacacg gttgtgtccc  23760
aaatgggctc tgagccagcg agggccgtct gcactttggc ctcacagaag gatgtcggag  23820
ggagaaatga agtgtgggtg ggggtcccgg gccacgctag acatgtgctt tcttttcctc  23880
gggctctggc aggtgaccgt ggcctgcgag gagggctgga ccctgactgg ctgcagtgcc  23940
ctccctggga cctcccacgt cctgggggcc tacgccgtag acaacacgtg tgtagtcagg  24000
agccgggacg tcagcactac aggcagcacc agcgaagggg ccgtgacagc cgttgccatc  24060
tgctgccgga gccggcacct ggcgcaggcc tcccaggagc tccagtgaca gccccatccc  24120
aggatgggtg tctggggagg gtcaagggct ggggctgagc tttaaaatgg ttccgacttg  24180
tccctctctc agccctccat ggcctggcac gagggggatgg ggatgcttcc gcctttccgg  24240
ggctgctggc ctggcccttg agtggggcag cctccttgcc tggaactcac tcactctggg  24300
tgcctcctcc ccaggtggag gtgccaggaa gctccctccc tcactgtggg gcatttcacc  24360
attcaaacag gtcgagctgt gctcgggtgc tgccagctgc tcccaatgtg ccgatgtccg  24420
tgggcagaat gactttttatt gagctcttgt tccgtgccag gcattcaatc ctcaggtctc  24480
caccaaggag gcaggattct tcccatggat aggggagggg gcggtagggg ctgcagggac  24540
aaacatcgtt gggggggtgag tgtgaaaggt gctgatggcc ctcatctcca gctaactgtg  24600
gagaagcccc tgggggctcc ctgattaatg gaggcttagc tttctggatg gcatctagcc  24660
agaggctgga gacaggtgcg cccctggtgg tcacaggctg tgccttggtt tcctgagcca  24720
cctttactct gctctatgcc aggctgtgct agcaacaccc aaaggtggcc tgcggggagc  24780
catcacctag gactgactcg gcagtgtgca gtggtgcatg cactgtctca gccaacccgc  24840
tccactaccc ggcagggtac acattcgcac ccctacttca cagaggaaga aacctggaac  24900
cagagggggc gtgcctgcca agctcacaca gcaggaactg agccagaaac gcagattggg  24960
ctggctctga agccaagcct cttcttactt cacccggctg ggctcctcat ttttacgggt  25020
aacagtgagg ctgggaaggg gaacacagac caggaagctc ggtgagtgat ggcagaacga  25080
```

-continued

```
tgcctgcagg catggaactt tttccgttat cacccaggcc tgattcactg gcctggcgga   25140
gatgcttcta aggcatggtc gggggagagg gccaacaact gtccctcctt gagcaccagc   25200
cccacccaag caagcagaca tttatctttt gggtctgtcc tctctgttgc cttttttacag  25260 ccaactttc tagacctgtt ttgctttgt aacttgaaga tatttattct gggttttgta   25320
gcatttttat taatatggtg acttttaaa ataaaaacaa acaaacgttg tcctaac       25377
```

<210> SEQ ID NO 105
<211> LENGTH: 692
<212> TYPE: PRT
<213> ORGANISM: Homo sapiens

<400> SEQUENCE: 105

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
        50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
                100                 105                 110

His Val Phe His Gly Leu Leu Pro Gly Phe Leu Val Lys Met Ser Gly
            115                 120                 125

Asp Leu Leu Glu Leu Ala Leu Lys Leu Pro His Val Asp Tyr Ile Glu
        130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
        210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
                260                 265                 270

Lys Ser Gln Leu Val Gln Pro Val Gly Pro Leu Val Val Leu Leu Pro
            275                 280                 285

Leu Ala Gly Gly Tyr Ser Arg Val Leu Asn Ala Ala Cys Gln Arg Leu
        290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
```

-continued

```
                  325                 330                 335
Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
            370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
            450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
            515                 520                 525

Leu Pro Gln Ala Asn Cys Ser Val His Thr Ala Pro Pro Ala Glu Ala
            530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
            595                 600                 605

Lys Val Lys Glu His Gly Ile Pro Ala Pro Gln Glu Gln Val Thr Val
            610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
            675                 680                 685

Gln Glu Leu Gln
    690
```

```
<210> SEQ ID NO 106
<211> LENGTH: 3166
<212> TYPE: DNA
<213> ORGANISM: Homo sapiens

<400> SEQUENCE: 106
```

-continued

```
ctgctcagtt catccctaga ggcagctgct ccaggtaatg ccctctgggg aggggaaaga      60
ggaggggagg aggatgaaga ggggcaagag gagctccctg cccagcccag ccagcaagcc     120
tggagaagca cttgctagag ctaaggaagc ctcggagctg gacgggtgcc ccccacccct     180
catcataacc tgaagaacat ggaggcccgg gaggggtgtc acttgcccaa agctacacag     240
ggggtggggc tggaagtggc tccaagtgca ggttcccccc tcattcttca ggcttagggc     300
tggaggaagc cttagacagc ccagtcctac cccagacagg gaaactgagg cctggagagg     360
gccagaaatc acccaaagac acacagcatg ttggctggac tggacggaga tcagtccaga     420
ccgcaggtgc cttgatgttc agtctggtgg gtttttctgct ccatcccacc cacctccctt     480
tgggcctcga tccctcgccc ctcaccagtc ccccttctga gagcccgtat tagcagggag     540
ccggccccta ctccttctgg cagacccagc taaggttcta ccttaggggc cacgccacct     600
ccccagggag gggtccagag gcatggggac ctggggtgcc cctcacagga cacttccttg     660
caggaacaga ggtgccatgc agccccgggt actccttgtt gttgccctcc tggcgctcct     720
ggcctctgcc cgtaagcact tggtgggact gggctggggg caggtggag gcaacttggg     780 gatcccagtc ccaatggggtg gtcaagcagg agcccagggc tcgtccagag gccgatccac     840
cccactcagc cctgctcttt cctcaggagc ttcagaggcc gaggatgcct cccttctcag     900
cttcatgcag ggttacatga agcacgccac caagaccgcc aaggatgcac tgagcagcgt     960
gcaggagtcc caggtggccc agcaggccag gtacacccgc tggcctccct ccccatcccc    1020
cctgccagct gcctccattc ccacccgccc ctgccctggt gagatcccaa caatggaatg    1080
gaggtgctcc agcctcccct gggcctgtgc ctcttcagcc tcctctttcc tcacagggcc    1140
tttgtcaggc tgctgcggga gagatgacag agttgagact gcattcctcc caggtccctc    1200
ctttctcccc ggagcagtcc tagggcgtgc cgttttagcc ctcatttcca tttttccttc    1260
ctttcccttt ctttctcttt ctatttcttt ctttctttct ttctttcttt ctttctttct    1320
ttctttcttt ctttctttct ttctttcttt cctttctttc tttcctttct ttctttcctt    1380
tctttctttc tttcctttct ttctctttct ttctttcttt cctttttctt tctttccctc    1440
tcttcctttc tctctttctt tcttcttctt ttttttttaa tggagtctcc ctctgtcacc    1500
taggctggag tgcagtggtg ccatctcggc tcactgcaac ctccgtctcc cgggttcaac    1560
ccattctcct gcctcagcct cccaagtagc tgggattaca ggcacgcgcc accacaccca    1620
gctaattttt gtattttttag cagagatggg gtttcaccat gttggccagg ttggtcttga    1680
attcctgacc tcaggggatc ctcctgcctc ggcctcccaa agtgctggga ttacaggcat    1740
gagccactgc gcctggcccc attttccttt tctgaaggtc tggctagagc agtggtcctc    1800
agcctttttg gcaccaggga ccagtttgt ggtggacaat ttttccatgg gccagcgggg    1860 atggtttttgg gatgaagctg ttccacctca gatcatcagg cattagattc tcataaggag    1920
ccctccacct agatccctgg catgtgcagt tcacaatagg gttcacactc ctatgagaat    1980
gtaaggccac ttgatctgac aggaggcgga gctcaggcgg tattgctcac tcacccacca    2040
ctcacttcgt gctgtgcagc ccggctccta acagtccatg gaccagtacc tatctatgac    2100
ttgggggttg gggaccccctg ggctaggggt ttgccttggg aggccccacc tgacccaatt    2160
caagcccgtg agtgcttctg ctttgttcta agacctgggg ccagtgtgag cagaagtgtg    2220
tccttcctct cccatcctgc ccctgcccat cagtactctc ctctccccta ctcccttctc    2280
cacctcaccc tgactggcat tagctggcat agcagaggtg ttcataaaca ttcttagtcc    2340
ccagaaccgg ctttgggggta ggtgttattt tctcactttg cagatgagaa aattgaggct    2400
```

```
cagagcgatt aggtgacctg ccccagatca cacaactaat caatcctcca atgactttcc      2460
aaatgagagg ctgcctccct ctgtcctacc ctgctcagag ccaccaggtt gtgcaactcc      2520
aggcggtgct gtttgcacag aaaacaatga cagccttgac ctttcacatc tccccaccct      2580
gtcactttgt gcctcaggcc caggggcata aacatctgag gtgacctgga gatggcaggg      2640
tttgacttgt gctggggttc ctgcaaggat atctcttctc ccagggtggc agctgtgggg      2700
gattcctgcc tgaggtctca gggctgtcgt ccagtgaagt tgagagggtg gtgtggtcct      2760
gactggtgtc gtccagtggg gacatgggtg tgggtcccat ggttgcctac agaggagttc      2820
tcatgccctg ctctgttgct tcccctgact gatttagggg ctgggtgacc gatggcttca      2880
gttccctgaa agactactgg agcaccgtta aggacaagtt ctctgagttc tgggatttgg      2940
accctgaggt cagaccaact tcagccgtgg ctgcctgaga cctcaatacc ccaagtccac      3000
ctgcctatcc atcctgcgag ctccttgggt cctgcaatct ccagggctgc ccctgtaggt      3060
tgcttaaaag ggacagtatt ctcagtgctc tcctacccca cctcatgcct ggcccccctc      3120
caggcatgct ggcctcccaa taaagctgga caagaagctg ctatga                     3166
```

```
<210> SEQ ID NO 107
<211> LENGTH: 99
<212> TYPE: PRT
<213> ORGANISM: Homo sapiens

<400> SEQUENCE: 107

Met Gln Pro Arg Val Leu Leu Val Val Ala Leu Leu Ala Leu Leu Ala
1               5                   10                  15

Ser Ala Arg Ala Ser Glu Ala Glu Asp Ala Ser Leu Leu Ser Phe Met
            20                  25                  30

Gln Gly Tyr Met Lys His Ala Thr Lys Thr Ala Lys Asp Ala Leu Ser
        35                  40                  45

Ser Val Gln Glu Ser Gln Val Ala Gln Gln Ala Arg Gly Trp Val Thr
        50                  55                  60

Asp Gly Phe Ser Ser Leu Lys Asp Tyr Trp Ser Thr Val Lys Asp Lys
65                  70                  75                  80

Phe Ser Glu Phe Trp Asp Leu Asp Pro Glu Val Arg Pro Thr Ser Ala
                85                  90                  95

Val Ala Ala
```

```
<210> SEQ ID NO 108
<211> LENGTH: 14994
<212> TYPE: DNA
<213> ORGANISM: Homo sapiens

<400> SEQUENCE: 108
aatgacaaac tgaaaaaatc tattgtttgt tatatatata acaaagaatt agtatccaca        60
atatgtaaat aattcctaaa attagtcaga aagagacaaa cttaaaaaga gggtaacaag       120
gaggggagca aattatgtac ataaccagat gattcgcaaa gacggcaaca gagatggcca       180
gcaaaacaaa ctagatatat acttgtctat tagatttatc aacatttttt gccttttttca      240 ttaaaagcat ttgtaaaagg atataggaaa agaggaactc tcatatactc ctggcaggga       300
tgtaaattgg tacaacccctt ttgaaggaca atctgacaaa agcaatcgta agttacaagt      360
caacatctat gaatgtatat gaaaatattt atatacatac atcaccacca taaaagcatt       420
ttctatacat actgtttata attagaaaat tggaaacaaa tgattaaaag ggggctgatt       480
```

-continued

```
aaattaaggt tcatctatat aacaggatta tgcagctatt aaaaaggacg tggtaactct    540
atagacattc ataggaaaat aaattttaaa atactaagat cctgaatgat atatatatca    600
tgagctatta tacataacaa gatcccactt gtgttataaa aaattatgtt tagtcattca    660
aagggtctgg tatgatagac ccaaaatgtt aatagagtcg agattttat ttttttatagg    720 tttttgaaat acctgaattt tcacaataag tactttgcac attaaaaatc ttagctgggc    780
atggtggctc acgcttgtaa tcccagcact ctgggaggcc aaggtaggca gatcacctga    840
ggtcaggagt tcgagaccag tctggccaac atggtgaaac cccgtctcta ctaaaaatac    900
aaaaattagc caggcttggt tggggggtgcc tgtaattcca gatactcggg aagctgagac    960
aggagaatcg cttgaaccca ggaggggggaa gttgcagtga gctgagatca cgacgctgca    1020
ctccagcctg ggcaacaaag agcaaaactc cgtctcaaaa ataaataaag aaaaaatctt    1080
tacatgtcca aagatacggc tgttcaacta aaaaatatat atgtataaaa cttaacatgt    1140
taatagtgaa cacacaaaac agtaagatag ataaaaattat tccttcaaag ctcacttaac    1200
ctctggatct acactgtcca aaaagacggt ctaatgagac aattgagcac ttgataggtg    1260
agtggttcta actgagatat gttctcagta taaaacatac aataggatct tcctatacaa    1320
cattaattaa aaaacaaact attgtagtta aaaaggaaaa aattagagat actatgtaaa    1380
aaagagccaa aataccttgt attttatttg aaagacatat ctccataaga ttacacaacc    1440
tcgtgtagga taaaggactt tgctttgctt ggaatttaaa caatttaggc tcttaaatgt    1500
cctaaaattc tctgtagcta agaaattttt atattggttc ctaggaacta ggaatcctta    1560
aattaggccc tacatttgct tacaagttta ttttccttgg cataaaattt tttagttttt    1620
acattactgg ttatatttga tcagggttct atttaaatag gcacaagttc aagcaaagat    1680
cagattctgc ttttagcagt gtgtactcag acaggaagta ttaaaaggca ggcagaaaat    1740
cctttataaa attactactt tcaatgcatt ttcccacgtt gaaatgcttc tgcagtttat    1800
aattaggcaa attactttaa ttataatcaa taatgctgtt caaattacta taagaattat    1860
acagatattt ataccaagag acaatatact agaaaccaag actacgtgac cattacctct    1920
actctgtcag tgttatttgt gagaaattgc acaaattttg caaaaagtgt tagtatccta    1980
ctacagtagg atataatata gaaggaaata atttcataaa gcctgtcttt ggtactagtg    2040
ctcagttact ttcattaact aaaaaagggg ctactcttca aattcccttc tctaaaaaga    2100
atgtactata tcaaaagggg gtaaacacta ctacgtatac attctgcact tagaaatccc    2160
tatatgttga ttttatcatt ctcttattca ataaatattg tttctacaat gtgtaaggca    2220
ttactgtact aaagcattat aaggaatata agttaaaaac acatacaaat cttgccaatc    2280
aacagcttat agtgtaatag gggagagaag ctggcccatc tatattctcc ctcaactagc    2340
aagtggatga aatatcaggg tcaatagtta taagccacaa aagctgacag cttaattaag    2400
agaagttttg aaatatgtat ttcatgacca ataattacaa ctgtaacttt tctatttaaa    2460
gaaggagaaa atttgaattt cttctctagc tcaacataca cttctataat tccattacat    2520
gaaccagagt aaagggtaag atggaaatga agaatatttt cttacccttt tgtggttcta    2580
tattggacac ttaaaaatca tacacaacct aatcaaagaa tgtaattctt taaaaaggta    2640
cgagaccaaa attcagaaaa tctagactat aacaaaattt ctcaatttac attatcttaa    2700
tatgcaatta attttcacca gtaaaatact atagtatggg tacaaatgca ttgattagtt    2760
ctaattacaa aaatggctaa tatataatac tgtgtagtgt ttatgataca tcagataatg    2820
ttctaagtgc tctgaaaata taaacttttta atctttatata cgaccctata aaataggtgt    2880
```

-continued

```
tattctcact ggagagatga gaaaacaggg gttcagagat gtgaagtaat ttgaccaaag    2940
gtcacaaagc tgaagaatat gaaatccggg attctgattc aggcagtctt attccagaat    3000
catgctctta accactatgg aatactgcct ctactgtaac tattataccc aaaaccctta    3060
atcctaagtc atcaaaagga agagcctcta ttttacacaa tgaagaggca tttctaagaa    3120
tagaaattta gggacgagca cagtggctta ctcctttaat atcagcactt tgagaggctg    3180
atatgggagg ttcacttgaa gtcaggagtt caaggtcagc ttgggcaaca tagtgaaaca    3240
cagtctctac aaaatattta aaaattagct gggtgtggtg gcatgcatct atagtctcag    3300
ctacttggga gacagaggga ggaggcttgc tcgagcccag gagttcgtgg ctatagtgag    3360
ctatgatcat gccactgcac tccagcctgg acaacagagc aagaccctgt ctctaaaaaa    3420
gaaaagaaat ttggaaatgg tttattttgt attaacaatt tataatttac actgaaattt    3480
attatgataa aacttttccc tgtgttaaaa agctattaac tttatgaaaa atttctttta    3540
ggtaaggttg attatatata cccacacaca tacacaggtt aaaagttagt ttcatgtgac    3600
ataataacta gcattttgag cactacctgt ttgcccagca ctgttctaag tgctctacat    3660
gtattattgt taaattatca taacactatg aattatgtac tataattacc ccagctttac    3720
agatgaggag actaatccat ggggaggtta agtaacttgt ccaaggccag acagctagag    3780
ccggcttttg gacccacacc acagtctgac tccagcaccc atattcttaa caatttcacc    3840
atattaatat gtcaagatta agcagtttta aaggatgcta ttttctcaca aatttcttaa    3900
tatgaacact caataagaat aatcactaat ataagcattt agtatttttt taacactaag    3960
ttggaagcat agtggaacat ttatttttag aaatattatt aattggctgg gctcacgctt    4020
gtaatcggct gggctcatgc ctgtaaattt tgggaggcca aggtaaaaga attgcttgag    4080
cccagtattt ccagaccagc atgggcaata cattaagaca tcatctttaa aaaaaaaatg    4140
ttattaatct cctctttttg ttaaatgtat attatcaaaa ttgttactaa gctaacaaac    4200
ttcagaaaaa cttatgatgg gcaagctgct tgtgacattg aaggtattta agattcaatt    4260
ctagtttggt cctagatgac cacatatcca ttgttccttc aacgagcaca tggtaaagag    4320
cctagaacac agagacacag aacacagtgg agaaaaggga gtgaaatgtc tttaatgaca    4380
cttactatat atgggatttt gtgacaatat acaaggatgg ttaagacata taaggtgatg    4440
caaaaaaaca tattaacaat tatagtgaca aaaaatgagg agcatataat tatacattga    4500
tttatacaga gtaccagagg aacacagcat tgagagccgt aacaccacct gagggagtgg    4560
agaaaggctt cagagagaaa gtgttttttg gaatggatca ctgtttccaa aagaactaaa    4620
gtacagtttg agaaatgcat acttaattca ttactttttt cccctcaact ttaataataa    4680
atttacccaa caaaaaagtt tatttttgac ttgtaaatct cttaaaatca taaaaaagta    4740
aaattagctt ttaaaaacag gtagtcacca tagcattgaa tgtgtagttt ataatacagc    4800
aaagttaaat acaatttcaa attacctatt aagttagttg ctcatttctt tgatttcatt    4860
tagcattgat ctaactcaat gtggaagaag gttacattcg tgcaagttaa cacggcttaa    4920
tgattaacta tgttcaccta ccaaccttac ctttttctggg caaatattgg tatatataga    4980
gttaagaagt ctaggtctgc ttccagaaga aaacagttcc acgttgcttg aaattgaaaa    5040
tcaagataaa aatgttcaca attaagctcc ttctttttat tgttcctcta gttatttcct    5100
ccagaattga tcaagacaat tcatcatttg attctctatc tccagagcca aaatcaagat    5160
ttgctatgtt agacgatgta aaaattttag ccaatggcct ccttcagttg ggacatggtc    5220
```

-continued

```
ttaaagactt tgtccataag acgaagggcc aaattaatga catatttcaa aaactcaaca      5280
tatttgatca gtcttttttat gatctatcgc tgcaaaccag tgaaatcaaa gaagaagaaa     5340
aggaactgag aagaactaca tataaactac aagtcaaaaa tgaagaggta aagaatatgt      5400
cacttgaact caactcaaaa cttgaaagcc tcctagaaga aaaaattcta cttcaacaaa      5460
aagtgaaata tttagaagag caactaacta acttaattca aaatcaacct gaaactccag      5520
aacacccaga agtaacttca cttaaagtaa gtagaaaata aagagggttc atgtttatgt      5580
tttcaatgtg gatcttttaa aaaaaatatt tctaaggcat gccatttgaa atactttgtt      5640
gcattgttga aatacttttt tttccaagaa aaataatctc cagaaaataa aatttcctat      5700
tataatttca agttagtttt ttgtttccct aatgttatat atgaaaacac tgaaaatttg      5760
cattttatat gaaaattaca aatcggttaa attatacaat ctagaacact atgtcattac      5820
actattgtaa attactgaag gtaagtaaaa agttaaaaaa aatttaaaac tattctccag      5880
tgtttaaaac agattaaata atacagtaaa tggaaaagat ttattcatat gaaaatatgc      5940
tgggcttttt cttttaattg aagttcagaa aatcaaattt tagagatagt acaatttaaa      6000
taaaatgtta aggacaaaaa tatgtgctat ttgaaagaag catacaaggg gaaggaattg      6060
ccaatattca tttttcaaat ccattattag tttaaaaatt tagattatga tagtgttaca      6120
ggaaattaat agaaaagaaa gaggaaagca acttataacc aacctactct ctatatccag      6180
acttttgtag aaaaacaaga taatagcatc aaagaccttc tccagaccgt ggaagaccaa      6240
tataaacaat taaaccaaca gcatagtcaa ataaaagaaa tagaaaatca ggtaagtcag      6300
tattttaatg gtatgtccca tctttcacac aggtctgtaa aaacactgaa tcctaaaatt      6360
atttacaagc tttaactgga tcatgagtaa aattatcaca tcagcataac tgttaaaatt      6420
gcaggctctg aagctaataa actacctgca tttaaaccat ggctctaaaa ctttgtgtga      6480
ccttgaataa attacttcac cccttttatct ctcagtttcc tcacatatac tacaaagata      6540
ataacagaac ttataggatt attgtaagaa aaaaaattaa ttcatagcag ccaatgtcat      6600
cttactaaaa ttcaaattag atcatgtttc tctttgctca aaaccacaca atagctttcc      6660
atttcactca tattggctct ttagaccaag attacccaac ccttcgtcat ctcactgact      6720
tcacctcctc tactctagtt attctgaccg ctttaccagt attcaaacac atcaaacata      6780
ctgccacctc aaagcctttg cccttgttgt ttcctctaac tggaacgctc ttctgccctg      6840
gtatctacgt ggcccactct ctgatttccc ttagggtcgt tatcaaacaa aaaattccca      6900
atgaagactt acaaggtcac ttaaccaaaa atcacaaccg cctggtccca tccctgaaaa      6960
cttctacttc cttagctact tttctcctgc acactcacct ttatttaaca taacataaat      7020
tttagttatt tatctcttct attcctgcac taaaatgtaa gctctgtgaa tacagggatt      7080
ttttccatta tcttcatatt ttccattatt tgtatatact ccagaatata gaatactgta      7140
tggcacacag taggcatttc tgttgaatta ataaatgtaa tgtcatattc acacagaagc      7200
gtgtgctatg attattatta cttggattac tagaaatagt gtgcctcata attaaaggtc      7260
aacattcaac aatgtaatta atctacaatg taaacatctg gtgaagtgac agagggaagc      7320
acttgtttag aaaaaagcta tgtcagaatc catgtattct aatatgcagt acaatagttt      7380
aaaaatatta ataatactct caaacagcta ttcaagagga ttcaaaaaac ataatataaa      7440
ctcagagaaa ctggtaaaca aaatcatttt caagagatat aaaacaaata ttattaccaa      7500
tttccactaa acaaacataa tgttagtagt gctgctaaaa ggttttttat caactacttt      7560
tggtttccat actttccttc ttatgatgtt attattctaa attctttttca attatatctt      7620
```

-continued

```
ttactatgat taaatgaacc tgctccccaa agcaaaatgt tactatagta atatacattg   7680
tgtctaaaaa taaaaatgtg tgaagaaacc aaaacaatga atttctgagt tggaagaaga   7740
gttagatcat ttaactttct catatttaaa ttaaaaaaac aaaactctaa aaatttaagt   7800
aactttaaga tcacatagtt acttagtaga aaagagtaat acccagcaag caaactttac   7860
aatagatcct tttaaataag gtcctaggaa atatcattca tgccagcatc aaaaaactaa   7920
cactaataat gcaagatatt atatattctg cttttcttac tgtcaatgag aaaaactatc   7980
attcaataaa ttgcaaaccc aacacactta aataaaaata aaatgttact gctaaactaa   8040
cgataaacta ctgaatatat agaaagtaag caaacaaact tgccaacctg ccaacatcta   8100
cagatatgtt tacaggtcaa aaattatcaa attatcaaga aagcctggtt caaattatgt   8160
attatgtctt tatcacaggt ctgaagatca gtaagaccta aaactgaaaa ttattaaact   8220
taaaatctga acagaatatc aaatatattt tattcatata aataaaagaa tacattacaa   8280
tattctaagc aaagcagtct ctacttttgg ccttgctctg ttttccgacc aatgtctgct   8340
tttttgcctt gctttatttt tttatcttat aaataatgt ccctgattaa atattttgag   8400
aacaggtaat ctgtacaatc tgaataacac tgtttatcta aatatcaaac accgttataa   8460
cattatgaac tgaaagacaa actgtacttc tgacatcctt actcagattt cccctaattg   8520
tatattcagt atcattttaa aaaacagatt tatattcttt tatcagctca gaaggactag   8580
tattcaagaa cccacagaaa tttctctatc ttccaagcca agagcaccaa gaactactcc   8640
ctttcttcag ttgaatgaaa taagaaatgt aaaacatgat ggtaagacac tttggtgggt   8700
ttccttcttg aagctattat tatcaaattc cctattctta ggacttgttc tagactaaaa   8760
gatagttaag agatatccat caaatacaat gtatcaacct aaactggatg ctggggttct   8820
ttttacaccc tataaaagac atacctaaga caatcagaga aatacaaata tggacttgat   8880
tattagataa tatagaaggt ttattaattt tcttagatgt gatcatggta ttgcagtttt   8940
aaaggagaac aatctcctgt ttaagagata catgctgaaa tatttacgga gttaaaggtc   9000
actggactcc agactggtga tagaacaaga ctctgtctct aaaaaataat taattttta   9060 aaagaaaata gtttggtaag atgattctta cattcttaaa taacacgcca tctaagaaaa   9120
atgctttaac ataaacatta ctgaaaaaat gctacatttg ccacaacttc ataaaatgtc   9180
aagtgaaatc tcaagctcca aagatattat tcctattact aaatctgatg taataacatt   9240
ttattgattc taggcattcc tgctgaatgt accaccattt ataacagagg tgaacataca   9300
agtggcatgt atgccatcag acccagcaac tctcaagttt ttcatgtcta ctgtgatgtt   9360
atatcaggta aaacctgtct aaggagaata gacagtagtt agttcaactt actcattacg   9420
tattaggaag attaacctgg ttatcattgt tttatacata tatatatgaa atatatatga   9480
gtattcgtat aaatataata cttttacctt gtttatgtat ttactcaata ttctcctttt   9540
cctctaaaat aatctgaagt gactattatc aataagttta ctatgccaaa attcattaat   9600
tgcctttcac ttaactttg ggaccataat aaataataaa atgtattgcc ataacattaa   9660
taaactacct tacaaaacca ccaattaaaa tcaaacaaac aaaaaagtgt tatttacatc   9720
tgtcaacata aatctactaa aaatacatga tttcattcat tatattcagg tagtccatgg   9780
acattaattc aacatcgaat agatggatca caaaacttca atgaaacgtg ggagaactac   9840
aaatatggtt ttgggaggct tgatggtaag gggactacat tcaatcattc attcacttgc   9900
taatctacaa atatttactg agaacctctt atggaccagg tattaggaaa agtagtaacg   9960
```

-continued

```
aacgagaagc agtctcagcc ttcatataat ttattatcaa acaattacac atttgttagt   10020
aaattacact tattacaact gttattattt gaattatatt tatcacaatt acatgtctgt   10080
tcttaaatat acttatcaca atttaattcc acggcttaca atgatcataa ctataattat   10140
taaagacaat tttgattaaa tgttatgtca taagtagtaa ctgttacaaa taagctgtga   10200
aaagaaccac tcctagcatt agtcactcta ttctctcatt aacgttttac atatcaatta   10260
attggaagtt aaaaggacca ggaaactcag acatacagta tacattttaa aatttcaatt   10320
atttaaatat aatatataga atgtatggct tataatgaat tagttaactc aatgcaaatt   10380
attctatttt gattacaaat agtaaaataa gcaagataaa ataacagatg tttaaaatcc   10440
aaaaagcaca tacaaaaatc catgaatgat gtctaagtac tcacttataa agtagaagac   10500
attcattatt atatcaaatt tttaaatgct cagtactatt tgaccattta aaaattttgt   10560
attcaaacta ccagtgaaag ccctacctag aaggtatact cagtgataag ttttgtagct   10620
ccaaatcttc taatagtgag tgtaacccca aaataaaagg ctgacaggta agtcgagaat   10680
actcacttaa ttctggtaag aaagcaaccc atttgtactt gtatttacca gcaatcctta   10740
aaatgaagct tcctactaac tcaatagcaa taagacaata gtgaatgttt aatgaaaaca   10800
gtattttata aatactttaa taaaaaggat tgtgatgaag aacaatctat ttatatttgt   10860
tatttgtttt taattccaat aaaaataatt tttaaaatta cagaaaaaag ttattaagaa   10920
ccatgctttt aaatttaaaa tgatttttta aatttattcc tgtctttttc tacaaagaaa   10980
gcatacatta agcaaatacc aaaggccagg tttacatttg aagaaagtga cattattatt   11040
actcaagtct ctaggaatac ttaacacatc tcttgactgt atatggatgt taataaatag   11100
ctgacagtaa agtttatcca tataaagact tgcaaatatt cctctaccaa tgacgagact   11160
ttaaaatatc tataataatg taacacattt cactggtgaa acatgtcttg tcatatgcat   11220
tatagaaagg ataatcagac tttcagttat attaatattt ttaacatttt tgtgcacata   11280
gctatcttca ataaaattgt tttaaaaggt attattttaa gatacactaa aatgatcaag   11340
ggattcaaga ctaaacaact caattagttg caccaataaa aaacacttaa aaaaactgtc   11400
agtgtccaac ctgtacttaa taactcacag atttttaaaa cttttctttt caggagaatt   11460
ttggttgggc ctagagaaga tatactccat agtgaagcaa tctaattatg ttttacgaat   11520
tgagttggaa gactggaaag acaacaaaca ttatattgaa tattcttttt acttgggaaa   11580
tcacgaaacc aactatacgc tacatctagt tgcgattact ggcaatgtcc ccaatgcaat   11640
cccggaaaac aaagatttgg tgtttttctac ttgggatcac aaagcaaaag gacacttcaa   11700
ctgtccagag ggttattcag gtatcttttt ctgataccaa tactttattt tcatatcttc   11760
aaagtatctt cccacattat tagctattat ctgcaatgac aacttttaaa aatccgaatc   11820
ccaaataagc gttttctctc tagacgaaaa cctcttaact ataatgaaag tgttcattct   11880
agttcaatca ggtattttac ctctaatctt cctcagattt tctatttttt ggtagtgtat   11940
agattattta tacagattat ttaaaattgg gacttataca gattatttaa aactgggata   12000
catgcatcta aaacactgta atatttataa gaaaggaaga taaacttacg gggaaataca   12060
gtaacagtaa ctacatacga gtctgtaccc attaaattgc atatctatct cctttaggag   12120
gctggtggtg gcatgatgag tgtggagaaa acaacctaaa tggtaaatat aacaaaccaa   12180
gagcaaaatc taagccagag aggagaagag gattatcttg gaagtctcaa aatggaaggt   12240
tatactctat aaaatcaacc aaaatgttga tccatccaac agattcagaa agctttgaat   12300
gaactgaggc aaatttaaaa ggcaataatt taaacattaa cctcattcca agttaatgtg   12360
```

-continued

```
gtctaataat ctggtattaa atccttaaga gaaagcttga gaaatagatt ttttttatct  12420
taaagtcact gtctatttaa gattaaacat acaatcacat aaccttaaag aataccgttt  12480
acatttctca atcaaaattc ttataatact atttgtttta aattttgtga tgtgggaatc  12540
aattttagat ggtcacaatc tagattataa tcaataggtg aacttattaa ataacttttc  12600
taaataaaaa atttagagac ttttatttta aaaggcatca tatgagctaa tatcacaact  12660
ttcccagttt aaaaaactag tactcttgtt aaaactctaa acttgactaa atacagagga  12720
ctggtaattg tacagttctt aaatgttgta gtattaattt caaaactaaa aatcgtcagc  12780
acagagtatg tgtaaaaatc tgtaatacaa atttttaaac tgatgcttca ttttgctaca  12840
aaataatttg gagtaaatgt ttgatatgat ttatttatga aacctaatga agcagaatta  12900
aatactgtat taaaataagt tcgctgtctt taaacaaatg gagatgacta ctaagtcaca  12960
ttgactttaa catgaggtat cactatacct tatttgttaa aatatatact gtatacattt  13020
tatatatttt aacacttaat actatgaaaa caaataattg taaaggaatc ttgtcagatt  13080
acagtaagaa tgaacatatt tgtggcatcg agttaaagtt tatatttccc ctaaatatgc  13140
tgtgattcta atacattcgt gtaggttttc aagtagaaat aaacctcgta acaagttact  13200
gaacgtttaa acagcctgac aagcatgtat atatgtttaa aattcaataa acaaagaccc  13260
agtccctaaa ttatagaaat ttaaattatt cttgcatgtt tatcgacatc acaacagatc  13320
cctaaatccc taaatcccta aagattagat acaaattttt taccacagta tcacttgtca  13380
gaatttattt ttaaatatga ttttttaaaa ctgccagtaa gaaattttaa attaaaccca  13440
tttgttaaag gatatagtgc ccaagttata tggtgaccta cctttgtcaa tacttagcat  13500
tatgtatttc aaattatcca atatacatgt catatatatt tttatatgtc acatatataa  13560
aagatatgta tgatctatgt gaatcctaag taaatatttt gttccagaaa agtacaaaat  13620
aataaaggta aaaataatct ataattttca ggaccacaga ctaagctgtc gaaattaacg  13680
ctgatttttt tagggccaga ataccaaaat ggctcctctc ttcccccaaa attggacaat  13740
ttcaaatgca aaataattca ttatttaata tatgagttgc ttcctctatt tggtttcctt  13800
aaaaaaaaaa aaaactctca taggacatgt ttcattttgt tcctttcagg agtagtaaat  13860
tagacgtttt ccccatataa agcttttttc taccagaaag atacttctgg tagaagaaga  13920
gaaaggagct ctttatggtt cacacgactg tctcctgtcc taactacttt gcttaaagtg  13980
ctcaaattcc atcactactc acagttgtct aatctaagtc taatcccctt tgatctctca  14040
gactaccttc cctttatct ctctactact taataataag aatatctttt tttcaaactt  14100
gaccttcatt ttgctttcac aatactatac tctccatgga ttatccctta tctgaatcca  14160
tctttataac cctattcctt tctcatattt agtactgtgg gccaatggac aaccttcaat  14220
catcttttct acactgaccc tcagacattc tatctgctct cacggactcc tttatttacc  14280
atgaataaag ttccaaaatc tacatattca tcccaagtct ctttccagtt ccccttctta  14340
cattgcctat ttgccatttc tcccttcaat accctatact tcactcaaat tcaacatacc  14400
aaaaataaaa ggccaggcac ggtggctcac acctgtaatc ccaggacttt gggaggctga  14460
ggcaggtgga tcacctgagg tcaggagtct gaccagcctg accaatatgg tgaaaccccg  14520
tctctaccta aaatacaaaa attagccagg cgtggtggca tgtgcctaca gtcccagcta  14580
ctcaagaggc tgagacagga gaatcgcttg aacccaggag gcggaggttg cagtgagctg  14640
agatcacacc aatgcactgg gtgacagaac aagactgact caaaaaaaaa taaataacaa  14700
```

-continued

```
attccccagc cccttactgc tactgctatc cctttctacc cacctttccc tcctttatac  14760
tctttcacac catcttcctc acttctttat atccattaat atgaccagca tgttcccagt  14820
cacagaagcc tggaacccgg aagacatctc tggctttca ctcaactttg taaactacct  14880
cttttgtatc ataagccacc aagttcaata caatcttctc ttgaaacgtc tcttaatctt  14940
ataagctttc ttccccaaag actgtcttta acttcagtgc tagattatat aagt       14994
```

```
<210> SEQ ID NO 109
<211> LENGTH: 460
<212> TYPE: PRT
<213> ORGANISM: Homo sapiens

<400> SEQUENCE: 109

Met Phe Thr Ile Lys Leu Leu Leu Phe Ile Val Pro Leu Val Ile Ser
1               5                   10                  15

Ser Arg Ile Asp Gln Asp Asn Ser Ser Phe Asp Ser Leu Ser Pro Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu Glu
                85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
            115                 120                 125

Glu Glu Lys Ile Leu Leu Gln Gln Lys Val Lys Tyr Leu Glu Glu Gln
    130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Leu Leu Gln Thr Val Glu Asp Gln Tyr Lys Gln Leu Asn Gln Gln
            180                 185                 190

His Ser Gln Ile Lys Glu Ile Glu Asn Gln Leu Arg Arg Thr Ser Ile
            195                 200                 205

Gln Glu Pro Thr Glu Ile Ser Leu Ser Ser Lys Pro Arg Ala Pro Arg
    210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
            275                 280                 285

Ile Asp Gly Ser Gln Asn Phe Asn Glu Thr Trp Glu Asn Tyr Lys Tyr
    290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
```

-continued

```
                   325                 330                 335
Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
            355                 360                 365

Val Pro Asn Ala Ile Pro Glu Asn Lys Asp Leu Val Phe Ser Thr Trp
        370                 375                 380

Asp His Lys Ala Lys Gly His Phe Asn Cys Pro Glu Gly Tyr Ser Gly
    385                 390                 395                 400

Gly Trp Trp Trp His Asp Glu Cys Gly Glu Asn Asn Leu Asn Gly Lys
                405                 410                 415

Tyr Asn Lys Pro Arg Ala Lys Ser Lys Pro Glu Arg Arg Gly Leu
            420                 425                 430

Ser Trp Lys Ser Gln Asn Gly Arg Leu Tyr Ser Ile Lys Ser Thr Lys
            435                 440                 445

Met Leu Ile His Pro Thr Asp Ser Glu Ser Phe Glu
    450                 455                 460

<210> SEQ ID NO 110
<211> LENGTH: 4548
<212> TYPE: PRT
<213> ORGANISM: Homo sapiens

<400> SEQUENCE: 110

Met Glu His Lys Glu Val Val Leu Leu Leu Leu Phe Leu Lys Ser
1               5                   10                  15

Ala Ala Pro Glu Gln Ser His Val Val Gln Asp Cys Tyr His Gly Asp
            20                  25                  30

Gly Gln Ser Tyr Arg Gly Thr Tyr Ser Thr Thr Val Thr Gly Arg Thr
            35                  40                  45

Cys Gln Ala Trp Ser Ser Met Thr Pro His Gln His Asn Arg Thr Thr
    50                  55                  60

Glu Asn Tyr Pro Asn Ala Gly Leu Ile Met Asn Tyr Cys Arg Asn Pro
65                  70                  75                  80

Asp Ala Val Ala Ala Pro Tyr Cys Tyr Thr Arg Asp Pro Gly Val Arg
                85                  90                  95

Trp Glu Tyr Cys Asn Leu Thr Gln Cys Ser Asp Ala Glu Gly Thr Ala
            100                 105                 110

Val Ala Pro Pro Thr Val Thr Pro Val Pro Ser Leu Glu Ala Pro Ser
        115                 120                 125

Glu Gln Ala Pro Thr Glu Gln Arg Pro Gly Val Gln Glu Cys Tyr His
        130                 135                 140

Gly Asn Gly Gln Ser Tyr Arg Gly Thr Tyr Ser Thr Thr Val Thr Gly
145                 150                 155                 160

Arg Thr Cys Gln Ala Trp Ser Ser Met Thr Pro His Ser His Ser Arg
            165                 170                 175

Thr Pro Glu Tyr Tyr Pro Asn Ala Gly Leu Ile Met Asn Tyr Cys Arg
            180                 185                 190

Asn Pro Asp Ala Val Ala Ala Pro Tyr Cys Tyr Thr Arg Asp Pro Gly
        195                 200                 205

Val Arg Trp Glu Tyr Cys Asn Leu Thr Gln Cys Ser Asp Ala Glu Gly
    210                 215                 220

Thr Ala Val Ala Pro Pro Thr Val Thr Pro Val Pro Ser Leu Glu Ala
225                 230                 235                 240
```

-continued

Pro Ser Glu Gln Ala Pro Thr Glu Gln Arg Pro Gly Val Gln Glu Cys
            245                 250                 255

Tyr His Gly Asn Gly Gln Ser Tyr Arg Gly Thr Tyr Ser Thr Thr Val
            260                 265                 270

Thr Gly Arg Thr Cys Gln Ala Trp Ser Ser Met Thr Pro His Ser His
            275                 280                 285

Ser Arg Thr Pro Glu Tyr Tyr Pro Asn Ala Gly Leu Ile Met Asn Tyr
        290                 295                 300

Cys Arg Asn Pro Asp Ala Val Ala Ala Pro Tyr Cys Tyr Thr Arg Asp
    305                 310                 315                 320

Pro Gly Val Arg Trp Glu Tyr Cys Asn Leu Thr Gln Cys Ser Asp Ala
            325                 330                 335

Glu Gly Thr Ala Val Ala Pro Pro Thr Val Thr Pro Val Pro Ser Leu
            340                 345                 350

Glu Ala Pro Ser Glu Gln Ala Pro Thr Glu Gln Arg Pro Gly Val Gln
            355                 360                 365

Glu Cys Tyr His Gly Asn Gly Gln Ser Tyr Arg Gly Thr Tyr Ser Thr
        370                 375                 380

Thr Val Thr Gly Arg Thr Cys Gln Ala Trp Ser Ser Met Thr Pro His
    385                 390                 395                 400

Ser His Ser Arg Thr Pro Glu Tyr Tyr Pro Asn Ala Gly Leu Ile Met
            405                 410                 415

Asn Tyr Cys Arg Asn Pro Asp Ala Val Ala Ala Pro Tyr Cys Tyr Thr
            420                 425                 430

Arg Asp Pro Gly Val Arg Trp Glu Tyr Cys Asn Leu Thr Gln Cys Ser
            435                 440                 445

Asp Ala Glu Gly Thr Ala Val Ala Pro Pro Thr Val Thr Pro Val Pro
        450                 455                 460

Ser Leu Glu Ala Pro Ser Glu Gln Ala Pro Thr Glu Gln Arg Pro Gly
    465                 470                 475                 480

Val Gln Glu Cys Tyr His Gly Asn Gly Gln Ser Tyr Arg Gly Thr Tyr
            485                 490                 495

Ser Thr Thr Val Thr Gly Arg Thr Cys Gln Ala Trp Ser Ser Met Thr
            500                 505                 510

Pro His Ser His Ser Arg Thr Pro Glu Tyr Tyr Pro Asn Ala Gly Leu
            515                 520                 525

Ile Met Asn Tyr Cys Arg Asn Pro Asp Ala Val Ala Ala Pro Tyr Cys
        530                 535                 540

Tyr Thr Arg Asp Pro Gly Val Arg Trp Glu Tyr Cys Asn Leu Thr Gln
    545                 550                 555                 560

Cys Ser Asp Ala Glu Gly Thr Ala Val Ala Pro Pro Thr Val Thr Pro
            565                 570                 575

Val Pro Ser Leu Glu Ala Pro Ser Glu Gln Ala Pro Thr Glu Gln Arg
            580                 585                 590

Pro Gly Val Gln Glu Cys Tyr His Gly Asn Gly Gln Ser Tyr Arg Gly
            595                 600                 605

Thr Tyr Ser Thr Thr Val Thr Gly Arg Thr Cys Gln Ala Trp Ser Ser
            610                 615                 620

Met Thr Pro His Ser His Ser Arg Thr Pro Glu Tyr Tyr Pro Asn Ala
    625                 630                 635                 640

Gly Leu Ile Met Asn Tyr Cys Arg Asn Pro Asp Ala Val Ala Ala Pro
            645                 650                 655

Tyr Cys Tyr Thr Arg Asp Pro Gly Val Arg Trp Glu Tyr Cys Asn Leu

-continued

```
                660                   665                   670

Thr Gln Cys Ser Asp Ala Glu Gly Thr Ala Val Ala Pro Pro Thr Val
        675                   680                   685

Thr Pro Val Pro Ser Leu Glu Ala Pro Ser Glu Gln Ala Pro Thr Glu
        690                   695                   700

Gln Arg Pro Gly Val Gln Glu Cys Tyr His Gly Asn Gly Gln Ser Tyr
705                   710                   715                   720

Arg Gly Thr Tyr Ser Thr Thr Val Thr Gly Arg Thr Cys Gln Ala Trp
                725                   730                   735

Ser Ser Met Thr Pro His Ser His Ser Arg Thr Pro Glu Tyr Tyr Pro
                740                   745                   750

Asn Ala Gly Leu Ile Met Asn Tyr Cys Arg Asn Pro Asp Ala Val Ala
                755                   760                   765

Ala Pro Tyr Cys Tyr Thr Arg Asp Pro Gly Val Arg Trp Glu Tyr Cys
        770                   775                   780

Asn Leu Thr Gln Cys Ser Asp Ala Glu Gly Thr Ala Val Ala Pro Pro
785                   790                   795                   800

Thr Val Thr Pro Val Pro Ser Leu Glu Ala Pro Ser Glu Gln Ala Pro
                805                   810                   815

Thr Glu Gln Arg Pro Gly Val Gln Glu Cys Tyr His Gly Asn Gly Gln
                820                   825                   830

Ser Tyr Arg Gly Thr Tyr Ser Thr Thr Val Thr Gly Arg Thr Cys Gln
                835                   840                   845

Ala Trp Ser Ser Met Thr Pro His Ser His Ser Arg Thr Pro Glu Tyr
        850                   855                   860

Tyr Pro Asn Ala Gly Leu Ile Met Asn Tyr Cys Arg Asn Pro Asp Ala
865                   870                   875                   880

Val Ala Ala Pro Tyr Cys Tyr Thr Arg Asp Pro Gly Val Arg Trp Glu
                885                   890                   895

Tyr Cys Asn Leu Thr Gln Cys Ser Asp Ala Glu Gly Thr Ala Val Ala
                900                   905                   910

Pro Pro Thr Val Thr Pro Val Pro Ser Leu Glu Ala Pro Ser Glu Gln
                915                   920                   925

Ala Pro Thr Glu Gln Arg Pro Gly Val Gln Glu Cys Tyr His Gly Asn
        930                   935                   940

Gly Gln Ser Tyr Arg Gly Thr Tyr Ser Thr Thr Val Thr Gly Arg Thr
945                   950                   955                   960

Cys Gln Ala Trp Ser Ser Met Thr Pro His Ser His Ser Arg Thr Pro
                965                   970                   975

Glu Tyr Tyr Pro Asn Ala Gly Leu Ile Met Asn Tyr Cys Arg Asn Pro
                980                   985                   990

Asp Ala Val Ala Ala Pro Tyr Cys  Tyr Thr Arg Asp Pro  Gly Val Arg
        995                   1000                  1005

Trp Glu  Tyr Cys Asn Leu Thr  Gln Cys Ser Asp Ala  Glu Gly Thr
        1010                  1015                  1020

Ala Val  Ala Pro Pro Thr Val  Thr Pro Val Pro Ser  Leu Glu Ala
        1025                  1030                  1035

Pro Ser  Glu Gln Ala Pro Thr  Glu Gln Arg Pro Gly  Val Gln Glu
        1040                  1045                  1050

Cys Tyr  His Gly Asn Gly Gln  Ser Tyr Arg Gly Thr  Tyr Ser Thr
        1055                  1060                  1065

Thr Val  Thr Gly Arg Thr Cys  Gln Ala Trp Ser Ser  Met Thr Pro
        1070                  1075                  1080
```

-continued

```
His Ser  His Ser Arg Thr Pro  Glu Tyr Tyr Pro Asn  Ala Gly Leu
    1085                1090                1095

Ile Met  Asn Tyr Cys Arg Asn  Pro Asp Ala Val Ala  Ala Pro Tyr
    1100                1105                1110

Cys Tyr  Thr Arg Asp Pro Gly  Val Arg Trp Glu Tyr  Cys Asn Leu
    1115                1120                1125

Thr Gln  Cys Ser Asp Ala Glu  Gly Thr Ala Val Ala  Pro Pro Thr
    1130                1135                1140

Val Thr  Pro Val Pro Ser Leu  Glu Ala Pro Ser Glu  Gln Ala Pro
    1145                1150                1155

Thr Glu  Gln Arg Pro Gly Val  Gln Glu Cys Tyr His  Gly Asn Gly
    1160                1165                1170

Gln Ser  Tyr Arg Gly Thr Tyr  Ser Thr Thr Val Thr  Gly Arg Thr
    1175                1180                1185

Cys Gln  Ala Trp Ser Ser Met  Thr Pro His Ser His  Ser Arg Thr
    1190                1195                1200

Pro Glu  Tyr Tyr Pro Asn Ala  Gly Leu Ile Met Asn  Tyr Cys Arg
    1205                1210                1215

Asn Pro  Asp Ala Val Ala Ala  Pro Tyr Cys Tyr Thr  Arg Asp Pro
    1220                1225                1230

Gly Val  Arg Trp Glu Tyr Cys  Asn Leu Thr Gln Cys  Ser Asp Ala
    1235                1240                1245

Glu Gly  Thr Ala Val Ala Pro  Pro Thr Val Thr Pro  Val Pro Ser
    1250                1255                1260

Leu Glu  Ala Pro Ser Glu Gln  Ala Pro Thr Glu Gln  Arg Pro Gly
    1265                1270                1275

Val Gln  Glu Cys Tyr His Gly  Asn Gly Gln Ser Tyr  Arg Gly Thr
    1280                1285                1290

Tyr Ser  Thr Thr Val Thr Gly  Arg Thr Cys Gln Ala  Trp Ser Ser
    1295                1300                1305

Met Thr  Pro His Ser His Ser  Arg Thr Pro Glu Tyr  Tyr Pro Asn
    1310                1315                1320

Ala Gly  Leu Ile Met Asn Tyr  Cys Arg Asn Pro Asp  Ala Val Ala
    1325                1330                1335

Ala Pro  Tyr Cys Tyr Thr Arg  Asp Pro Gly Val Arg  Trp Glu Tyr
    1340                1345                1350

Cys Asn  Leu Thr Gln Cys Ser  Asp Ala Glu Gly Thr  Ala Val Ala
    1355                1360                1365

Pro Pro  Thr Val Thr Pro Val  Pro Ser Leu Glu Ala  Pro Ser Glu
    1370                1375                1380

Gln Ala  Pro Thr Glu Gln Arg  Pro Gly Val Gln Glu  Cys Tyr His
    1385                1390                1395

Gly Asn  Gly Gln Ser Tyr Arg  Gly Thr Tyr Ser Thr  Thr Val Thr
    1400                1405                1410

Gly Arg  Thr Cys Gln Ala Trp  Ser Ser Met Thr Pro  His Ser His
    1415                1420                1425

Ser Arg  Thr Pro Glu Tyr Tyr  Pro Asn Ala Gly Leu  Ile Met Asn
    1430                1435                1440

Tyr Cys  Arg Asn Pro Asp Ala  Val Ala Ala Pro Tyr  Cys Tyr Thr
    1445                1450                1455

Arg Asp  Pro Gly Val Arg Trp  Glu Tyr Cys Asn Leu  Thr Gln Cys
    1460                1465                1470
```

-continued

```
Ser Asp Ala Glu Gly Thr Ala  Val Ala Pro Pro  Thr Val Thr Pro
    1475             1480                1485

Val Pro  Ser Leu Glu Ala Pro  Ser Glu Gln Ala Pro   Thr Glu Gln
    1490             1495                1500

Arg Pro  Gly Val Gln Glu Cys  Tyr His Gly Asn Gly   Gln Ser Tyr
    1505             1510                1515

Arg Gly  Thr Tyr Ser Thr Thr  Val Thr Gly Arg Thr   Cys Gln Ala
    1520             1525                1530

Trp Ser  Ser Met Thr Pro His  Ser His Ser Arg Thr   Pro Glu Tyr
    1535             1540                1545

Tyr Pro  Asn Ala Gly Leu Ile  Met Asn Tyr Cys Arg   Asn Pro Asp
    1550             1555                1560

Ala Val  Ala Ala Pro Tyr Cys  Tyr Thr Arg Asp Pro   Gly Val Arg
    1565             1570                1575

Trp Glu  Tyr Cys Asn Leu Thr  Gln Cys Ser Asp Ala   Glu Gly Thr
    1580             1585                1590

Ala Val  Ala Pro Pro Thr Val  Thr Pro Val Pro Ser   Leu Glu Ala
    1595             1600                1605

Pro Ser  Glu Gln Ala Pro Thr  Glu Gln Arg Pro Gly   Val Gln Glu
    1610             1615                1620

Cys Tyr  His Gly Asn Gly Gln  Ser Tyr Arg Gly Thr   Tyr Ser Thr
    1625             1630                1635

Thr Val  Thr Gly Arg Thr Cys  Gln Ala Trp Ser Ser   Met Thr Pro
    1640             1645                1650

His Ser  His Ser Arg Thr Pro  Glu Tyr Tyr Pro Asn   Ala Gly Leu
    1655             1660                1665

Ile Met  Asn Tyr Cys Arg Asn  Pro Asp Ala Val Ala   Ala Pro Tyr
    1670             1675                1680

Cys Tyr  Thr Arg Asp Pro Gly  Val Arg Trp Glu Tyr   Cys Asn Leu
    1685             1690                1695

Thr Gln  Cys Ser Asp Ala Glu  Gly Thr Ala Val Ala   Pro Pro Thr
    1700             1705                1710

Val Thr  Pro Val Pro Ser Leu  Glu Ala Pro Ser Glu   Gln Ala Pro
    1715             1720                1725

Thr Glu  Gln Arg Pro Gly Val  Gln Glu Cys Tyr His   Gly Asn Gly
    1730             1735                1740

Gln Ser  Tyr Arg Gly Thr Tyr  Ser Thr Thr Val Thr   Gly Arg Thr
    1745             1750                1755

Cys Gln  Ala Trp Ser Ser Met  Thr Pro His Ser His   Ser Arg Thr
    1760             1765                1770

Pro Glu  Tyr Tyr Pro Asn Ala  Gly Leu Ile Met Asn   Tyr Cys Arg
    1775             1780                1785

Asn Pro  Asp Ala Val Ala Ala  Pro Tyr Cys Tyr Thr   Arg Asp Pro
    1790             1795                1800

Gly Val  Arg Trp Glu Tyr Cys  Asn Leu Thr Gln Cys   Ser Asp Ala
    1805             1810                1815

Glu Gly  Thr Ala Val Ala Pro  Pro Thr Val Thr Pro   Val Pro Ser
    1820             1825                1830

Leu Glu  Ala Pro Ser Glu Gln  Ala Pro Thr Glu Gln   Arg Pro Gly
    1835             1840                1845

Val Gln  Glu Cys Tyr His Gly  Asn Gly Gln Ser Tyr   Arg Gly Thr
    1850             1855                1860

Tyr Ser  Thr Thr Val Thr Gly  Arg Thr Cys Gln Ala   Trp Ser Ser
```

-continued

```
                 1865                   1870                   1875

Met Thr  Pro His Ser His  Ser Arg Thr Pro Glu  Tyr Tyr Pro Asn
         1880                   1885                   1890

Ala Gly  Leu Ile Met Asn  Tyr Cys Arg Asn Pro  Asp Ala Val Ala
         1895                   1900                   1905

Ala Pro  Tyr Cys Tyr Thr  Arg Asp Pro Gly Val  Arg Trp Glu Tyr
         1910                   1915                   1920

Cys Asn  Leu Thr Gln Cys  Ser Asp Ala Glu Gly  Thr Ala Val Ala
         1925                   1930                   1935

Pro Pro  Thr Val Thr Pro  Val Pro Ser Leu Glu  Ala Pro Ser Glu
         1940                   1945                   1950

Gln Ala  Pro Thr Glu Gln  Arg Pro Gly Val Gln  Glu Cys Tyr His
         1955                   1960                   1965

Gly Asn  Gly Gln Ser Tyr  Arg Gly Thr Tyr Ser  Thr Thr Val Thr
         1970                   1975                   1980

Gly Arg  Thr Cys Gln Ala  Trp Ser Ser Met Thr  Pro His Ser His
         1985                   1990                   1995

Ser Arg  Thr Pro Glu Tyr  Tyr Pro Asn Ala Gly  Leu Ile Met Asn
         2000                   2005                   2010

Tyr Cys  Arg Asn Pro Asp  Ala Val Ala Ala Pro  Tyr Cys Tyr Thr
         2015                   2020                   2025

Arg Asp  Pro Gly Val Arg  Trp Glu Tyr Cys Asn  Leu Thr Gln Cys
         2030                   2035                   2040

Ser Asp  Ala Glu Gly Thr  Ala Val Ala Pro Pro  Thr Val Thr Pro
         2045                   2050                   2055

Val Pro  Ser Leu Glu Ala  Pro Ser Glu Gln Ala  Pro Thr Glu Gln
         2060                   2065                   2070

Arg Pro  Gly Val Gln Glu  Cys Tyr His Gly Asn  Gly Gln Ser Tyr
         2075                   2080                   2085

Arg Gly  Thr Tyr Ser Thr  Thr Val Thr Gly Arg  Thr Cys Gln Ala
         2090                   2095                   2100

Trp Ser  Ser Met Thr Pro  His Ser His Ser Arg  Thr Pro Glu Tyr
         2105                   2110                   2115

Tyr Pro  Asn Ala Gly Leu  Ile Met Asn Tyr Cys  Arg Asn Pro Asp
         2120                   2125                   2130

Ala Val  Ala Ala Pro Tyr  Cys Tyr Thr Arg Asp  Pro Gly Val Arg
         2135                   2140                   2145

Trp Glu  Tyr Cys Asn Leu  Thr Gln Cys Ser Asp  Ala Glu Gly Thr
         2150                   2155                   2160

Ala Val  Ala Pro Pro Thr  Val Thr Pro Val Pro  Ser Leu Glu Ala
         2165                   2170                   2175

Pro Ser  Glu Gln Ala Pro  Thr Glu Gln Arg Pro  Gly Val Gln Glu
         2180                   2185                   2190

Cys Tyr  His Gly Asn Gly  Gln Ser Tyr Arg Gly  Thr Tyr Ser Thr
         2195                   2200                   2205

Thr Val  Thr Gly Arg Thr  Cys Gln Ala Trp Ser  Ser Met Thr Pro
         2210                   2215                   2220

His Ser  His Ser Arg Thr  Pro Glu Tyr Tyr Pro  Asn Ala Gly Leu
         2225                   2230                   2235

Ile Met  Asn Tyr Cys Arg  Asn Pro Asp Ala Val  Ala Ala Pro Tyr
         2240                   2245                   2250

Cys Tyr  Thr Arg Asp Pro  Gly Val Arg Trp Glu  Tyr Cys Asn Leu
         2255                   2260                   2265
```

-continued

```
Thr Gln  Cys Ser Asp Ala Glu  Gly Thr Ala Val Ala  Pro Pro Thr
    2270                 2275                 2280

Val Thr  Pro Val Pro Ser Leu  Glu Ala Pro Ser Glu  Gln Ala Pro
    2285                 2290                 2295

Thr Glu  Gln Arg Pro Gly Val  Gln Glu Cys Tyr His  Gly Asn Gly
    2300                 2305                 2310

Gln Ser  Tyr Arg Gly Thr Tyr  Ser Thr Thr Val Thr  Gly Arg Thr
    2315                 2320                 2325

Cys Gln  Ala Trp Ser Ser Met  Thr Pro His Ser His  Ser Arg Thr
    2330                 2335                 2340

Pro Glu  Tyr Tyr Pro Asn Ala  Gly Leu Ile Met Asn  Tyr Cys Arg
    2345                 2350                 2355

Asn Pro  Asp Ala Val Ala Ala  Pro Tyr Cys Tyr Thr  Arg Asp Pro
    2360                 2365                 2370

Gly Val  Arg Trp Glu Tyr Cys  Asn Leu Thr Gln Cys  Ser Asp Ala
    2375                 2380                 2385

Glu Gly  Thr Ala Val Ala Pro  Pro Thr Val Thr Pro  Val Pro Ser
    2390                 2395                 2400

Leu Glu  Ala Pro Ser Glu Gln  Ala Pro Thr Glu Gln  Arg Pro Gly
    2405                 2410                 2415

Val Gln  Glu Cys Tyr His Gly  Asn Gly Gln Ser Tyr  Arg Gly Thr
    2420                 2425                 2430

Tyr Ser  Thr Thr Val Thr Gly  Arg Thr Cys Gln Ala  Trp Ser Ser
    2435                 2440                 2445

Met Thr  Pro His Ser His Ser  Arg Thr Pro Glu Tyr  Tyr Pro Asn
    2450                 2455                 2460

Ala Gly  Leu Ile Met Asn Tyr  Cys Arg Asn Pro Asp  Ala Val Ala
    2465                 2470                 2475

Ala Pro  Tyr Cys Tyr Thr Arg  Asp Pro Gly Val Arg  Trp Glu Tyr
    2480                 2485                 2490

Cys Asn  Leu Thr Gln Cys Ser  Asp Ala Glu Gly Thr  Ala Val Ala
    2495                 2500                 2505

Pro Pro  Thr Val Thr Pro Val  Pro Ser Leu Glu Ala  Pro Ser Glu
    2510                 2515                 2520

Gln Ala  Pro Thr Glu Gln Arg  Pro Gly Val Gln Glu  Cys Tyr His
    2525                 2530                 2535

Gly Asn  Gly Gln Ser Tyr Arg  Gly Thr Tyr Ser Thr  Thr Val Thr
    2540                 2545                 2550

Gly Arg  Thr Cys Gln Ala Trp  Ser Ser Met Thr Pro  His Ser His
    2555                 2560                 2565

Ser Arg  Thr Pro Glu Tyr Tyr  Pro Asn Ala Gly Leu  Ile Met Asn
    2570                 2575                 2580

Tyr Cys  Arg Asn Pro Asp Ala  Val Ala Ala Pro Tyr  Cys Tyr Thr
    2585                 2590                 2595

Arg Asp  Pro Gly Val Arg Trp  Glu Tyr Cys Asn Leu  Thr Gln Cys
    2600                 2605                 2610

Ser Asp  Ala Glu Gly Thr Ala  Val Ala Pro Pro Thr  Val Thr Pro
    2615                 2620                 2625

Val Pro  Ser Leu Glu Ala Pro  Ser Glu Gln Ala Pro  Thr Glu Gln
    2630                 2635                 2640

Arg Pro  Gly Val Gln Glu Cys  Tyr His Gly Asn Gly  Gln Ser Tyr
    2645                 2650                 2655
```

-continued

```
Arg Gly Thr Tyr Ser Thr Thr  Val Thr Gly Arg Thr  Cys Gln Ala
    2660                2665            2670

Trp Ser  Ser Met Thr Pro His  Ser His Ser Arg Thr  Pro Glu Tyr
    2675                2680            2685

Tyr Pro  Asn Ala Gly Leu Ile  Met Asn Tyr Cys Arg  Asn Pro Asp
    2690                2695            2700

Ala Val  Ala Ala Pro Tyr Cys  Tyr Thr Arg Asp Pro  Gly Val Arg
    2705                2710            2715

Trp Glu  Tyr Cys Asn Leu Thr  Gln Cys Ser Asp Ala  Glu Gly Thr
    2720                2725            2730

Ala Val  Ala Pro Pro Thr Val  Thr Pro Val Pro Ser  Leu Glu Ala
    2735                2740            2745

Pro Ser  Glu Gln Ala Pro Thr  Glu Gln Arg Pro Gly  Val Gln Glu
    2750                2755            2760

Cys Tyr  His Gly Asn Gly Gln  Ser Tyr Arg Gly Thr  Tyr Ser Thr
    2765                2770            2775

Thr Val  Thr Gly Arg Thr Cys  Gln Ala Trp Ser Ser  Met Thr Pro
    2780                2785            2790

His Ser  His Ser Arg Thr Pro  Glu Tyr Tyr Pro Asn  Ala Gly Leu
    2795                2800            2805

Ile Met  Asn Tyr Cys Arg Asn  Pro Asp Ala Val Ala  Ala Pro Tyr
    2810                2815            2820

Cys Tyr  Thr Arg Asp Pro Gly  Val Arg Trp Glu Tyr  Cys Asn Leu
    2825                2830            2835

Thr Gln  Cys Ser Asp Ala Glu  Gly Thr Ala Val Ala  Pro Pro Thr
    2840                2845            2850

Val Thr  Pro Val Pro Ser Leu  Glu Ala Pro Ser Glu  Gln Ala Pro
    2855                2860            2865

Thr Glu  Gln Arg Pro Gly Val  Gln Glu Cys Tyr His  Gly Asn Gly
    2870                2875            2880

Gln Ser  Tyr Arg Gly Thr Tyr  Ser Thr Thr Val Thr  Gly Arg Thr
    2885                2890            2895

Cys Gln  Ala Trp Ser Ser Met  Thr Pro His Ser His  Ser Arg Thr
    2900                2905            2910

Pro Glu  Tyr Tyr Pro Asn Ala  Gly Leu Ile Met Asn  Tyr Cys Arg
    2915                2920            2925

Asn Pro  Asp Ala Val Ala Ala  Pro Tyr Cys Tyr Thr  Arg Asp Pro
    2930                2935            2940

Gly Val  Arg Trp Glu Tyr Cys  Asn Leu Thr Gln Cys  Ser Asp Ala
    2945                2950            2955

Glu Gly  Thr Ala Val Ala Pro  Pro Thr Val Thr Pro  Val Pro Ser
    2960                2965            2970

Leu Glu  Ala Pro Ser Glu Gln  Ala Pro Thr Glu Gln  Arg Pro Gly
    2975                2980            2985

Val Gln  Glu Cys Tyr His Gly  Asn Gly Gln Ser Tyr  Arg Gly Thr
    2990                2995            3000

Tyr Ser  Thr Thr Val Thr Gly  Arg Thr Cys Gln Ala  Trp Ser Ser
    3005                3010            3015

Met Thr  Pro His Ser His Ser  Arg Thr Pro Glu Tyr  Tyr Pro Asn
    3020                3025            3030

Ala Gly  Leu Ile Met Asn Tyr  Cys Arg Asn Pro Asp  Ala Val Ala
    3035                3040            3045

Ala Pro  Tyr Cys Tyr Thr Arg  Asp Pro Gly Val Arg  Trp Glu Tyr
```

-continued

```
        3050              3055              3060

Cys Asn Leu Thr Gln Cys Ser  Asp Ala Glu Gly Thr  Ala Val Ala
    3065              3070              3075

Pro Pro  Thr Val Thr Pro Val  Pro Ser Leu Glu Ala  Pro Ser Glu
    3080              3085              3090

Gln Ala  Pro Thr Glu Gln Arg  Pro Gly Val Gln Glu  Cys Tyr His
    3095              3100              3105

Gly Asn  Gly Gln Ser Tyr Arg  Gly Thr Tyr Ser Thr  Thr Val Thr
    3110              3115              3120

Gly Arg  Thr Cys Gln Ala Trp  Ser Ser Met Thr Pro  His Ser His
    3125              3130              3135

Ser Arg  Thr Pro Glu Tyr Tyr  Pro Asn Ala Gly Leu  Ile Met Asn
    3140              3145              3150

Tyr Cys  Arg Asn Pro Asp Ala  Val Ala Ala Pro Tyr  Cys Tyr Thr
    3155              3160              3165

Arg Asp  Pro Gly Val Arg Trp  Glu Tyr Cys Asn Leu  Thr Gln Cys
    3170              3175              3180

Ser Asp  Ala Glu Gly Thr Ala  Val Ala Pro Pro Thr  Val Thr Pro
    3185              3190              3195

Val Pro  Ser Leu Glu Ala Pro  Ser Glu Gln Ala Pro  Thr Glu Gln
    3200              3205              3210

Arg Pro  Gly Val Gln Glu Cys  Tyr His Gly Asn Gly  Gln Ser Tyr
    3215              3220              3225

Arg Gly  Thr Tyr Ser Thr Thr  Val Thr Gly Arg Thr  Cys Gln Ala
    3230              3235              3240

Trp Ser  Ser Met Thr Pro His  Ser His Ser Arg Thr  Pro Glu Tyr
    3245              3250              3255

Tyr Pro  Asn Ala Gly Leu Ile  Met Asn Tyr Cys Arg  Asn Pro Asp
    3260              3265              3270

Ala Val  Ala Ala Pro Tyr Cys  Tyr Thr Arg Asp Pro  Gly Val Arg
    3275              3280              3285

Trp Glu  Tyr Cys Asn Leu Thr  Gln Cys Ser Asp Ala  Glu Gly Thr
    3290              3295              3300

Ala Val  Ala Pro Pro Thr Val  Thr Pro Val Pro Ser  Leu Glu Ala
    3305              3310              3315

Pro Ser  Glu Gln Ala Pro Thr  Glu Gln Arg Pro Gly  Val Gln Glu
    3320              3325              3330

Cys Tyr  His Gly Asn Gly Gln  Ser Tyr Arg Gly Thr  Tyr Ser Thr
    3335              3340              3345

Thr Val  Thr Gly Arg Thr Cys  Gln Ala Trp Ser Ser  Met Thr Pro
    3350              3355              3360

His Ser  His Ser Arg Thr Pro  Glu Tyr Tyr Pro Asn  Ala Gly Leu
    3365              3370              3375

Ile Met  Asn Tyr Cys Arg Asn  Pro Asp Pro Val Ala  Ala Pro Tyr
    3380              3385              3390

Cys Tyr  Thr Arg Asp Pro Ser  Val Arg Trp Glu Tyr  Cys Asn Leu
    3395              3400              3405

Thr Gln  Cys Ser Asp Ala Glu  Gly Thr Ala Val Ala  Pro Pro Thr
    3410              3415              3420

Ile Thr  Pro Ile Pro Ser Leu  Glu Ala Pro Ser Glu  Gln Ala Pro
    3425              3430              3435

Thr Glu  Gln Arg Pro Gly Val  Gln Glu Cys Tyr His  Gly Asn Gly
    3440              3445              3450
```

-continued

```
Gln Ser  Tyr Gln Gly Thr Tyr  Phe Ile Thr Val Thr  Gly Arg Thr
    3455                3460                3465

Cys Gln  Ala Trp Ser Ser Met  Thr Pro His Ser His  Ser Arg Thr
    3470                3475                3480

Pro Ala  Tyr Tyr Pro Asn Ala  Gly Leu Ile Lys Asn  Tyr Cys Arg
    3485                3490                3495

Asn Pro  Asp Pro Val Ala Ala  Pro Trp Cys Tyr Thr  Thr Asp Pro
    3500                3505                3510

Ser Val  Arg Trp Glu Tyr Cys  Asn Leu Thr Arg Cys  Ser Asp Ala
    3515                3520                3525

Glu Trp  Thr Ala Phe Val Pro  Pro Asn Val Ile Leu  Ala Pro Ser
    3530                3535                3540

Leu Glu  Ala Phe Phe Glu Gln  Ala Leu Thr Glu Glu  Thr Pro Gly
    3545                3550                3555

Val Gln  Asp Cys Tyr Tyr His  Tyr Gly Gln Ser Tyr  Arg Gly Thr
    3560                3565                3570

Tyr Ser  Thr Thr Val Thr Gly  Arg Thr Cys Gln Ala  Trp Ser Ser
    3575                3580                3585

Met Thr  Pro His Gln His Ser  Arg Thr Pro Glu Asn  Tyr Pro Asn
    3590                3595                3600

Ala Gly  Leu Thr Arg Asn Tyr  Cys Arg Asn Pro Asp  Ala Glu Ile
    3605                3610                3615

Arg Pro  Trp Cys Tyr Thr Met  Asp Pro Ser Val Arg  Trp Glu Tyr
    3620                3625                3630

Cys Asn  Leu Thr Gln Cys Leu  Val Thr Glu Ser Ser  Val Leu Ala
    3635                3640                3645

Thr Leu  Thr Val Val Pro Asp  Pro Ser Thr Glu Ala  Ser Ser Glu
    3650                3655                3660

Glu Ala  Pro Thr Glu Gln Ser  Pro Gly Val Gln Asp  Cys Tyr His
    3665                3670                3675

Gly Asp  Gly Gln Ser Tyr Arg  Gly Ser Phe Ser Thr  Thr Val Thr
    3680                3685                3690

Gly Arg  Thr Cys Gln Ser Trp  Ser Ser Met Thr Pro  His Trp His
    3695                3700                3705

Gln Arg  Thr Thr Glu Tyr Tyr  Pro Asn Gly Gly Leu  Thr Arg Asn
    3710                3715                3720

Tyr Cys  Arg Asn Pro Asp Ala  Glu Ile Ser Pro Trp  Cys Tyr Thr
    3725                3730                3735

Met Asp  Pro Asn Val Arg Trp  Glu Tyr Cys Asn Leu  Thr Gln Cys
    3740                3745                3750

Pro Val  Thr Glu Ser Ser Val  Leu Ala Thr Ser Thr  Ala Val Ser
    3755                3760                3765

Glu Gln  Ala Pro Thr Glu Gln  Ser Pro Thr Val Gln  Asp Cys Tyr
    3770                3775                3780

His Gly  Asp Gly Gln Ser Tyr  Arg Gly Ser Phe Ser  Thr Thr Val
    3785                3790                3795

Thr Gly  Arg Thr Cys Gln Ser  Trp Ser Ser Met Thr  Pro His Trp
    3800                3805                3810

His Gln  Arg Thr Thr Glu Tyr  Tyr Pro Asn Gly Gly  Leu Thr Arg
    3815                3820                3825

Asn Tyr  Cys Arg Asn Pro Asp  Ala Glu Ile Arg Pro  Trp Cys Tyr
    3830                3835                3840
```

-continued

```
Thr Met  Asp Pro Ser Val Arg  Trp Glu Tyr Cys Asn  Leu Thr Gln
    3845             3850           3855

Cys Pro  Val Met Glu Ser Thr  Leu Leu Thr Thr Pro  Thr Val Val
    3860             3865           3870

Pro Val  Pro Ser Thr Glu Leu  Pro Ser Glu Glu Ala  Pro Thr Glu
    3875             3880           3885

Asn Ser  Thr Gly Val Gln Asp  Cys Tyr Arg Gly Asp  Gly Gln Ser
    3890             3895           3900

Tyr Arg  Gly Thr Leu Ser Thr  Thr Ile Thr Gly Arg  Thr Cys Gln
    3905             3910           3915

Ser Trp  Ser Ser Met Thr Pro  His Trp His Arg Arg  Ile Pro Leu
    3920             3925           3930

Tyr Tyr  Pro Asn Ala Gly Leu  Thr Arg Asn Tyr Cys  Arg Asn Pro
    3935             3940           3945

Asp Ala  Glu Ile Arg Pro Trp  Cys Tyr Thr Met Asp  Pro Ser Val
    3950             3955           3960

Arg Trp  Glu Tyr Cys Asn Leu  Thr Arg Cys Pro Val  Thr Glu Ser
    3965             3970           3975

Ser Val  Leu Thr Thr Pro Thr  Val Ala Pro Val Pro  Ser Thr Glu
    3980             3985           3990

Ala Pro  Ser Glu Gln Ala Pro  Pro Glu Lys Ser Pro  Val Val Gln
    3995             4000           4005

Asp Cys  Tyr His Gly Asp Gly  Arg Ser Tyr Arg Gly  Ile Ser Ser
    4010             4015           4020

Thr Thr  Val Thr Gly Arg Thr  Cys Gln Ser Trp Ser  Ser Met Ile
    4025             4030           4035

Pro His  Trp His Gln Arg Thr  Pro Glu Asn Tyr Pro  Asn Ala Gly
    4040             4045           4050

Leu Thr  Glu Asn Tyr Cys Arg  Asn Pro Asp Ser Gly  Lys Gln Pro
    4055             4060           4065

Trp Cys  Tyr Thr Thr Asp Pro  Cys Val Arg Trp Glu  Tyr Cys Asn
    4070             4075           4080

Leu Thr  Gln Cys Ser Glu Thr  Glu Ser Gly Val Leu  Glu Thr Pro
    4085             4090           4095

Thr Val  Val Pro Val Pro Ser  Met Glu Ala His Ser  Glu Ala Ala
    4100             4105           4110

Pro Thr  Glu Gln Thr Pro Val  Val Arg Gln Cys Tyr  His Gly Asn
    4115             4120           4125

Gly Gln  Ser Tyr Arg Gly Thr  Phe Ser Thr Thr Val  Thr Gly Arg
    4130             4135           4140

Thr Cys  Gln Ser Trp Ser Ser  Met Thr Pro His Arg  His Gln Arg
    4145             4150           4155

Thr Pro  Glu Asn Tyr Pro Asn  Asp Gly Leu Thr Met  Asn Tyr Cys
    4160             4165           4170

Arg Asn  Pro Asp Ala Asp Thr  Gly Pro Trp Cys Phe  Thr Met Asp
    4175             4180           4185

Pro Ser  Ile Arg Trp Glu Tyr  Cys Asn Leu Thr Arg  Cys Ser Asp
    4190             4195           4200

Thr Glu  Gly Thr Val Val Ala  Pro Pro Thr Val Ile  Gln Val Pro
    4205             4210           4215

Ser Leu  Gly Pro Pro Ser Glu  Gln Asp Cys Met Phe  Gly Asn Gly
    4220             4225           4230

Lys Gly  Tyr Arg Gly Lys Lys  Ala Thr Thr Val Thr  Gly Thr Pro
```

-continued

```
    4235              4240              4245

Cys Gln  Glu Trp Ala Ala Gln  Glu Pro His Arg His  Ser Thr Phe
    4250              4255              4260

Ile Pro  Gly Thr Asn Lys Trp  Ala Gly Leu Glu Lys  Asn Tyr Cys
    4265              4270              4275

Arg Asn  Pro Asp Gly Asp Ile  Asn Gly Pro Trp Cys  Tyr Thr Met
    4280              4285              4290

Asn Pro  Arg Lys Leu Phe Asp  Tyr Cys Asp Ile Pro  Leu Cys Ala
    4295              4300              4305

Ser Ser  Ser Phe Asp Cys Gly  Lys Pro Gln Val Glu  Pro Lys Lys
    4310              4315              4320

Cys Pro  Gly Ser Ile Val Gly  Gly Cys Val Ala His  Pro His Ser
    4325              4330              4335

Trp Pro  Trp Gln Val Ser Leu  Arg Thr Arg Phe Gly  Lys His Phe
    4340              4345              4350

Cys Gly  Gly Thr Leu Ile Ser  Pro Glu Trp Val Leu  Thr Ala Ala
    4355              4360              4365

His Cys  Leu Lys Lys Ser Ser  Arg Pro Ser Ser Tyr  Lys Val Ile
    4370              4375              4380

Leu Gly  Ala His Gln Glu Val  Asn Leu Glu Ser His  Val Gln Glu
    4385              4390              4395

Ile Glu  Val Ser Arg Leu Phe  Leu Glu Pro Thr Gln  Ala Asp Ile
    4400              4405              4410

Ala Leu  Leu Lys Leu Ser Arg  Pro Ala Val Ile Thr  Asp Lys Val
    4415              4420              4425

Met Pro  Ala Cys Leu Pro Ser  Pro Asp Tyr Met Val  Thr Ala Arg
    4430              4435              4440

Thr Glu  Cys Tyr Ile Thr Gly  Trp Gly Glu Thr Gln  Gly Thr Phe
    4445              4450              4455

Gly Thr  Gly Leu Leu Lys Glu  Ala Gln Leu Leu Val  Ile Glu Asn
    4460              4465              4470

Glu Val  Cys Asn His Tyr Lys  Tyr Ile Cys Ala Glu  His Leu Ala
    4475              4480              4485

Arg Gly  Thr Asp Ser Cys Gln  Gly Asp Ser Gly Gly  Pro Leu Val
    4490              4495              4500

Cys Phe  Glu Lys Asp Lys Tyr  Ile Leu Gln Gly Val  Thr Ser Trp
    4505              4510              4515

Gly Leu  Gly Cys Ala Arg Pro  Asn Lys Pro Gly Val  Tyr Ala Arg
    4520              4525              4530

Val Ser  Arg Phe Val Thr Trp  Ile Glu Gly Met Met  Arg Asn Asn
    4535              4540              4545
```

```
<210> SEQ ID NO 111
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111 cttctttta ttgttcctct agttatttcc tccagaattg atcaagacta ttcatcattt      60
gattctctat ctcca                                                      75

<210> SEQ ID NO 112
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
aaaatcaaga taaaaatgtt cac                                            23

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
agctccttct ttttattgtt cct                                            23

<210> SEQ ID NO 114
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
cctccagaat tgatcaagac aat                                            23

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
atcaagacaa ttcatcattt gat                                            23

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
atcatttgat tctctatctc cag                                            23

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gattctctat ctccagagcc aaa                                            23

<210> SEQ ID NO 118
<211> LENGTH: 23
```

<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 118
tctatctcca gagccaaaat caa                                              23

<210> SEQ ID NO 119
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 119
gctatgttag acgatgtaaa aat                                              23

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 120
atgacatatt tcaaaaactc aac                                              23

<210> SEQ ID NO 121
<211> LENGTH: 76
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 121
ttcctccaga attgatcaag acaattcatc atttgattct ctatctccag agccaaaatc     60
aagatttgct atgtta                                                     76

<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 122
gatcagtctt tttatgatct atc                                             23

<210> SEQ ID NO 123
<211> LENGTH: 75
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 123
atcaagacaa ttcatcattt gattctctat ctccagagcc aaaatcaaga tttgctatgt     60
tagacgatgt aaaaa                                                      75

```
<210> SEQ ID NO 124
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (41)..(41)
<223> OTHER INFORMATION: a, c, t, g, unknown or other
<220> FEATURE:
<221> NAME/KEY: modified_base
<222> LOCATION: (45)..(45)
<223> OTHER INFORMATION: a, c, t, g, unknown or other
<220> FEATURE:
<221> NAME/KEY: modified_base
<222> LOCATION: (55)..(55)
<223> OTHER INFORMATION: a, c, t, g, unknown or other
<220> FEATURE:
<221> NAME/KEY: modified_base
<222> LOCATION: (57)..(57)
<223> OTHER INFORMATION: a, c, t, g, unknown or other
<220> FEATURE:
<221> NAME/KEY: modified_base
<222> LOCATION: (74)..(74)
<223> OTHER INFORMATION: a, c, t, g, unknown or other

<400> SEQUENCE: 124
tctacttcaa caaaaagtga aatatttaga agagcaacta nctancttaa ttcanantca        60
acctgaaact ccana                                                         75

<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
aaaatcaacc tgaaactcca gaa                                                23

<210> SEQ ID NO 126
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
ttttatcagc tcagaaggac tagtattcaa gaacccacag aaatttctct atcttccaag        60
ccaagagcac caaga                                                         75

<210> SEQ ID NO 127
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
tcttgatcaa ttctggagga aat                                                23

<210> SEQ ID NO 128
<211> LENGTH: 23
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
atttggccct tcgtcttatg gac                                           23

<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
cactggtttg cagcgataga tca                                           23

<210> SEQ ID NO 130
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ttgacttgta gtttatatgt agt                                           23

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
tttacctctt cattttgac ttg                                            23

<210> SEQ ID NO 132
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
tttcttctag gaggctttca agt                                           23

<210> SEQ ID NO 133
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
cactttttgt tgaagtagaa ttt                                           23

<210> SEQ ID NO 134
<211> LENGTH: 23
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 134
agttagttag ttgctcttct aaa                                              23

<210> SEQ ID NO 135
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
tgaattaagt tagttagttg ctc                                              23

<210> SEQ ID NO 136
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
ttttatcagc tcagaaggac tag                                              23

<210> SEQ ID NO 137
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
tagtattcaa gaacccacag aaatttctct atcttccaag ccaagagcac caagaactac     60
tccctttctt cagtt                                                       75

<210> SEQ ID NO 138
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
ctctatcttc caagccaaga gca                                              23

<210> SEQ ID NO 139
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ctgtgggttc ttgaatacta gtc                                              23

<210> SEQ ID NO 140
<211> LENGTH: 23

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
aactgaagaa agggagtagt tct                                          23

<210> SEQ ID NO 141
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
cattcaactg aagaaaggga gta                                          23

<210> SEQ ID NO 142
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
cttatttcat tcaactgaag aaa                                          23

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
ttatcttgat tttcaatttc aag                                          23

<210> SEQ ID NO 144
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
ccgtggaaga ccaatataaa caattaaacc aacagcatag tcaaataaaa gaaatagaaa     60
atcaggtaag tcagt                                                   75

<210> SEQ ID NO 145
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
tctatttctt ttatttgact atg                                          23

<210> SEQ ID NO 146
```

-continued

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
gactatgctg ttggtttaat tgt                                                  23

<210> SEQ ID NO 147
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
tttatattgg tcttccacgg tct                                                  23

<210> SEQ ID NO 148
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
gtcttccacg gtctggagaa ggt                                                  23

<210> SEQ ID NO 149
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
tcttgttttt ctacaaaagt ctg                                                  23

<210> SEQ ID NO 150
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
tattgattct aggcattcct gct                                                  23

<210> SEQ ID NO 151
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
taggcattcc tgctgaatgt acc                                                  23

<210> SEQ ID NO 152
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ctgctgaatg taccaccatt tat                                           23

<210> SEQ ID NO 153
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
ataacagagg tgaacataca agt                                           23

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
agcaggaatg cctagaatca ata                                           23

<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
cattcattat attcaggtag tcc                                           23

<210> SEQ ID NO 156
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
attatattca ggtagtccat gga                                           23

<210> SEQ ID NO 157
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
tattcaggta gtccatggac att                                           23

<210> SEQ ID NO 158
<211> LENGTH: 74
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 158
aatacatgat ttcattcatt atattcaggt agtccatgga cattaattca acatcgaata        60
gatggatcac aaaa                                                          74

<210> SEQ ID NO 159
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
attcaacatc gaatagatgg atc                                                23

<210> SEQ ID NO 160
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
aacatcgaat agatggatca caa                                                23

<210> SEQ ID NO 161
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
aatgtagtcc ccttaccatc aag                                                23

<210> SEQ ID NO 162
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
gtagttctcc cacgtttcat tga                                                23

<210> SEQ ID NO 163
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
aagttttgtg atccatctat tcg                                                23

<210> SEQ ID NO 164
<211> LENGTH: 23
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
gatgttgaat taatgtccat gga                                            23

<210> SEQ ID NO 165
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
atgtccatgg actacctgaa tat                                            23

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
agttggaaga ctggaaagac aac                                            23

<210> SEQ ID NO 167
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tattgaatat tctttttact tgg                                            23

<210> SEQ ID NO 168
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
aatattcttt ttacttggga aat                                            23

<210> SEQ ID NO 169
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
tttttacttg ggaaatcacg aaa                                            23

<210> SEQ ID NO 170
<211> LENGTH: 76
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 170
tatacgctac atctagttgc gattactggc aatgtcccca atgcaatccc ggaaaacaaa      60
gatttggtgt tttcta                                                     76

<210> SEQ ID NO 171
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
accaactata cgctacatct agttgcgatt actggcaatg tccccaatgc aatcccggaa      60
aacaaagatt tggtg                                                      75

<210> SEQ ID NO 172
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gggacattgc cagtaatcgc aac                                             23

<210> SEQ ID NO 173
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
ccagtaatcg caactagatg tag                                             23

<210> SEQ ID NO 174
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gattactggc aatgtcccca atg                                             23

<210> SEQ ID NO 175
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
gaagactgga aagacaacaa acattatatt gaatattctt tttacttggg aaatcacaaa      60
accaactata cgcta                                                      75

-continued

```
<210> SEQ ID NO 176
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
gtaaaacata attagattgc ttc                                          23

<210> SEQ ID NO 177
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gattgcttca ctatggagta tat                                          23

<210> SEQ ID NO 178
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
cttcactatg gagtatatct tct                                          23

<210> SEQ ID NO 179
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
tcttggaagt ctcaaaatgg aag                                          23

<210> SEQ ID NO 180
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
gcctcagttc attcaaagct ttc                                          23

<210> SEQ ID NO 181
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
tgagacttcc aagataatcc tct                                          23
```

-continued

<210> SEQ ID NO 182
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
accatttagg ttgttttctc cac                                        23

<210> SEQ ID NO 183
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
attgttcctc tagttatttc ctc                                        23

<210> SEQ ID NO 184
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
ttgttcctct agttatttcc tcc                                        23

<210> SEQ ID NO 185
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
tccataagac gaagggccaa att                                        23

<210> SEQ ID NO 186
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
tatgatctat cgctgcaaac cag                                        23

<210> SEQ ID NO 187
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
atgatctatc gctgcaaacc agt                                        23

-continued

```
<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
attgaatatt ctttttactt ggg                                             23

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
gagttgagtt caagtgacat att                                             23

<210> SEQ ID NO 190
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
ttacgaattg agttggaaga ctggaaagac aacaaacatt atattgaata ttcttttttac   60 ttgggaaatc acgaa                                                      75

<210> SEQ ID NO 191
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
ggaaagacaa caaacattat att                                             23

<210> SEQ ID NO 192
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
aaatgttgat ccatccaaca gattcagaaa gctttgaatg aactgaggca aatttaaaag    60
gcaataattt aaaca                                                      75

<210> SEQ ID NO 193
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
```

-continued gaaagctttg aatgaactga ggc                                                                    23

<210> SEQ ID NO 194
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
tacttcaaca aaaagtgaaa tatttagaag agcaactaac taacttaatt caaaatcaac        60
ctgaaactcc agaac                                                          75

<210> SEQ ID NO 195
<211> LENGTH: 99
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (80)..(99)
<223> OTHER INFORMATION: a, c, u, g, unknown or other

<400> SEQUENCE: 195
ggucuagagg acagaauuca acgggugugc uaauggccac uuuccaggug gcaaagcccg        60
uugagcuucg aaguggcacn nnnnnnnnnn nnnnnnnnn                                99

<210> SEQ ID NO 196
<211> LENGTH: 116
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (97)..(116)
<223> OTHER INFORMATION: a, c, u, g, unknown or other

<400> SEQUENCE: 196
ggcgagguuc ugucuuuugg ucaggacaac cgucuagcua uaagugcugc aggggugaga        60
aacuccuagc uggacgaugu cucgaggcau uagcacnnnn nnnnnnnnnn nnnnn            116

CHEMICALLY MODIFIED GUIDE RNAs FOR GENOME EDITING WITH Cas12b

CROSS REFERENCE TO RELATED APPLICATIONS

This application claims benefit under 35 U.S.C. § 119 from Provisional Application Ser. No. 63/007,814, filed Apr. 9, 2020, the disclosures of which are incorporated herein by reference in their entirety.

SEQUENCE LISTING

The instant application contains a Sequence Listing which has been submitted electronically in XML file format and is hereby incorporated by reference in its entirety. Said XML copy, created on Dec. 9, 2022, is named 53989-709_831_SL.xml and is 6,524,890 bytes in size.

FIELD OF DISCLOSURE

Described herein are compositions related to chemically modified guide polynucleotides (e.g., guide RNAs, single guide RNAs, crRNAs, tracrRNAs, etc.) including compositions that comprise such guide polynucleotides. Also described herein are methods of using guide polynucleotides in gene modification of a target gene and methods of treating a disease or a condition.

BACKGROUND

All publications herein are incorporated by reference to the same extent as if each individual publication or patent application was specifically and individually indicated to be incorporated by reference. The following description includes information that may be useful in understanding the present disclosure. It is not an admission that any of the information provided herein is prior art or relevant to the presently claimed invention, or that any publication specifically or implicitly referenced is prior art. In the event of inconsistent usages between this document and those documents incorporated by reference, the usage in the incorporated reference(s) should be considered supplementary to that of this document; for any irreconcilable inconsistencies, the usage in this document controls.

SUMMARY OF THE DISCLOSURE

In one aspect, provided herein is a single guide RNA that comprises (i) a spacer sequence and (ii) a scaffold or tracr sequence, wherein the spacer sequence is designed to be complementary to a target polynucleotide sequence in a gene of interest when in close proximity to the target complementary polynucleotide, wherein the scaffold sequence is a substrate for a Cas12b protein to facilitate the formation of Cas12b protein-guide RNA complex, the ribonucleoprotein (RNP) complex, and wherein the single guide RNA comprises one or more chemical modification(s). In some embodiments, the scaffold sequence is of about 97 nucleotides long and constitutes or encompasses the 5'-end of the single guide RNA, and the spacer sequence, is about 20 to 40 nucleotides long, which constitutes or encompasses the 3'-end of the single guide RNA. In one aspect of the invention, the guide RNA Ca12b protein complex exerts modifications to the gene of interest to modulate the encoded protein production or to modify functional property of the protein. In one aspect the gene of interest is PCSK9 and in another aspect the target gene of interest is ANGPTL3.

In some embodiments, the chemical modification is in the spacer sequence. In some embodiments, the chemical modification is in the scaffold or tracr sequence. In some embodiments, the chemical modification is in a stem loop structure of the scaffold sequence. In yet other aspects, the target gene of interest may be selected from a group of genes that are capable of being modified by a Cas12b nuclease combined with a chemically modified gRNA scaffold as described herein and a spacer sequence that is complementary to DNA sequence of a target gene of interest, including, but not limited to, for example the gene sequences disclosed herein for PCSK9, APOC3, ANGPTL3 and/or Lp(a).

In some embodiments, the single guide RNA comprises an unmodified nucleotide. In some embodiments, the unmodified nucleotide comprises a 2'-hydroxyl that, when the guide RNA in close proximity to the Cas12b protein facilitates the interaction between the guide RNA and Cas12b protein. In some embodiments, the unmodified nucleotide comprises a 2'-hydroxyl that is in contact with the Cas12b protein when contacted with the Cas12b protein. In some embodiments, the unmodified nucleotide comprises a 2'-hydroxyl that is in close proximity with a second unmodified nucleotide of the single guide RNA. In some embodiments, the second unmodified nucleotide is at the 5'-end of the first unmodified nucleotide and in some embodiments the second unmodified nucleotide is at the 3'-end of the first unmodified nucleotide. In some embodiments, the unmodified nucleotide comprises a 2'-hydroxyl that is in close proximity with one or more modified nucleotide(s). In the embodiment the modified nucleotide is at the 5'-end and/or at the 3'-end of the first unmodified nucleotide.

In some embodiments, the unmodified nucleotide is at a nucleotide position selected from positions 8-10, 12-15, 22-24, 32-38, 40, 41, 43, 44, 53-56, 63, 66-69, 88-97, 99-103, 106-108, 111-116 as numbered in SEQ ID NO: 1 or a corresponding position thereof. In some embodiments, the chemical modification is at a nucleotide position selected from positions 1-7, 11, 16-21, 25-31, 39, 42, 45-52, 57-62, 64, 65, 70-87, 98, 104, 105, 109, and 110 as numbered in SEQ ID NO: 1 or a corresponding position thereof.

In some embodiments, the chemical modification(s) comprise(s) one or more 2'-OMe sugar modification(s). In some embodiments, the chemical modification comprises one or more nebularin, deoxynebularin or 2'-O-methylnebularine a combination thereof. In some embodiments, the nebularine, the 2'-O-methylnebularine, or the 2'-deoxynebularine replaces an adenosine in the single guide RNA as compared to an otherwise unmodified guide RNA. In some embodiments, the nebularine, the 2'-O-methylnebularine, or the 2'-deoxynebularine replaces a guanosine in the single guide RNA as compared to an otherwise unmodified guide RNA. In some embodiments, the nebularine, the 2'-O-methylnebularine, or the 2'-deoxynebularine replaces a chemically modified or unmodified adenosine in the chemically modified single guide RNA. In some embodiments, the nebularine, the 2'-O-methylnebularine, or the 2'-deoxynebularine replaces a chemically modified or unmodified adenosine guanosine in the chemically modified single guide RNA.

In some embodiments, the chemical modification(s) comprise(s) one or more phosphorothioate linkage(s). In some embodiments, the chemically modified single guide RNA comprises a phosphorothioate linkage at a 5' end or at a 3' end. In some embodiments, the chemically modified single guide RNA comprises two and no more than two phosphorothioate linkages at the 5' end. In some embodiments, the single guide RNA comprises two and no more than two contiguous phosphorothioate linkages at the 3' end. In some embodiments, the single guide RNA comprises three phosphorothioate linkages at the 3' end. In some embodiments, the single guide RNA comprises three phosphorothioate linkages at the 5' end.

In some embodiments, the chemically modified single guide RNA comprises the sequence 5'-NsNsN-3', 5'-NsNsNsS-3', 5'-nsnsnsn-3', or 5'-nsnsn-3' at the 3' end, wherein, each uppercase N independently indicates unmodified nucleotide adenosine, cytidine, guanosine and/or uridine; and lowercase letters indicates modified nucleotides including but not limited to 2'-H, 2'-OMe and base modification; and each s independently indicates phosphorothioate backbone modification. In some embodiments, each one of the last four nucleotides at the 3'end of the single guide RNA comprises a 2'-OMe modification.

In some embodiments, the chemically modified single guide RNA comprises the sequence 5'-UsUsU-3', 5'-UsUsUsU-3', 5'-ususus-3', or 5'-ususu-3' at the 3' end. In some embodiments, each one of the last four nucleotides at the 3'end of the single guide RNA comprises a 2'-OMe modification.

In some embodiments, the target polynucleotide sequence is in a PCSK9 gene. In some embodiments, the target polynucleotide sequence is in a ANTPLT3 gene.

In some embodiments, the chemical modification on the single guide RNA enhances binding of the modified guide RNA to the Cas12b protein as compared to an unmodified single guide RNA.

In another aspect, provided herein is the chemically modified single guide RNA comprising a sequence selected from any one of SEQ ID NOs: 2-89, wherein the guide RNA comprises one or more chemical modifications.

In another aspect, provided herein is the chemically modified single guide RNA comprising a sequence of SEQ ID NO: 2, wherein the guide RNA comprises chemical modifications of the guide RNA of GB0002, GB0003, GB0007 or GB0008 of Table 1.

In another aspect, provided wherein the chemical modification on a single guide RNA comprising a sequence of Table 1, wherein a, u, g, and c indicate 2'-OMe modified adenine, uridine, guanine, and cytidine at structure directed select positions in combination with s, X, x and dX; wherein each 's', each 'X', each 'x' and 'dX' respectively indicate a phosphorothioate linkage, a nebularine, a 2'-O-methylnebularine, and a 2'-deoxynebularine. In some embodiments, the nebularine, the 2'-O-methylnebularine, or the 2'-deoxynebularine replaces a adenosine in the single guide RNA as compared to an otherwise unmodified guide RNA. In some embodiments, the nebularine, the 2'-O-methylnebularine, or the 2'-deoxynebularine replaces a guanosine in the single guide RNA as compared to an otherwise unmodified guide RNA.

In another aspect, provided herein is a ribonucleoprotein complex comprising the chemically modified single guide RNA and a Cas12b protein, wherein the complex comprises increased stability as compared to a complex with an unmodified single guide RNA and a Cas12b protein, wherein the stability is measured by half-life of the complex ex vivo or in vitro.

In another aspect, provided herein is a composition for gene modification comprising the chemically modified single guide RNA as provided herein and a Cas12b protein or a nucleic acid sequence encoding the Cas12b protein, wherein the nucleic acid sequence is an mRNA. In some embodiments, the composition further comprises a vector that comprises the nucleic acid sequence encoding the Cas12b protein. In some embodiments, the composition further comprises a pharmaceutically acceptable carrier.

In another aspect, provided herein is a lipid nanoparticle ("LNP") comprising the composition as provided herein. For example, the LNP may encapsulate an mRNA that encodes for the Cas12b protein and a gRNA that is comprised of a spacer that is complementary to a target polynucleotide of a target gene of interest.

In another aspect, provided herein is a method for modifying a targeted polynucleotide sequence in a gene of interest in a cell using the structure guided chemically modified single guide RNA and a Cas12b protein complex called ribonucleoprotein complex (RNP), the composition as provided herein, wherein the single guide RNA directs the Cas12b protein to effect a modification in the target polynucleotide sequence in the cell.

In some embodiments, the targeted polynucleotide sequence is present in a gene of interest. In some embodiments, the targeted polynucleotide sequence is present in a PCSK9 gene. In some embodiments, the targeted polynucleotide sequence is present in an ANGPTL3 gene.

In some embodiments, the cell of interest is a mammalian cell.

In some embodiments, the modification to the gene produced by the modified single guide comprising Cas12b RNP complex results in less off-target effect in the cell as compared to an unmodified single guide RNA comprising Cas12b RNP complex. In some embodiments, the single guide RNA exhibits increased stability in the cell compared to an unmodified single guide RNA, wherein the stability is measured by half-life of the single guide RNA in the cell.

In some embodiments, the modification to the target polynucleotide sequence or target gene is a double stranded break, a non-sense mutation, a frameshift mutation, a splice site alteration, or an inversion.

In some embodiments, the modification to the gene results in reducing or abolishing expression of functional protein encoded by the gene. In some embodiments, the modified gene is PCSK9 which results in reducing or abolishing expression of functional PCSK9 protein in the cell. In some embodiments, the modified gene is ANGPTL3 which result in reducing or abolishing expression of functional ANGPTL3 protein in the cell.

In another aspect, provided herein is a method for treating or preventing a condition in a subject in need thereof by administering the RNP complex comprising chemically modified single guide RNA and Cas12b protein, wherein the spacer of single guide RNA that is designed to be complementary to the targeted polynucleotide sequence of the gene hybridize with the target to facilitate the Cas12b protein to effect a modification to the target polynucleotide sequence of the gene, thereby producing a therapeutic effect for treating or preventing certain disease condition.

In some embodiments, the disease condition is atherosclerotic vascular disease such as hypertriglyceridemia and diabetes.

In some embodiments, the target polynucleotide sequence is in an ANGPTL3 gene. In some embodiments, the modification reduces expression of functional ANGPTL3 protein encoded by the ANGPTL3 gene in the subject. In some embodiments, the condition is a atherosclerotic vascular disease, hypertriglyceridemia, or diabetes.

In some embodiments, the subject post-treatment/post-administration exhibits a reduced blood LDL cholesterol level, and/or a reduced blood triglycerides level as compared to pre-administration.

In another aspect, provided herein is a single guide RNA that comprises (i) a spacer sequence and (ii) a tracr sequence, wherein the spacer sequence hybridizes with a target polynucleotide sequence in a PCSK9 gene or an ANGPTL3 gene when contacted with the target polynucleotide, wherein the scaffold sequence binds a Cas12b protein when contacted with the Cas12b protein, and wherein the single guide RNA comprises a chemical modification.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 discloses SEQ ID NOS 111 and 114, respectively, in order of appearance.

FIG. 2 discloses SEQ ID NOS 121 and 116, respectively, in order of appearance.

FIG. 3 discloses SEQ ID NOS 123 and 118, respectively, in order of appearance.

FIG. 4 discloses SEQ ID NOS 124 and 94, respectively, in order of appearance.

FIG. 5 discloses SEQ ID NOS 126 and 96, respectively, in order of appearance.

FIG. 6 discloses SEQ ID NOS 137-138, respectively, in order of appearance.

FIG. 7 discloses SEQ ID NOS 144 and 90, respectively, in order of appearance.

FIG. 8 discloses SEQ ID NOS 158 and 91, respectively, in order of appearance.

FIG. 9 discloses SEQ ID NOS 170 and 97, respectively, in order of appearance.

FIG. 10 discloses SEQ ID NOS 171 and 174, respectively, in order of appearance.

FIG. 11 discloses SEQ ID NOS 175 and 188, respectively, in order of appearance.

FIG. 12 discloses SEQ ID NOS 190-191, respectively, in order of appearance.

FIG. 13 discloses SEQ ID NOS 192-193, respectively, in order of appearance.

FIG. 14 discloses SEQ ID NOS 194 and 101, respectively, in order of appearance.

FIG. 18 discloses SEQ ID NO: 1.

FIG. 19A discloses SEQ ID NO: 195 and FIG. 19B discloses SEQ ID NO: 196.

FIG. 20 is an alignment of a reference unmodified guide RNA for ANGPTL3 (SEQ ID NO: 1) along with corresponding chemically modified guides, GB0002, GB0003, GB0007, and GB0008. Underlined nucleotides depict the spacer sequence for the unmodified and modified guides (positions 98 to 120). Letters indicate: A: Adensine, C: Cytidine; G: Guanosine, U: Uridine; T: thymidine; a: 2'-O-methyladenosine (2'-OMe-A); c: 2'-O-methylcytidine (2'-OMe-C); g: 2'-O-methylguanosine (2'-OMe-G); u: 2'-O-methyluridine (2'-OMe-U); and s: phosphorothioate (PS) linkage. FIG. 20 discloses SEQ ID NOS 1, 197-198 AND 202-203

DETAILED DESCRIPTION OF THE DISCLOSURE

Figure 1:
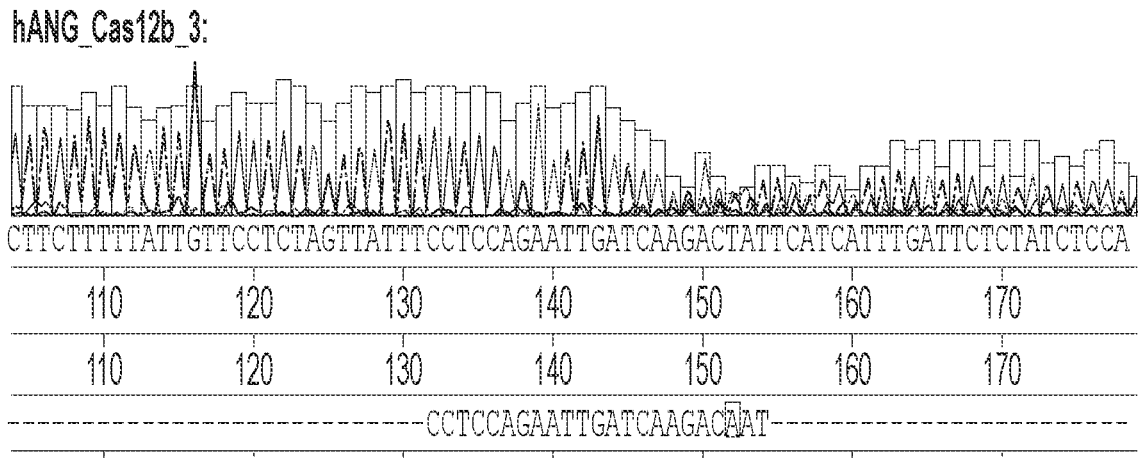
FIG. 1 depicts a Sanger sequencing chromatogram demonstrating Cas12b editing in cells. HEK293 cells were transfected 1:1 with a plasmid encoding Cas12b and a plasmid encoding the hANG_Cas12b_3 gRNA. The gRNA protospacer is aligned to the sanger sequencing chromatogram.
Figure 2:
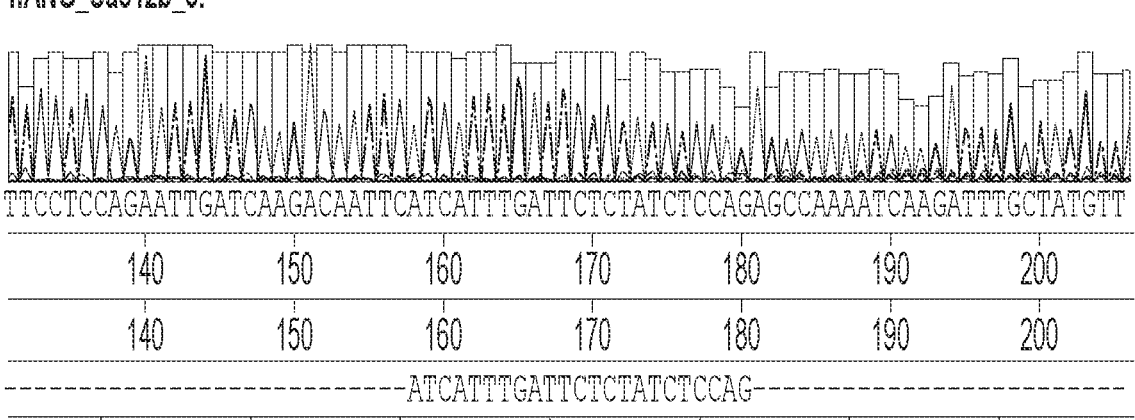
FIG. 2 depicts a Sanger sequencing chromatogram demonstrating Cas12b editing in cells. HEK293 cells were transfected 1:1 with a plasmid encoding Cas12b and a plasmid encoding the hANG_Cas12b_5 gRNA. The gRNA protospacer is aligned to the sanger sequencing chromatogram.
Figure 3:
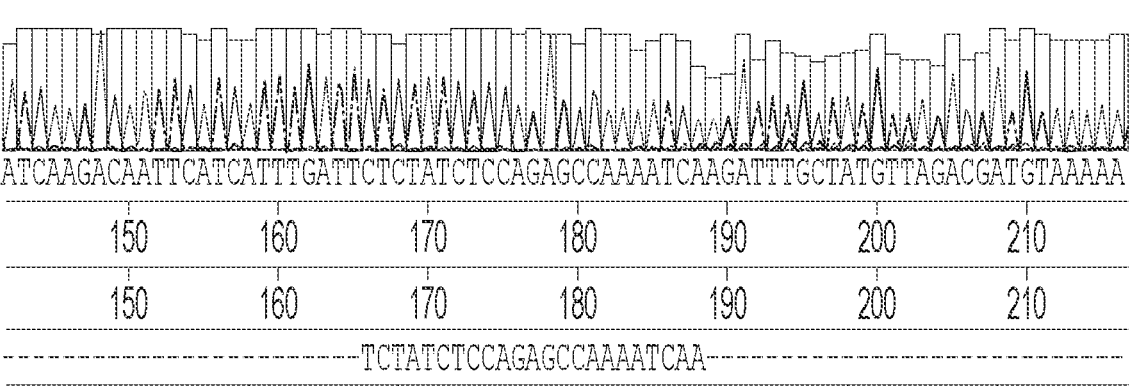
FIG. 3 depicts a Sanger sequencing chromatogram demonstrating Cas12b editing in cells. HEK293 cells were transfected 1:1 with a plasmid encoding Cas12b and a plasmid encoding the hANG_Cas12b_7 gRNA. The gRNA protospacer is aligned to the sanger sequencing chromatogram.
Figure 4:
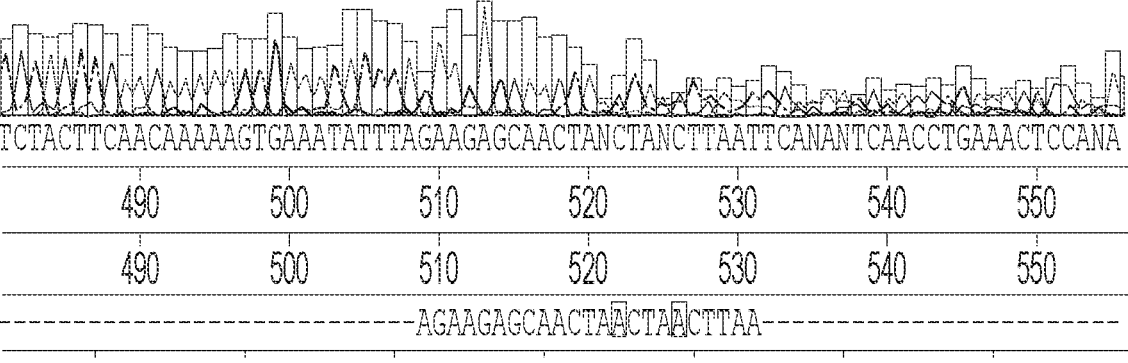
FIG. 4 depicts a Sanger sequencing chromatogram demonstrating Cas12b editing in cells. HEK293 cells were transfected 1:1 with a plasmid encoding Cas12b and a plasmid encoding the hANG_Cas12b_14 gRNA. The gRNA protospacer is aligned to the sanger sequencing chromatogram.
Figure 5:
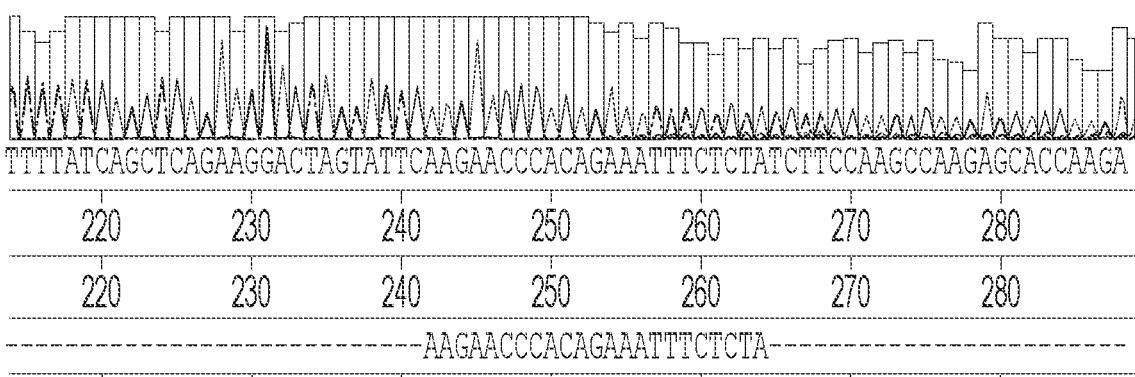
FIG. 5 depicts a Sanger sequencing chromatogram demonstrating Cas12b editing in cells. HEK293 cells were transfected 1:1 with a plasmid encoding Cas12b and a plasmid encoding the hANG_Cas12b_33 gRNA. The gRNA protospacer is aligned to the sanger sequencing chromatogram.
Figure 6:
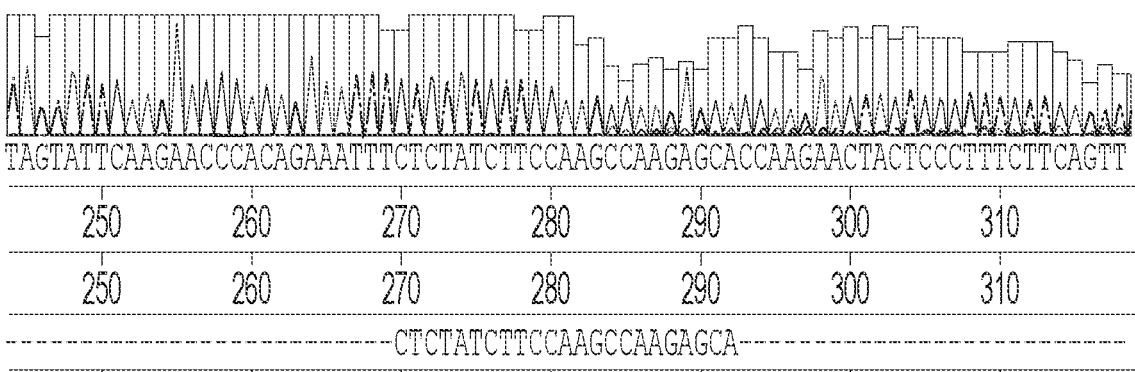
FIG. 6 depicts a Sanger sequencing chromatogram demonstrating Cas12b editing in cells. HEK293 cells were transfected 1:1 with a plasmid encoding Cas12b and a plasmid encoding the hANG_Cas12b_34 gRNA. The gRNA protospacer is aligned to the sanger sequencing chromatogram.
Figure 7:
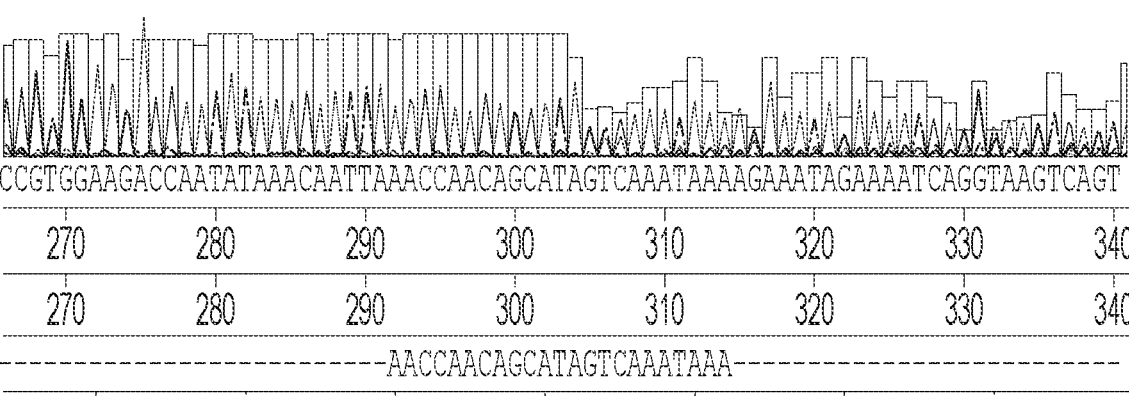
FIG. 7 depicts a Sanger sequencing chromatogram demonstrating Cas12b editing in cells. HEK293 cells were transfected 1:1 with a plasmid encoding Cas12b and a plasmid encoding the hANG_Cas12b_42 gRNA. The gRNA protospacer is aligned to the sanger sequencing chromatogram.
Figure 8:
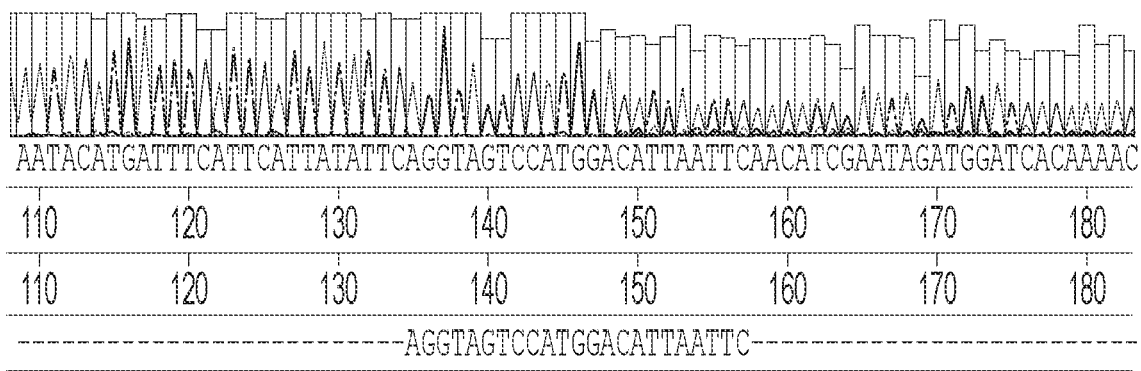
FIG. 8 depicts a Sanger sequencing chromatogram demonstrating Cas12b editing in cells. HEK293 cells were transfected 1:1 with a plasmid encoding Cas12b and a plasmid encoding the hANG_Cas12b_64 gRNA. The gRNA protospacer is aligned to the sanger sequencing chromatogram.
Figure 9:
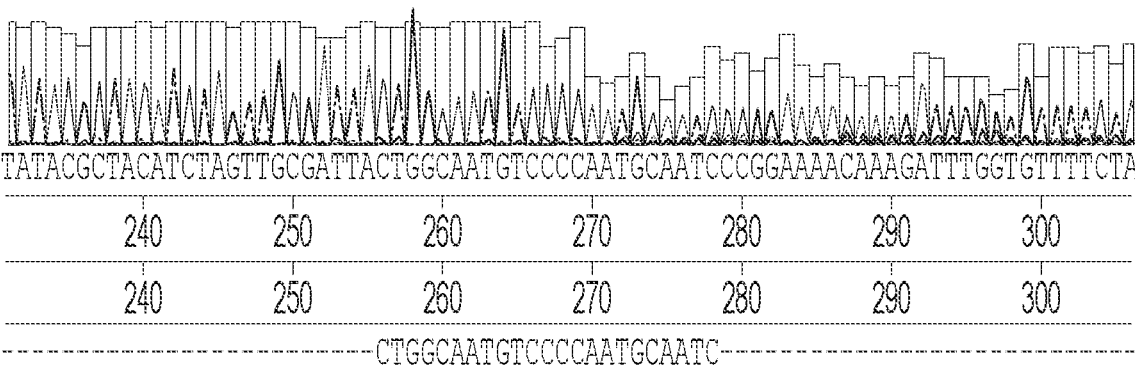
FIG. 9 depicts a Sanger sequencing chromatogram demonstrating Cas12b editing in cells. HEK293 cells were transfected 1:1 with a plasmid encoding Cas12b and a plasmid encoding the hANG_Cas12b_82 gRNA. The gRNA protospacer is aligned to the sanger sequencing chromatogram.
Figure 10:
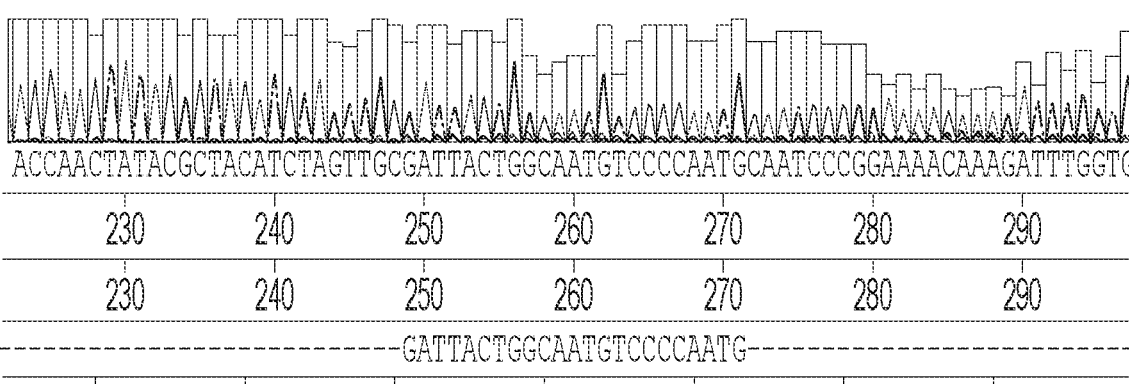
FIG. 10 depicts a Sanger sequencing chromatogram demonstrating Cas12b editing in cells. HEK293 cells were transfected 1:1 with a plasmid encoding Cas12b and a plasmid encoding the hANG_Cas12b_84 gRNA. The gRNA protospacer is aligned to the sanger sequencing chromatogram.
Figure 11:
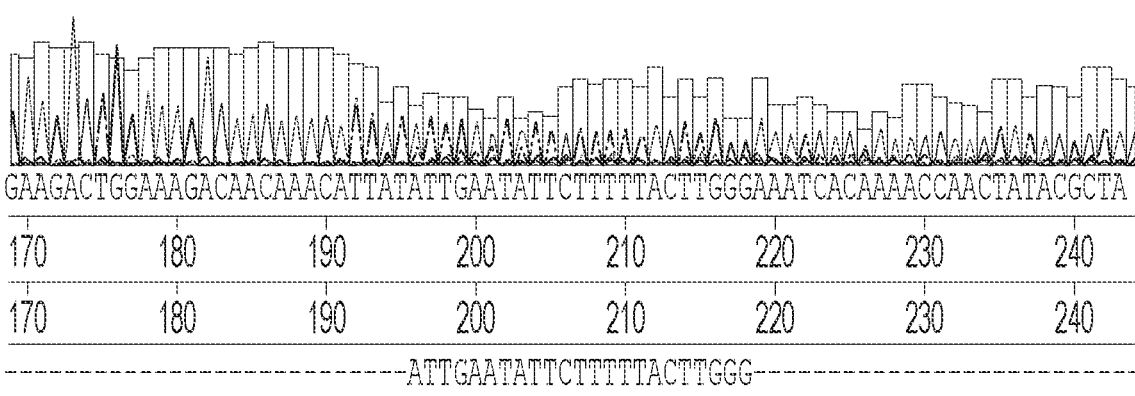
FIG. 11 depicts a Sanger sequencing chromatogram demonstrating Cas12b editing in cells. HEK293 cells were transfected 1:1 with a plasmid encoding Cas12b and a plasmid encoding the hANG_Cas12b_87 gRNA. The gRNA protospacer is aligned to the sanger sequencing chromatogram.
Figure 12:
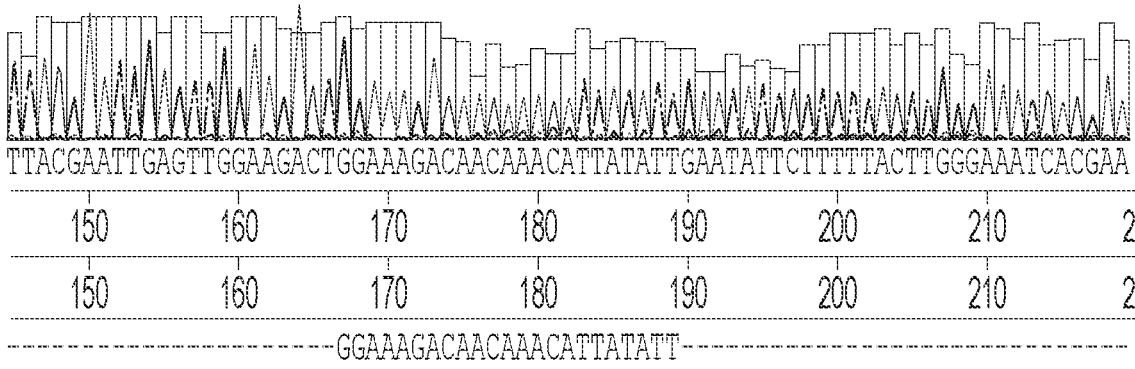
FIG. 12 depicts a Sanger sequencing chromatogram demonstrating Cas12b editing in cells. HEK293 cells were transfected 1:1 with a plasmid encoding Cas12b and a plasmid encoding the hANG_Cas12b_88 gRNA. The gRNA protospacer is aligned to the sanger sequencing chromatogram.
Figure 13:
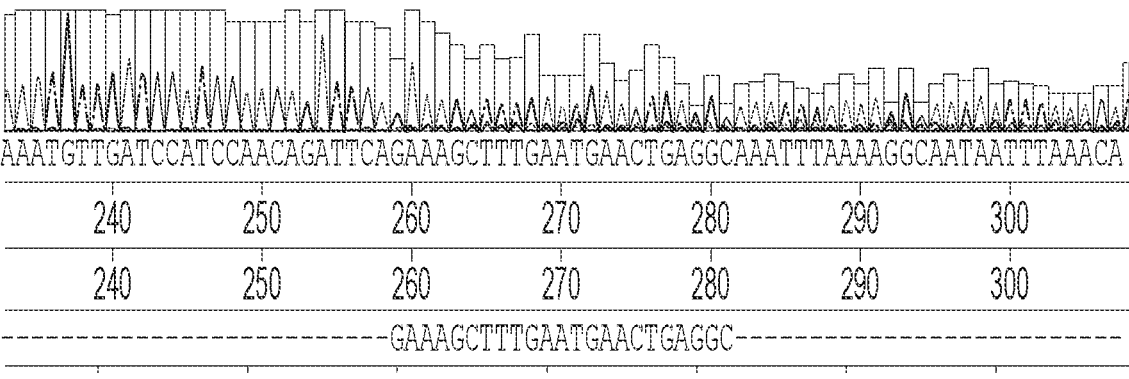
FIG. 13 depicts a Sanger sequencing chromatogram demonstrating Cas12b editing in cells. HEK293 cells were transfected 1:1 with a plasmid encoding Cas12b and a plasmid encoding the hANG_Cas12b_95 gRNA. The gRNA protospacer is aligned to the sanger sequencing chromatogram.
Figure 14:
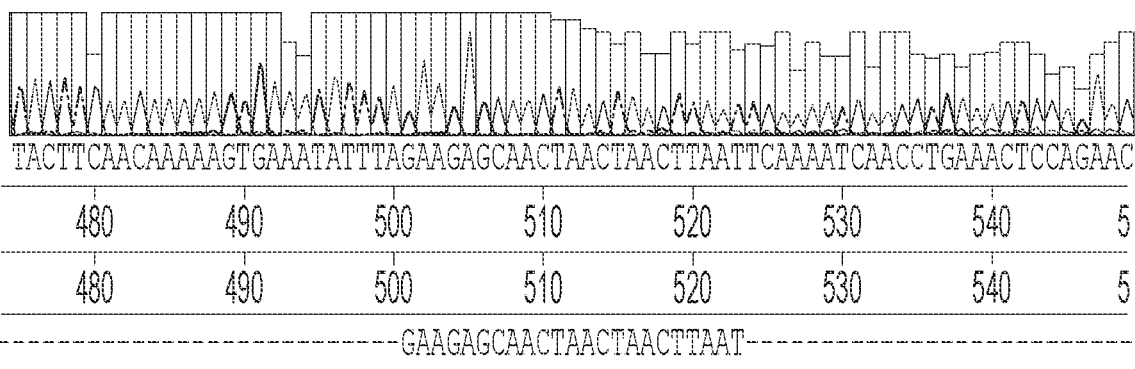
FIG. 14 depicts a Sanger sequencing chromatogram demonstrating Cas12b editing in cells. HEK293 cells were transfected 1:1 with a plasmid encoding Cas12b and a plasmid encoding the hANG_Cas12b_117 gRNA. The gRNA protospacer is aligned to the sanger sequencing chromatogram.

Certain specific details of this description are set forth in order to provide a thorough understanding of various embodiments. However, one skilled in the art will understand that the present disclosure may be practiced without these details. In other instances, well-known structures have not been shown or described in detail to avoid unnecessarily obscuring descriptions of the embodiments. Further, headings provided herein are for convenience only and do not interpret the scope or meaning of the claimed disclosure.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods, and materials are described below.

Certain Definitions

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

In this application, the use of the singular includes the plural unless specifically stated otherwise. It must be noted that, as used in the specification, the singular forms "a," "an" and "the" include plural referents unless the context clearly dictates otherwise.

In this application, the use of "or" means "and/or" unless stated otherwise. Furthermore, use of the term "including" as well as other forms, such as "include", "includes," and "included," is not limiting.

The terms "modified" and "chemically modified" are interchangeably use and/or represent chemically modified or chemical modification in a given context, for example, "modified polynucleotide" and "chemically modified polynucleotide" indicates chemical modification on the polynucleotide.

Reference in the specification to "embodiments," "some embodiments," "an embodiment," "one embodiment" or "other embodiments" means that a particular feature, structure, or characteristic described in connection with the embodiments is included in at least some embodiments, but not necessarily all embodiments, of the disclosure.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the disclosure, and vice versa. Furthermore, compositions of the disclosure can be used to achieve methods of the disclosure.

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 comprises 1 to 10, 1 to 20, 1 to 30, and 1 to 40 in one direction, or 50 to 40, 50 to 30, 50 to 20, and 50 to 10 in the other direction.

The terms "nucleic acid," "nucleotides," and "polynucle-otides," as used herein, are used interchangeably and refer to a polymer containing at least two nucleotides (i.e., deoxy-ribonucleotides or ribonucleotides) in either single- or double-stranded form and includes DNA and RNA. "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic deriva-tives of purines and pyrimidines, which include, but are not limited to, modifications which place new reactive groups such as, but not limited to, amines, alcohols, thiols, car-boxylates, and alkylhalides. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs and/or modified residues include, without limitation, phosphorothioates, phosphoramidates, methyl phosphonates, chiral-methyl phosphonates, 2'-O-methyl ribonucleotides, and peptide-nucleic acids (PNAs).

The term "nucleic acid" includes any oligonucleotide or polynucleotide, with fragments containing up to 60 nucleo-tides generally termed oligonucleotides, and longer frag-ments termed polynucleotides. A deoxyribooligonucleotide consists of a 5-carbon sugar called deoxyribose joined covalently to phosphate at the 5' and 3' carbons of this sugar to form an alternating, unbranched polymer. DNA may be in the form of, e.g., antisense molecules, plasmid DNA, pre-condensed DNA, a PCR product, vectors, expression cas-settes, chimeric sequences, chromosomal DNA, or deriva-tives and combinations of these groups. A ribooligonucleotide consists of a similar repeating structure where the 5-carbon sugar is ribose. Accordingly, the terms "polynucleotide" and "oligonucleotide" can refer to a poly-mer or oligomer of nucleotide or nucleoside monomers consisting of naturally-occurring bases, sugars and inter-sugar (backbone) linkages. The terms "polynucleotide" and "oligonucleotide" can also include polymers or oligomers comprising non-naturally occurring monomers, or portions thereof, which function similarly. Such modified or substi-tuted oligonucleotides are often preferred over native forms because of properties such as, for example, enhanced cel-lular uptake, reduced immunogenicity, and increased stabil-ity in the presence of nucleases.

The "nucleic acid" described herein may include one or more nucleotide variants, including nonstandard nucleotide (s), non-natural nucleotide(s), nucleotide analog(s), and/or modified nucleotides. Examples of modified nucleotides include, but are not limited to diaminopurine, 5-fluorouracil, 5-bromouracil, 5-chlorouracil, 5-iodouracil, hypoxanthine, xantine, 4-acetylcytosine, 5-(carboxyhydroxylmethyl)ura-cil, 5-carboxymethylaminomethyl-2-thiouridine, 5-car-boxymethylaminomethyluracil, dihydrouracil, beta-D-ga-lactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methyl-aminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, ura-cil-5-oxyacetic acid (v), wybutoxosine, pseudouracil, queo-sine, 2-thiocytosine, 5-methyl-2-thiouracil, 2-thiouracil, 4-thiouracil, 5-methyluracil, uracil-5-oxyacetic acid meth-ylester, 5-methyl-2-thiouracil, 3-(3-amino-3-N-2-carboxypropyl) uracil, (acp3)w, 2,6-diaminopurine and the like. In some cases, nucleotides may include modifications in their phosphate moieties, including modifications to a triphos-phate moiety. Non-limiting examples of such modifications include phosphate chains of greater length (e.g., a phosphate chain having, 4, 5, 6, 7, 8, 9, 10 or more phosphate moieties) and modifications with thiol moieties (e.g., alpha-thiotri-phosphate and beta-thiotriphosphates).

The nucleic acid described herein may be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety, or phosphate backbone.

Examples of modified sugar moieties include, but are not limited to, 2'-O-methyl, 2'-O-methoxyethyl, 2'-O-amino-ethyl, 2'-Flouro, N3'→P5' phosphoramidate, 2'dimethylami-nooxyethoxy, 2' 2'dimethylaminoethoxyethoxy, 2'-guani-dinidium, 2'-O-guanidinium ethyl, carbamate modified sugars, and bicyclic modified sugars. 2'-O-methyl or 2'-O-methoxyethyl modifications promote the A-form or RNA-like conformation in oligonucleotides, increase binding affinity to RNA, and have enhanced nuclease resistance. Modified sugar moieties can also include having an extra bridge bond (e.g., a methylene bridge joining the 2'-O and 4'-C atoms of the ribose in a locked nucleic acid) or sugar analog such as a morpholine ring (e.g., as in a phosphoro-diamidate morpholino).

Backbone modifications can include, but are not limited to, a phosphorothioate, a phosphorodithioate, a phospho-roselenoate, a phosphorodiselenoate, a phosphoroanilothio-ate, a phosphoraniladate, a phosphoramidate, and a phos-phorodiamidate linkage. A phosphorothioate linkage substitutes a sulfur atom for a non-bridging oxygen in the phosphate backbone and delay nuclease degradation of oligonucleotides. A phosphorodiamidate linkage (N3'→P5') allows prevents nuclease recognition and degradation. Back-bone modifications can also include having peptide bonds instead of phosphorous in the backbone structure (e.g., N-(2-aminoethyl)-glycine units linked by peptide bonds in a peptide nucleic acid), or linking groups including carbamate, amides, and linear and cyclic hydrocarbon groups. Oligo-nucleotides with modified backbones are reviewed in Mick-lefield, Backbone modification of nucleic acids: synthesis, structure and therapeutic applications, Curr. Med. Chem., 8 (10): 1157-79, 2001 and Lyer et al., Modified oligonucle-otides-synthesis, properties and applications, Curr. Opin. Mol. Ther., 1 (3): 344-358, 1999.

Unless otherwise indicated, a particular nucleic acid sequence also implicitly encompasses conservatively modi-fied variants thereof (e.g., degenerate codon substitutions), alleles, orthologs, SNPs, and complementary sequences as well as the sequence explicitly indicated. Specifically, degenerate codon substitutions may be achieved by gener-ating sequences in which the third position of one or more selected (or all) codons is substituted with mixed-base and/or deoxyinosine residues (Batzer et al., Nucleic Acid Res., 19:5081 (1991); Ohtsuka et al., J. Biol. Chem., 260: 2605-2608 (1985); Rossolini et al., Mol. Cell. Probes, 8:91-98 (1994).

The present disclosure encompasses isolated or substan-tially purified nucleic acid molecules and compositions containing those molecules. As used herein, an "isolated" or "purified" DNA molecule or RNA molecule is a DNA molecule or RNA molecule that exists apart from its native environment. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in some embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

The term "protospacer" "or "target polynucleotide sequence" and its grammatical equivalents as used herein can refer to a PAM-adjacent nucleic acid sequence upon which the "spacer sequence" of the guide RNA (gRNA) is adapted from protospacer as an RNA version thereof. A protospacer can be a nucleotide sequence within gene, genome, or chromosome that is targeted by a gRNA. In the native state, a protospacer is adjacent to a PAM (protospacer adjacent motif). The site of cleavage by an RNA-guided nuclease is within a protospacer sequence. For example, when a gRNA targets a specific protospacer, the Cas protein will generate a double strand break within the protospacer sequence, thereby cleaving the protospacer. Following cleavage, disruption of the protospacer can result though non-homologous end joining (NHEJ) or homology-directed repair (HDR). Disruption of the protospacer can result in the deletion of the protospacer. Additionally or alternatively, disruption of the protospacer can result in an exogenous nucleic acid sequence being inserted into or replacing the protospacer.

The terms "gene editing," or "gene modification" and its grammatical equivalents as used herein can refer to genetic engineering in which one or more nucleotides are inserted, replaced, or removed from a genome. Gene editing can be performed using a nuclease (e.g., a natural-existing nuclease or an artificially engineered nuclease). Gene modification can include introducing a double stranded break, a non-sense mutation, a frameshift mutation, a splice site alteration, or an inversion in a polynucleotide sequence, e.g., a target polynucleotide sequence.

As used herein, the terms "protein," "polypeptide," and "peptide" are used interchangeably and refer to a polymer of amino acid residues linked via peptide bonds and which may be composed of two or more polypeptide chains. The terms "polypeptide," "protein," and "peptide" refer to a polymer of at least two amino acid monomers joined together through amide bonds. An amino acid may be the L-optical isomer or the D-optical isomer. More specifically, the terms "polypeptide," "protein," and "peptide" refer to a molecule composed of two or more amino acids in a specific order; for example, the order as determined by the base sequence of nucleotides in the gene or RNA coding for the protein. Proteins are essential for the structure, function, and regulation of the body's cells, tissues, and organs, and each protein has unique functions. Examples are hormones, enzymes, antibodies, and any fragments thereof. In some cases, a protein can be a portion of the protein, for example, a domain, a subdomain, or a motif of the protein. In some cases, a protein can be a variant (or mutation) of the protein, wherein one or more amino acid residues are inserted into, deleted from, and/or substituted into the naturally occurring (or at least a known) amino acid sequence of the protein. A protein or a variant thereof can be naturally occurring or recombinant. Methods for detection and/or measurement of polypeptides in biological material are well known in the art and include, but are not limited to, Western-blotting, flow cytometry, ELISAs, RIAs, and various proteomics techniques. An exemplary method to measure or detect a polypeptide is an immunoassay, such as an ELISA. This type of protein quantitation can be based on an antibody capable of capturing a specific antigen, and a second antibody capable of detecting the captured antigen. Exemplary assays for detection and/or measurement of polypeptides are described in Harlow, E. and Lane, D. Antibodies: A Laboratory Manual, (1988), Cold Spring Harbor Laboratory Press.

As used herein, a "lipid nanoparticle (LNP) composition" or a "nanoparticle composition" is a composition comprising one or more described lipids. LNP compositions are typically sized on the order of micrometers or smaller and may include a lipid bilayer. Nanoparticle compositions encompass lipid nanoparticles (LNPs), liposomes (e.g., lipid vesicles), and lipoplexes. For example, a nanoparticle composition may be a liposome having a lipid bilayer with a diameter of 500 nm or less. The LNPs described herein can have a mean diameter of from about 1 nm to about 2500 nm, from about 10 nm to about 1500 nm, from about 20 nm to about 1000 nm, from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, or from about 70 nm to about 80 nm. The LNPs described herein can have a mean diameter of about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, or greater. The LNPs described herein can be substantially non-toxic.

CRISPR/CAS System

CRISPR is an adaptive immune system that provides protection against mobile genetic elements (viruses, transposable elements and conjugative plasmids). CRISPR clusters contain spacers, sequences complementary to antecedent mobile elements, and target invading nucleic acids. A CRISPR/Cas system comprises a non-coding RNA molecule (e.g., guide RNA) that binds to DNA (e.g., target DNA sequence) and Cas proteins (e.g., Cas9, Cas12b) with nuclease functionality (e.g., two nuclease domains). See, e.g., Sander, et al., Nature Biotechnology, 32:347-355 (2014); see also e.g., Hsu, et al., Cell 157(6):1262-1278 (2014). The general mechanism and recent advances of CRISPR system is discussed in Cong, et al., Science, 339(6121): 819-823 (2013); Fu, et al., Nature Biotechnology, 31, 822-826 (2013); Chu, et al., Nature Biotechnology 33, 543-548 (2015); Shmakov, et al., Molecular Cell, 60, 1-13 (2015); Makarova, et al., Nature Reviews Microbiology, 13, 1-15 (2015). CRISPR/Cas systems can be used to introduce site-specific cleavage of a target DNA. The locations for site-specific cleavage are determined by both 1) base-pairing complementarity between the guide RNA (gRNA) and the target DNA sequence that is complementary to a protospacer sequence and 2) a short motif in the target DNA referred to as the protospacer adjacent motif (PAM). CRISPR/Cas systems (e.g., Type II CRISPR/Cas system) can be used to generate, e.g., an engineered cell in which a target gene is disrupted or mutated. A Cas enzyme (e.g., Cas9, Cas 12b) can be used to catalyze DNA cleavage. A Cas9 protein (e.g., a *Streptococcus pyogenes* Cas9 or any closely related Cas9), for example, can derive an enzymatic action to generate double stranded breaks at target site sequences which hybridize to about 20 nucleotides of a guide sequence (e.g., gRNA) and that have a protospacer-adjacent motif (PAM) following the target sequence.

CRISPR/Cas system comprises Class 1 or Class 2 system components, including ribonucleic acid protein complexes. The Class 2 Cas nuclease families of proteins are enzymes with DNA endonuclease activity, and they can be directed to cleave a desired nucleic acid target by designing an appropriate guide RNA, as described further herein. A Class 2 CRISPR/Cas system component may be from a Type II, Type IIA, Type IIB, Type IIC, Type V, or Type VI system. Class 2 Cas nucleases include, for example, Cas9 (also known as Csn1 or Csx12), Csn2, Cas4, Cas12a (Cpf1), Cas12b (C2c1), Cas12c (C2c3), Cas13a (C2c2), Cas13b, Cas13c, and Cas13d proteins.

Other non-limiting examples of Cas proteins include Cas1, Cas1B, Cas2, Cas3, Cas4, Cas5, Cas6, Cas7, Cas8, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Cpf1, Cas9HiFi, homologues thereof, or modified versions thereof.

CRISPR clusters (e.g., spacers, sequences complementary to antecedent mobile elements, and target invading nucleic acids) are transcribed and processed into CRISPR RNA (crRNA). In Type II CRISPR systems correct processing of pre-crRNA requires a trans-activating crRNA (tracrRNA), endogenous ribonuclease 3 (rnc) and a Class 2 Cas nuclease. The tracrRNA serves as a guide for ribonuclease 3-aided processing of pre-crRNA. Subsequently, Cas nuclease/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNAs. However, single guide RNAs (sgRNA) can be engineered so as to incorporate aspects of both the crRNA and tracrRNA into a single RNA species (Jinek M., et al., Science (2012) 337:816-821). Cas nucleases recognize a short motif in the CRISPR repeat sequences (the PAM or protospacer adjacent motif) to help distinguish self versus non-self. For example, Cas9 nuclease sequences and structures are well known to those of skill in the art (see, e.g., Ferretti, et al., Proc. Natl. Acad. Sci. U.S.A. (2001) 98:4658-4663; Deltcheva, et al., Nature (2011) 471:602-607; and Jinek, et al., Science (2012) 337:816-821, the entire contents of each of which are incorporated herein by reference). CAS12B (C2C1)

The term "Cas12b (C2C1)," as used herein, refers to a type V-B CRISPR-Cas system RNA-guided DNA endonuclease that has a double-stranded DNA cleavage activity. For example, a crRNA in combination with a minimal 78 nt (nucleotides) tracrRNA or a fused sgRNA is sufficient for Cas12b-mediated DNA cleavage. For instance, in some embodiments, a 14 nt direct repeat (DR) hybridizes with tracrRNA to form a crRNA:tracrRNA duplex, which is then loaded onto Cas12b to guide DNA recognition and cleavage. Cas12b contains a RuvC-like nuclease domain and a putative Nuc domain, generating a staggered double-stranded break at the target locus, with a 5' overhang, or a "sticky end" at the PAM distal side of the target sequence (See, e.g., Garneau et al, Nature. 2010; 468:67-71; Gasiunas et al., Proc Natl Acad Sci USA. 2012; 109:E2579-2586, the entire contents of which are incorporated herein by reference). In some embodiments, the 5' overhang is 7 nt. (See, e.g., Lewis and Ke, Mol Cell. 2017, 65(3):377-379 and Liu et al., Molecular cell, 2017, 65(2):310-32, the entire contents of which are incorporated herein by reference). Cas12b is sometimes also referred to as Cpf2.

In some embodiments, Cas12b originates from a bacterium selected from the group consisting of: *Alicyclobacillus kakegawensis, Alicyclobacillus acidoterrestris, Alicycloba-cillus contaminans, Alicyclobacillus macrosporangiidus, Bacillus* sp. V3-13, *Bacillus hisashii, Candidatus lindow-bacteria* bacterium RIFCSPLOW02, *Desulfovibrio inopina-tus, Desulfonatronum thiodismutans, Elusimicrobia* bacterium RIFOXYA12, *Lentisphaeria* bacterium, *Omnitrophica* WOR 2 bacterium RIFCSPHIGH02, *Opitutaceae* bacterium TAV5, *Phycisphaerae* bacterium ST-NAGAB-D1, *Plancto-mycetes* bacterium RBG_13_46_10, *Spirochaetes* bacterium GWB1 27 13, *Verrucomicrobiaceae* bacterium UBA2429, *Tuberibacillus calidus, Bacillus thermoamylovorans, Brevi-bacillus* sp. CF112, *Bacillus* sp. NSP2.1, *Desulfatirhabdium butyrativorans, Alicyclobacillus herbarius, Citrobacter fre-undii, Brevibacillus agri, Methylobacterium nodulans* and *Laceyella sediminis*. In some embodiments, Cas12b originates from a bacterium selected from the group consisting of: *Alicyclobacillus, Desulfovibrio, Desulfonatronum, Opi-tutaceae, Tuberibacillus, Bacillus, Brevibacillus, Candida-tus, Desulfatirhabdium, Citrobacter, Desulfatirhabdium butyrativorans, Desulfonatronum thiodismutans, Elusimi-crobia, Methylobacterium, Methylobacterium nodulans, Omnitrophica, Phycisphaerae, Planctomycetes, Spiro-chaetes, Verrucomicrobiaceae, Lentisphaeria,* and *Lac-eyella, Laceyella sediminis*.

In some embodiment, Cas12b recognizes the T-rich PAM at the 5' end of the protospacer sequence to mediate DNA interference. In some embodiments, Cas12b PAM sequences may be T-rich sequences. In some embodiments, the PAM sequence is 5' TTN 3' or 5' ATTN 3', wherein N is any nucleotide. In some embodiments, the PAM sequence is 5' TTC 3'. In some embodiments, the *Alicyclobacillus acido-terrestris* ATCC 49025 C2cl protein (AacC2cl) cleaves target sites preceded by a 5' TTN PAM, where N is A, C, G, or T, more preferably where N is A, G, or T. In some embodiments, the *Bacillus thermoamylovorans* strain B4166 C2cl protein (BthC2cl) cleaves sites preceded by a ATTN, where N is A/C/G or T.

An exemplary *Bacillus hisashii* Cas12b has an amino acid sequence of

```
                                        (SEQ ID NO: 102)
MATRSFILKIEPNEEVKKGLWKTHEVLNHGIAYYMNILKLIRQEAIY

EHHEQDPKNPKKVSKAEIQAELWDFVLKMQKCNSFTHEVDKDEVFNI

LRELYEELVPSSVEKKGEANQLSNKFLYPLVDPNSQSGKGTASSGRK

PRWYNLKIAGDPSWEEEKKKWEEDKKKDPLAKILGKLAEYGLIPLFI

PYTDSNEPIVKEIKWMEKSRNQSVRRLDKDMFIQALERFLSWESWNL

KVKEEYEKVEKEYKTLEERIKEDIQALKALEQYEKERQEQLLRDTLN

TNEYRLSKRGLRGWREIIQKWLKMDENEPSEKYLEVFKDYQRKHPRE

AGDYSVYEFLSKKENHFIWRNHPEYPYLYATFCEIDKKKKDAKQQAT

FTLADPINHPLWVRFEERSGSNLNKYRILTEQLHTEKLKKKLTVQLD

RLIYPTESGGWEEKGKVDIVLLPSRQFYNQIFLDIEEKGKHAFTYKD
```

```
                     -continued
ESIKFPLKGTLGGARVQFDRDHLRRYPHKVESGNVGRIYFNMTVNIE

PTESPVSKSLKIHRDDFPKVVNFKPKELTEWIKDSKGKKLKSGIESL

EIGLRVMSIDLGQRQAAAASIFEVVDQKPDIEGKLFFPIKGTELYAV

HRASFNIKLPGETLVKSREVLRKAREDNLKLMNQKLNFLRNVLHFQQ

FEDITEREKRVTKWISRQENSDVPLVYQDELIQIRELMYKPYKDWVA

FLKQLHKRLEVEIGKEVKHWRKSLSDGRKGLYGISLKNIDEIDRTRK

FLLRWSLRPTEPGEVRRLEPGQRFAIDQLNHLNALKEDRLKKMANTI

IMHALGYCYDVRKKKWQAKNPACQIILFEDLSNYNPYEERSRFENSK

LMKWSRREIPRQVALQGEIYGLQVGEVGAQFSSRFHAKTGSPGIRCS

VVTKEKLQDNRFFKNLQREGRLTLDKIAVLKEGDLYPDKGGEKFISL

SKDRKCVTTHADINAAQNLQKRFWTRTHGFYKVYCKAYQVDGQTVYI

PESKDQKQKIIEEFGEGYFILKDGVYEWVNAGKLKIKKGSSKQSSSE

LVDSDILKDSFDLASELKGEKLMLYRDPSGNVFPSDKWMAAGVFFGK

LERILISKLTNQYSISTIEDDSSKQSM
```

In some embodiments, Cas12b is *Bacillus hisashii* Cas12b. In some embodiments, Cas12b has a mutation. In some embodiments, Cas12b is *Bacillus hisashii* Cas12b that has a mutation. In some embodiments, Cas12b is *Bacillus hisashii* Cas12b that has K846R mutation. In some embodiments, Cas12b is *Bacillus hisashii* Cas12b that has S893R mutation. In some embodiments, Cas12b is *Bacillus hisashii* Cas12b that has E837G mutation. In some embodiments, Cas12b is *Bacillus hisashii* Cas12b that has K846R mutation, S893R mutation, E837G mutation, and any combination thereof. In some embodiments, Cas12b is *Bacillus hisashii* Cas12b that has K846R/S893R/E837G mutations.

In some embodiments, the recombinant Cas12b protein comprises one or more nuclear localization signals. In some embodiments, the recombinant Cas12b protein is catalytically inactive. In some embodiments, the recombinant Cas12b protein is associated with one or more functional domains.

Guide RNAs

The guide RNA (gRNA) is capable of guiding the Class 2 Cas nuclease to a target sequence on a target nucleic acid molecule where the target sequence is complementary to the protospacer sequence, where the gRNA hybridizes with and the Cas nuclease cleaves or modulates the target sequence. In some embodiments, a gRNA binds with and provides specificity of cleavage by a Class 2 nuclease. In some embodiments, the gRNA and the Cas protein may form a ribonucleoprotein (RNP), e.g., a CRISPR/Cas complex. In some embodiments, the CRISPR complex may be a Type II CRISPR/Class 2 Cas nuclease. In some embodiments, the CRISPR/Cas complex may be a Type V CRISPR/Cas complex, such as a Cas12b/guide RNA complex. In some embodiments, the Cas nuclease may be a single-protein Cas nuclease, e.g., a Cas12b protein. In some embodiments, the gRNA targets cleavage by a Cas12b protein.

A gRNA for Cas12b editing can comprise at least two distinct regions: a first distinct region at the 5' end called the scaffold sequence comprises of stem loops and single strands that recognize and bind to the Cas12b protein, and the second distinct regions at the 3' end of the scaffold sequence is designed to be complementary to a target site in a chromosomal sequence (i.e., spacer region) that facilitate binding of the Cas12b protein-gRNA complex to the targeted section of the gene of interest to effect Cas12b/guide RNA-mediated gene modification. Further, scaffold regions of each gRNA can be identical in all gRNAs as it is the protein binding domain of the gRNA. The spacer region of each guide RNA can also be different such that each gRNA guides a protein, e.g., Cas12b, to a specific target site. A scaffold region of a gRNA may form a secondary structure. In some embodiments, a secondary structure formed by a gRNA can comprise a stem (or hairpin) and a loop. The length of a loop and/or a stem can vary. In some embodiments, a loop can range from about 3 to about 10 nucleotides in length. In some embodiments, a stem can range from about 6 to about 20 nucleotides in length. A stem can comprise one or more bulges of 1 to 10 nucleotides or about 10 nucleotides. In some embodiments, the overall length of a second region can range from about 16 to 60 nucleotides in length. In some embodiments, a loop can be about 4 nucleotides in length. In some embodiments, a stem can be about 12 in length. A third region of scaffold sequence can be essentially single-stranded. In addition, the length of the spacer at the 3'-end of the Cas12b gRNA can vary. In some embodiments, the spacer sequence can be more than 3 or more than 4 nucleotides in length. For example, the length of the spacer at the 3' end of the gRNA can range from about 20 to 40 nucleotides in length.

A gRNA for a CRISPR/Cas12b system can comprise a CRISPR RNA (crRNA) and a trans-activating crRNA (tracrRNA, tracr sequence, or scaffold sequence). As used herein, tracrRNA, tracr sequence, or scaffold sequence are used interchangeably. In some embodiments, the crRNA comprises a targeting or spacer sequence that is complementary to and capable of hybridizing with the target sequence on the target nucleic acid molecule. The crRNA may also comprise a portion that is complementary to and capable of hybridizing with a portion of the tracrRNA. In some embodiments, the crRNA may parallel the structure of a naturally occurring crRNA transcribed from a CRISPR locus of a bacteria, where the targeting sequence acts as the spacer of the CRISPR/Cas12b system, and a portion of a repeat sequence flanking the spacers on the CRISPR locus. The gRNA may target any sequence of interest via the targeting sequence of the crRNA. In some embodiments, the degree of complementarity between the targeting sequence of the gRNA and the target sequence on the target nucleic acid molecule is at least about 60%, 65%, 70%, 75%, 80%, 85%, 90%, 95%, 97%, 98%, 99%, or 100%. In some embodiments, the targeting sequence of the gRNA and the target sequence on the target nucleic acid molecule may be 100% complementary. In other embodiments, the targeting sequence of the gRNA and the target sequence on the target nucleic acid molecule may contain at least one mismatch. For example, the targeting sequence of the gRNA and the target sequence on the target nucleic acid molecule may contain 1, 2, 3, 4, 5, 6, 7, 8, 9, or 10 mismatches.

In some embodiments, the length of the targeting sequence depends on the CRISPR/Cas system and components used. For example, different Cas proteins from different bacterial species have varying optimal targeting sequence lengths. Accordingly, the targeting sequence comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more than 50 nucleotides in length. In some embodiments, the targeting sequence comprised 20-40 nucleotides in length. In some embodiments, the targeting sequence comprises 20-25 nucleotides in length. In some embodiments, the targeting sequence comprises 24 nucleotides in length. In some embodiments, the targeting sequence comprises 23 nucleotides in length.

In some embodiments, the guide RNA is a "dual guide RNA" or "dgRNA". In some embodiments, the dgRNA comprises a first RNA molecule comprising a crRNA, and a second RNA molecule comprising a tracrRNA. The first and second RNA molecules may form a RNA duplex via the base pairing between the crRNA and the tracrRNA (e.g. repeat and anti-repeat). In some embodiments, the guide RNA is a "single guide RNA" or "sgRNA." In some embodiments, the sgRNA comprises a crRNA covalently linked to a tracrRNA. In some embodiments, the crRNA and the tracrRNA may be covalently linked via a linker. In some embodiments, the single-molecule guide RNA comprises a stem-loop structure via the base pairing between the crRNA and the tracrRNA. In some embodiments, the sgRNA is a "Cas12b sgRNA" capable of mediating RNA-guided DNA cleavage by a Cas12b protein. In certain embodiments, the guide RNA comprises a crRNA and tracrRNA sufficient for forming an active complex with a Cas12b protein and mediating RNA-guided DNA cleavage. The terms "guide RNA," "single guide RNA," "gRNA," and "sgRNA" are used interchangeably throughout this application. In some embodiments, more than one guide RNA can be used; each guide RNA contains a different targeting sequence, such that the CRISPR/Cas12b system cleaves more than one target sequence. In some embodiments, one or more guide RNAs may have the same or differing properties such as activity or stability within a CRISPR/Cas12b complex. Where more than one guide RNA is used, each guide RNA can be encoded on the same or on different expression cassettes. The promoters used to drive expression of the more than one guide RNA may be the same or different.

In some embodiments, the gRNA or mRNA encoding Cas12b nuclease is modified. The modifications can comprise chemical alterations, synthetic modifications, nucleotide additions, and/or nucleotide subtractions and modified nucleosides or nucleotides can be present in a gRNA. A gRNA or Cas nuclease-encoding mRNA comprising one or more modified nucleosides or nucleotides is called a "modified" RNA to describe the presence of one or more non-naturally and/or naturally occurring components or configurations that are used instead of or in addition to the canonical A, G, C, and U residues. In some embodiments, a modified RNA is synthesized with a non-canonical nucleoside or nucleotide. Modified nucleosides and nucleotides can include one or more of: (i) alteration, e.g., replacement, of one or both of the non-linking phosphate oxygens and/or of one or more of the linking phosphate oxygens in the phosphodiester backbone linkage (an exemplary backbone modification); (ii) alteration, e.g., replacement, of a constituent of the ribose sugar, e.g., of the 2' hydroxyl on the ribose sugar (an exemplary sugar modification); (iii) wholesale replacement of the phosphate moiety with "dephospho" linkers (an exemplary backbone modification); (iv) modification or replacement of a naturally occurring nucleobase, including with a non-canonical nucleobase (an exemplary base modification); (v) replacement or modification of the ribose-phosphate backbone (an exemplary backbone modification); (vi) modification of the 3' end or 5' end of the oligonucleotide, e.g., removal, addition, modification, or replacement of a terminal phosphate group or conjugation of a moiety, cap, or linker (such 3' or 5' cap modifications comprises a sugar and/or backbone modification); and (vii) modification or replacement of the sugar (an exemplary sugar modification). The modifications can enhance genome editing by CRISPR/Cas12b. A modification can alter chirality of a gRNA. In some cases, chirality may be uniform or stereopure after a modification. A guide RNA can also be truncated. Truncation can be used to reduce undesired off-target mutagenesis. The truncation can comprise any number of nucleotide deletions. For example, the truncation can comprise 1, 2, 3, 4, 5, 10, 15, 20, 25, 30, 40, 50 or more nucleotides.

Methods for selecting, designing, and validating gRNAs and targeting sequences (or spacer sequences) are described herein and known to those skilled in the art. Software tools can be used to optimize the gRNAs corresponding to a target nucleic acid sequence, e.g., to minimize total off-target activity across the genome. For example, for each possible targeting domain choice using *B. hisashii* Cas12b, all off-target sequences (preceding selected PAMs, e.g., NAG or NGG) may be identified across the genome that contain up to certain number (e.g., 1, 2, 3, 4, 5, 6, 7, 8, 9, or 10) of mismatched base-pairs. First regions of gRNAs complementary to a target site can be identified, and all first regions (e.g., crRNAs) can be ranked according to its total predicted off-target score; the top-ranked targeting domains represent those that are likely to have the greatest on-target and the least off-target activity. In some embodiments, a DNA sequence searching algorithm can be used to identify a target sequence in crRNAs of a gRNA for use with Cas12b. A custom gRNA design software based on the public tool cas-offinder, which scores guides after calculating their genome-wide off-target propensity, can be also used to design a gRNA (e.g., Bae, et al., Cas-OFFinder: A fast and versatile algorithm that searches for potential off-target sites of Cas9 RNA-guided endonucleases. Bioinformatics 30, 1473-1475 (2014)). In some embodiments, RepeatMasker program can be used to screen repeat elements and regions of low complexity in the input DNA sequences. In addition, the number of residues that could unintentionally be targeted (e.g., off-target residues that could potentially reside on ssDNA within the target nucleic acid locus) may be minimized to reduce the impact of potential substrate promiscuity of the Cas12b editing system. Candidate gRNAs can be functionally evaluated by using methods known in the art and/or as set forth herein.

The gRNAs described herein can be synthesized chemically, enzymatically, or a combination thereof. For example, the gRNA can be synthesized using standard phosphoramidite-based solid-phase synthesis methods. Alternatively, the gRNA can be synthesized in vitro by operably linking DNA encoding the gRNA to a promoter control sequence that is recognized by a phage RNA polymerase. Examples of suitable phage promoter sequences include, but are not limited to, T7, T3, SP6 promoter sequences, or variations thereof. In some embodiments, gRNA comprises two separate molecules (e.g., crRNA and tracrRNA) and one molecule (e.g., crRNA) can be chemically synthesized and the other molecule (e.g., tracrRNA) can be enzymatically synthesized.

Cas12b Guide RNAs

Described herein are guide RNAs that have improved properties or functionalities for a a CRISPR/Cas12b gene editing system. In some embodiments, the guide RNA comprises two RNA molecules, i.e., a crRNA, and a tracrRNA. In some embodiments, the two molecules are connected by a linker. In some embodiments, the two molecules are connected by a non-nucleic acid linker. In some embodiments, the two molecules are connected by a peptide linker or a chemical linker. In some embodiments, the guide RNA is a single molecule or single guide RNA.

Figure 18:
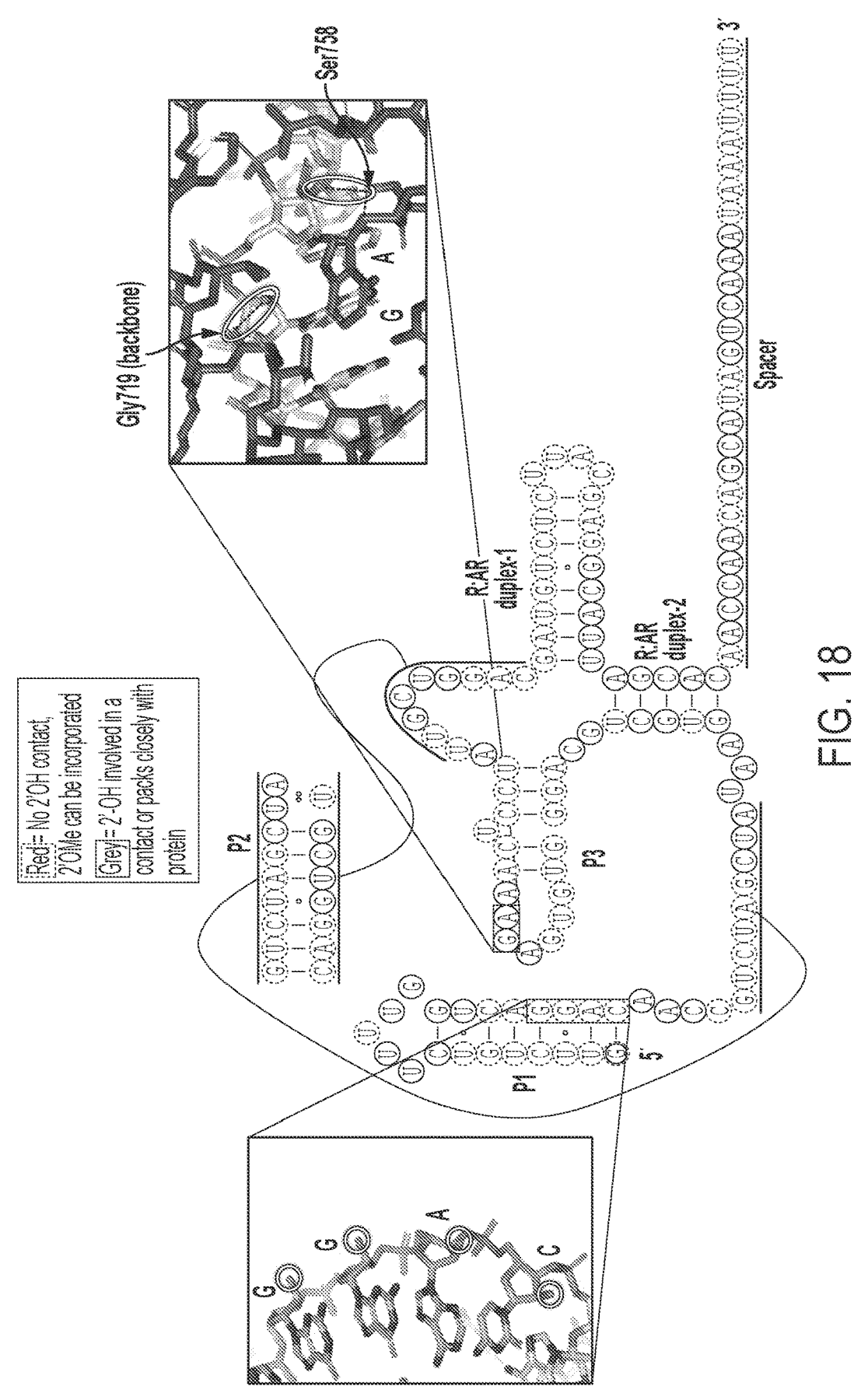
FIG. 18 illustrates key details from a structure-based approach to: 1) identify bases where 2'-O-methyl could be substituted in lieu of 2'-hydroxyl groups to offer stability to an exemplary Cas12b gRNA, while not causing steric hindrance with either the protein or gRNA; 2) introduce changes to the gRNA sequence to improve stability and/or improve nuclease activity.
Figure 19A:
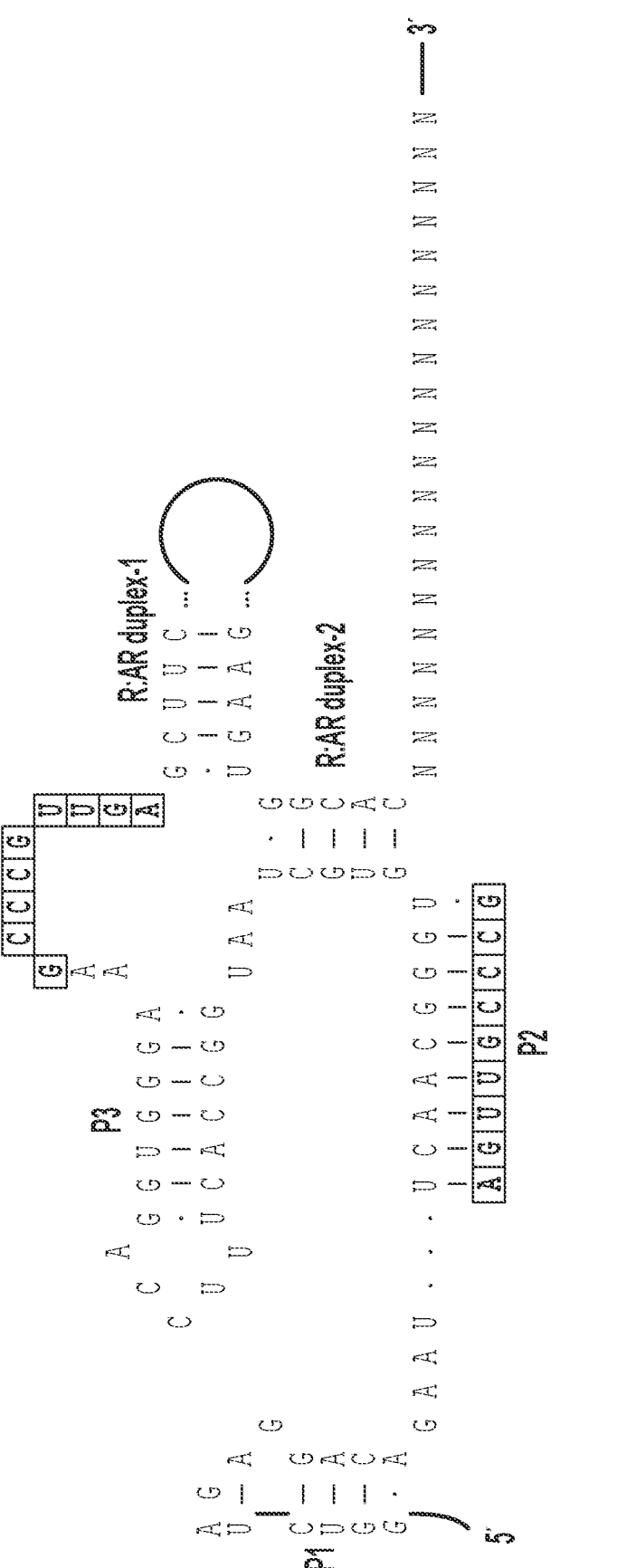
FIG. 19A-19B show exemplary sgRNAs for *Alicyclobacillus acidoterrestris* Cas12b (FIG. 19A) and *Bacillus thermoamylovorans* Cas12b (FIG. 19B).
Figure 19B:
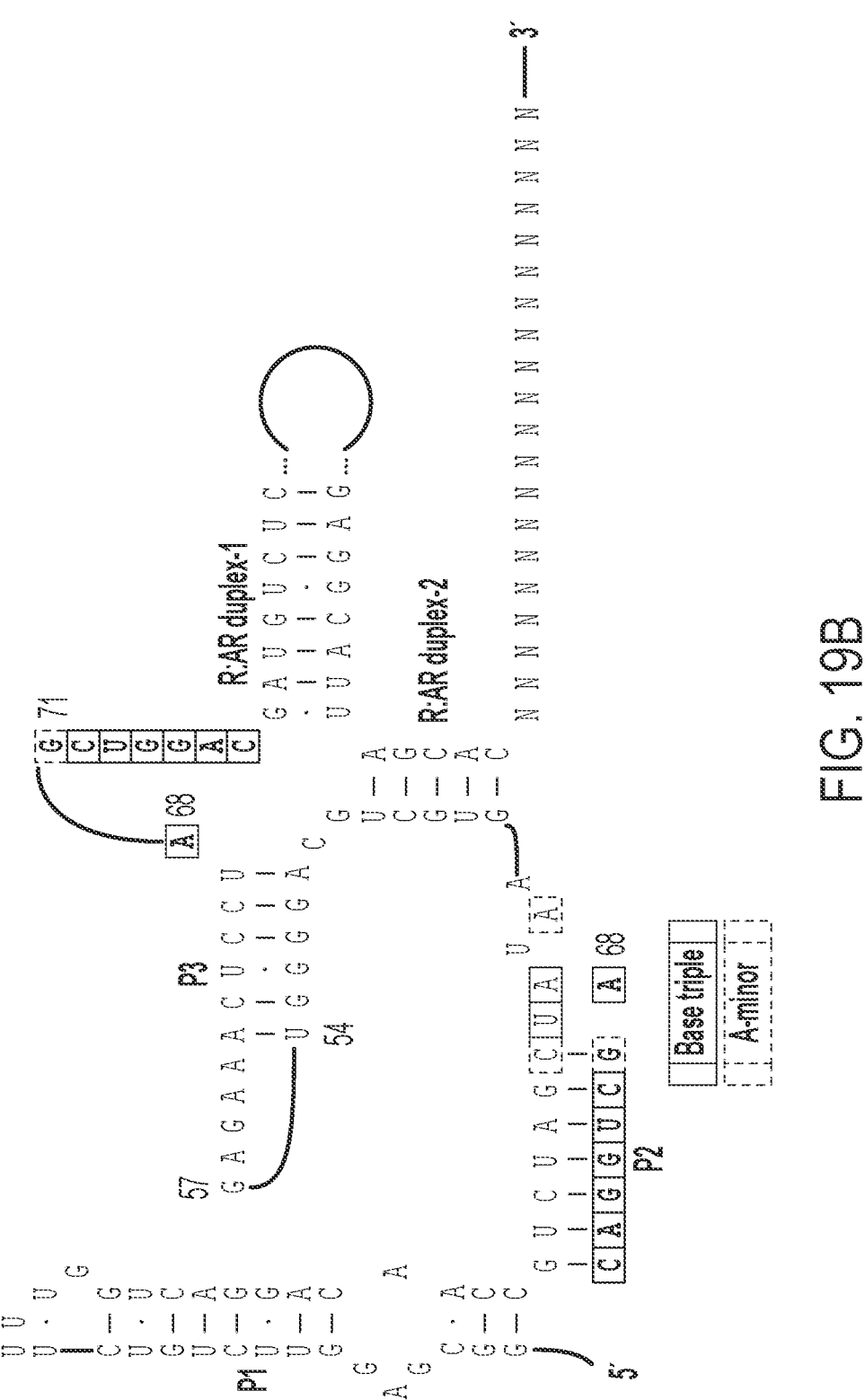

Illustrative Cas12b single guide RNAs and their interactions with Cas12b protein are depicted in FIGS. 18-19.

In some embodiments, a guide RNA comprises a total of 50-150 nucleotides in length. In some embodiments, a guide RNA comprises a total of 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 nucleotides in length. In some embodiments, a guide RNA comprises a total of about 50 to about 60, about 50 to about 70, about 50 to about 80, about 50 to about 90, about 50 to about 100, about 50 to about 110, about 50 to about 120, about 50 to about 130, about 50 to about 140, about 60 to about 70, about 60 to about 80, about 60 to about 90, about 60 to about 100, about 60 to about 110, about 60 to about 120, about 60 to about 130, about 60 to about 140, about 70 to about 80, about 70 to about 90, about 70 to about 100, about 70 to about 110, about 70 to about 120, about 70 to about 130, about 70 to about 140, about 80 to about 90, about 80 to about 100, about 80 to about 110, about 80 to about 120, about 80 to about 130, about 80 to about 140, about 90 to about 100, about 90 to about 110, about 90 to about 120, about 90 to about 130, about 90 to about 140, about 100 to about 110, about 100 to about 120, about 100 to about 130, about 100 to about 140, about 110 to about 120, about 110 to about 130, about 110 to about 140, about 120 to about 130, about 120 to about 140, or about 130 to about 140 nucleotides in length. In some embodiments, a guide RNA comprises a total of about 50, about 60, about 70, about 80, about 90, about 100, about 110, about 120, about 130, or about 140 nucleotides in length. In some embodiments, a guide RNA comprises a total of at least about 50, about 60, about 70, about 80, about 90, about 100, about 110, about 120, or about 130 nucleotides in length. In some embodiments, a guide RNA comprises a total of at most about 60, about 70, about 80, about 90, about 100, about 110, about 120, about 130, or about 140 nucleotides in length. In some embodiment, a guide RNA comprises a total of 121, 122, 123, 124, 125, 126, 127, 128, or 129 nucleotides in length. In another embodiment, a guide RNA comprises a total of 124 nucleotides in length.

In some embodiments, a guide RNA comprises a spacer region or sequence (i.e., the target sequence) of 10 to 40 nucleotides in length. Illustrative spacer sequences are depicted in the single guide RNAs shown in FIGS. 18-19. In some embodiments, a guide RNA comprises a spacer sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length. In some embodiments, a guide RNA comprises a spacer sequence of about 10 to about 40 nucleotides in length. In some embodiments, a guide RNA comprises a spacer sequence of about 10 to about 15, about 10 to about 20, about 10 to about 25, about 10 to about 30, about 15 to about 20, about 15 to about 25, about 15 to about 30, about 20 to about 25, about 20 to about 30, about 25 to about 30 nucleotides, about 30 to about 35 nucleotides, or about 35 to about 40 nucleotides in length. In some embodiments, a guide RNA comprises a spacer sequence of about 10, about 15, about 20, about 25, about 30, about 35, or about 40 nucleotides in length. In some embodiments, a guide RNA comprises a spacer sequence of at least about 10, about 15, about 20, about 25, or about 30 nucleotides in length. In some embodiments, a guide RNA comprises a spacer sequence of at most about 15, about 20, about 25, about 30, or about 35 nucleotides in length. In some embodiment, a guide RNA comprises a spacer sequence of 10, 21, 22, 23, 24, 25, 26, 27, 28, 29, 30, 31, 32, 33, 34, or 35 nucleotides in length. In another embodiment, a guide RNA comprises a spacer sequence of 27 nucleotides in length. In some embodiments, the guide RNA comprises a sequence of 15, 16, 17, 18, 19, 20, 21, 22, 23, 24, 25, 26, 27, 28, 29, 30, 31, 32, 33, 34, 35, 36, 37, 38, 39, or 40 contiguous nucleotides that is complementary to a target sequence.

In some embodiments, a guide RNA comprises a scaffold sequence. The scaffold sequence acts as a substrate for a Cas12b protein to facilitate the formation of Cas12b protein-guide RNA complex. Illustrative scaffold sequences are depicted in the single guide RNAs shown in FIGS. 18-19. In some embodiments, the scaffold sequence comprises a tracrRNA sequence, or a stem loop structure. In some embodiments, the scaffold sequence comprises a tracrRNA sequence, and a stem loop structure. In some embodiments, a guide RNA comprises a scaffold sequence of from 30 to 130 nucleotides in length. In some embodiments, a guide RNA comprises a scaffold sequence of 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, or 130 nucleotides in length. In some embodiments, a guide RNA comprises a scaffold sequence of from about 30 to about 130 nucleotides in length. In some embodiments, a guide RNA comprises a scaffold sequence of from about 30 to about 40, about 30 to about 50, about 30 to about 60, about 30 to about 70, about 30 to about 75, about 30 to about 80, about 30 to about 90, about 30 to about 100, about 30 to about 110, about 30 to about 120, about 30 to about 130, about 40 to about 50, about 40 to about 60, about 40 to about 70, about 40 to about 75, about 40 to about 80, about 40 to about 90, about 40 to about 100, about 40 to about 110, about 40 to about 120, about 40 to about 130, about 50 to about 60, about 50 to about 70, about 50 to about 75, about 50 to about 80, about 50 to about 90, about 50 to about 100, about 50 to about 110, about 50 to about 120, about 50 to about 130, about 60 to about 70, about 60 to about 75, about 60 to about 80, about 60 to about 90, about 60 to about 100, about 60 to about 110, about 60 to about 120, about 60 to about 130, about 70 to about 75, about 70 to about 80, about 70 to about 90, about 70 to about 100, about 70 to about 110, about 70 to about 120, about 70 to about 130, about 75 to about 80, about 75 to about 90, about 75 to about 100, about 75 to about 110, about 75 to about 120, about 75 to about 130, about 80 to about 90, about 80 to about 100, about 80 to about 110, about 80 to about 120, about 80 to about 130, about 90 to about 100, about 90 to about 110, about 90 to about 120, about 90 to about 130, about 100 to about 110, about 100 to about 120, about 100 to about 130, about 110 to about 120, about 110 to about 130, or about 120 to about 130 nucleotides in length. In some embodiments, a guide RNA comprises a scaffold sequence of from about 30, about 40, about 50, about 60, about 70, about 75, about 80, about 90, about 100, about 110, about 120, or about 130 nucleotides in length. In some embodiments, a guide RNA comprises a scaffold sequence of from at least about 30, about 40, about 50, about 60, about 70, about 75, about 80, about 90, about 100, about 110, or about 120 nucleotides in length. In some embodiments, a guide RNA comprises a scaffold sequence of from at most about 40, about 50, about 60, about 70, about 75, about 80, about 90, about 100, about 110, about 120, or about 130 nucleotides in length.

In some embodiments, a guide RNA comprises a sequence comprising a stem loop structure. In some embodiments, a guide RNA comprises a sequence comprising a stem loop structure of from 8 to 35 nucleotides in length. In some embodiments, a guide RNA comprises a sequence comprising a stem loop structure that is 8, 9, 10, 11, 12, 13, 14, 15, 16, 17, 18, 19, 20, 21, 22, 23, 24, 25, 26, 27, 28, 29, 30, 31, 32, 33, 34, or 35 nucleotides in length. In some embodiments, a guide RNA comprises a sequence comprising a stem structure of from 2 to 16 nucleotides in length. In some embodiments, a guide RNA comprises a sequence comprising a stem structure of 2, 3, 4, 5, 6, 7, 8, 9, 10, 11, 12, 13, 14, 15, or 16 nucleotides in length. In some embodiments, a guide RNA comprises a sequence comprising a loop structure of from 3 to 31 nucleotides in length. In some embodiments, a guide RNA comprises a sequence comprising a loop structure of 3, 4, 5, 6, 7, 8, 9, 10, 11, 12, 13, 14, 15, 16, 17, 18, 19, 20, 21, 22, 23, 24, 25, 26, 27, 28, 29, 30, or 31 nucleotides in length.

In some embodiments, the guide RNA comprises a crRNA. In some embodiments, the crRNA comprises one or more chemically modified nucleotides. In some embodiments, the chemically modified crRNA may be 30 to 50 nucleotides in length. In some embodiments, the chemically modified crRNA may be of 30, 31, 32, 33, 34, 35, 36, 37, 38, 39, 40, 41, 42, 43, 44, 45, 46, 47, 48, 49, or 50 nucleotides in length. In some embodiments, the chemically modified crRNA may be of from about 30 to about 50 nucleotides in length. In some embodiments, the chemically modified crRNA may be of from about 30 to about 32, about 30 to about 34, about 30 to about 36, about 30 to about 38, about 30 to about 40, about 30 to about 42, about 30 to about 44, about 30 to about 46, about 30 to about 48, about 30 to about 50, about 32 to about 34, about 32 to about 36, about 32 to about 38, about 32 to about 40, about 32 to about 42, about 32 to about 44, about 32 to about 46, about 32 to about 48, about 32 to about 50, about 34 to about 36, about 34 to about 38, about 34 to about 40, about 34 to about 42, about 34 to about 44, about 34 to about 46, about 34 to about 48, about 34 to about 50, about 36 to about 38, about 36 to about 40, about 36 to about 42, about 36 to about 44, about 36 to about 46, about 36 to about 48, about 36 to about 50, about 38 to about 40, about 38 to about 42, about 38 to about 44, about 38 to about 46, about 38 to about 48, about 38 to about 50, about 40 to about 42, about 40 to about 44, about 40 to about 46, about 40 to about 48, about 40 to about 50, about 42 to about 44, about 42 to about 46, about 42 to about 48, about 42 to about 50, about 44 to about 46, about 44 to about 48, about 44 to about 50, about 46 to about 48, about 46 to about 50, or about 48 to about 50 nucleotides in length. In some embodiments, the chemically modified crRNA may be of from about 30, about 32, about 34, about 36, about 38, about 40, about 42, about 44, about 46, about 48, or about 50 nucleotides in length. In some embodiments, the chemically modified crRNA may be of from at least about 30, about 32, about 34, about 36, about 38, about 40, about 42, about 44, about 46, or about 48 nucleotides in length. In some embodiments, the chemically modified crRNA may be of from at most about 32, about 34, about 36, about 38, about 40, about 42, about 44, about 46, about 48, or about 50 nucleotides in length.

In some embodiments, the guide RNA comprises a tracrRNA. In some embodiments, the tracrRNA comprises one or more chemically modified nucleotides. In some embodiments, the chemically modified tracrRNA comprises a total of from 50 to 130 nucleotides in length. In some embodiments, the chemically modified tracrRNA comprises a total of 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, or 130 nucleotides in length. In some embodiments, the chemically modified tracrRNA comprises a total of about 30 to about 130 nucleotides in length. In some embodiments, the chemically modified tracrRNA comprises a total of about 30 to about 40, about 30 to about 50, about 30 to about 60, about 30 to about 70, about 30 to about 75, about 30 to about 80, about 30 to about 90, about 30 to about 100, about 30 to about 110, about 30 to about 120, about 30 to about 130, about 40 to about 50, about 40 to about 60, about 40 to about 70, about 40 to about 75, about 40 to about 80, about 40 to about 90, about 40 to about 100, about 40 to about 110, about 40 to about 120, about 40 to about 130, about 50 to about 60, about 50 to about 70, about 50 to about 75, about 50 to about 80, about 50 to about 90, about 50 to about 100, about 50 to about 110, about 50 to about 120, about 50 to about 130, about 60 to about 70, about 60 to about 75, about 60 to about 80, about 60 to about 90, about 60 to about 100, about 60 to about 110, about 60 to about 120, about 60 to about 130, about 70 to about 75, about 70 to about 80, about 70 to about 90, about 70 to about 100, about 70 to about 110, about 70 to about 120, about 70 to about 130, about 75 to about 80, about 75 to about 90, about 75 to about 100, about 75 to about 110, about 75 to about 120, about 75 to about 130, about 80 to about 90, about 80 to about 100, about 80 to about 110, about 80 to about 120, about 80 to about 130, about 90 to about 100, about 90 to about 110, about 90 to about 120, about 90 to about 130, about 100 to about 110, about 100 to about 120, about 100 to about 130, about 110 to about 120, about 110 to about 130, or about 120 to about 130 nucleotides in length. In some embodiments, the chemically modified tracrRNA comprises a total of about 30, about 40, about 50, about 60, about 70, about 75, about 80, about 90, about 100, about 110, about 120, or about 130 nucleotides in length. In some embodiments, the chemically modified tracrRNA comprises a total of at least about 30, about 40, about 50, about 60, about 70, about 75, about 80, about 90, about 100, about 110, or about 120 nucleotides in length. In some embodiments, the chemically modified tracrRNA comprises a total of at most about 40, about 50, about 60, about 70, about 75, about 80, about 90, about 100, about 110, about 120, or about 130 nucleotides in length.

In one aspect, provided herein is a single guide RNA that comprises (i) a spacer sequence and (ii) a scaffold sequence, wherein the spacer sequence is designed to be complementary and hybridize with a targeted polynucleotide sequence in a gene of interest, and wherein the scaffold sequence is a substrate for a Cas12b protein to facilitate the formation of Cas12b protein-guide RNA complex, the ribonucleoprotein (RNP) complex. In some embodiments, the scaffold sequence is of about 95 to 105 nucleotide long and constitute the 5'-end of the single guide RNA, and the spacer sequence that constitute the 3'-end of the single guide RNA is about 20 to 40 nucleotide long. In some embodiments, the scaffold sequence is of about 97 nucleotide long and constitute the 5'-end of the single guide RNA, and the spacer sequence that constitute the 3'-end of the single guide RNA is about 20 to 40 nucleotide long. In some embodiments, the scaffold sequence is of about 97 nucleotide long and constitute the 5'-end of the single guide RNA, and the spacer sequence that constitute the 3'-end of the single guide RNA is 23 nucleotide long.

Structure-Based Modification of Cas12b Guide RNAs

Also provided herein are chemical modifications to the guide RNAs described herein. In one aspect, the modifications are from a structurally based design that examines the interaction of the Cas12b protein and guide RNA, as exemplified FIG. 18, 19b and FIG. 19b. Nucleotide positions on the guide RNA are identified as targets for modification based on proximity to the nuclease and function.

In some embodiments, the structure of a guide RNA is maintained or modified based on the ribonucleoprotein (RNP)-sgRNA alignment. For example, in some embodiments, the guide RNA is designed to maintain or modify the stem-loop guide intramolecular interactions, e.g., the W-C base pairing at the stem. For another example, in some embodiments, the designed chemically modified guide RNA is designed to maintain or modify the loop nucleotide alignment with protein. In another example, in some embodiments, the designed chemically modified guide RNA is designed to maintain or modify the interaction of base (H-bond), 2'-hydroxyl (2'-OH), 4'-oxygen (ring-oxygen) of the sugar moiety, or phosphate linkage of each nucleotide to amino acid side chains of the protein. In another example, in some embodiments, the structure of the designed chemically modified guide RNA is maintained or modified based on the spatial arrangement of nucleotide within RNP, e.g., steric interaction, and room to accommodate bulky substitution like 2'-OMe and phosphorothioate (PS).

In some embodiments, an X-ray crystal approach is used for designing chemically modified Cas12b sgRNAs. For example, in some embodiments, selective 2'-hydroxyl substitution with 2'-O-methyl groups in Cas12b sgRNAs may improve the half-life of the sgRNA and sustain potency inside the cell. In some embodiments, modification of 2'-hydroxyl groups at sites where critical hydrogen bonds are formed between the sgRNA and the Cas12b protein is avoided, so as not to detriment RNP formation in the cytosol.

In some embodiments, a Cas12b protein is a Cas12b nuclease from *Bacillus hisashii* that contains 3 single mutations, e.g., K846R/S893R/E837G mutations that result in improved activity (see, e.g., Strecker et al. Nature communications 2019, 10(1): 212, of which entire contents are incorporated herein by reference).

In some embodiments, structure-based spacer and tracr designs are informed by the crystal structures of different Cas12b proteins in a ternary complex with gRNA and target or non-target DNAs. For example, in some embodiments, structure-based spacer and tracr designs are informed by the crystal structure of *Bacillus thermoamylovorans* Cas12b in a ternary complex with sgRNA and DNA (FIG. 19A) (see, e.g., Wu et al. Cell research 2017, 27(5):705 and Liang et al. Molecular cell 2017, 65(2):310-322, of which entire contents are incorporated herein by reference), which has 99% identity to the *Bacillus hisashii* Cas12b triple mutant construct having K846R/S893R/E837G mutations (FIG. 19B) (see, e.g., Wu et al. Cell research 2017, 27(5):705 and Strecker et al. Nature communications 2019, 10(1): 212, of which entire contents are incorporated herein by reference). By comparison, *Alicyclobacillus acidoterrestris* Cas12b has 33% to *Bacillus hisashii* Cas12b. In some embodiments, the crystal structure from *B. thermoamylovorans* is used as a model to determine where 2' modifications would be tolerated in *Bacillus hisashii* Cas12b.

In some embodiments, any positions in the crystal structure where there appeared to be a hydrogen bond between the 2'OH of a given nucleotide and the Cas12b protein (or another part of the guide RNA) are left unmodified. In some embodiments, any positions where a clash was predicted to occur between a 2'-O-Me and the protein are left unmodified. In some embodiments, at sites where the 2'OH is solvent-exposed or otherwise distant from protein residues, a 2'-O-Me substitution is made. In some embodiments, the entire guide RNA is modified according to the aforementioned strategy. In some embodiments, only the tracr region of the guide RNA is modified according to the aforementioned strategy. In some embodiments, only the spacer region of the guide RNA is modified according to the aforementioned strategy. In some embodiments, specific stem loops of the tracr are left unmodified and it is identified whether the effect of incorporating 2'-O-Me substitutions in these structural regions is beneficial or not.

In some embodiments, the guide RNA is modified by the structure-based incorporation of 2' modifications. In some embodiment, it is avoided to place 2'OMe modifications at sites that appear important for guide RNA structure or RNP formation. For example, in some embodiments, 2'-hydroxyls that do not form contacts may be converted to 2'-O-methyl groups to impart improved chemical stability. For another example, in some embodiments, 2'-hydroxyls that form contacts with protein or other regions of the gRNA may be left unmodified, since modification may have a negative impact on RNP formation and therefore nuclease activity. FIG. 18 shows exemplary structure-based incorporation of 2' modifications.

In one aspect, the guide RNA comprises a chemical modification. In some embodiments, the chemical modifications include but not limited to sugar and nucleobase modifications and combinations thereof. In some embodiments, the guide RNA comprises a modification at a specific nucleotide position. In some embodiments, the guide RNA comprises one or more modifications at one or more specific positions.

In some embodiments, the chemical modification is in the spacer sequence of the RNA. In some embodiments, the chemical modification is in the scaffold sequence of the RNA. In some embodiments, the chemical modification is in a stem loop structure of the scaffold sequence. In some embodiments, the chemical modification is in the crRNA sequence of the guide RNA. In some embodiments, the chemical modification is in the tracrRNA sequence of the guide RNA.

In some embodiments, the chemical modification comprises a 2'-OMe modification. In some embodiments, the chemical modification comprises a nebularin. In some embodiments, the chemical modification comprises a deoxynebularin. In some embodiments, the chemical modification comprises a 2'-O-MOE modification. In some embodiments, the chemical modification comprises a 2'-F modification.

In some embodiments, the chemically modified guide RNA comprises modifications, such as, for example, 2'-O-methyl modifications, 2'-O-(2-methoxyethyl) modifications, 2'-fluoro modifications, phosphorothioate modifications, inverted abasic modifications, deoxyribonucleotides, bicylic ribose analog (e.g., locked nucleic acid (LNA), C-ethylene-bridged nucleic acid (ENA), bridged nucleic acid (BNA), unlocked nucleic acid (UNA)), base or nucleobase modifications, internucleoside linkage modifications, ribonebularine, 2'-O-methylnebularine, or 2'-deoxynebularine. Other examples of modifications include, but are not limited to, 5'adenylate, 5' guanosine-triphosphate cap, 5'N7-Methyl-guanosine-triphosphate cap, 5'triphosphate cap, 3'phosphate, 3'thiophosphate, 5'phosphate, 5'thiophosphate, Cis-Syn thymidine dimer, trimers, C12 spacer, C3 spacer, C6 spacer, dSpacer, PC spacer, rSpacer, Spacer 18, Spacer 9,3'-3' modifications, 5'-5' modifications, abasic, acridine, azobenzene, biotin, biotin BB, biotin TEG, cholesteryl TEG, desthiobiotin TEG, DNP TEG, DNP-X, DOTA, dT-Biotin, dual biotin, PC biotin, psoralen C2, psoralen C6, TINA, 3'DABCYL, black hole quencher 1, black hole quencer 2, DABCYL SE, dT-DABCYL, IRDye QC-1, QSY-21, QSY-35, QSY-7, QSY-9, carboxyl linker, thiol linkers, 2'deoxy-ribonucleoside analog purine, 2'deoxyribonucleoside analog pyrimidine, ribonucleoside analog, 2'-O-methyl ribonucleoside analog, sugar modified analogs, wobble/universal bases, fluorescent dye label, 2'fluoro RNA, 2'O-methyl RNA, methylphosphonate, phosphodiester DNA, phosphodiester RNA, phosphothioate DNA, phosphorothioate RNA, UNA, pseudouridine-5'-triphosphate, 5-methylcyti-dine-5'-triphosphate, 2-O-methyl 3phosphorothioate or any combinations thereof.

In some embodiments, the chemically modified guide RNA comprises modification on the sugar group. In some embodiments, modified sugar group may control oligonucleotide binding affinity for complementary strands, duplex formation, or interaction with nucleases. Examples of chemical modifications to the sugar group include, but are not limited to, 2'-O-methyl (2'-OMe), 2'-fluoro (2'-F), 2'-deoxy, 2'-O-(2-methoxyethyl) (2'-MOE), 2'-NH2, 2'-O-Allyl, 2'-O-Ethylamine, 2'-O-Cyanoethyl, 2'-O-Acetalester, or a bicyclic nucleotide such as locked nucleic acid (LNA), 2'-(5-constrained ethyl (S-cEt)), constrained MOE, or 2'-0, 4'-C-aminomethylene bridged nucleic acid (2',4'-BNA$^{NC}$). In some embodiments, 2'-O-methyl modification can increase binding affinity of oligonucleotides. In some embodiments, 2'-O-methyl modification can enhance nuclease stability of oligonucleotides. In some embodiments, 2'-fluoro modification can increase oligonucleotide binding affinity and nuclease stability.

In some embodiments, the chemically modified guide RNA binds the Cas12b protein with increased binding affinity as compared to an unmodified single guide RNA. In some embodiments, the chemically modified single guide RNA binds the Cas12b protein with increased binding affinity by at least 5%, at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, at least 1000%, at least 2000%, at least 3000%, at least 4000%, at least 5000%, at least 6000%, at least 7000%, at least 8000%, at least 9000%, at least 10000%, at least 20000%, at least 30000%, at least 40000%, at least 50000%, at least 60000%, at least 70000%, at least 80000%, at least 90000%, or at least 100000% as compared to an unmodified single guide RNA. In some embodiments, the chemically modified guide RNA binds the Cas12b protein with increased binding affinity by at least 2 fold, at least 3 fold, at least 4 fold, at least 5 fold, at least 10 fold, at least 20 fold, at least 25 fold, at least 30 fold, at least 40 fold, at least 50 fold, at least 60 fold, at least 70 fold, at least 80 fold, at least 90 fold, at least 100 fold or >100 fold, at least 200 fold, at least 300 fold, at least 400 fold, at least 500 fold, at least 600 fold, at least 700 fold, at least 800 fold, at least 900 fold, at least 1000 fold, at least 2000 fold, at least 3000 fold, at least 4000 fold, at least 5000 fold, at least 6000 fold, at least 7000 fold, at least 8000 fold, at least 9000 fold, or at least 10000 fold as compared to an unmodified guide RNA.

In some embodiments, the chemically modified guide RNA increases the editing efficiency as compared to an unmodified guide RNA. In some embodiments, the chemically modified single guide RNA increases the editing efficiency by at least 5%, at least 10%, at least 20%, at least 30%, at least 40%, at least 50%, at least 60%, at least 70%, at least 80%, at least 90%, at least 100% or >100%, at least 200%, at least 300%, at least 400%, at least 500%, at least 600%, at least 700%, at least 800%, at least 900%, at least 1000%, at least 2000%, at least 3000%, at least 4000%, at least 5000%, at least 6000%, at least 7000%, at least 8000%, at least 9000%, at least 10000%, at least 20000%, at least 30000%, at least 40000%, at least 50000%, at least 60000%, at least 70000%, at least 80000%, at least 90000%, or at least 100000% as compared to an unmodified guide RNA. In some embodiments, the chemically modified single guide RNA increases editing efficiency by at least 2 fold, at least 3 fold, at least 4 fold, at least 5 fold, at least 10 fold, at least 20 fold, at least 25 fold, at least 30 fold, at least 40 fold, at least 50 fold, at least 60 fold, at least 70 fold, at least 80 fold, at least 90 fold, at least 100 fold or >100 fold, at least 200 fold, at least 300 fold, at least 400 fold, at least 500 fold, at least 600 fold, at least 700 fold, at least 800 fold, at least 900 fold, at least 1000 fold, at least 2000 fold, at least 3000 fold, at least 4000 fold, at least 5000 fold, at least 6000 fold, at least 7000 fold, at least 8000 fold, at least 9000 fold, or at least 10000 fold as compared to an unmodified guide RNA.

In some embodiments, the chemically modified guide RNA increases the stability of the Cas12b-gRNA complex as compared to an unmodified single guide RNA. In some embodiments, the single guide RNA increases the stability of the Cas12b-gRNA complex by at least 5%, at least 10%, at least 20%, at least 30%, at least 40%, at least 50%, at least 60%, at least 70%, at least 80%, at least 90%, at least 100%, or higher at least 200%, at least 300%, at least 400%, at least 500%, at least 600%, at least 700%, at least 800%, at least 900%, at least 1000%, at least 2000%, at least 3000%, at least 4000%, at least 5000%, at least 6000%, at least 7000%, at least 8000%, at least 9000%, at least 10000%, at least 20000%, at least 30000%, at least 40000%, at least 50000%, at least 60000%, at least 70000%, at least 80000%, at least 90000%, or at least 100000% as compared to an unmodified single guide RNA. In some embodiments, the chemically modified guide RNA increases the stability of the Cas12b-gRNA complex by at least 2 fold, at least 3 fold, at least 4 fold, at least 5 fold, at least 10 fold, at least 20 fold, at least 25 fold, at least 30 fold, at least 40 fold, at least 50 fold, at least 60 fold, at least 70 fold, at least 80 fold, at least 90 fold, at least 100 fold or >100 fold, at least 200 fold, at least 300 fold, at least 400 fold, at least 500 fold, at least 600 fold, at least 700 fold, at least 800 fold, at least 900 fold, at least 1000 fold, at least 2000 fold, at least 3000 fold, at least 4000 fold, at least 5000 fold, at least 6000 fold, at least 7000 fold, at least 8000 fold, at least 9000 fold, or at least 10000 fold as compared to an unmodified guide RNA.

In some embodiments, the chemically modified guide RNA increases the stability of the guide RNA in vitro as compared to an unmodified guide RNA. In some embodiments, the chemically modified single guide RNA increases the stability of the guide RNA in vitro by at least 5%, at least 10%, at least 20%, at least 30%, at least 40%, at least 50%, at least 60%, at least 70%, at least 80%, at least 90%, at least 100% or >100%, at least 200%, at least 300%, at least 400%, at least 500%, at least 600%, at least 700%, at least 800%, at least 900%, at least 1000%, at least 2000%, at least 3000%, at least 4000%, at least 5000%, at least 6000%, at least 7000%, at least 8000%, at least 9000%, at least 10000%, at least 20000%, at least 30000%, at least 40000%, at least 50000%, at least 60000%, at least 70000%, at least 80000%, at least 90000%, or at least 100000% as compared to an unmodified single guide RNA. In some embodiments, the chemically modified guide RNA increases the stability of the guide RNA in vitro by at least 2 fold, at least 3 fold, at least 4 fold, at least 5 fold, at least 10 fold, at least 20 fold, at least 25 fold, at least 30 fold, at least 40 fold, at least 50 fold, at least 60 fold, at least 70 fold, at least 80 fold, at least 90 fold, at least 100 fold or >100 fold, at least 200 fold, at least 300 fold, at least 400 fold, at least 500 fold, at least 600 fold, at least 700 fold, at least 800 fold, at least 900 fold, at least 1000 fold, at least 2000 fold, at least 3000 fold, at least 4000 fold, at least 5000 fold, at least 6000 fold, at least 7000 fold, at least 8000 fold, at least 9000 fold, or at least 10000 fold as compared to an unmodified guide RNA.

In some embodiments, the chemically modified guide RNA increases the stability of the guide RNA in vivo as compared to an unmodified guide RNA. In some embodiments, the chemically modified single guide RNA increases the stability of the guide RNA in vivo by at least 5%, at least 10%, at least 20%, at least 30%, at least 40%, at least 50%, at least 60%, at least 70%, at least 80%, at least 90%, at least 100% or >100% at least 200%, at least 300%, at least 400%, at least 500%, at least 600%, at least 700%, at least 800%, at least 900%, at least 1000%, at least 2000%, at least 3000%, at least 4000%, at least 5000%, at least 6000%, at least 7000%, at least 8000%, at least 9000%, at least 10000%, at least 20000%, at least 30000%, at least 40000%, at least 50000%, at least 60000%, at least 70000%, at least 80000%, at least 90000%, or at least 100000% as compared to an unmodified guide RNA. In some embodiments, the chemically modified guide RNA increases the stability of the guide RNA in vivo by at least 2 fold, at least 3 fold, at least 4 fold, at least 5 fold, at least 10 fold, at least 20 fold, at least 25 fold, at least 30 fold, at least 40 fold, at least 50 fold, at least 60 fold, at least 70 fold, at least 80 fold, at least 90 fold, at least 100 fold or >100 fold, at least 200 fold, at least 300 fold, at least 400 fold, at least 500 fold, at least 600 fold, at least 700 fold, at least 800 fold, at least 900 fold, at least 1000 fold, at least 2000 fold, at least 3000 fold, at least 4000 fold, at least 5000 fold, at least 6000 fold, at least 7000 fold, at least 8000 fold, at least 9000 fold, or at least 10000 fold as compared to an unmodified guide RNA.

In some embodiments, the chemically modified guide RNA increases the stability of the guide RNA ex vivo as compared to an unmodified guide RNA. In some embodiments, the chemically modified single RNA increases the stability of the guide RNA ex vivo by at least 5%, at least 10%, at least 20%, at least 30%, at least 40%, at least 50%, at least 60%, at least 70%, at least 80%, at least 90%, at least 100% or >100% at least 200%, at least 300%, at least 400%, at least 500%, at least 600%, at least 700%, at least 800%, at least 900%, at least 1000%, at least 2000%, at least 3000%, at least 4000%, at least 5000%, at least 6000%, at least 7000%, at least 8000%, at least 9000%, at least 10000%, at least 20000%, at least 30000%, at least 40000%, at least 50000%, at least 60000%, at least 70000%, at least 80000%, at least 90000%, or at least 100000% as compared to an unmodified guide RNA. In some embodiments, the chemically modified guide RNA increases the stability of the guide RNA ex vivo by at least 2 fold, at least 3 fold, at least 4 fold, at least 5 fold, at least 10 fold, at least 20 fold, at least 25 fold, at least 30 fold, at least 40 fold, at least 50 fold, at least 60 fold, at least 70 fold, at least 80 fold, at least 90 fold, at least 100 fold or >100 fold, at least 200 fold, at least 300 fold, at least 400 fold, at least 500 fold, at least 600 fold, at least 700 fold, at least 800 fold, at least 900 fold, at least 1000 fold, at least 2000 fold, at least 3000 fold, at least 4000 fold, at least 5000 fold, at least 6000 fold, at least 7000 fold, at least 8000 fold, at least 9000 fold, or at least 10000 fold as compared to an unmodified guide RNA.

In some embodiments, the chemically modified guide RNA increases the resistance to degradation in a cell as compared to an unmodified guide RNA. In some embodiments, the chemically modified guide RNA increases the resistance to degradation in a cell by at least 5%, at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, at least 1000%, at least 2000%, at least 3000%, at least 4000%, at least 5000%, at least 6000%, at least 7000%, at least 8000%, at least 9000%, at least 10000%, at least 20000%, at least 30000%, at least 40000%, at least 50000%, at least 60000%, at least 70000%, at least 80000%, at least 90000%, or at least 100000% as compared to an unmodified guide RNA. In some embodiments, the modified guide RNA increases the resistance to degradation in a cell by at least 2 fold, at least 3 fold, at least 4 fold, at least 5 fold, at least 10 fold, at least 20 fold, at least 25 fold, at least 30 fold, at least 40 fold, at least 50 fold, at least 60 fold, at least 70 fold, at least 80 fold, at least 90 fold, at least 100 fold, at least 200 fold, at least 300 fold, at least 400 fold, at least 500 fold, at least 600 fold, at least 700 fold, at least 800 fold, at least 900 fold, at least 1000 fold, at least 2000 fold, at least 3000 fold, at least 4000 fold, at least 5000 fold, at least 6000 fold, at least 7000 fold, at least 8000 fold, at least 9000 fold, or at least 10000 fold as compared to an unmodified guide RNA.

In some embodiments, the chemical modification on the guide RNA results in less off-target effect in the cell as compared to an unmodified guide RNA. In some embodiments, the modification results in at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 98%, at least 99%, at least 99.5%, at least 99.9%, or 100% less off-target effect in the cell as compared to an unmodified guide RNA. In some embodiments, the modification results in at least 2 fold, at least 3 fold, at least 4 fold, at least 5 fold, at least 10 fold, at least 20 fold, at least 25 fold, at least 30 fold, at least 40 fold, at least 50 fold, at least 60 fold, at least 70 fold, at least 80 fold, at least 90 fold, at least 100 fold, at least 200 fold, at least 300 fold, at least 400 fold, at least 500 fold, at least 600 fold, at least 700 fold, at least 800 fold, at least 900 fold, at least 1000 fold, at least 2000 fold, at least 3000 fold, at least 4000 fold, at least 5000 fold, at least 6000 fold, at least 7000 fold, at least 8000 fold, at least 9000 fold, or at least 10000 fold less off-target effect in the cell as compared to an unmodified guide RNA.

In some embodiments, the chemically modified guide RNA exhibits increased stability in the cell compared to an unmodified guide RNA, wherein the stability is measured by half-life of the guide RNA in the cell. In some embodiments, the guide RNA exhibits increased stability in the cell by at least 5%, at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, at least 1000%, at least 2000%, at least 3000%, at least 4000%, at least 5000%, at least 6000%, at least 7000%, at least 8000%, at least 9000%, at least 10000%, at least 20000%, at least 30000%, at least 40000%, at least 50000%, at least 60000%, at least 70000%, at least 80000%, at least 90000%, or at least 100000% compared to an unmodified single guide RNA. In some embodiments, the single guide RNA exhibits increased stability in the cell by at least 2 fold, at least 3 fold, at least 4 fold, at least 5 fold, at least 10 fold, at least 20 fold, at least 25 fold, at least 30 fold, at least 40 fold, at least 50 fold, at least 60 fold, at least 70 fold, at least 80 fold, at least 90 fold, at least 100 fold, or higher compared to an unmodified single guide RNA.

In some embodiments, the chemically modified guide RNA exhibits increased half-life in the cell compared to an unmodified guide RNA. In some embodiments, the chemically modified guide RNA exhibits increased half-life in the cell by at least 5%, at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, at least 1000%, at least 2000%, at least 3000%, at least 4000%, at least 5000%, at least 6000%, at least 7000%, at least 8000%, at least 9000%, at least 10000%, at least 20000%, at least 30000%, at least 40000%, at least 50000%, at least 60000%, at least 70000%, at least 80000%, at least 90000%, or at least 100000% compared to an unmodified guide RNA. In some embodiments, the chemically modified guide RNA exhibits increased half-life in the cell by at least 2 fold, at least 3 fold, at least 4 fold, at least 5 fold, at least 10 fold, at least 20 fold, at least 25 fold, at least 30 fold, at least 40 fold, at least 50 fold, at least 60 fold, at least 70 fold, at least 80 fold, at least 90 fold, at least 100 fold, at least 200 fold, at least 300 fold, at least 400 fold, at least 500 fold, at least 600 fold, at least 700 fold, at least 800 fold, at least 900 fold, at least 1000 fold, at least 2000 fold, at least 3000 fold, at least 4000 fold, at least 5000 fold, at least 6000 fold, at least 7000 fold, at least 8000 fold, at least 9000 fold, or at least 10000 fold as compared to an unmodified guide RNA.

In some embodiments, the chemically modified guide RNA comprises modification on the phosphate group. Examples of chemical modifications to the phosphate group includes, but are not limited to, a phosphorothioate (PS), phosphonoacetate (PACE), thiophosphonoacetate (thio-PACE), amide, triazole, phosphonate, or phosphotriester modification. In some embodiments, PS linkage can refer to a bond where a sulfur is substituted for one bridging phosphate oxygen in a phosphodiester linkage, e.g., between nucleotides.

In some embodiments, the chemically modified guide RNA comprises a phosphorothioate (PS) linkage at a 5' end or at a 3' end. In some embodiments, a guide RNA comprises a phosphorothioate (PS) linkage at a 5' end. In some embodiments, the chemically modified guide RNA comprises a phosphorothioate (PS) linkage at a 3' end. In some embodiments, the chemically modified guide RNA comprises a phosphorothioate (PS) linkage at a 5' end and at a 3' end. In some embodiments, the chemically modified guide RNA comprises one, two, three, four or more than four phosphorothioate linkages at the 5' end or at the 3' end. In some embodiments, the chemically modified guide RNA comprises three phosphorothioate (PS) linkages at the 5' end or at the 3' end. In some embodiments, the chemically modified guide RNA comprises three phosphorothioate linkages at the 3' end. In some embodiments, the chemically modified guide RNA comprises two and no more than two (i.e., only two)

phosphorothioate (PS) linkages at the 5' end or at the 3' end. In some embodiments, the chemically modified guide RNA comprises two and no more than two (i.e., only two) contiguous phosphorothioate (PS) linkages at the 5' end or at the 3' end. In some embodiments, the chemically modified guide RNA comprises three contiguous phosphorothioate (PS) linkages at the 5' end or at the 3' end. In some embodiments, the chemically modified guide RNA comprises two and no more than two (i.e., only two) contiguous phosphorothioate (PS) linkages at the 5' end and three contiguous phosphorothioate (PS) linkages at the 3' end. In some embodiments, the chemically modified guide RNA comprises two and no more than two (i.e., only two) contiguous phosphorothioate (PS) linkages at the 3' end and three contiguous phosphorothioate (PS) linkages at the 5' end. In some embodiments, the chemically modified guide RNA comprises two or three phosphorothioate (PS) linkages after the first 3 nucleotides on the 5' end or before the last three nucleotides on the 3' end. In some embodiments, the chemically modified guide RNA comprises two or three contiguous phosphorothioate (PS) linkages after the first 3 nucleotides on the 5' end or before the last three nucleotides on the 3' end.

In some embodiments, the chemically modified guide RNA comprises modifications on the nucleobase. Examples of chemical modifications to the nucleobase include, but are not limited to, 2-thiouridine, 4-thiouridine, N6-methyladenosine, pseudouridine, 2,6-diaminopurine, inosine, thymidine, 5-methylcytosine, 5-substituted pyrimidine, isoguanine, isocytosine, or halogenated aromatic groups.

In some embodiments, chemically modified guide RNA comprises nebularine. In some embodiments, nebularine is a purine ribonucleoside that is derived from a beta-D-ribose and is 9H-purine attached to a beta-D-ribofuranosyl residue at position 9 via a glycosidic (N-glycosyl) linkage. In some embodiments, nebularine is a purine ribonucleoside with no exocyclic functional moiety or substitution. In some embodiments, nebularine is a purine ribonucleoside. In some embodiments, nebularine is a purine D-ribonucleoside. In some embodiments, nebularine is further modified chemically. In this application, "X," "x," and "dX" may be used to depict a ribonebularine modification, a 2'-O-methylnebularine modification, and a 2'-deoxynebularine modification, respectively, in guide RNA sequences (e.g., Table 1). In some embodiments, substitution of a nucleotide (e.g., A) of a guide RNA sequence (e.g., spacer region or tracr region) with nebularine may reduce off-target effects without affecting the guide RNA activity. In some embodiments, the nebularine, the deoxynebularine, or 2'-O-methylnebularine replaces an adenine in an unmodified guide RNA. In some embodiments, the nebularine, the deoxynebularine, or 2'-O-methylnebularine is in the spacer sequence. In some embodiments, the nebularine, the deoxynebularine, or 2'-O-methylnebularine is in the scaffold sequence. In some embodiments, the nebularine, the deoxynebularine, or 2'-O-methylnebularine is in a tracrRNA sequence in the scaffold sequence. In some embodiments, the nebularine, the deoxynebularine, or 2'-O-methylnebularine is in a crRNA sequence in the scaffold sequence. In some embodiments, the nebularine, the deoxynebularine, or 2'-O-methylnebularine is in a stem loop structure in the scaffold sequence.

In some embodiments, the modified guide RNA comprises from 1 to 150 chemically modified nucleotides. In some embodiments, a guide RNA comprises a total of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 chemically modified nucleotides. In some embodiments, the chemically modified guide RNA comprises a total of about 1 to about 45 chemically modified nucleotides. In some embodiments, the chemically modified guide RNA comprises a total of about 1 to about 3, about 1 to about 5, about 1 to about 10, about 1 to about 15, about 1 to about 20, about 1 to about 25, about 1 to about 30, about 1 to about 35, about 1 to about 40, about 1 to about 45, about 3 to about 5, about 3 to about 10, about 3 to about 15, about 3 to about 20, about 3 to about 25, about 3 to about 30, about 3 to about 35, about 3 to about 40, about 3 to about 45, about 5 to about 10, about 5 to about 15, about 5 to about 20, about 5 to about 25, about 5 to about 30, about 5 to about 35, about 5 to about 40, about 5 to about 45, about 10 to about 15, about 10 to about 20, about 10 to about 25, about 10 to about 30, about 10 to about 35, about 10 to about 40, about 10 to about 45, about 15 to about 20, about 15 to about 25, about 15 to about 30, about 15 to about 35, about 15 to about 40, about 15 to about 45, about 20 to about 25, about 20 to about 30, about 20 to about 35, about 20 to about 40, about 20 to about 45, about 25 to about 30, about 25 to about 35, about 25 to about 40, about 25 to about 45, about 30 to about 35, about 30 to about 40, about 30 to about 45, about 35 to about 40, about 35 to about 45, about 40 to about 45, or about 45 to about 50 chemically modified nucleotides. In some embodiments, the chemically modified guide RNA comprises a total of about 1, about 3, about 5, about 10, about 15, about 20, about 25, about 30, about 35, about 40, about 45, or about 50 chemically modified nucleotides. In some embodiments, the chemically modified guide RNA comprises a total of at least about 1, about 3, about 5, about 10, about 15, about 20, about 25, about 30, about 35, about 40, about 45, or about 50 chemically modified nucleotides. In some embodiments, the chemically modified guide RNA comprises a total of at most about 3, about 5, about 10, about 15, about 20, about 25, about 30, about 35, about 40, about 45, or about 50 chemically modified nucleotides. In some embodiments, the chemically modified guide RNA comprises a total of about 50 to about 140 chemically modified nucleotides. In some embodiments, the chemically modified guide RNA comprises a total of about 50 to about 60, about 50 to about 70, about 50 to about 80, about 50 to about 90, about 50 to about 100, about 50 to about 110, about 50 to about 120, about 50 to about 130, about 50 to about 140, about 60 to about 70, about 60 to about 80, about 60 to about 90, about 60 to about 100, about 60 to about 110, about 60 to about 120, about 60 to about 130, about 60 to about 140, about 70 to about 80, about 70 to about 90, about 70 to about 100, about 70 to about 110, about 70 to about 120, about 70 to about 130, about 70 to about 140, about 80 to about 90, about 80 to about 100, about 80 to about 110, about 80 to about 120, about 80 to about 130, about 80 to about 140, about 90 to about 100, about 90 to about 110, about 90 to about 120, about 90 to about 130, about 90 to about 140, about 100 to about 110, about 100 to about 120, about 100 to about 130, about 100 to about 140, about 110 to about 120, about 110 to about 130, about 110 to about 140, about 120 to about 130, about 120 to about 140, or about 130 to about 140 chemically modified nucleotides. In some embodiments, the chemically modified guide RNA comprises a total of about 50, about 60, about 70, about 80, about 90, about 100, about 110, about 120, about 130, or about 140 chemically modified nucleotides. In some embodiments, the chemically modified guide RNA comprises a total of at least about 50, about 60, about 70, about 80, about 90, about 100, about 110, about 120, or about 130 chemically modified nucleotides. In some embodiments, the chemically modified guide RNA comprises a total of at most about 60, about 70, about 80, about 90, about 100, about 110, about 120, about 130, or about 140 chemically modified nucleotides. In some embodiment, the chemically modified guide RNA comprises a total of 121, 122, 123, 124, 125, 126, 127, 128, or 129 chemically modified nucleotides. In another embodiment, the modified guide RNA comprises a total of 124 chemically modified nucleotides.

In some embodiments, the modified guide RNA comprises about 1% to about 100% chemically modified nucleotides. In some embodiments, the chemically modified guide RNA comprises about 1% to about 10%, about 1% to about 20%, about 1% to about 30%, about 1% to about 40%, about 1% to about 50%, about 1% to about 60%, about 1% to about 70%, about 1% to about 80%, about 1% to about 90%, about 1% to about 95%, about 1% to about 100%, about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 10% to about 100%, about 20% to about 30%, about 20% to about 40%, about 20% to about 50%, about 20% to about 60%, about 20% to about 70%, about 20% to about 80%, about 20% to about 90%, about 20% to about 95%, about 20% to about 100%, about 30% to about 40%, about 30% to about 50%, about 30% to about 60%, about 30% to about 70%, about 30% to about 80%, about 30% to about 90%, about 30% to about 95%, about 30% to about 100%, about 40% to about 50%, about 40% to about 60%, about 40% to about 70%, about 40% to about 80%, about 40% to about 90%, about 40% to about 95%, about 40% to about 100%, about 50% to about 60%, about 50% to about 70%, about 50% to about 80%, about 50% to about 90%, about 50% to about 95%, about 50% to about 100%, about 60% to about 70%, about 60% to about 80%, about 60% to about 90%, about 60% to about 95%, about 60% to about 100%, about 70% to about 80%, about 70% to about 90%, about 70% to about 95%, about 70% to about 100%, about 80% to about 90%, about 80% to about 95%, about 80% to about 100%, about 90% to about 95%, about 90% to about 100%, or about 95% to about 100% chemically modified nucleotides. In some embodiments, the chemically modified nucleotide comprises about 1%, about 10%, about 20%, about 30%, about 40%, about 50%, about 60%, about 70%, about 80%, about 90%, about 95%, or about 100% chemically modified nucleotides. In some embodiments, the chemically modified guide RNA comprises at least about 1%, about 10%, about 20%, about 30%, about 40%, about 50%, about 60%, about 70%, about 80%, about 90%, or about 95% chemically modified nucleotides. In some embodiments, the chemically modified guide RNA comprises at most about 10%, about 20%, about 30%, about 40%, about 50%, about 60%, about 70%, about 80%, about 90%, about 95%, or about 100% chemically modified nucleotides.

In some embodiments, the chemically modified guide RNA has a chemically modified nucleotide on one or more of the positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 in the 5'-3' direction in the guide RNA sequence.

In some embodiments, the chemically modified guide RNA has a chemically modified nucleotide on one or more of the positions which are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 nucleotides from the 5' end of the guide RNA sequence.

In some embodiments, the chemically modified guide RNA has a chemically modified nucleotide on one or more the positions where are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 nucleotides from the 3' end of the guide RNA sequence.

In some embodiments, the chemically modified guide RNA has a one or more chemical modifications in the spacer region, i.e., the targeting or crRNA sequence. In some embodiments, the spacer sequence comprises a total of from 1 to 40 chemically modified nucleotides. In some embodiments, the spacer region comprises a total of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 chemically modified nucleotides. In some embodiments, the spacer sequence comprises a total of about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 23, about 25, about 26, about 27, about 28, about 29 or about 30 chemically modified nucleotides. In some embodiments, the spacer sequence comprises a total of at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 23, about 25, about 26, about 27, about 28, about 29 or about 30 chemically modified nucleotides. In some embodiments, the spacer sequence comprises a total of at most about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 23, about 25, about 26, about 27, about 28, about 29 or about 30 chemically modified nucleotides. In some embodiments, the spacer sequence comprises a total of about 10 to about 30 chemically modified nucleotides. In some embodiments, the spacer sequence comprises a total of about 10 to about 15, about 10 to about 20, about 10 to about 25, about 10 to about 30, about 15 to about 20, about 15 to about 25, about 15 to about 30, about 20 to about 25, about 20 to about 30, or about 25 to about 30 chemically modified nucleotides. In some embodiments, the spacer sequence comprises a total of about 10, about 15, about 20, about 25, or about 30 chemically modified nucleotides. In some embodiments, the spacer sequence comprises a total of at least about 10, about 15, about 20, or about 25 chemically modified nucleotides. In some embodiments, the spacer sequence comprises a total of at most about 15, about 20, about 25, or about 30 chemically modified nucleotides. In one embodiment, the spacer sequence comprises a total of 27 chemically modified nucleotides. In another embodiment, the spacer sequence comprises a total of 13 chemically modified nucleotides.

In some embodiments, the spacer sequence comprises from 1% to 100% chemically modified nucleotides. In some embodiments, the spacer sequence comprises about 1% to about 100% chemically modified nucleotides. In some embodiments, the spacer sequence comprises about 1% to about 10%, about 1% to about 20%, about 1% to about 30%, about 1% to about 40%, about 1% to about 50%, about 1% to about 60%, about 1% to about 70%, about 1% to about 80%, about 1% to about 90%, about 1% to about 95%, about 1% to about 100%, about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 10% to about 100%, about 20% to about 30%, about 20% to about 40%, about 20% to about 50%, about 20% to about 60%, about 20% to about 70%, about 20% to about 80%, about 20% to about 90%, about 20% to about 95%, about 20% to about 100%, about 30% to about 40%, about 30% to about 50%, about 30% to about 60%, about 30% to about 70%, about 30% to about 80%, about 30% to about 90%, about 30% to about 95%, about 30% to about 100%, about 40% to about 50%, about 40% to about 60%, about 40% to about 70%, about 40% to about 80%, about 40% to about 90%, about 40% to about 95%, about 40% to about 100%, about 50% to about 60%, about 50% to about 70%, about 50% to about 80%, about 50% to about 90%, about 50% to about 95%, about 50% to about 100%, about 60% to about 70%, about 60% to about 80%, about 60% to about 90%, about 60% to about 95%, about 60% to about 100%, about 70% to about 80%, about 70% to about 90%, about 70% to about 95%, about 70% to about 100%, about 80% to about 90%, about 80% to about 95%, about 80% to about 100%, about 90% to about 95%, about 90% to about 100%, or about 95% to about 100% chemically modified nucleotides. In some embodiments, the spacer sequence comprises about 1%, about 10%, about 20%, about 30%, about 40%, about 50%, about 60%, about 70%, about 80%, about 90%, about 95%, or about 100% chemically modified nucleotides. In some embodiments, the spacer sequence comprises at least about 1%, about 10%, about 20%, about 30%, about 40%, about 50%, about 60%, about 70%, about 80%, about 90%, or about 95% chemically modified nucleotides. In some embodiments, the spacer sequence comprises at most about 10%, about 20%, about 30%, about 40%, about 50%, about 60%, about 70%, about 80%, about 90%, about 95%, or about 100% chemically modified nucleotides.

In some embodiments, the chemically modified spacer sequence has a chemically modified nucleotide on one or more of the positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 in the 5'-3' direction in the spacer sequence.

In some embodiments, the chemically modified spacer region has a chemically modified nucleotide on one or more of the positions which are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 nucleotides from the 5' end of the spacer sequence.

In some embodiments, the chemically modified spacer region has a chemically modified nucleotide on one or more the positions which are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 nucleotides from the 3' end of the spacer sequence.

In some embodiments, the chemically modified guide RNA has a one or more chemical modifications in the scaffold sequence. In some embodiments, the scaffold sequence comprises a total of from 1 to 130 chemically modified nucleotides. In some embodiments, the chemically modified guide RNA comprises a scaffold sequence of from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, or 130 chemically modified nucleotides. In some embodiments, the scaffold sequence comprises a total of from about 1 to about 50 chemically modified nucleotides. In some embodiments, the scaffold sequence comprises a total of from about 5 to about 50, about 10 to about 50, about 15 to about 50, about 20 to about 50, about 25 to about 50, about 30 to about 50, about 35 to about 50, about 40 to about 50, about 45 to about 50, about 1 to about 45, about 1 to about 40, about 1 to about 35, about 1 to about 30, about 1 to about 25, about 1 to about 20, about 1 to about 15, about 1 to about 10, about 1 to about 5 chemically modified nucleotides. In some embodiments, the scaffold sequence comprises a total of from about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49 or about 50 chemically modified nucleotides. In some embodiments, the scaffold sequence comprises a total of from at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49 or about 50 chemically modified nucleotides. In some embodiments, the scaffold sequence comprises a total of from at most about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49 or about 50 chemically modified nucleotides. In some embodiments, the scaffold sequence comprises a total of from about 10 to about 30 chemically modified nucleotides. In some embodiments, the scaffold sequence comprises a total of from about 10 to about 15, about 10 to about 20, about 10 to about 25, about 10 to about 30, about 10 to about 35, about 10 to about 40, about 15 to about 45, about 15 to about 20, about 15 to about 25, about 15 to about 30, about 15 to about 35, about 15 to about 40, about 15 to about 45, about 20 to about 25, about 20 to about 30, about 25 to about 30, about 25 to about 35, about 25 to about 40, about 25 to about 45, about 30 to about 35, about 30 to about 40, about 30 to about 45, about 35 to about 40, or about 35 to about 45 chemically modified nucleotides. In some embodiments, the scaffold sequence comprises a total of from about 10, about 15, about 20, about 25, about 30, about 35, about 40, or about 45 chemically modified nucleotides. In some embodiments, the scaffold sequence comprises a total of from at least about 10, about 15, about 20, or about 25 chemically modified nucleotides. In some embodiments, the spacer region comprises a total of at most about 15, about 20, about 25, about 30, about 35, about 40, or about 45 chemically modified nucleotides. In some embodiments, the scaffold sequence comprises a total of from about 30 to about 130 chemically modified nucleotides. In some embodiments, the scaffold sequence comprises a total of from about 30 to about 40, about 30 to about 50, about 30 to about 60, about 30 to about 70, about 30 to about 75, about 30 to about 80, about 30 to about 90, about 30 to about 100, about 30 to about 110, about 30 to about 120, about 30 to about 130, about 40 to about 50, about 40 to about 60, about 40 to about 70, about 40 to about 75, about 40 to about 80, about 40 to about 90, about 40 to about 100, about 40 to about 110, about 40 to about 120, about 40 to about 130, about 50 to about 60, about 50 to about 70, about 50 to about 75, about 50 to about 80, about 50 to about 90, about 50 to about 100, about 50 to about 110, about 50 to about 120, about 50 to about 130, about 60 to about 70, about 60 to about 75, about 60 to about 80, about 60 to about 90, about 60 to about 100, about 60 to about 110, about 60 to about 120, about 60 to about 130, about 70 to about 75, about 70 to about 80, about 70 to about 90, about 70 to about 100, about 70 to about 110, about 70 to about 120, about 70 to about 130, about 75 to about 80, about 75 to about 90, about 75 to about 100, about 75 to about 110, about 75 to about 120, about 75 to about 130, about 80 to about 90, about 80 to about 100, about 80 to about 110, about 80 to about 120, about 80 to about 130, about 90 to about 100, about 90 to about 110, about 90 to about 120, about 90 to about 130, about 100 to about 110, about 100 to about 120, about 100 to about 130, about 110 to about 120, about 110 to about 130, or about 120 to about 130 chemically modified nucleotides. In some embodiments, the scaffold sequence comprises a total of from about 30, about 40, about 50, about 60, about 70, about 75, about 80, about 90, about 100, about 110, about 120, or about 130 chemically modified nucleotides. In some embodiments, the scaffold sequence comprises a total of from at least about 30, about 40, about 50, about 60, about 70, about 75, about 80, about 90, about 100, about 110, or about 120 chemically modified nucleotides. In some embodiments, the scaffold sequence comprises a total of from at most about 40, about 50, about 60, about 70, about 75, about 80, about 90, about 100, about 110, about 120, or about 130 chemically modified nucleotides. In one embodiment, the scaffold sequence comprises a total of 60 chemically modified nucleotides. In another embodiment, the scaffold sequence comprises a total of 36 chemically modified nucleotides.

In some embodiments, the scaffold sequence comprises from 1% to 100% chemically modified nucleotides. In some embodiments, the scaffold sequence comprises about 1% to about 100% chemically modified nucleotides. In some embodiments, the scaffold sequence comprises about 1% to about 10%, about 1% to about 20%, about 1% to about 30%, about 1% to about 40%, about 1% to about 50%, about 1% to about 60%, about 1% to about 70%, about 1% to about 80%, about 1% to about 90%, about 1% to about 95%, about 1% to about 100%, about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 10% to about 100%, about 20% to about 30%, about 20% to about 40%, about 20% to about 50%, about 20% to about 60%, about 20% to about 70%, about 20% to about 80%, about 20% to about 90%, about 20% to about 95%, about 20% to about 100%, about 30% to about 40%, about 30% to about 50%, about 30% to about 60%, about 30% to about 70%, about 30% to about 80%, about 30% to about 90%, about 30% to about 95%, about 30% to about 100%, about 40% to about 50%, about 40% to about 60%, about 40% to about 70%, about 40% to about 80%, about 40% to about 90%, about 40% to about 95%, about 40% to about 100%, about 50% to about 60%, about 50% to about 70%, about 50% to about 80%, about 50% to about 90%, about 50% to about 95%, about 50% to about 100%, about 60% to about 70%, about 60% to about 80%, about 60% to about 90%, about 60% to about 95%, about 60% to about 100%, about 70% to about 80%, about 70% to about 90%, about 70% to about 95%, about 70% to about 100%, about 80% to about 90%, about 80% to about 95%, about 80% to about 100%, about 90% to about 95%, about 90% to about 100%, or about 95% to about 100% chemically modified nucleotides. In some embodiments, the scaffold sequence comprises about 1%, about 10%, about 20%, about 30%, about 40%, about 50%, about 60%, about 70%, about 80%, about 90%, about 95%, or about 100% chemically modified nucleotides. In some embodiments, the scaffold sequence comprises at least about 1%, about 10%, about 20%, about 30%, about 40%, about 50%, about 60%, about 70%, about 80%, about 90%, or about 95% chemically modified nucleotides. In some embodiments, the scaffold sequence comprises at most about 10%, about 20%, about 30%, about 40%, about 50%, about 60%, about 70%, about 80%, about 90%, about 95%, or about 100% chemically modified nucleotides.

In some embodiments, the chemically modified scaffold sequence has a chemically modified nucleotide on one or more of the positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, or 130 in the 5'-3' direction in the scaffold sequence.

In some embodiments, the chemically modified scaffold region has a chemically modified nucleotide on one or more of the positions which are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, or 129 nucleotides from the 5' end of the scaffold sequence.

In some embodiments, the chemically modified scaffold region has a chemically modified nucleotide on one or more of the positions which are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, or 129 nucleotides from the 3' end of the scaffold sequence.

In some embodiments, the modified crRNA comprises a total of from 1 to 50 chemically modified nucleotides. In some embodiments, the chemically modified crRNA comprises a total of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 chemically modified nucleotides. In some embodiments, the chemically modified crRNA comprises a total of about 1 to about 10 chemically modified nucleotides. In some embodiments, the chemically modified crRNA comprises a total of about 1 to about 2, about 1 to about 3, about 1 to about 4, about 1 to about 5, about 1 to about 6, about 1 to about 7, about 1 to about 8, about 1 to about 9, about 1 to about 10, about 2 to about 3, about 2 to about 4, about 2 to about 5, about 2 to about 6, about 2 to about 7, about 2 to about 8, about 2 to about 9, about 2 to about 10, about 3 to about 4, about 3 to about 5, about 3 to about 6, about 3 to about 7, about 3 to about 8, about 3 to about 9, about 3 to about 10, about 4 to about 5, about 4 to about 6, about 4 to about 7, about 4 to about 8, about 4 to about 9, about 4 to about 10, about 5 to about 6, about 5 to about 7, about 5 to about 8, about 5 to about 9, about 5 to about 10, about 6 to about 7, about 6 to about 8, about 6 to about 9, about 6 to about 10, about 7 to about 8, about 7 to about 9, about 7 to about 10, about 8 to about 9, about 8 to about 10, or about 9 to about 10 chemically modified nucleotides. In some embodiments, the chemically modified crRNA comprises a total of about 1, about 2, about 3, about 4, about 5, about 6, about 7, about 8, about 9, or about 10 chemically modified nucleotides. In some embodiments, the chemically modified crRNA comprises a total of at least about 1, about 2, about 3, about 4, about 5, about 6, about 7, about 8, or about 9 chemically modified nucleotides. In some embodiments, the chemically modified crRNA comprises a total of at most about 2, about 3, about 4, about 5, about 6, about 7, about 8, about 9, or about 10 chemically modified nucleotides. In some embodiments, the chemically modified crRNA comprises a total of about 10 to about 30 chemically modified nucleotides. In some embodiments, the chemically modified crRNA comprises a total of about 10 to about 15, about 10 to about 20, about 10 to about 25, about 10 to about 30, about 15 to about 20, about 15 to about 25, about 15 to about 30, about 20 to about 25, about 20 to about 30, or about 25 to about 30 chemically modified nucleotides. In some embodiments, the chemically modified crRNA comprises a total of about 10, about 15, about 20, about 25, or about 30 chemically modified nucleotides. In some embodiments, the chemically modified crRNA comprises a total of at least about 10, about 15, about 20, or about 25 chemically modified nucleotides. In some embodiments, the chemically modified crRNA comprises a total of at most about 15, about 20, about 25, or about 30 chemically modified nucleotides. In some embodiments, the chemically modified crRNA comprises a total of from about 30 to about 50 chemically modified nucleotides. In some embodiments, the chemically modified crRNA comprises a total of from about 30 to about 32, about 30 to about 34, about 30 to about 36, about 30 to about 38, about 30 to about 40, about 30 to about 42, about 30 to about 44, about 30 to about 46, about 30 to about 48, about 30 to about 50, about 32 to about 34, about 32 to about 36, about 32 to about 38, about 32 to about 40, about 32 to about 42, about 32 to about 44, about 32 to about 46, about 32 to about 48, about 32 to about 50, about 34 to about 36, about 34 to about 38, about 34 to about 40, about 34 to about 42, about 34 to about 44, about 34 to about 46, about 34 to about 48, about 34 to about 50, about 36 to about 38, about 36 to about 40, about 36 to about 42, about 36 to about 44, about 36 to about 46, about 36 to about 48, about 36 to about 50, about 38 to about 40, about 38 to about 42, about 38 to about 44, about 38 to about 46, about 38 to about 48, about 38 to about 50, about 40 to about 42, about 40 to about 44, about 40 to about 46, about 40 to about 48, about 40 to about 50, about 42 to about 44, about 42 to about 46, about 42 to about 48, about 42 to about 50, about 44 to about 46, about 44 to about 48, about 44 to about 50, about 46 to about 48, about 46 to about 50, or about 48 to about 50 chemically modified nucleotides. In some embodiments, the chemically modified crRNA comprises a total of from about 30, about 32, about 34, about 36, about 38, about 40, about 42, about 44, about 46, about 48, or about 50 chemically modified nucleotides. In some embodiments, the chemically modified crRNA comprises a total of from at least about 30, about 32, about 34, about 36, about 38, about 40, about 42, about 44, about 46, or about 48 chemically modified nucleotides. In some embodiments, the chemically modified crRNA comprises a total of from at most about 32, about 34, about 36, about 38, about 40, about 42, about 44, about 46, about 48, or about 50 chemically modified nucleotides.

In some embodiments, the modified crRNA comprises from 1% to 100% chemically modified nucleotides. In some embodiments, the crRNA comprises about 1% to about 100% chemically modified nucleotides. In some embodiments, the crRNA comprises about 1% to about 10%, about 1% to about 20%, about 1% to about 30%, about 1% to about 40%, about 1% to about 50%, about 1% to about 60%, about 1% to about 70%, about 1% to about 80%, about 1% to about 90%, about 1% to about 95%, about 1% to about 100%, about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 10% to about 100%, about 20% to about 30%, about 20% to about 40%, about 20% to about 50%, about 20% to about 60%, about 20% to about 70%, about 20% to about 80%, about 20% to about 90%, about 20% to about 95%, about 20% to about 100%, about 30% to about 40%, about 30% to about 50%, about 30% to about 60%, about 30% to about 70%, about 30% to about 80%, about 30% to about 90%, about 30% to about 95%, about 30% to about 100%, about 40% to about 50%, about 40% to about 60%, about 40% to about 70%, about 40% to about 80%, about 40% to about 90%, about 40% to about 95%, about 40% to about 100%, about 50% to about 60%, about 50% to about 70%, about 50% to about 80%, about 50% to about 90%, about 50% to about 95%, about 50% to about 100%, about 60% to about 70%, about 60% to about 80%, about 60% to about 90%, about 60% to about 95%, about 60% to about 100%, about 70% to about 80%, about 70% to about 90%, about 70% to about 95%, about 70% to about 100%, about 80% to about 90%, about 80% to about 95%, about 80% to about 100%, about 90% to about 95%, about 90% to about 100%, or about 95% to about 100% chemically modified nucleotides. In some embodiments, the crRNA comprises about 1%, about 10%, about 20%, about 30%, about 40%, about 50%, about 60%, about 70%, about 80%, about 90%, about 95%, or about 100% chemically modified nucleotides. In some embodiments, the crRNA comprises at least about 1%, about 10%, about 20%, about 30%, about 40%, about 50%, about 60%, about 70%, about 80%, about 90%, or about 95% chemically modified nucleotides. In some embodiments, the crRNA comprises at most about 10%, about 20%, about 30%, about 40%, about 50%, about 60%, about 70%, about 80%, about 90%, about 95%, or about 100% chemically modified nucleotides.

In some embodiments, the chemically modified crRNA has a chemically modified nucleotide on one or more of the positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 in the 5'-3' direction in the crRNA sequence.

In some embodiments, the chemically modified crRNA has a chemically modified nucleotide on one or more of the positions which are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides from the 5' end of the crRNA sequence.

In some embodiments, the chemically modified crRNA has a chemically modified nucleotide on one or more of the positions which are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides from the 3' end of the crRNA sequence.

In some embodiments, the chemically modified tracrRNA comprises a total of from 1 to 130 chemically modified nucleotides. In some embodiments, the chemically modified tracrRNA comprises a total of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, or 130 chemically modified nucleotides. In some embodiments, the chemically modified tracrRNA comprises a total of about 1 to about 10 chemically modified nucleotides. In some embodiments, the chemically modified tracrRNA comprises a total of about 1 to about 2, about 1 to about 3, about 1 to about 4, about 1 to about 5, about 1 to about 6, about 1 to about 7, about 1 to about 8, about 1 to about 9, about 1 to about 10, about 2 to about 3, about 2 to about 4, about 2 to about 5, about 2 to about 6, about 2 to about 7, about 2 to about 8, about 2 to about 9, about 2 to about 10, about 3 to about 4, about 3 to about 5, about 3 to about 6, about 3 to about 7, about 3 to about 8, about 3 to about 9, about 3 to about 10, about 4 to about 5, about 4 to about 6, about 4 to about 7, about 4 to about 8, about 4 to about 9, about 4 to about 10, about 5 to about 6, about 5 to about 7, about 5 to about 8, about 5 to about 9, about 5 to about 10, about 6 to about 7, about 6 to about 8, about 6 to about 9, about 6 to about 10, about 7 to about 8, about 7 to about 9, about 7 to about 10, about 8 to about 9, about 8 to about 10, or about 9 to about 10 chemically modified nucleotides. In some embodiments, the chemically modified tracrRNA comprises a total of about 1, about 2, about 3, about 4, about 5, about 6, about 7, about 8, about 9, or about 10 chemically modified nucleotides. In some embodiments, the chemically modified tracrRNA comprises a total of at least about 1, about 2, about 3, about 4, about 5, about 6, about 7, about 8, or about 9 chemically modified nucleotides. In some embodiments, the chemically modified tracrRNA comprises a total of at most about 2, about 3, about 4, about 5, about 6, about 7, about 8, about 9, or about 10 chemically modified nucleotides. In some embodiments, the chemically modified tracrRNA comprises a total of about 10 to about 30 chemically modified nucleotides. In some embodiments, the chemically modified tracrRNA comprises a total of about 10 to about 15, about 10 to about 20, about 10 to about 25, about 10 to about 30, about 15 to about 20, about 15 to about 25, about 15 to about 30, about 20 to about 25, about 20 to about 30, or about 25 to about 30 chemically modified nucleotides. In some embodiments, the chemically modified tracrRNA comprises a total of about 10, about 15, about 20, about 25, or about 30 chemically modified nucleotides. In some embodiments, the chemically modified tracrRNA comprises a total of at least about 10, about 15, about 20, or about 25 chemically modified nucleotides. In some embodiments, the spacer region comprises a total of at most about 15, about 20, about 25, or about 30 chemically modified nucleotides. In some embodiments, the chemically modified tracrRNA comprises a total of about 30 to about 130 chemically modified nucleotides. In some embodiments, the chemically modified tracrRNA comprises a total of about 30 to about 40, about 30 to about 50, about 30 to about 60, about 30 to about 70, about 30 to about 75, about 30 to about 80, about 30 to about 90, about 30 to about 100, about 30 to about 110, about 30 to about 120, about 30 to about 130, about 40 to about 50, about 40 to about 60, about 40 to about 70, about 40 to about 75, about 40 to about 80, about 40 to about 90, about 40 to about 100, about 40 to about 110, about 40 to about 120, about 40 to about 130, about 50 to about 60, about 50 to about 70, about 50 to about 75, about 50 to about 80, about 50 to about 90, about 50 to about 100, about 50 to about 110, about 50 to about 120, about 50 to about 130, about 60 to about 70, about 60 to about 75, about 60 to about 80, about 60 to about 90, about 60 to about 100, about 60 to about 110, about 60 to about 120, about 60 to about 130, about 70 to about 75, about 70 to about 80, about 70 to about 90, about 70 to about 100, about 70 to about 110, about 70 to about 120, about 70 to about 130, about 75 to about 80, about 75 to about 90, about 75 to about 100, about 75 to about 110, about 75 to about 120, about 75 to about 130, about 80 to about 90, about 80 to about 100, about 80 to about 110, about 80 to about 120, about 80 to about 130, about 90 to about 100, about 90 to about 110, about 90 to about 120, about 90 to about 130, about 100 to about 110, about 100 to about 120, about 100 to about 130, about 110 to about 120, about 110 to about 130, or about 120 to about 130 chemically modified nucleotides. In some embodiments, the chemically modified tracrRNA comprises a total of about 30, about 40, about 50, about 60, about 70, about 75, about 80, about 90, about 100, about 110, about 120, or about 130 chemically modified nucleotides. In some embodiments, the chemically modified tracrRNA comprises a total of at least about 30, about 40, about 50, about 60, about 70, about 75, about 80, about 90, about 100, about 110, or about 120 chemically modified nucleotides. In some embodiments, the chemically modified tracrRNA comprises a total of at most about 40, about 50, about 60, about 70, about 75, about 80, about 90, about 100, about 110, about 120, or about 130 chemically modified nucleotides.

In some embodiments, the chemically modified tracrRNA comprises about 1% to about 100% chemically modified nucleotides. In some embodiments, the chemically modified tracrRNA comprises about 1% to about 10%, about 1% to about 20%, about 1% to about 30%, about 1% to about 40%, about 1% to about 50%, about 1% to about 60%, about 1% to about 70%, about 1% to about 80%, about 1% to about 90%, about 1% to about 95%, about 1% to about 100%, about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 10% to about 100% about 20% to about 30%, about 20% to about 40%, about 20% to about 50%, about 20% to about 60%, about 20% to about 70%, about 20% to about 80%, about 20% to about 90%, about 20% to about 95%, about 20% to about 100%, about 30% to about 40%, about 30% to about 50%, about 30% to about 60%, about 30% to about 70%, about 30% to about 80%, about 30% to about 90%, about 30% to about 95%, about 30% to about 100%, about 40% to about 50%, about 40% to about 60%, about 40% to about 70%, about 40% to about 80%, about 40% to about 90%, about 40% to about 95%, about 40% to about 100%, about 50% to about 60%, about 50% to about 70%, about 50% to about 80%, about 50% to about 90%, about 50% to about 95%, about 50% to about 100%, about 60% to about 70%, about 60% to about 80%, about 60% to about 90%, about 60% to about 95%, about 60% to about 100%, about 70% to about 80%, about 70% to about 90%, about 70% to about 95%, about 70% to about 100%, about 80% to about 90%, about 80% to about 95%, about 80% to about 100%, about 90% to about 95%, about 90% to about 100%, or about 95% to about 100% chemically modified nucleotides. In some embodiments, the chemically modified tracrRNA comprises about 1%, about 10%, about 20%, about 30%, about 40%, about 50%, about 60%, about 70%, about 80%, about 90%, about 95%, or about 100% chemically modified nucleotides. In some embodiments, the chemically modified tracrRNA comprises at least about 1%, about 10%, about 20%, about 30%, about 40%, about 50%, about 60%, about 70%, about 80%, about 90%, or about 95% chemically modified nucleotides. In some embodiments, the chemically modified tracrRNA comprises at most about 10%, about 20%, about 30%, about 40%, about 50%, about 60%, about 70%, about 80%, about 90%, about 95%, or about 100% chemically modified nucleotides.

In some embodiments, the chemically modified tracrRNA has a chemically modified nucleotide on one or more of the positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, or 130 in the 5'-3' direction in the tracrRNA sequence.

In some embodiments, the chemically modified tracrRNA has a chemically modified nucleotide on one or more of the positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, or 129 nucleotides from the 5' end of the tracrRNA sequence.

In some embodiments, the chemically modified tracrRNA has a chemically modified nucleotide on one or more of the positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, or 129 nucleotides from the 3' end of the tracrRNA sequence.

In some embodiments, the chemically modified guide RNA comprises phosphorothioate (PS) linkages at the 5' or 3' end of the gRNA sequence. In some embodiments, the chemically modified guide RNA comprises 0, 1, 2, 3, 4, or 5 PS linkages at the 5' end of the guide RNA sequence. In some embodiments, the chemically modified guide RNA comprises 0, 1, 2, 3, 4, or 5 PS linkages at the 3' end of the guide RNA sequence. In some embodiments, the chemically modified guide RNA comprises 0, 1, 2, 3, 4, or 5 PS linkages, or any combinations thereof at each of 5' and 3' end of the guide RNA sequence. In some embodiments, the chemically modified guide RNA comprises 0, 1, 2 or 3 PS linkages, or any combinations thereof at each of 5' and 3' end of the guide RNA sequence. In some embodiments, the chemically modified guide RNA comprises 1 PS linkage at each of 5' and 3' end of the guide RNA sequence. In some embodiments, the chemically modified guide RNA comprises 2 PS linkages at each of 5' and 3' end of the guide RNA sequence. In some embodiments, the chemically modified guide RNA comprises 3 PS linkages at each of 5' and 3' end of the guide RNA sequence. In some embodiments, the chemically modified guide RNA comprises 4 PS linkages at each of 5' and 3' end of the guide RNA sequence. In some embodiments, the chemically modified guide RNA comprises 5 PS linkages at each of 5' and 3' end of the guide RNA sequence. In some embodiments, the chemically modified guide RNA comprises 3 PS linkages at the 5' end and 0 PS linkage (i.e., no modification) at the 3' end of the guide RNA sequence. In some embodiments, the chemically modified guide RNA comprises 3 PS linkages at the 5' end and 1 PS linkage at the 3' end of the guide RNA sequence. In some embodiments, the chemically modified guide RNA comprises 3 PS linkages at the 5' end and 2 PS linkages at the 3' end of the guide RNA sequence. In some embodiments, the chemically modified guide RNA comprises 3 PS linkages at the 5' end and 4 PS linkages at the 3' end of the guide RNA sequence. In some embodiments, the chemically modified guide RNA comprises 3 PS linkages at the 5' end and 5 PS linkages at the 3' end of the guide RNA sequence. In some embodiments, the chemically modified guide RNA comprises 2 PS linkages at the 5' end and 0 PS linkage (i.e., no modification) at the 3' end of the guide RNA sequence. In some embodiments, the chemically modified guide RNA comprises 2 PS linkages at the 5' end and 1 PS linkage at the 3' end of the guide RNA sequence. In some embodiments, the chemically modified guide RNA comprises 2 PS linkages at the 5' end and 3 PS linkages at the 3' end of the guide RNA sequence. In some embodiments, the chemically modified guide RNA comprises 2 PS linkages at the 5' end and 4 PS linkages at the 3' end of the guide RNA sequence. In some embodiments, the chemically modified guide RNA comprises 2 PS linkages at the 5' end and 5 PS linkages at the 3' end of the guide RNA sequence.

In some embodiments, the chemically modified guide RNA comprises 2 and no more than 2 contiguous phosphorothioate (PS) linkages at the 5' end. In some embodiments, the chemically modified guide RNA comprises 2 and no more than 2 contiguous phosphorothioate (PS) linkages at the 3' end. In some embodiments, the chemically modified guide RNA comprises 3 contiguous phosphorothioate (PS) linkages at the 5' end. In some embodiments, the chemically modified guide RNA comprises 3 contiguous phosphorothioate (PS) linkages at the 3' end. In some embodiments, the chemically modified guide RNA comprises the sequence 5'-UsUsU-3' at the 3'end or at the 5' end, wherein U indicates a uridine and wherein s indicates a phosphorothioate (PS) linkage. In some embodiments, the chemically modified guide RNA comprises 3 phosphorothioate (PS) linkages at the 5' end. In some embodiments, the chemically modified guide RNA comprises 3 phosphorothioate (PS) linkages at the 3' end. In some embodiments, the chemically modified guide RNA comprises the two phosphorothioate linkages at the 5' end, wherein the two phosphorothioate (PS) linkages are two contiguous phosphorothioate (PS) linkages at the first two nucleotide positions of the 5' end. In some embodiments, the chemically modified guide RNA comprises the two phosphorothioate linkages at the 5' end, wherein the two phosphorothioate (PS) linkages are within the first 3-10 nucleotides of the 5' end. In some embodiments, the chemically modified guide RNA comprises the two phosphorothioate (PS) linkages at the 3' end, wherein the two phosphorothioate (PS) linkages are two contiguous phosphorothioate (PS) linkages at the first two nucleotide positions of the 3' end. In some embodiments, the chemically modified guide RNA comprises the two phosphorothioate (PS) linkages at the 3' end, wherein the two phosphorothioate (PS) linkages are within the first 3-10 nucleotides of the 3' end. In some embodiments, the chemically modified guide RNA comprises the sequence 5'-UsUsUs-3' at the 3' end, wherein U indicates a uridine and s indicates a phosphorothioate (PS) linkage. In some embodiments, the chemically modified guide RNA comprises the sequence 5'-UsUsU-3' at the 3'end, wherein U indicates a uridine and s indicates a phosphorothioate (PS) linkage.

In some embodiments, the chemically modified guide RNA comprises PS linkages at the internal positions of the guide RNA sequence. In some embodiments, the chemically modified guide RNA comprises 1, 2, 3, 4, 5, 6, 7, 8, 9, or 10 PS linkages at the internal positions of the guide RNA sequence. In some embodiments, the chemically modified guide RNA comprises 1 PS linkage at the internal position of the guide RNA sequence. In some embodiments, the chemically modified guide RNA comprises 2 PS linkages at the internal positions of the guide RNA sequence. In some embodiments, the chemically modified guide RNA comprises 3 PS linkages at the internal positions of the guide RNA sequence. In some embodiments, the chemically modified guide RNA comprises 4 PS linkages at the internal positions of the guide RNA sequence. In some embodiments, the chemically modified guide RNA comprises 5 PS linkages at the internal positions of the guide RNA sequence. In some embodiments, the chemically modified guide RNA comprises 6 PS linkages at the internal positions of the guide RNA sequence. In some chemically modified embodiments, the guide RNA comprises 7 PS linkages at the internal positions of the guide RNA sequence. In some embodiments, the chemically modified guide RNA comprises 8 PS linkages at the internal positions of the guide RNA sequence. In some embodiments, the chemically modified guide RNA comprises 9 PS linkages at the internal positions of the guide RNA sequence. In some embodiments, the chemically modified the guide RNA comprises 10 PS linkages at the internal positions of the guide RNA sequence.

In some embodiments, the chemically modified guide RNA comprises PS linkages at the 5' end, the 3' end, or at the internal positions, or any combination thereof, of the guide RNA sequence. In some embodiments, the chemically modified guide RNA comprises 0, 1, 2, 3, 4, 5, 6, 7, 8, 9, or 10 PS linkages at the 5'end, the 3' end, or at the internal positions, or any combination thereof, of the guide RNA sequence.

In some embodiments, the chemically modified guide RNA comprises 2 PS linkages at the 5' end, 3 PS linkages at the 3' end, and 0 PS linkage (i.e., no modification) at the internal position of the guide RNA sequence. In some embodiments, the chemically modified guide RNA comprises 2 PS linkages at the 5' end, 3 PS linkages at the 3' end, and 1 PS linkage at the internal position of the guide RNA sequence. In some embodiments, the chemically modified guide RNA comprises 2 PS linkages at the 5' end, 3 PS linkages at the 3' end, and 2 PS linkages at the internal positions of the guide RNA sequence. In some embodiments, the chemically modified guide RNA comprises 2 PS linkages at the 5' end, 3 PS linkages at the 3' end, and 3 PS linkages at the internal positions of the guide RNA sequence. In some embodiments, the chemically modified guide RNA comprises 2 PS linkages at the 5' end, 3 PS linkages at the 3' end, and 4 PS linkages at the internal positions of the guide RNA sequence. In some embodiments, the chemically modified guide RNA comprises 2 PS linkages at the 5' end, 3 PS linkages at the 3' end, and 5 PS linkages at the internal positions of the guide RNA sequence. In some embodiments, the chemically modified guide RNA comprises 2 PS linkages at the 5' end, 3 PS linkages at the 3' end, and 6 PS linkages at the internal positions of the guide RNA sequence.

In some embodiments, the chemically modified guide RNA comprises 3 PS linkages at the 5' end, 2 PS linkages at the 3' end, and 0 PS linkage (i.e., no modification) at the internal position of the guide RNA sequence. In some embodiments, the chemically modified guide RNA comprises 3 PS linkages at the 5' end, 2 PS linkages at the 3' end, and 1 PS linkage at the internal position of the guide RNA sequence. In some embodiments, the chemically modified guide RNA comprises 3 PS linkages at the 5' end, 2 PS linkages at the 3' end, and 2 PS linkages at the internal positions of the guide RNA sequence. In some embodiments, the chemically modified guide RNA comprises 3 PS linkages at the 5' end, 2 PS linkages at the 3' end, and 3 PS linkages at the internal positions of the guide RNA sequence. In some embodiments, the chemically modified guide RNA comprises 3 PS linkages at the 5' end, 2 PS linkages at the 3' end, and 4 PS linkages at the internal positions of the guide RNA sequence. In some embodiments, the chemically modified guide RNA comprises 3 PS linkages at the 5' end, 2 PS linkages at the 3' end, and 5 PS linkages at the internal positions of the guide RNA sequence. In some embodiments, the chemically modified guide RNA comprises 3 PS linkages at the 5' end, 2 PS linkages at the 3' end, and 6 PS linkages at the internal positions of the guide RNA sequence.

In some embodiments, the chemically modified guide RNA comprises 2 PS linkages at the 5' end, 2 PS linkages at the 3' end, and 0 PS linkage (i.e., no PS backbone modification) at the internal position of the guide RNA sequence. In some embodiments, the chemically modified guide RNA comprises 2 PS linkages at the 5' end and 2 PS linkages at the 3' end and 1 PS linkage at the internal position of the guide RNA sequence. In some embodiments, the chemically modified guide RNA comprises 2 PS linkages at the 5' end and 2 PS linkages at the 3' end and 2 PS linkages at the internal positions of the guide RNA sequence. In some embodiments, the chemically modified guide RNA comprises 2 PS linkages at the 5' end and 2 PS linkages at the 3' end and 3 PS linkages at the internal positions of the guide RNA sequence. In some embodiments, the chemically modified guide RNA comprises 2 PS linkages at the 5' end and 2 PS linkages at the 3' end and 4 PS linkages at the internal positions of the guide RNA sequence. In some embodiments, the chemically modified guide RNA comprises 2 PS linkages at the 5' end and 2 PS linkages at the 3' end and 5 PS linkages at the internal positions of the guide RNA sequence. In some embodiments, the chemically modified guide RNA comprises 2 PS linkages at the 5' end and 2 PS linkages at the 3' end and 6 PS linkages at the internal positions of the guide RNA sequence.

In some embodiments, the chemically modified guide RNA comprises 3 PS linkages at the 5' end, 3 PS linkages at the 3' end, and 0 PS linkage (i.e., no modification) at the internal position of the guide RNA sequence. In some embodiments, the chemically modified guide RNA comprises 3 PS linkages at the 5' end and 3 PS linkages at the 3' end and 1 PS linkage at the internal position of the guide RNA sequence. In some embodiments, the chemically modified guide RNA comprises 3 PS linkages at the 5' end and 3 PS linkages at the 3' end and 2 PS linkages at the internal positions of the guide RNA sequence. In some embodiments, the chemically modified guide RNA comprises 3 PS linkages at the 5' end and 3 PS linkages at the 3' end and 3 PS linkages at the internal positions of the guide RNA sequence. In some embodiments, the chemically modified guide RNA comprises 3 PS linkages at the 5' end and 3 PS linkages at the 3' end and 4 PS linkages at the internal positions of the guide RNA sequence. In some embodiments, the chemically modified guide RNA comprises 3 PS linkages at the 5' end and 3 PS linkages at the 3' end and 5 PS linkages at the internal positions of the guide RNA sequence. In some embodiments, the chemically modified guide RNA comprises 3 PS linkages at the 5' end and 3 PS linkages at the 3' end and 6 PS linkages at the internal positions of the guide RNA sequence.

In some embodiments, the chemically modified guide RNA comprises additional modified or unmodified nucleotide (N) with phosphodiester linkage, wherein N is an A, C, G, U, dA (deoxyA), dC (deoxyC), dG (deoxyG), or T, and any combinations thereof. In some embodiments, the guide RNA comprises 1, 2, 3, 4, or 5 additional N with phosphodiester linkage, wherein N is an A, G, U, dA, dG, dC, or T, and any combinations thereof. In some embodiments, the chemically modified guide RNA comprises 1, 2, 3, 4, or 5 additional N with phosphodiester linkage at the 5' or 3' end. In one embodiment, the chemically modified guide RNA comprises 1, 2, 3, 4, or 5 additional N with phosphodiester linkage at the 5' end. In a preferred embodiment, the guide RNA comprises 1, 2, 3, 4, or 5 additional N with phosphodiester linkage at the 3' end. In some embodiments, the chemically modified guide RNA comprises 1, 2, 3, 4, or 5 additional N with phosphodiester linkage and each N is the same modified or unmodified nucleotide. For example, the chemically modified guide RNA comprises 4 additional N with phosphodiester linkage and each N of the 4 additional N is A, C, G, U, dA, dC, dG, or T. For example, the guide RNA comprises 4 additional N with phosphodiester linkage and each N of the 4 additional N is A. For example, the chemically modified guide RNA comprises 3 additional N with phosphodiester linkage and each N of the 3 additional N is A, C, G, U, dA, dC, dG, or T. For example, the chemically modified guide RNA comprises 3 additional N with phosphodiester linkage and each N of the 3 additional N is A. For example, the chemically modified guide RNA comprises 3 additional N with phosphodiester linkage and each N of the 3 additional N is C. For example, the chemically modified guide RNA comprises 3 additional N with phosphodiester linkage and each N of the 3 additional N is G. For example, the chemically modified guide RNA comprises 3 additional N with phosphodiester linkage and each N of the 3 additional N is U. For example, the guide RNA comprises 3 additional N with phosphodiester linkage and each N of the 3 additional N is dA. For example, the chemically modified guide RNA comprises 3 additional N with phosphodiester linkage and each N of the 3 additional N is dC. For example, the chemically modified guide RNA comprises 3 additional N with phosphodiester linkage and each N of the 3 additional N is dG. For example, the guide RNA comprises 3 additional N with phosphodiester linkage and each N of the 3 additional N is T.

In some embodiments, the chemically modified guide RNA comprises additional Uracil (U) with phosphodiester linkage at the 5' or 3' end. In one embodiment, the chemically modified guide RNA comprises additional U with phosphodiester linkage at the 5' end. In a preferred embodiment, the chemically modified guide RNA comprises additional U with phosphodiester linkage at the 3' end. In some embodiments, the chemically modified guide RNA comprises 1, 2, 3, 4, or 5 additional U with phosphodiester linkage at the 5' or 3' end. In some embodiments, the chemically modified guide RNA comprises 1 additional U with phosphodiester linkage at the 5' end. In some embodiments, the chemically modified guide RNA comprises 1 additional U with phosphodiester linkage at the 3' end. In some embodiments, the guide RNA comprises 2 additional U with phosphodiester linkage at the 5' end. In some embodiments, the chemically modified guide RNA comprises 2 additional U with phosphodiester linkage at the 3' end. In some embodiments, the chemically modified guide RNA comprises 3 additional U with phosphodiester linkage at the 5' end. In a preferred embodiment, the guide RNA comprises 3 additional U with phosphodiester linkage at the 3' end. In some embodiments, the chemically modified guide RNA comprises 4 additional U with phosphodiester linkage at the 5' end. In some embodiments, the guide RNA comprises 4 additional U with phosphodiester linkage at the 3' end. In some embodiments, the chemically modified guide RNA comprises 5 additional U with phosphodiester linkage at the 5' end. In some embodiments, the chemically modified guide RNA comprises 5 additional U with phosphodiester linkage at the 3' end.

In some embodiments, the chemically modified guide RNA comprises a ribonebularine (depicted as "X" in this application, e.g., in Table 1). In some embodiments, the chemically modified guide RNA comprises 0, 1, 2, 3, 4, 5, 6, 7, 8, 9, or 10 ribonebularines. In some embodiments, the chemically modified guide RNA does not comprise ribonebularine. In some embodiments, the chemically modified guide RNA comprises 1 ribonebularine. In some embodiments, the chemically modified guide RNA comprises 2 ribonebularines. In some embodiments, the guide RNA comprises 3 ribonebularines. In some embodiments, the chemically modified guide RNA comprises 4 ribonebularines. In some embodiments, the chemically modified guide RNA comprises 5 ribonebularines. In some embodiments, the g chemically modified guide polynucleotide comprises 6 ribonebularines. In some embodiments, the chemically modified guide RNA comprises 7 ribonebularines. In some embodiments, the chemically modified guide RNA comprises 8 ribonebularines. In some embodiments, the chemically modified guide RNA comprises 9 ribonebularines. In some embodiments, the chemically modified guide RNA comprises 10 ribonebularines. In some embodiments, the nebularine replaces an adenine in an unmodified guide RNA. In some embodiments, the nebularine is in the spacer sequence. In some embodiments, the nebularine is in a tracrRNA sequence in the scaffold sequence. In some embodiments, the nebularine is in a crRNA sequence in the scaffold sequence. In some embodiments, the nebularine is in a stem loop structure in the scaffold sequence.

In some embodiments, the chemically modified guide RNA comprises a 2'-O-methylnebularine (depicted as "x" in this application, e.g., in Table 1). In some embodiments, the chemically modified guide RNA comprises 0, 1, 2, 3, 4, 5, 6, 7, 8, 9, or 10 2'-O-methylnebularines. In some embodiments, the chemically modified guide RNA does not comprise 2'-O-methylnebularine. In some embodiments, the chemically modified guide RNA comprises 1 2'-O-methylnebularine. In some embodiments, the chemically modified guide RNA comprises 2 2'-O-methylnebularines. In some embodiments, the chemically modified guide RNA comprises 3 2'-O-methylnebularines. In some embodiments, the chemically modified guide RNA comprises 4 2'-O-methylnebularines. In some embodiments, the chemically modified guide RNA comprises 5 2'-O-methylnebularines. In some embodiments, the chemically modified guide RNA comprises 6 2'-O-methylnebularines. In some embodiments, the chemically modified guide RNA comprises 7 2'-O-methylnebularines. In some embodiments, the chemically modified guide RNA comprises 8 2'-O-methylnebularines. In some embodiments, the chemically modified guide RNA comprises 9 2'-O-methylnebularines. In some embodiments, the chemically modified guide RNA comprises 10 2'-O-methylnebularines. In some embodiments, the 2'-O-methylnebularine replaces an adenine in an unmodified guide RNA. In some embodiments, the 2'-O-methylnebularine is in the spacer sequence. In some embodiments, the 2'-O-methylnebularine is in a tracrRNA sequence in the scaffold sequence. In some embodiments, the 2'-O-methylnebularine is in a crRNA sequence in the scaffold sequence. In some embodiments, the 2'-O-methylnebularine is in a stem loop structure in the scaffold sequence.

In some embodiments, the chemically modified guide RNA comprises a 2'-deoxynebularine (depicted as "dX" in this application, e.g., in Table 1). In some embodiments, the chemically modified guide RNA comprises 0, 1, 2, 3, 4, 5, 6, 7, 8, 9, or 10 2'-deoxynebularine. In some embodiments, the chemically modified guide RNA does not comprise 2'-deoxynebularine. In some embodiments, the chemically modified guide RNA comprises 1 2'-deoxynebularine. In some embodiments, the chemically modified guide RNA comprises 2 2'-deoxynebularine. In some embodiments, the chemically modified guide RNA comprises 3 2'-deoxynebularines. In some embodiments, the chemically modified guide RNA comprises 4 2'-deoxynebularines. In some embodiments, the chemically modified guide RNA comprises 5 2'-deoxynebularines. In some embodiments, the chemically modified guide RNA comprises 6 2'-deoxynebularines. In some embodiments, the chemically modified guide RNA comprises 7 2'-deoxynebularines. In some embodiments, the chemically modified guide RNA comprises 8 2'-deoxynebularines. In some embodiments, the chemically modified guide RNA comprises 9 2'-deoxynebularines. In some embodiments, the chemically modified guide RNA comprises 10 2'-deoxynebularines. In some embodiments, the 2'-deoxynebularine replaces an adenine in an unmodified guide RNA. In some embodiments, the 2'-deoxynebularine is in the spacer sequence. In some embodiments, the 2'-deoxynebularine is in a tracrRNA sequence in the scaffold sequence. In some embodiments, the 2'-deoxynebularine is in a crRNA sequence in the scaffold sequence. In some embodiments, the 2'-deoxynebularine is in a stem loop structure in the scaffold sequence.

In some embodiments, the chemically modified guide RNA comprises a 2'-O-methylribonucleotide (2'-OMe). In some embodiments, the guide RNA comprises from about 0 to about 70 2'-OMe. In some embodiments, the chemically modified guide RNA comprises 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 2'-OMe. In some embodiments, the chemically modified guide RNA comprises from about 0 to about 70 2'-OMe. In some embodiments, the chemically modified guide RNA comprises from about 0 to about 10, about 0 to about 20, about 0 to about 30, about 0 to about 35, about 0 to about 40, about 0 to about 45, about 0 to about 50, about 0 to about 55, about 0 to about 60, about 0 to about 65, about 0 to about 70, about 10 to about 20, about 10 to about 30, about 10 to about 35, about 10 to about 40, about 10 to about 45, about 10 to about 50, about 10 to about 55, about 10 to about 60, about 10 to about 65, about 10 to about 70, about 20 to about 30, about 20 to about 35, about 20 to about 40, about 20 to about 45, about 20 to about 50, about 20 to about 55, about 20 to about 60, about 20 to about 65, about 20 to about 70, about 30 to about 35, about 30 to about 40, about 30 to about 45, about 30 to about 50, about 30 to about 55, about 30 to about 60, about 30 to about 65, about 30 to about 70, about 35 to about 40, about 35 to about 45, about 35 to about 50, about 35 to about 55, about 35 to about 60, about 35 to about 65, about 35 to about 70, about 40 to about 45, about 40 to about 50, about 40 to about 55, about 40 to about 60, about 40 to about 65, about 40 to about 70, about 45 to about 50, about 45 to about 55, about 45 to about 60, about 45 to about 65, about 45 to about 70, about 50 to about 55, about 50 to about 60, about 50 to about 65, about 50 to about 70, about 55 to about 60, about 55 to about 65, about 55 to about 70, about 60 to about 65, about 60 to about 70, or about 65 to about 70 2'-OMe. In some embodiments, the chemically modified guide RNA comprises from about 0, about 10, about 20, about 30, about 35, about 40, about 45, about 50, about 55, about 60, about 65, or about 70 2'-OMe. In some embodiments, the chemically modified guide RNA comprises from at least about 0, about 10, about 20, about 30, about 35, about 40, about 45, about 50, about 55, about 60, or about 65 2'-OMe. In some embodiments, the chemically modified guide RNA comprises from at most about 10, about 20, about 30, about 35, about 40, about 45, about 50, about 55, about 60, about 65, or about 70 2'-OMe. In some embodiments, the chemically modified guide RNA does not comprise 2'-OMe. In some embodiments, the chemically modified guide RNA comprises 62 2'-OMe. In some embodiments, the chemically modified guide RNA comprises 54 2'-OMe.

In some embodiments, the chemically modified guide RNA comprises 2'-OMe at the 5' end of the guide RNA sequence. In some embodiments, the chemically modified guide RNA comprises 2'-OMe at the 3' end of the guide RNA sequence. In some embodiments, the chemically modified guide RNA comprises 2'-OMe at the internal positions of the guide RNA sequence. In some embodiments, the chemically modified guide RNA comprises 2'-OMe at the 5' end, 3' end, or internal positions of the guide RNA sequence. In some embodiments, the chemically modified guide RNA comprises 2'-OMe at the 5' end, 3' end, and internal positions of the guide RNA sequence.

In some embodiments, each one of the last nucleotides at the 3'end of the chemically modified single guide RNA comprises a 2'-OMe modification. In some embodiments, each one of the last two nucleotides at the 3'end of the chemically modified single guide RNA comprises a 2'-OMe modification. In some embodiments, each one of the last three nucleotides at the 3'end of the chemically modified single guide RNA comprises a 2'-OMe modification. In some embodiments, each one of the last four nucleotides at the 3'end of the chemically modified single guide RNA comprises a 2'-OMe modification. In some embodiments, each one of the last five nucleotides at the 3'end of the chemically modified single guide RNA comprises a 2'-OMe modification. In some embodiments, each one of the last six nucleotides at the 3'end of the chemically modified single guide RNA comprises a 2'-OMe modification. In some embodiments, each one of the last seven nucleotides at the 3'end of the chemically modified single guide RNA comprises a 2'-OMe modification. In some embodiments, each one of the last eight nucleotides at the 3'end of the chemically modified single guide RNA comprises a 2'-OMe modification. In some embodiments, each one of the last nine nucleotides at the 3'end of the chemically modified single guide RNA comprises a 2'-OMe modification. In some embodiments, each one of the last ten nucleotides at the 3'end of the chemically modified single guide RNA comprises a 2'-OMe modification.

In some embodiments, the chemically modified guide RNA has a one or more chemical modifications in the 5' end of the guide RNA sequence. In some embodiments, the chemically modified guide RNA comprises one or more chemically modified nucleotides in the 5' end of the guide RNA sequence. In some embodiments, the chemically modified guide RNA has a one or more chemical modifications in the 3' end of the guide RNA sequence. In some embodiments, the chemically modified guide RNA comprises one or more chemically modified nucleotides in the 3' end of the guide RNA sequence.

In some embodiments, the chemically modified guide RNA comprises 1 additional Us at the 3' end, with phosphodiester linkage (3' UUU). In some embodiments, the chemically modified guide RNA comprises 2 additional Us at the 3' end, with phosphodiester linkage (3' UUU). In some embodiments, the chemically modified guide RNA comprises 3 additional Us at the 3' end, with phosphodiester linkage (3' UUU). In some embodiments, the chemically modified guide RNA comprises 4 additional Us at the 3' end, with phosphodiester linkage (3' UUU). In some embodiments, the chemically modified guide RNA comprises 5 additional Us at the 3' end, with phosphodiester linkage (3' UUU). In some embodiments, the chemically modified guide RNA comprises 6 additional Us at the 3' end, with phosphodiester linkage (3' UUU). In some embodiments, the chemically modified guide RNA comprises 7 additional Us at the 3' end, with phosphodiester linkage (3' UUU). In some embodiments, the chemically modified guide RNA comprises have 3 additional Us at the 3' end, with phosphodiester linkage (3' UUU). In some embodiments, the chemically modified guide RNA comprises 8 additional Us at the 3' end, with phosphodiester linkage (3' UUU). In some embodiments, the chemically modified guide RNA comprises 9 additional Us at the 3' end, with phosphodiester linkage (3' UUU). In some embodiments, the chemically modified guide RNA comprises 10 additional Us at the 3' end, with phosphodiester linkage (3' UUU).

In some embodiments, the chemically modified guide RNA comprises one or more combination(s) of all the aforementioned nucleobase, sugar and backbone modifications at select position(s). In some embodiments, the chemically modified guide RNA comprises a 2'-O-methylribonucleotide (2'-OMe) and PS linkages. In some embodiments, the chemically modified single guide RNA comprises the sequence 5'-NsNsN-3', 5'-NsNsNsS-3', 5'-nsnsnsn-3', or 5'-nsnsn-3' at the 3' end, wherein, each uppercase N independently indicates unmodified nucleotide adenosine, cytidine, guanosine and/or uridine; and lowercase letters indicates modified nucleotides including but not limited to 2'-H, 2'-OMe and base modification; and each s independently indicates phosphorothioate backbone modification. In some embodiments, each one of the last four nucleotides at the 3'end of the single guide RNA comprises a 2'-OMe modification.

In some embodiments, the chemically modified guide RNA comprises 2'-OMe modified Us at the 3' end. In some embodiments, the chemically modified guide RNA comprises 2'-OMe modified Us at the 3' end with PS linkages (3' UsUsUsU). In some embodiments, the chemically modified guide RNA comprises 2'-OMe modified Us at the 3' end without PS linkages (3'usususu). In some embodiments, the chemically modified single guide RNA comprises the sequence 5'-UsUsU, 5'-UsUsUsU-3', 5'-usususu-3', or 5'-ususu-3' at the 3' end. In some embodiments, the chemically modified single guide RNA comprises the sequence 5'-UsUsU at the 3' end. In some embodiments, the chemically modified single guide RNA comprises the sequence 5'-UsUsUsU-3' at the 3' end. In some embodiments, the chemically modified single guide RNA comprises the sequence 5'-usususu-3' at the 3' end. In some embodiments, the chemically modified single guide RNA comprises the sequence 5'-ususu-3' at the 3' end.

In some embodiments, the guide RNA comprises an unmodified nucleotide. In some embodiments, the unmodified nucleotide comprises a 2'hydroxyl (2'OH) that is in close proximity to the Cas12b protein when contacted with the Cas12b protein. "Close proximity" as used herein in some embodiments, refers to a hydrogen bond (real or predicted) between the 2'hydroxyl of a given nucleotide and the Cas12b protein in a three-dimensional complex. In other embodiments, "close proximity" refers to physical distance between the 2'hydroxyl and the Cas12b protein, such as 1, 2, 3, 4, 5, 6, 7, 8, 9, or 10 angstroms (Å) distance. In yet other embodiments, "close proximity" refers to other electrostatic or dipole-dipole interactions between the atoms of the 2'hydroxyl of a given nucleotide and the Cas12b protein. In some embodiments, the unmodified nucleotide comprises a 2'hydroxyl that is in contact with the Cas12b protein when contacted with the Cas12b protein. In some embodiments, the unmodified nucleotide comprises a 2'hydroxyl that is in close proximity with a second nucleotide in the guide RNA.

In some embodiments, the single guide RNA comprises an unmodified nucleotide. In some embodiments, the unmodified nucleotide comprises a 2'hydroxyl that is in close proximity to the Cas12b protein when contacted with the Cas12b protein. In some embodiments, the unmodified nucleotide comprises a 2'hydroxyl that is in contact with the Cas12b protein when contacted with the Cas12b protein. In some embodiments, the unmodified nucleotide comprises a 2'hydroxyl that is in close proximity with a second nucleotide in the single guide RNA.

Exemplary Modified Guide RNAs

```
Reference Guide Sequence
                                        SEQ ID NO: 1
GUUCUGUCUUUUGGUCAGGACAACCGUCUAGCUAUAAGUGCUGCAGG

GUGUGAGAAACUCCUAUUGCUGGACGAUGUCUCUUACGAGGCAUUAG

CACAACCAACAGCAUAGUCAAAUAAAUUUU,
gRNA scaffold sequence: positions 1 to 97 of
SEQ ID NO: 1.
Underlined sequence: ANGPTL3 spacer (positions
98 to 120 of SEQ ID NO: 1)
```

SEQ ID NO:1 is an exemplary Cas12b unmodified guide RNA sequence of 124 nucleotides in length which can be modified according to the modifications described herein. In some embodiments, a chemically modified guide RNA comprises SEQ ID NO:1 with one or more modifications. In some embodiments, a chemically modified guide RNA comprises SEQ ID NO:1 as a single guide RNA. In some embodiments, a chemically modified guide RNA comprises SEQ ID NO:1 as a dual guide RNA. In some embodiments, a chemically modified guide RNA comprises a scaffold sequence and a spacer sequence, wherein the scaffold sequence comprises a sequence at positions 1 to 97 of SEQ ID NO: 1 or a chemically modified version thereof. In these embodiments, the spacer sequence is contemplated to target a polynucleotide in a gene of interest, e.g., ANGPTL3, and can also be chemically modified.

In some embodiments, a guide RNA comprises the sequence of SEQ ID NO: 1. In embodiments, a guide RNA comprises a sequence at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.5%, and 100% identity to the sequence of SEQ ID NO: 1. In some embodiments, a guide RNA is SEQ ID NO: 1. In embodiments, a guide RNA is a sequence at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.5%, and 100% identity to the sequence of SEQ ID NO: 1.

In some embodiments, a single guide RNA comprises one or more unmodified nucleotide independently at a nucleotide position selected from positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124 as numbered in SEQ ID NO: 1 or a corresponding position thereof. In some embodiments, a single guide RNA comprises an unmodified nucleotide independently at a nucleotide position selected from positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124 as numbered in SEQ ID NO: 1 or a corresponding position thereof. In some embodiments, a single guide RNA comprises one or more unmodified nucleotide at a nucleotide position selected from positions 8-10, 12-15, 22-24, 32-38, 40, 41, 43, 44, 53-56, 63, 66-69, 88-97, 99-103, 106-108, 111-116 as numbered in SEQ ID NO: 1 or a corresponding position thereof. In some embodiments, the unmodified nucleotide is at a nucleotide position selected from positions 1, 8-10, 12-15, 22-24, 32-38, 40, 41, 43, 44, 53-56, 63, 66-69, 88-97, 99-103, 106-108, 111-116 as numbered in SEQ ID NO: 1 or a corresponding position thereof.

In some embodiments, a single guide RNA comprises one or more chemical modification independently at a nucleotide position selected from positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124 as numbered in SEQ ID NO: 1 or a corresponding position thereof. In some embodiments, a single guide RNA comprises a chemical modification independently at a nucleotide position selected from positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124 as numbered in SEQ ID NO: 1 or a corresponding position thereof. In some embodiments, a single guide RNA comprises one or more chemical modification at a nucleotide position selected from positions 2-7, 11, 16-21, 25-31, 39, 42, 45-52, 57-62, 64, 65, 70-87, 98, 104, 105, 109, and 110 as numbered in SEQ ID NO: 1 or a corresponding position thereof. In some embodiments, the chemical modification is at a nucleotide position selected from positions 2-7, 11, 16-21, 25-31, 39, 42, 45-52, 57-62, 64, 65, 70-87, 98, 104, 105, 109, and 110 as numbered in SEQ ID NO: 1 or a corresponding position thereof. In some embodiments, the chemical modification comprises a 2'-OMe modification. In some embodiments, the chemical modification comprises a nebularin. In some embodiments, the chemical modification comprises a deoxynebularin.

In some embodiments, the guide RNA comprises one or more structure based site-specific chemical modification(s) as illustrated in Table 1. Table 1 as shown below depicts exemplary guide RNAs which incorporate one or more modifications described herein and comprises an RNA spacer sequence which is analogous to a protospacer polynucleotide in the ANGPTL3 gene. FIG. 20 depicts an alignment of the reference guide RNA (SEQ ID NO:1) along with exemplary chemically modified guide RNAs, GB0002, GB0003, GB0007, GB0008. FIG. 20 further shows where which the modifications at certain positions as well as the spacer (positions 98 to 120) and scaffold sequence (positions 1 to 97) of these guide RNAs. As shown in FIG. 20, GB002 has modified nucleotides at positions 1-3, 5, 16, 21, 25, 29, 30, 44, 45, 49, 50, 62, 63, 67-69, 72, 75, 76, 79, 82-84 and 117-120, GB003 has modified nucleotides at positions 1, 2, 3, 5, 16, 21, 25, 29, 30, 33, 35, 37, 39, 44, 45, 47, 49-51, 62, 63, 65, 67-69, 72, 75, 76, 79, 82-84, 86, 87, 89, 92, 95 and 117-120. GB007 has modified nucleotides at positions 1-7, 11, 16-21, 25-31, 39, 42, 45-52, 57-62, 64, 65, 70-87, and 117-120, and GB008 has modified nucleotides at positions 1-7, 11, 16-21, 25-31, 45-52, 57-62, 64, 65, 70-87 and 117-120. Conversely, GB002 has unmodified nucleotides at positions 4, 6-15, 17-20, 22-24, 27, 28, 31-43, 46-48, 51-61, 64-66, 70, 71, 73, 74, 77, 78, 80, 81, 85-116, GB003 has unmodified nucleotides at positions 4, 6-15, 17-20, 22-24, 27, 28, 31, 32, 34, 36, 38, 40-43, 46, 48, 52-61, 64, 66, 70, 71, 73, 74, 77, 78, 80, 81, 85, 88, 90, 91, 93, 94 and 96-116. GB007 has unmodified nucleotides at positions 8-10, 12-15, 22-24, 32-38, 40, 41, 43, 44, 53-56, 63, 66-69 and 88-116, and GB008 has unmodified nucleotides at positions 8-10, 12-15, 22-24, 32-44, 53-56, 63, 66-69 and 88-116.

It is further contemplated, in some embodiments, that the exemplary guide RNAs of Table 1 can have the ANGPTL3 spacer sequence swapped with different spacer sequences to target other genes of interest, such as PCSK9, APOC3, and the like. Furthermore, the modifications on spacer sequences of other genes are also contemplated, in some embodiments, to correspond to the modifications used in the exemplary ANGPTL3 spacer sequences. Thus, in some embodiments, are guide RNAs that comprise a scaffold sequence in one of the gRNAs in Table 1 and a different spacer sequence than the spacer sequence in one of the gRNAs in Table 1.

In another aspect, provided herein is a guide RNA, including single guides thereof, comprising a gRNA sequence of Table 1, wherein a, u, g, and c indicate 2'-OMe modified adenine, uridine, guanine, and cytidine, wherein s indicates a phosphorothioate linkage, wherein X indicates a nebularine, and wherein dX indicates a 2'-deoxynebularine. In some embodiments, a guide RNA comprises a sequence at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.5%, and 100% identity to any one of the gRNA sequences of Table 1. In some embodiments, a guide RNA is a sequence at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.5%, and 100% identity to any one of the gRNA sequences of Table 1. In some embodiments, a guide RNA is any one of the sequences of Table 1.

One aspect provided herein is a single guide RNA comprising a sequence selected from any one of SEQ ID NOs: 2-89, wherein a, u, g, and c indicate 2'-OMe modified adenine, uridine, guanine, and cytidine, and wherein s indicates a phosphorothioate linkage. In some embodiments, a single guide RNA comprises a sequence at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 860%, 87%, 88%, 89%, 90%, 90.5%, 91%, 91.5%, 920%, 92.5%, 93%, 93.5%, 94%, 94.5%, 95%, 95.5%, 96%, 96.5%, 97%, 97.5%, 98%, 98.5%, 99%, 99.5%, and 100% identity to any one of SEQ ID NOs: 2-89. In some embodiments, a single guide RNA is a sequence at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.5%, and 100% identity to any one of SEQ ID NOs: 2-89. In some embodiments, a single guide RNA is any one of SEQ ID NOs: 2-89 having one or more chemical modifications.

In some embodiments, the single guide RNA comprises a chemically modified nucleotide selected from positions 1-3, 5, 16, 21, 25, 29, 30, 44, 45, 49, 50, 62, 63, 67-69, 72, 75, 76, 79, 82-84 and 117-120 as numbered in SEQ ID NO: 1 or a corresponding position thereof.

In some embodiments, the single guide RNA comprises a chemically modified nucleotide selected from positions 1, 2, 3, 5, 16, 21, 25, 29, 30, 33, 35, 37, 39, 44, 45, 47, 49-51, 62, 63, 65, 67-69, 72, 75, 76, 79, 82-84, 86, 87, 89, 92, 95 and 117-120 as numbered in SEQ ID NO: 1 or a corresponding position thereof.

In some embodiments, the single guide RNA comprises a chemically modified nucleotide selected from positions 1-7, 11, 16-21, 25-31, 39, 42, 45-52, 57-62, 64, 65, 70-87, and 117-120 as numbered in SEQ ID NO: 1 or a corresponding position thereof.

In some embodiments, the single guide RNA comprises a chemically modified nucleotide selected from positions 1-7, 11, 16-21, 25-31, 45-52, 57-62, 64, 65, 70-87 and 117-120 as numbered in SEQ ID NO: 1 or a corresponding position thereof.

In some embodiments, the single guide RNA comprises an unmodified nucleotide at a nucleotide position selected from positions 4, 6-15, 17-20, 22-24, 27, 28, 31-43, 46-48, 51-61, 64-66, 70, 71, 73, 74, 77, 78, 80, 81, and 85-116 as numbered in in SEQ ID NO: 1 or a corresponding position thereof.

In some other embodiments, the single guide RNA comprises an unmodified nucleotide at a nucleotide position selected from positions 4, 6-15, 17-20, 22-24, 27, 28, 31, 32, 34, 36, 38, 40-43, 46, 48, 52-61, 64, 66, 70, 71, 73, 74, 77, 78, 80, 81, 85, 88, 90, 91, 93, 94 and 96-116 as numbered in SEQ ID NO: 1 or a corresponding position thereof.

In some other embodiments, the single guide RNA comprises an unmodified nucleotide at a nucleotide position selected from positions 8-10, 12-15, 22-24, 32-38, 40, 41, 43, 44, 53-56, 63, 66-69 and 88-116 as numbered in SEQ ID NO: 1 or a corresponding position thereof.

In some other embodiments, the single guide RNA comprises an unmodified nucleotide at a nucleotide position selected from positions 8-10, 12-15, 22-24, 32-44, 53-56, 63, 66-69 and 88-116 as numbered in SEQ ID NO: 1 or a corresponding position thereof.

TABLE 1

| | | | | Exemplary Cas12b gRNAs targeting human ANGPTL3 gene |
|---|---|---|---|---|
| gRNA ID | Proto-Spacer SEQ ID NO: | Exemplary ANGPTL3 Protospacer (5'-3') | gRNA SEQ ID NO: | gRNA (5'-3') with Modified Exemplary Spacer |
| GB0001 | 90 | AACCAACAGCAT AGTCAAATAAA | 2 | gsususCUGUCUUUUGGUCAGGACAACC GUCUAGCUAUAAGUGCUGCAGGGUGU GAGAAACUCCUAUUGCUGGACGAUGU CUCUUACGAGGCAUUAGCACAACCAA CAGCAUAGUCAAAusasasa |
| GB0002 | 90 | AACCAACAGCAT AGTCAAATAAA | 197 | gsususCuGUCUUUUGGUcAGGAcAACcgU CuaGCUAUAAGUGCUGcaGGGugUGAGA AACUCCuaUUGcugGAcGAugUCuCUuacG AGGCAUUAGCACAACCAACAGCAUAG UCAAAusasasa |
| GB0003 | 90 | AACCAACAGCAT AGTCAAATAAA | 198 | gsususCuGUCUUUUGGUcAGGAcAACcgU CuaGCuAuAaGuGCUGcaGgGuguGAGAAA CUCCuaUuGcugGAcGAugUCuCUuacGagG cAUuAGcACAACCAACAGCAUAGUCAA Ausasasa |
| GB0004 | 90 | AACCAACAGCAT AGTCAAATAAA | 199 | gsususCUGUCUUUUGGUCAGGACAACC GUCUAGCUAUAAGUGCUGCAGGGUGU GAGAAACUCCUAUUGCUGGACGAUGU CUCUUACGAGGCAUUAGCACAACCAA CAGCAUAGUcAAAusasasa |
| GB0005 | 90 | AACCAACAGCAT AGTCAAATAAA | 200 | gsususCuGUCUUUUGGUcAGGAcAACcgU CuaGCUAUAAGUGCUGcaGGGugUGAGA AACUCCuaUUGcugGAcGAugUCuCUuacG AGGCAUUAGCACAACCAACAGCAuAG UcAAAusasasa |

TABLE 1-continued

| gRNA ID | Proto-Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| GB0006 | 90 | AACCAACAGCAT AGTCAAATAAA | 201 | gsususCuGUCUUUUGGUcAGGAcAACcgU CuaGCuAuAaGuGCUGcaGgGuguGAGAAA CUCCuaUuGcugGAcGAugUCuCUuacGagG cAUuAGcACAACCAACAGCAuAGUcAA Ausasasa |
| GB0007 | 90 | AACCAACAGCAT AGTCAAATAAA | 202 | gsususcuguCUUuUGGUcaggacAACcgucuag CUAUAAGuGCuGCagggugugAGAAacuccu AuuGCUGgacgaugucucuuacgagGCAUUAG CACAACCAACAGCAUAGUCAAAusasasa |
| GB0008 | 90 | AACCAACAGCAT AGTCAAATAAA | 203 | gsususcuguCUUuUGGUcaggacAACcgucuag CUAUAAGUGCUGCagggugugAGAAacucc uAuuGCUGgacgaugucucuuacgagGCAUUAG CACAACCAACAGCAUAGUCAAAusasasa |
| GB0009 | 90 | AACCAACAGCAT AGTCAAATAAA | 204 | gsususCUGUCUUUUGGUCAGGACAACcg ucuagCUAUAAGuGCuGCagggugugAGAa cuccuAuuGCUGgacgaugucucuuacgagGCAU UAGCACAACCAACAGCAUAGUCAAAus asasa |
| GB0010 | 90 | AACCAACAGCAT AGTCAAATAAA | 205 | gsususcuguCUUuUGGUcaggacAACcgucuag CUAUAAGuGCuGCAGGGUGUGAGAAA CUCCUAuuGCUGgacgaugucucuuacgagGC AUUAGCACAACCAACAGCAUAGUCAA Ausasasa |
| GB0011 | 90 | AACCAACAGCAT AGTCAAATAAA | 206 | gsususCUGUCUUUUGGUCAGGACAACC GUCUAGCUAUAAGUGCUGCAGGGUGU GAGAAACUCCUAUUGCUGGACGAUGU CUCUUACGAGGCAUUAGCACaACCAAc aGCAuaGUCAAAusasasa |
| GB0012 | 90 | AACCAACAGCAT AGTCAAATAAA | 207 | gsususcuguCUUuUGGUcaggacAACcgucuag CUAUAAGuGCuGCagggugugAGAAacuccu AuuGCUGgacgaugucucuuacgagGCAUUAG CACaACCAAcaGCAuaGUCAAAusasasa |
| GB0013 | 90 | AACCAACAGCAT AGTCAAATAAA | 208 | gsususCUGUCUUUUGGUCAGGACAACC GUCUAGCUAUAAGUGCUGCAGGGUGU GAGAAACUCCUAUUGCUGGACGAUGU CUCUUACGAGGCAUUAGCACaACcAAc aGcAuaGUCAAAusasasa |
| GB0014 | 90 | AACCAACAGCAT AGTCAAATAAA | 209 | gsususcuguCUUuUGGUcaggacAACcgucuag CuAUAAGuGCuGCagggugugAGAAacuccu AuuGCUGgacgaugucucuuacgagGcAUUAGC ACaACcAAcaGcAuaGUCAAAusasasa |
| GB0015 | 90 | AACCAACAGCAT AGTCAAATAAA | 3 | gsususCUGUCUUUUGGUCAGGACAACC GUCUAGCUAUAAGUGCUGCAGGGUGU GAGAAACUCCUAUUGCUGGACGAUGU CUCUUACGAGGCAUUAGCACAACCAA CAGCAUAGUCAAAUAAAusususu |
| GB0016 | 90 | AACCAACAGCAT AGTCAAATAAA | 4 | gsususCUGUCUUUUGGUCAGGACAACC GUCUAGCUAUAAGUGCUGCAGGGUGU GAGAAACUCCUAUUGCUGGACGAUGU CUCUUACGAGGCAUUAGCACAACCAA CAGCAUGUCAAAuaaausususu |
| GB0017 | 90 | AACCAACAGCAT AGTCAAATAAA | 210 | gsususcuguCUUuUGGUcaggacAACcgucuag CUAUAAGuGCuGCagggugugAGAAacuccu AuuGCUGgacgaugucucuuacgagGCAUUAG CACAACCAACAGCAUAGUCAAAuAAA usususu |
| GB0018 | 90 | AACCAACAGCAT AGTCAAATAAA | 211 | gsususCUGUCUUUUGGUCAGGACAACC GUCUAGCUAUAAGUGCUGCAGGGUGU GAGAAACUCCUAUUGCUGGACGAUGU CUCUUACGAGGCAUUAGCACaACCAAc aGCAuaGUCAAAuaaausususu |

TABLE 1-continued

| | | Exemplary ANGPTL3 | | |
|---|---|---|---|---|
| gRNA ID | Proto-Spacer SEQ ID NO: | Protospacer (5'-3') | gRNA SEQ ID NO: | gRNA (5'-3') with Modified Exemplary Spacer |
| GB0019 | 90 | AACCAACAGCAT AGTCAAATAAA | 212 | gsususcuguCUUuUGGUcaggacAACcgucuag CUAUAAGuGCuGCagggugugAGAAacuccu AuuGCUGgacgaugucucuuacgagGCAUUAG CAC<u>AACCAACAGCAUAGUCAAAUAAA</u> ususu |
| GB0020 | 90 | AACCAACAGCAT AGTCAAATAAA | 213 | gsususcuguCUUuUGGUcaggacAACcgucuag CUAUAAGuGCuGCagggugugAGAAacuccu AuuGCUGgacgaugucucuuacgagGCAUUAG CAC<u>AACCAACAGCAUAGUCAAA</u>uaaaus ususu |
| GB0021 | 90 | AACCAACAGCAT AGTCAAATAAA | 214 | gsususcuguCUUuUGGUcaggacAACcgucuag CUAUAAGuGCuGCagggugugAGAAacuccu AuuGCUGgacgaugucucuuacgagGCAUUAG CAC<u>aACCAAcaGCuaGUCAAA</u>uaaaususu su |
| GB0022 | 91 | AGGTAGTCCATG GACATTAATTC | 5 | gsususCUGUCUUUUGGUCAGGACAACC GUCUAGCUAUAAGUGCUGCAGGGGUGU GAGAAACUCCUAUUGCUGGACGAUGU CUCUUACGAGGCAUUAGCAC<u>AGGUAG UCCAUGGACAUUA</u>asususc |
| GB0023 | 91 | AGGTAGTCCATG GACATTAATTC | 215 | gsususCUGUCUUUUGGUCAGGACAACC GUCUAGCUAUAAGUGCUGCAGGGGUGU GAGAAACUCCUAUUGCUGGACGAUGU CUCUUACGAGGCAUUAGCAC<u>aGGuAGu cCAugg</u>ACAUuAasususc |
| GB0024 | 91 | AGGTAGTCCATG GACATTAATTC | 216 | gsususCUGUCUUUUGGUCAGGACAACC GUCUAGCUAUAAGUGCUGCAGGGGUGU GAGAAACUCCUAUUGCUGGACGAUGU CUCUUACGAGGCAUUAGCAC<u>AGGUAG</u> ucCAUggACAUUAasususc |
| GB0025 | 91 | AGGTAGTCCATG GACATTAATTC | 217 | gsususCuGUCUUUUGGUcAGGAcAACcgU CuaGCUAUAAGUGCUGcaGGGugUGAGA AACUCCuaUUGcugGAcGAugUCuCUuacG AGGCAUUAGCAC<u>AGGUAGUCCAUGGA CAUUA</u>asususc |
| GB0026 | 91 | AGGTAGTCCATG GACATTAATTC | 218 | gsususCuGUCUUUUGGUcAGGAcAACcgU CuaGCuAuAaGuGCUGcaGgGuguGAGAAA CUCCuaUuGcugGAcGAugUCuCUuacGagG cAUuAGcAC<u>AGGUAGUCCAUGGACAUU Aa</u>sususc |
| GB0027 | 91 | AGGTAGTCCATG GACATTAATTC | 219 | gsususcuguCUUuUGGUcaggacAACcgucuag CUAUAAGuGCuGCagggugugAGAAacuccu AuuGCUGgacgaugucucuuacgagGCAUUAG CAC<u>AGGUAGUCCAUGGACAUUA</u>asusus <u>c</u> |
| GB0028 | 91 | AGGTAGTCCATG GACATTAATTC | 220 | gsususcuguCUUuUGGUcaggacAACcgucuag CUAUAAGUGCUGCagggugugAGAAacucc uAuuGCUGgacgaugucucuuacgagGCAUUAG CAC<u>AGGUAGUCCAUGGACAUUA</u>asusus <u>c</u> |
| GB0029 | 91 | AGGTAGTCCATG GACATTAATTC | 221 | gsususCUGUCUUUUGGUCAGGACAACcg ucuagCUAUAAGuGCuGCagggugugAGAAa cuccuAuuGCUGgacgaugucucuuacgagGCAU UAGCAC<u>AGGUAGUCCAUGGACAUUAa</u>s <u>ususc</u> |
| GB0030 | 91 | AGGTAGTCCATG GACATTAATTC | 222 | gsususcuguCUUuUGGUcaggacAACcgucuag CUAUAAGuGCuGCAGGGGUGUGAGAAA CUCCUAuuGCUGgacgaugucucuuacgagGC AUUAGCAC<u>AGGUAGUCCAUGGACAUU Aa</u>sususc |

TABLE 1-continued

| | | | | |
|---|---|---|---|---|
| | | Exemplary Cas12b gRNAs targeting human ANGPTL3 gene | | |

| gRNA ID | Proto-Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| GB0031 | 91 | AGGTAGTCCATG GACATTAATTC | 223 | gsususCUGUCUUUUGGUCAGGACAACC GUCUAGCUAUAAGUGCUGCAGGGUGU GAGAAACUCCUAUUGCUGGACGAUGU CUCUUACGAGGCAUUAGCACaGGUAG ucCAUggACAUUAasususc |
| GB0032 | 91 | AGGTAGTCCATG GACATTAATTC | 224 | gsususcuguCUUuUGGUcaggacAACcgucuag CUAUAAGuGCuGCagggugugAGAAacuccu AuuGCUGgacgaugucucuuacgagGCAUUAG CACaGGUAGucCAUggACAUUAasususc |
| GB0033 | 91 | AGGTAGTCCATG GACATTAATTC | 225 | gsususcuguCUUuUGGUcaggacAACcgucuag CUAUAAGuGCuGCagggugugAGAAacuccu AuuGCUGgacgaugucucuuacgagGCAUUAG CACaGGuAGucCAuggACAUuAasususc |
| GB0034 | 91 | AGGTAGTCCATG GACATTAATTC | 226 | gsususcuguCUUuUGGUcaggacAACcgucuag CuUAAGuGCuGCagggugugAGAAacuccu AuuGCUGgacgaugucucuuacgagGcAUUAGC ACaGGuAGucCAuggACAUuAasususc |
| GB0035 | 91 | AGGTAGTCCATG GACATTAATTC | 6 | gsususcuguCUUuUGGUcaggacAACcgucuag CUAUAAGuCuGCagggugugAGAAacuccuA uuGCUGgacgaugucucuuacgagGCAUUAGC ACAGGUAGUCCAUGGACAUUAAUUCu sususu |
| GB0036 | 91 | AGGTAGTCCATG GACATTAATTC | 7 | gsususcuguCUUuUGGUcaggacAACcgucuag CUAUAAGuGCuGCagggugugAGAAacuccu AuuGCUGgacgaugucucuuacgagGCAUUAG CACAGGUAGUCCAUGGACAUUAauucus ususu |
| GB0037 | 91 | AGGTAGTCCATG GACATTAATTC | 227 | gsususcuguCUUuUGGUcaggacAACcgucuag CUAUAAGuGCuGCagggugugAGAAacuccu AuuGCUGgacgaugucucuuacgagGCAUUAG CACaGGUAGucCAUggACAUUAauucususu su |
| GB0038 | 92 | CAAAAACTCAAC ATATTTGATCA | 8 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACCAAAAA CUCAACAUAUUUGAUCAUsususu |
| GB0039 | 93 | TACTTCAACAAA AAGTGAAATAT | 9 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACUACUUC AACAAAAAGUGAAAUAUUsususu |
| GB0040 | 94 | AGAAGAGCAAC TAACTAACTTAA | 10 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACAGAAGA GCAACUAACUAACUUAAUsususu |
| GB0041 | 95 | TGGAGGAAATA ACTAGAGGAAC A | 11 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACUGGAGG AAAUAACUAGAGGAACAUsususu |
| GB0042 | 96 | AAGAACCCACA GAAATTTCTCTA | 12 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACAAGAAC CCACAGAAAUUUCUCUAUsususu |

TABLE 1-continued

Exemplary Cas12b gRNAs targeting human ANGPTL3 gene

| gRNA ID | Proto-Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| GB0043 | 90 | AACCAACAGCAT AGTCAAATAAA | 13 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCAC<u>AACCAA CAGCAUAGUCAAAUAAA</u>Ususus |
| GB0044 | 91 | aGGTAGTCCATG GACATTAATTC | 14 | gsusUCUGUCUUUUGGUCAGGACAACC GUCUAGCUAUAAGUGCUGCAGGGUGU GAGAAACUC CUAUUGCUGGACGAUGUCUCUUACGA GGCAUUAGCAC<u>AGGUAGUCCAUGGAC AUUAAUUC</u>Ususus |
| GB0045 | 97 | CTGGCAATGTCC CCAATGCAATC | 15 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCAC<u>CUGGCA AUGUCCCCAAUGCAAUC</u>Ususus |
| GB0046 | 98 | CATTGGGGACAT TGCCAGTAATC | 16 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCAC<u>CAUUGG GGACAUUGCCAGUAAUC</u>Ususus |
| GB0047 | 99 | CCCAAGTAAAAA GAATATTCAAT | 17 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCAC<u>CCCAAG UAAAAAGAAUAUUCAAU</u>Ususus |
| GB0048 | 100 | AATATAATGTTT GTTGTCTTTCC | 18 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCAC<u>AAUAUA AUGUUUGUUGUCUUUCC</u>Ususus |
| GB0049 | 101 | GAAGAGCAACT AACTAACTTAAT | 19 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCAC<u>GAAGAG CAACUAACUAACUUAAU</u>Ususus |
| GB00001 | 90 | AACCAACAGCAT AGTCAAATAAA | 20 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCAC<u>AACCAA CAGCAUAGUCAAA</u>usasasa |
| GB00002 | 90 | AACCAACAGCAT AGTCAAATAAA | 244 | gsusUCuGUCUUUUGGUcAGGAcAACcgU CuaGCUAUAAGUGCUGcaGGGugUGAGA AACUCCuaUUGcugGAcGAugUCuCUuacG AGGCAUUAGCAC<u>AACCAACAGCAUAG UCAAA</u>usasasa |
| GB00003 | 90 | AACCAACAGCAT AGTCAAATAAA | 245 | gsusUCuGUCUUUUGGUcAGGAcAACcgU CuaGCuAuAaGuGCUGcaGgGuguGAGAAA CUCCuaUuGcugGAcGAugUCuCUuacGagG cAUuAGcAC<u>AACCAACAGCAUAGUCAA A</u>usasasa |
| GB00004 | 90 | AACCAACAGCAT AGTCAAATAAA | 246 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCAC<u>AACCAA CAGCAuAGUcAAA</u>usasasa |
| GB00005 | 90 | AACCAACAGCAT AGTCAAATAAA | 247 | gsusUCuGUCUUUUGGUcAGGAcAACcgU CuaGCUAUAAGUGCUGcaGGGugUGAGA AACUCCuaUUGcugGAcGAugUCuCUuacG AGGCAUUAGCAC<u>AACCAACAGCAuAG UcAAA</u>usasasa |

TABLE 1-continued

Exemplary Cas12b gRNAs targeting human ANGPTL3 gene

| gRNA ID | Proto-Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| GB00006 | 90 | AACCAACAGCAT AGTCAAATAAA | 248 | gsusUCuGUCUUUUGGUcAGGAcAACcgU CuaGCuAuAaGuGCUGcaGgGuguGAGAAA CUCCuaUuGcugGAcGAugUCuCUuacGagG cAUuAGcACAACCAACAGCAuAGUcAA Ausasasa |
| GB00007 | 90 | AACCAACAGCAT AGTCAAATAAA | 249 | gsusUcuguCUUuUGGUcaggacAACcgucuag CUAUAAGuGCuGCagggugugAGAAacuccu AuuGCUGgacgaugucucuuacgagGCAUUAG CACAACCAACAGCAUAGUCAAusasasa |
| GB00008 | 90 | AACCAACAGCAT AGTCAAATAAA | 250 | gsusUcuguCUUuUGGUcaggacAACcgucuag CUAUAAGUGCUGCagggugugAGAAacucc uAuuGCUGgacgaugucucuuacgagGCAUUAG CACAACCAACAGCAUAGUCAAusasasa |
| GB00009 | 90 | AACCAACAGCAT AGTCAAATAAA | 251 | gsusUCUGUCUUUUGGUCAGGACAACcg ucuagCUAUAAGuGCuGCagggugugAGAAa cuccuAuuGCUGgacgaugucucuuacgagGCAU UAGCACAACCAACAGCAUAGUCAAus asasa |
| GB00010 | 90 | AACCAACAGCAT AGTCAAATAAA | 252 | gsusUcuguCUUuUGGUcaggacAACcgucuag CUAUAAGuGCuGCAGGGGUGUGAGAAA CUCCUAuuGCUGgacgaugucucuuacgagGC AUUAGCACAACCAACAGCAUAGUCAA Ausasasa |
| GB00011 | 90 | AACCAACAGCAT AGTCAAATAAA | 253 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACaACCAAc aGCAuaGUCAAusasasa |
| GB00012 | 90 | AACCAACAGCAT AGTCAAATAAA | 254 | gsusUcuguCUUuUGGUcaggacAACcgucuag CUAUAAGuGCuGCagggugugAGAAacuccu AuuGCUGgacgaugucucuuacgagGCAUUAG CACaACCAcaGCAuaGUCAAusasasa |
| GB00013 | 90 | AACCAACAGCAT AGTCAAATAAA | 255 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACaACcAAc aGcAuaGUCAAusasasa |
| GB00014 | 90 | AACCAACAGCAT AGTCAAATAAA | 256 | gsusUcuguCUUuUGGUcaggacAACcgucuag CuAUAAGuGCuGCagggugugAGAAacuccu AuuGCUGgacgaugucucuuacgagGcAUUAGC ACaACcAAcaGcAuaGUCAAusasasa |
| GB00015 | 90 | AACCAACAGCAT AGTCAAATAAA | 228 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACAACCAA CAGCAUAGUCAAAUAAAusususu |
| GB00016 | 90 | AACCAACAGCAT AGTCAAATAAA | 21 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACAACCAA CAGCAUGUCAAuaaausususu |
| GB00017 | 90 | AACCAACAGCAT AGTCAAATAAA | 229 | gsusUcuguCUUuUGGUcaggacAACcgucuag CUAUAAGuGCuGCagggugugAGAAacuccu AuuGCUGgacgaugucucuuacgagGCAUUAG CACAACCAACAGCAUAGUCAAAuAAA usususu |
| GB00018 | 90 | AACCAACAGCAT AGTCAAATAAA | 230 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACaACCAAc aGCAuaGUCAAuaaausususu |

TABLE 1-continued

Exemplary Cas12b gRNAs targeting human ANGPTL3 gene

| gRNA ID | Proto-Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| GB00019 | 90 | AACCAACAGCAT AGTCAAATAAA | 231 | gsusUcguCUUuUGGUcaggacAACcgucuag CUAUAAGuGCuGCagggugugAGAAacuccu AuuGCUGgacgaugucucuuacgagGCAUUAG CACAACCAACAGCAUAGUCAAAUAAA usususu |
| GB00020 | 90 | AACCAACAGCAT AGTCAAATAAA | 232 | gsusUcguCUUuUGGUcaggacAACcgucuag CUAUAAGuGCuGCagggugugAGAAacuccu AuuGCUGgacgaugucucuuacgagGCAUUAG CACAACCAACAGCAUAGUCAAUaaaaus ususu |
| GB00021 | 90 | AACCAACAGCAT AGTCAAATAAA | 233 | gsusUcguCUUuUGGUcaggacAACcgucuag CUAUAAGuGCuGCagggugugAGAAacuccu AuuGCUGgacgaugucucuuacgagGCAUUAG CACaACCAAcaGCAuaGUCAAUaaaaususu su |
| GB00022 | 91 | AGGTAGTCCATG GACATTAATTC | 22 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACAGGUAG UCCAUGGACAUUAasususc |
| GB00023 | 91 | AGGTAGTCCATG GACATTAATTC | 272 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACaGGuAGu cCAuggACAUuAasususc |
| GB00024 | 91 | AGGTAGTCCATG GACATTAATTC | 273 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACAGGUAG ucCAUggACAUUAasususc |
| GB00025 | 91 | AGGTAGTCCATG GACATTAATTC | 274 | gsusUCuGUCUUUUGGUcAGGAcAACcgU CuaGCUAUAAGUGCUGcaGGGugUGAGA AACUCCuaUUGcugGAcGAugUCuCUuacG AGGCAUUAGCACAGGUAGUCCAUGGA CAUUAasususc |
| GB00026 | 91 | AGGTAGTCCATG GACATTAATTC | 275 | gsusUCuGUCUUUUGGUcAGGAcAACcgU CuaGCuAuAaGuGCUGcaGgGuguGAGAAA CUCCuaUuGcugGAcGAugUCuCUuacGagG cAUuAGcACAGGUAGUCCAUGGACAUU Aasususc |
| GB00027 | 91 | AGGTAGTCCATG GACATTAATTC | 276 | gsusUcguCUUuUGGUcaggacAACcgucuag CUAUAAGuGCuGCagggugugAGAAacuccu AuuGCUGgacgaugucucuuacgagGCAUUAG CACAGGUAGUCCAUGGACAUUAasusus c |
| GB00028 | 91 | AGGTAGTCCATG GACATTAATTC | 277 | gsusUcguCUUuUGGUcaggacAACcgucuag CUAUAAGUGCUGCagggugugAGAAacucc uAuuGCUGgacgaugucucuuacgagGCAUUAG CACAGGUAGUCCAUGGACAUUAasusus c |
| GB00029 | 91 | AGGTAGTCCATG GACATTAATTC | 278 | gsusUCUGUCUUUUGGUCAGGACAACcg ucuagCUAUAAGuGCuGCagggugugAGAAa cuccuAuuGCUGgacgaugucucuuacgagGCAU UAGCACAGGUAGUCCAUGGACAUUAas ususc |
| GB00030 | 91 | AGGTAGTCCATG GACATTAATTC | 279 | gsusUcguCUUuUGGUcaggacAACcgucuag CUAUAAGuGCuGCAGGGUGUGAGAAA CUCCUAuuGCUGgacgaugucucuuacgagGC AUUAGCACAGGUAGUCCAUGGACAUU Aasususc |

TABLE 1-continued

<u>Exemplary Cas12b gRNAs targeting human ANGPTL3 gene</u>

| gRNA ID | Proto- Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| GB00031 | 91 | AGGTAGTCCATG GACATTAATTC | 280 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACaGGUAG ucCAUggACAUUAasususc |
| GB00032 | 91 | AGGTAGTCCATG GACATTAATTC | 281 | gsusUcuguCUUuUGGUcaggacAACcgucuag CUAUAAGuGCuGCagggugugAGAAacuccu AuuGCUGgacgaugucucuuacgagGCAUUAG CACaGGUAGucCAUggACAUUAasususc |
| GB00033 | 91 | AGGTAGTCCATG GACATTAATTC | 282 | gsusUcuguCUUuUGGUcaggacAACcgucuag CUAUAAGuGCuGCagggugugAGAAacuccu AuuGCUGgacgaugucucuuacgagGCAUUAG CACaGGuAGucCAuggACAUuAasususc |
| GB00034 | 91 | AGGTAGTCCATG GACATTAATTC | 283 | gsusUcuguCUUuUGGUcaggacAACcgucuag CuAUAAGuGCuGCagggugugAGAAacuccu AuuGCUGgacgaugucucuuacgagGcAUUAGC ACaGGuAGucCAuggACAUuAasususc |
| GB00035 | 91 | AGGTAGTCCATG GACATTAATTC | 23 | gsusUcuguCUUuUGGUcaggacAACcgucuag CUAUAAGuCUuGCagggugugAGAAacuccuA uuGCUGgacgaugucucuuacgagGCAUUAGC ACAGGUAGUCCAUGGACAUUAAUUCu sususu |
| GB00036 | 91 | AGGTAGTCCATG GACATTAATTC | 240 | gsusUcuguCUUuUGGUcaggacAACcgucuag CUAUAAGuGCuGCagggugugAGAAacuccu AuuGCUGgacgaugucucuuacgagGCAUUAG CACAGGUAGUCCAUGGACAUUAauucus ususu |
| GB00037 | 91 | AGGTAGTCCATG GACATTAATTC | 241 | gsusUcuguCUUuUGGUcaggacAACcgucuag CUAUAAGuGCuGCagggugugAGAAacuccu AuuGCUGgacgaugucucuuacgagGCAUUAG CACaGGUAGucCAUggACAUUAauucususu su |
| GB00038 | 90 | AACCAACAGCAT AGTCAAATAAA | 257 | gsusuCUGUCUUUUGGUCAGGACAACCG UCUAGCUAUAAGUGCUGCAGGGUGUG AGAAACUCCUAUUGCUGGACGAUGUC UCUUACGAGGCAUUAGCACAACCAAC AGCAUAGUCAAAusasasa |
| GB00039 | 90 | AACCAACAGCAT AGTCAAATAAA | 258 | gsusuCuGUCUUUUGGUcAGGAcAACcgU CuaGCUAUAAGUGCUGcaGGGugUGAGA AACUCCuaUUGcugGAcGAugUCuCUuacG AGGCAUUAGCACAACCAACAGCAUAG UCAAAusasasa |
| GB00040 | 90 | AACCAACAGCAT AGTCAAATAAA | 259 | gsusuCuGUCUUUUGGUcAGGAcAACcgU CuaGCuAuAaGuGCUGcaGgGugUGAGAAA CUCCuaUuGcugGAcGAugUCuCUuacGagG cAUuAGcACAACCAACAGCAUAGUCAA Ausasasa |
| GB00041 | 90 | AACCAACAGCAT AGTCAAATAAA | 260 | gsusuCUGUCUUUUGGUCAGGACAACCG UCUAGCUAUAAGUGCUGCAGGGUGUG AGAAACUCCUAUUGCUGGACGAUGUC UCUUACGAGGCAUUAGCACAACCAAC AGCAuAGUcAAAusasasa |
| GB00042 | 90 | AACCAACAGCAT AGTCAAATAAA | 261 | gsusuCuGUCUUUUGGUcAGGAcAACcgU CuaGCUAUAAGUGCUGcaGGGugUGAGA AACUCCuaUUGcugGAcGAugUCuCUuacG AGGCAUUAGCACAACCAACAGCAuAG UcAAAusasasa |

TABLE 1-continued

Exemplary Cas12b gRNAs targeting human ANGPTL3 gene

| gRNA ID | Proto-Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| GB00043 | 90 | AACCAACAGCAT AGTCAAATAAA | 262 | gsusuCuGUCUUUUGGUcAGGAcAACcgU CuaGCuAuAaGuGCUGcaGgGuguGAGAAA CUCCuaUuGcugGAcAugUCuCUuacGagG cAUuAGcACAACCAACAGCAUAGUcAA Ausasasa |
| GB00044 | 90 | AACCAACAGCAT AGTCAAATAAA | 263 | gsusucuguCUUuUGGUcaggacAACcgucuagC UAUAAGuGCUgCagggugugAGAAacuccuA uuGCUGgacgaugucucuuacgagGCAUUAGC ACAACCAACAGCAUAGUCAAAusasasa |
| GB00045 | 90 | AACCAACAGCAT AGTCAAATAAA | 264 | gsusucuguCUUuUGGUcaggacAACcgucuagC UAUAAGUGCUGCagggugugAGAAacuccu AuuGCUGgacgaugucucuuacgagGCAUUAG CACAACCAACAGCAUAGUCAAAusasasa |
| GB00046 | 90 | AACCAACAGCAT AGTCAAATAAA | 265 | gsusuCUGUCUUUUGGUCAGGACAACcgu cuagCUAUAAGuGCuGCagggugugAGAAac uccuAuuGCUGgacgaugucucuuacgagGCAUU AGCACAACCAACAGCAUAGUCAAAusa sasa |
| GB00047 | 90 | AACCAACAGCAT AGTCAAATAAA | 266 | gsusucuguCUUuUGGUcaggacAACcgucuagC UAUAAGuGCuGCAGGGUGUGAGAAAC UCCUAuuGCUGgacgaugucucuuacgagGCA UUAGCACAACCAACAGCAUAGUCAAA usasasa |
| GB00048 | 90 | AACCAACAGCAT AGTCAAATAAA | 267 | gsusuCUGUCUUUUGGUCAGGACAACCG UCUAGCUAUAAGUGCUGCAGGGUGUG AGAAACUCCUAUUGCUGGACGAUGUC UCUUACGAGGCAUUAGCACaACCAAca GCAuaGUCAAAusasasa |
| GB00049 | 90 | AACCAACAGCAT AGTCAAATAAA | 268 | gsusucuguCUUuUGGUcaggacAACcgucuagC UAUAAGuGCuGCagggugugAGAAacuccuA uuGCUGgacgaugucucuuacgagGCAUUAGC ACaACCAAcaGCAuaGUCAAAusasasa |
| GB00050 | 90 | AACCAACAGCAT AGTCAAATAAA | 269 | gsusuCUGUCUUUUGGUCAGGACAACCG UCUAGCUAUAAGUGCUGCAGGGUGUG AGAAACUCCUAUUGCUGGACGAUGUC UCUUACGAGGCAUUAGCACaACcAAca GcAuaGUCAAAusasasa |
| GB00051 | 90 | AACCAACAGCAT AGTCAAATAAA | 270 | gsusucuguCUUuUGGUcaggacAACcgucuagC uAUAAGuGCuGCagggugugAGAAacuccuA uuGCUGgacgaugucucuuacgagGcAUUAGCA CaACcAAcaGcAuaGUCAAAusasasa |
| GB00052 | 90 | AACCAACAGCAT AGTCAAATAAA | 234 | gsusuCUGUCUUUUGGUCAGGACAACCG UCUAGCUAUAAGUGCUGCAGGGUGUG AGAAACUCCUAUUGCUGGACGAUGUC UCUUACGAGGCAUUAGCACAACCAAC AGCAUAGUCAAAUAAAusususu |
| GB00053 | 90 | AACCAACAGCAT AGTCAAATAAA | 271 | gsusuCUGUCUUUUGGUCAGGACAACCG UCUAGCUAUAAGUGCUGCAGGGUGUG AGAAACUCCUAUUGCUGGACGAUGUC UCUUACGAGGCAUUAGCACAACCAAC AGCAUGUCAAAuaaausususu |
| GB00054 | 90 | AACCAACAGCAT AGTCAAATAAA | 235 | gsusucuguCUUuUGGUcaggacAACcgucuagC UAUAAGuGCuGCagggugugAGAAacuccuA uuGCUGgacgaugucucuuacgagGCAUUAGC ACAACCAACAGCAUAGUCAAAuAAAus ususu |
| GB00055 | 90 | AACCAACAGCAT AGTCAAATAAA | 236 | gsusuCUGUCUUUUGGUCAGGACAACCG UCUAGCUAUAAGUGCUGCAGGGUGUG AGAAACUCCUAUUGCUGGACGAUGUC UCUUACGAGGCAUUAGCACaACcAAca GCAuaGUCAAAuaaausususu |

TABLE 1-continued

<u>Exemplary Cas12b gRNAs targeting human ANGPTL3 gene</u>

| gRNA ID | Proto-Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| GB00056 | 90 | AACCAACAGCAT AGTCAAATAAA | 237 | gsusucuguCUUuUGGUcaggacAACcgucuagC UAUAAGuGCuGCagggugugAGAAacuccuA uuGCUGgacgaugucucuuacgagGCAUUAGC ACAACCAACAGCAUAGUCAAAuAAAus ususu |
| GB00057 | 90 | AACCAACAGCAT AGTCAAATAAA | 238 | gsusucuguCUUuUGGUcaggacAACcgucuagC UAUAAGuGCuGCagggugugAGAAacuccuA uuGCUGgacgaugucucuuacgagGCAUUAGC ACAACCAACAGCAUAGUCAAAuaaausus usu |
| GB00058 | 90 | AACCAACAGCAT AGTCAAATAAA | 239 | gsusucuguCUUuUGGUcaggacAACcgucuagC UAUAAGuGCuGCagggugugAGAAacuccuA uuGCUGgacgaugucucuuacgagGCAUUAGC ACaACCAAcaGCAuaGUCAAAuaaausususu |
| GB00059 | 91 | AGGTAGTCCATG GACATTAATTC | 284 | gsusuCUGUCUUUUGGUCAGGACAACCG UCUAGCUAUAAGUGCUGCAGGGUGUG AGAAACUCCUAUUGCUGGACGAUGUC UCUUACGAGGCAUUAGCACAGGUAGU CCAUGGACAUUAasususc |
| GB00060 | 91 | AGGTAGTCCATG GACATTAATTC | 285 | gsusuCUGUCUUUUGGUCAGGACAACCG UCUAGCUAUAAGUGCUGCAGGGUGUG AGAAACUCCUAUUGCUGGACGAUGUC UCUUACGAGGCAUUAGCACaGGuAGuc CAuggACAUuAasususc |
| GB00061 | 91 | AGGTAGTCCATG GACATTAATTC | 286 | gsusuCUGUCUUUUGGUCAGGACAACCG UCUAGCUAUAAGUGCUGCAGGGUGUG AGAAACUCCUAUUGCUGGACGAUGUC UCUUACGAGGCAUUAGCACAGGUAGu cCAUggACAUUAasususc |
| GB00062 | 91 | AGGTAGTCCATG GACATTAATTC | 287 | gsusuCuGUCUUUUGGUcAGGAcAACcgU CuaGCUAUAAGUGCUGcaGGGugUGAGA AACUCCuaUUGcugGAcGAugUCuCUuacG AGGCAUUAGCACAGGUAGUCCAUGGA CAUUAasususc |
| GB00063 | 91 | AGGTAGTCCATG GACATTAATTC | 288 | gsusuCuGUCUUUUGGUcAGGAcAACcgU CuaGCuAuAaGuGCUGcaGgGugugGAGAAA CUCCuaUuGcugGAcGAugUCuCUuacGagG cAUuAGcACAGGUAGUCCAUGGACAUU Aasususc |
| GB00064 | 91 | AGGTAGTCCATG GACATTAATTC | 289 | gsusucuguCUUuUGGUcaggacAACcgucuagC UAUAAGuGCuGCagggugugAGAAacuccuA uuGCUGgacgaugucucuuacgagGCAUUAGC ACAGGUAGUCCAUGGACAUUAasususc |
| GB00065 | 91 | AGGTAGTCCATG GACATTAATTC | 290 | gsusucuguCUUuUGGUcaggacAACcgucuagC UAUAAGUGCUGCagggugugAGAAacuccu AuuGCUGgacgaugucucuuacgagGCAUUAG CACAGGUAGUCCAUGGACAUUAasusus c |
| GB00066 | 91 | AGGTAGTCCATG GACATTAATTC | 291 | gsusuCUGUCUUUUGGUCAGGACAACcgu cuagCUAUAAGuGCuGCagggugugAGAAac uccuAuuGCUGgacgaugucucuuacgagGCAUU AGCACAGGUAGUCCAUGGACAUUAasu susc |
| GB00067 | 91 | AGGTAGTCCATG GACATTAATTC | 292 | gsusucuguCUUuUGGUcaggacAACcgucuagC UAUAAGuGCuGCAGGGUGUGAGAAAC UCCUAuuGCUGgacgaugucucuuacgagGCA UUAGCACAGGUAGUCCAUGGACAUUA asususc |

TABLE 1-continued

Exemplary Cas12b gRNAs targeting human ANGPTL3 gene

| gRNA ID | Proto- Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| GB00068 | 91 | AGGTAGTCCATG GACATTAATTC | 293 | gsusuCUGUCUUUUGGUCAGGACAACCG UCUAGCUAUAAGUGCUGCAGGGUGUG AGAAACUCCUAUUGCUGGACGAUGUC UCUUACGAGGCAUUAGCACaGGuAGuc CAUggACAUUAasususc |
| GB00069 | 91 | AGGTAGTCCATG GACATTAATTC | 294 | gsusucuguCUUuUGGUcaggacAACcgucuagC UAUAAGuGCuGCagggugugAGAAacuccuA uuGCUGgacgaugucucuuacgagGCAUUAGC ACaGGUAGucCAUggACAUUAasususc |
| GB00070 | 91 | AGGTAGTCCATG GACATTAATTC | 295 | gsusucuguCUUuUGGUcaggacAACcgucuagC UAUAAGuGCuGCagggugugAGAAacuccuA uuGCUGgacgaugucucuuacgagGCAUUAGC ACaGGuAGucCAuggACAUuAasususc |
| GB00071 | 91 | AGGTAGTCCATG GACATTAATTC | 296 | gsusucuguCUUuUGGUcaggacAACcgucuagC uAUAAGuGCuGCagggugugAGAAacuccuA uuGCUGgacgaugucucuuacgagGcAUUAGCA CaGGuAGucCAuggACAUuAasususc |
| GB00072 | 91 | AGGTAGTCCATG GACATTAATTC | 297 | gsusucuguCUUuUGGUcaggacAACcgucuagC UAUAAGuCuGCagggugugAGAAacuccuAu uGCUGgacgaugucucuuacgagGCAUUAGCA CAGGUAGUCCAUGGACAUUAAUUCusu susu |
| GB00073 | 91 | AGGTAGTCCATG GACATTAATTC | 242 | gsusucuguCUUuUGGUcaggacAACcgucuagC UAUAAGuGCuGCagggugugAGAAacuccuA uuGCUGgacgaugucucuuacgagGCAUUAGC ACAGGUAGUCCAUGGACAUUAauucusus usu |
| GB00074 | 91 | AGGTAGTCCATG GACATTAATTC | 243 | gsusucuguCUUuUGGUcaggacAACcgucuagC UAUAAGuGCuGCagggugugAGAAacuccuA uuGCUGgacgaugucucuuacgagGCAUUAGC ACaGGUAGucCAUggACAUUAauucususus u |
| GB00075 | 90 | AACCAACAGCAT AGTCAAATAAA | 24 | gsususCUGUCUUUUGGUCAGGACAACC GUCUAGCUAUAAGUGCUGCAGGGUGU GAGAAACUCCUAUUGCUGGACGAUGU CUCUUACGAGGCAUUAGCACAACCAA CAGCAUAGUCAAAuasasa |
| GB00076 | 90 | AACCAACAGCAT AGTCAAATAAA | 298 | gsususCuGUCUUUUGGUcAGGAcAACcgU CuaGCUAUAAGUGCUGcaGGGugUGAGA AACUCCuaUUGcugGAcGAugUCuCUuacG AGGCAUUAGCACAACCAACAGCAUAG UCAAAuasasa |
| GB00077 | 90 | AACCAACAGCAT AGTCAAATAAA | 299 | gsususCuGUCUUUUGGUcAGGAcAACcgU CuaGCuAuAaGuGCUGcaGgGugUGAGAAA CUCCuaUuGcugGAcGAugUCuCUuacGagG cAUuAGcACAACCAACAGCAUAGUCAA Auasasa |
| GB00078 | 90 | AACCAACAGCAT AGTCAAATAAA | 300 | gsususCUGUCUUUUGGUCAGGACAACC GUCUAGCUAUAAGUGCUGCAGGGUGU GAGAAACUCCUAUUGCUGGACGAUGU CUCUUACGAGGCAUUAGCACAACCAA CAGCAuAGUcAAAuasasa |
| GB00079 | 90 | AACCAACAGCAT AGTCAAATAAA | 301 | gsususCuGUCUUUUGGUcAGGAcAACcgU CuaGCUAUAAGUGCUGcaGGGugUGAGA AACUCCuaUUGcugGAcGAugUCuCUuacG AGGCAUUAGCACAACCAACAGCAuAG UcAAAuasasa |

TABLE 1-continued

Exemplary Cas12b gRNAs targeting human ANGPTL3 gene

| gRNA ID | Proto- Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| GB00080 | 90 | AACCAACAGCAT AGTCAAATAAA | 302 | gsususCuGUCUUUUGGUcAGGAcAACcgU CuaGCuAuAaGuGCUGcaGgGuguGAGAAA CUCCuaUuGcugGAcGAugUCuCUuacGagG cAUuAGcACAACCAACAGCAuAGUcAA Auasasa |
| GB00081 | 90 | AACCAACAGCAT AGTCAAATAAA | 303 | gsususcuguCUUuUGGUcaggacAACcgucuag CUAUAAGuGCuGCagggugugAGAAacuccu AuuGCUGgacgaugucucuuacgagGCAUUAG CACAACCAACAGCAUAGUCAAAuasasa |
| GB00082 | 90 | AACCAACAGCAT AGTCAAATAAA | 304 | gsususcuguCUUuUGGUcaggacAACcgucuag CUAUAAGUGCuGCagggugugAGAAacucc uAuuGCUGgacgaugucucuuacgagGCAUUAG CACAACCAACAGCAUAGUCAAAuasasa |
| GB00083 | 90 | AACCAACAGCAT AGTCAAATAAA | 305 | gsususCUGUCUUUUGGUCAGGACAACcg ucuagCUAUAAGuGCuGCagggugugAGAAa cuccuAuuGCUGgacgaugucucuuacgagGCAU UAGCACAACCAACAGCAUAGUCAAAua sasa |
| GB00084 | 90 | AACCAACAGCAT AGTCAAATAAA | 306 | gsususcuguCUUuUGGUcaggacAACcgucuag CUAUAAGuGCuGCAGGGUGUGAGAAA CUCCUAuuGCUGgacgaugucucuuacgagGC AUUAGCACAACCAACAGCAUAGUCAA Auasasa |
| GB00085 | 90 | AACCAACAGCAT AGTCAAATAAA | 307 | gsususCUGUCUUUUGGUCAGGACAACC GUCUAGCUAUAAGUGCUGCAGGGUGU GAGAAACUCCUAUUGCUGGACGAUGU CUCUUACGAGGCAUUAGCACaACCAAc aGCAuaGUCAAAuasasa |
| GB00086 | 90 | AACCAACAGCAT AGTCAAATAAA | 308 | gsususcuguCUUuUGGUcaggacAACcgucuag CUAUAAGuGCuGCagggugugAGAAacuccu AuuGCUGgacgaugucucuuacgagGCAUUAG CACaACCAAcaGCAuaGUCAAAuasasa |
| GB00087 | 90 | AACCAACAGCAT AGTCAAATAAA | 309 | gsususCUGUCUUUUGGUCAGGACAACC GUCUAGCUAUAAGUGCUGCAGGGUGU GAGAAACUCCUAUUGCUGGACGAUGU CUCUUACGAGGCAUUAGCACaACcAAc aGcAuaGUCAAAuasasa |
| GB00088 | 90 | AACCAACAGCAT AGTCAAATAAA | 310 | gsususcuguCUUuUGGUcaggacAACcgucuag CuAUAAGuGCuGCagggugugAGAAacuccu AuuGCUGgacgaugucucuuacgagGcAUUAGC ACaACcAAcaGcAuaGUCAAAuasasa |
| GB00089 | 90 | AACCAACAGCAT AGTCAAATAAA | 25 | gsususCUGUCUUUUGGUCAGGACAACC GUCUAGCUAUAAGUGCUGCAGGGUGU GAGAAACUCCUAUUGCUGGACGAUGU CUCUUACGAGGCAUUAGCACAACCAA CAGCAUAGUCAAAUAAAuususu |
| GB00090 | 90 | AACCAACAGCAT AGTCAAATAAA | 26 | gsususCUGUCUUUUGGUCAGGACAACC GUCUAGCUAUAAGUGCUGCAGGGUGU GAGAAACUCCUAUUGCUGGACGAUGU CUCUUACGAGGCAUUAGCACAACCAA CAGCAUAGUCAAAuaaauusususu |
| GB00091 | 90 | AACCAACAGCAT AGTCAAATAAA | 311 | gsususcuguCUUuUGGUcaggacAACcgucuag CUAUAAGuGCuGCagggugugAGAAacuccu AuuGCUGgacgaugucucuuacgagGCAUUAG CACAACCAACAGCAUAGUCAAAuAAA uususu |
| GB00092 | 90 | AACCAACAGCAT AGTCAAATAAA | 312 | gsususCUGUCUUUUGGUCAGGACAACC GUCUAGCUAUAAGUGCUGCAGGGUGU GAGAAACUCCUAUUGCUGGACGAUGU CUCUUACGAGGCAUUAGCACaACCAAc aGCAuaGUCAAAuaaauusususu |

TABLE 1-continued

Exemplary Cas12b gRNAs targeting human ANGPTL3 gene

| gRNA ID | Proto-Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| GB00093 | 90 | AACCAACAGCAT AGTCAAATAAA | 313 | gsususcuguCUUuUGGUcaggacAACcgucuag CUAUAAGuGCuGCagggugugAGAAacuccu AuuGCUGgacgaugucucuuacgagGCAUUAG CACAACCAACAGCAUAGUCAAAUAAA uususu |
| GB00094 | 90 | AACCAACAGCAT AGTCAAATAAA | 314 | gsususcuguCUUuUGGUcaggacAACcgucuag CUAUAAGuGCuGCagggugugAGAAacuccu AuuGCUGgacgaugucucuuacgagGCAUUAG CACAACCAACAGCAUAGUCAAAuaaaauu susu |
| GB00095 | 90 | AACCAACAGCAT AGTCAAATAAA | 315 | gsususcuguCUUuUGGUcaggacAACcgucuag CUAUAAGuGCuGCagggugugAGAAacuccu AuuGCUGgacgaugucucuuacgagGCAUUAG CACaACCAAcaGCAuaGUCAAAuaaaauusus u |
| GB00096 | 91 | AGGTAGTCCATG GACATTAATTC | 27 | gsususCUGUCUUUUGGUCAGGACAACC GUCUAGCUAUAAGUGCUGCAGGGUGU GAGAAACUCCUAUUGCUGGACGAUGU CUCUUACGAGGCAUUAGCACAGGUAG UCCAUGGACAUUAaususc |
| GB00097 | 91 | AGGTAGTCCATG GACATTAATTC | 316 | gsususCUGUCUUUUGGUCAGGACAACC GUCUAGCUAUAAGUGCUGCAGGGUGU GAGAAACUCCUAUUGCUGGACGAUGU CUCUUACGAGGCAUUAGCACaGGuAGu cCAuggACAUuAaususc |
| GB00098 | 91 | AGGTAGTCCATG GACATTAATTC | 317 | gsususCUGUCUUUUGGUCAGGACAACC GUCUAGCUAUAAGUGCUGCAGGGUGU GAGAAACUCCUAUUGCUGGACGAUGU CUCUUACGAGGCAUUAGCACAGGUAG ucCAUggACAUUAaususc |
| GB00099 | 91 | AGGTAGTCCATG GACATTAATTC | 318 | gsususCuGUCUUUUGGUcAGGAcAACcgU CuaGCUAUAAGUGCUGcaGGGugUGAGA AACUCCuaUUGcugGAcGAugUCuCUuacG AGGCAUUAGCACAGGUAGUCCAUGGA CAUUAaususc |
| GB00100 | 91 | AGGTAGTCCATG GACATTAATTC | 319 | gsususCuGUCUUUUGGUcAGGAcAACcgU CuaGCuAuAaGuGCUGcaGgGuguGAGAAA CUCCuaUuGcugGAcGAugUCuCUuacGagG cAUuAGcACAGGUAGUCCAUGGACAUU Aaususc |
| GB00101 | 91 | AGGTAGTCCATG GACATTAATTC | 320 | gsususcuguCUUuUGGUcaggacAACcgucuag CUAUAAGuGCuGCagggugugAGAAacuccu AuuGCUGgacgaugucucuuacgagGCAUUAG CACAGGUAGUCCAUGGACAUUAaususc |
| GB00102 | 91 | AGGTAGTCCATG GACATTAATTC | 321 | gsususcuguCUUuUGGUcaggacAACcgucuag CUAUAAGUGCUGCagggugugAGAAacucc uAuuGCUGgacgaugucucuuacgagGCAUUAG CACAGGUAGUCCAUGGACAUUAaususc |
| GB00103 | 91 | AGGTAGTCCATG GACATTAATTC | 322 | gsususCUGUCUUUUGGUCAGGACAACcg ucuagCUAUAAGuGCuGCagggugugAGAAa cuccuAuuGCUGgacgaugucucuuacgagGCAU UAGCACAGGUAGUCCAUGGACAUUAa ususc |
| GB00104 | 91 | AGGTAGTCCATG GACATTAATTC | 323 | gsususcuguCUUuUGGUcaggacAACcgucuag CUAUAAGuGCuGCAGGGUGUGAGAAA CUCCUAuuGCUGgacgaugucucuuacgagGC AUUAGCACAGGUAGUCCAUGGACAUU Aaususc |

TABLE 1-continued

Exemplary Cas12b gRNAs targeting human ANGPTL3 gene

| gRNA ID | Proto-Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| GB00105 | 91 | AGGTAGTCCATG GACATTAATTC | 324 | gsususCUGUCUUUUGGUCAGGACAACC GUCUAGCUAUAAGUGCUGCAGGGGUGU GAGAAACUCCUAUUGCUGGACGAUGU CUCUUACGAGGCAUUAGCACaGGUAG ucCAUggACAUUAaususc |
| GB00106 | 91 | AGGTAGTCCATG GACATTAATTC | 325 | gsususcuguCUUuUGGUcaggacAACcgucuag CUAUAAGuGCuGCagggugugAGAAacuccu AuuGCUGgacgaugucucuuacgagGCAUUAG CACaGGUAGucCAUggACAUUAaususc |
| GB00107 | 91 | AGGTAGTCCATG GACATTAATTC | 27 | gsususcuguCUUuUGGUcaggacAACcgucuag CUAUAAGuGCuGCagggugugAGAAacuccu AuuGCUGgacgaugucucuuacgagGCAUUAG CACaGGuAGucCAuggACAUuAaususc |
| GB00108 | 91 | AGGTAGTCCATG GACATTAATTC | 27 | gsususcuguCUUuUGGUcaggacAACcgucuag CuAUAAGuGCuGCagggugugAGAAacuccu AuuGCUGgacgaugucucuuacgagGcAUUAGC ACaGGuAGucCAuggACAUuAaususc |
| GB00109 | 91 | AGGTAGTCCATG GACATTAATTC | 28 | gsususcuguCUUuUGGUcaggacAACcgucuag CUAUAAGuCuGCCagggugugAGAAacuccuA uuGCUGgacgaugucucuuacgagGCAUUAGC ACAGGUAGUCCAUGGACAUUAAUUCu ususu |
| GB00110 | 91 | AGGTAGTCCATG GACATTAATTC | 29 | gsususcuguCUUuUGGUcaggacAACcgucuag CUAUAAGuGCuGCagggugugAGAAacuccu AuuGCUGgacgaugucucuuacgagGCAUUAG CACAGGUAGUCCAUGGACAUUAauucuu susu |
| GB00111 | 91 | AGGTAGTCCATG GACATTAATTC | 328 | gsususcuguCUUuUGGUcaggacAACcgucuag CUAUAAGuGCuGCagggugugAGAAacuccu AuuGCUGgacgaugucucuuacgagGCAUUAG CACaGGUAGucCAUggACAUUAauucuusus u |
| GB00112 | 92 | CAAAAACTCAAC ATATTTGATCA | 30 | gsusUCUGUCUUUUGGUCAGGACAACC GUCUAGCUAUAAGUGCUGCAGGGGUGU GAGAAACUCCUAUUGCUGGACGAUGU CUCUUACGAGGCAUUAGCACCAAAAA CUCAACAUAUUUGAUCAUususu |
| GB00113 | 93 | TACTTCAACAAA AAGTGAAATAT | 31 | gsusUCUGUCUUUUGGUCAGGACAACC GUCUAGCUAUAAGUGCUGCAGGGGUGU GAGAAACUCCUAUUGCUGGACGAUGU CUCUUACGAGGCAUUAGCACUACUUC AACAAAAAGUGAAAUAUUususu |
| GB00114 | 94 | AGAAGAGCAACT AACTAACTTAA | 32 | gsusUCUGUCUUUUGGUCAGGACAACC GUCUAGCUAUAAGUGCUGCAGGGGUGU GAGAAACUCCUAUUGCUGGACGAUGU CUCUUACGAGGCAUUAGCACAGAAGA GCAACUAACUAACUUAAUususu |
| GB00115 | 95 | TGGAGGAAATAA CTAGAGGAACA | 33 | gsusUCUGUCUUUUGGUCAGGACAACC GUCUAGCUAUAAGUGCUGCAGGGGUGU GAGAAACUCCUAUUGCUGGACGAUGU CUCUUACGAGGCAUUAGCACUGGAGG AAAUAACUAGAGGAACAUususu |
| GB00116 | 96 | AAGAACCCACA GAAATTTCTCTA | 34 | gsusUCUGUCUUUUGGUCAGGACAACC GUCUAGCUAUAAGUGCUGCAGGGGUGU GAGAAACUCCUAUUGCUGGACGAUGU CUCUUACGAGGCAUUAGCACAAGAAC CCACAGAAAUUUCUCUAUususu |

TABLE 1-continued

Exemplary Cas12b gRNAs targeting human ANGPTL3 gene

| gRNA ID | Proto-Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| GB00117 | 90 | AACCAACAGCAT AGTCAAATAAA | 35 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACAACCAA CAGCAUAGUCAAAUAAAUususu |
| GB00118 | 91 | aGGTAGTCCATG GACATTAATTC | 36 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACAGGUAG UCCAUGGACAUUAAUUCUususu |
| GB00119 | 97 | CTGGCAATGTCC CCAATGCAATC | 37 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACCUGGCA AUGUCCCCAAUGCAAUCUususu |
| GB00120 | 98 | CATTGGGGACAT TGCCAGTAATC | 38 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACCAUUGG GGACAUUGCCAGUAAUCUususu |
| GB00121 | 99 | CCCAAGTAAAAA GAATATTCAAT | 39 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACCCCAAG UAAAAAGAAUAUUCAAUUususu |
| GB00122 | 100 | AATATAATGTTT GTTGTCTTTCC | 40 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACAAUAUA AUGUUUGUUGUCUUUCCUususu |
| GB00123 | 101 | GAAGAGCAACT AACTAACTTAAT | 41 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACGAAGAG CAACUAACUAACUUAAUUususu |
| GB00124 | 90 | AACCAACAGCAT AGTCAAATAAA | 42 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACAACCAA CAGCAUAGUCAAAuasasa |
| GB00125 | 90 | AACCAACAGCAT AGTCAAATAAA | 42 | gsusUCuGUCUUUUGGUcAGGAcAACcgU CuaGCUAUAAGUGCUGcaGGGugUGAGA AACUCCuaUUGcugGAcGAugUCUCUuacG AGGCAUUAGCACAACCAACAGCAUAG UCAAAuasasa |
| GB00126 | 90 | AACCAACAGCAT AGTCAAATAAA | 346 | gsusUCuGUCUUUUGGUcAGGAcAACcgU CuaGCuAuAaGuGCUGcaGgGugUGAGAAA CUCCuaUuGcugGAcGAugUCuCUuacGagG cAUuAGcACAACCAACAGCAUAGUCAA Auasasa |
| GB00127 | 90 | AACCAACAGCAT AGTCAAATAAA | 347 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACAACCAA CAGCAuAGUcAAAuasasa |
| GB00128 | 90 | AACCAACAGCAT AGTCAAATAAA | 348 | gsusUCuGUCUUUUGGUcAGGAcAACcgU CuaGCUAUAAGUGCUGcaGGGugUGAGA AACUCCuaUUGcugGAcGAugUCuCUuacG AGGCAUUAGCACAACCAACAGCAuAG UcAAAuasasa |

TABLE 1-continued

<u>Exemplary Cas12b gRNAs targeting human ANGPTL3 gene</u>

| gRNA ID | Proto-Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| GB00129 | 90 | AACCAACAGCAT AGTCAAATAAA | 349 | gsusUCuGUCUUUUGGUcAGGAcAACcgU CuaGCuAuAaGuGCUGcaGgGuguGAGAAA CUCCuaUuGcugGAcGAugUCuCUuacGagG cAUuAGcACAACCAACAGCAuAGUcAA Auasasa |
| GB00130 | 90 | AACCAACAGCAT AGTCAAATAAA | 350 | gsusUcuguCUUuUGGUcaggacAACcgucuag CUAUAAGuGCuGCagggugugAGAAacuccu AuuGCUGgacgaugucucuuacgagGCAUUAG CACAACCAACAGCAUAGUCAAuasasa |
| GB00131 | 90 | AACCAACAGCAT AGTCAAATAAA | 351 | gsusUcuguCUUuUGGUcaggacAACcgucuag CUAUAAGUGCUGCagggugugAGAAacucc uAuuGCUGgacgaugucucuuacgagGCAUUAG CACAACCAACAGCAUAGUCAAuasasa |
| GB00132 | 90 | AACCAACAGCAT AGTCAAATAAA | 352 | gsusUCUGUCUUUUGGUCAGGACAACcg ucuagCUAUAAGuGCuGCagggugugAGAAa cuccuAuuGCUGgacgaugucucuuacgagGCAU UAGCACAACCAACAGCAUAGUCAAua sasa |
| GB00133 | 90 | AACCAACAGCAT AGTCAAATAAA | 353 | gsusUcuguCUUuUGGUcaggacAACcgucuag CUAUAAGuGCuGCAGGGUGUGAGAAA CUCCUAuuGCUGgacgaugucucuuacgagGC AUUAGCACAACCAACAGCAUAGUCAA Auasasa |
| GB00134 | 90 | AACCAACAGCAT AGTCAAATAAA | 354 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACaACCAAc aGCAuaGUCAAAuasasa |
| GB00135 | 90 | AACCAACAGCAT AGTCAAATAAA | 355 | gsusUcuguCUUuUGGUcaggacAACcgucuag CUAUAAGuGCuGCagggugugAGAAacuccu AuuGCUGgacgaugucucuuacgagGCAUUAG CACaACCAacaGCAuaGUCAAuasasa |
| GB00136 | 90 | AACCAACAGCAT AGTCAAATAAA | 356 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACaACcAAc aGcAuaGUCAAAuasasa |
| GB00137 | 90 | AACCAACAGCAT AGTCAAATAAA | 357 | gsusUcuguCUUuUGGUcaggacAACcgucuag CuAUAAGuGCuGCagggugugAGAAacuccu AuuGCUGgacgaugucucuuacgagGcAUUAGC ACaACcAAcaGcAuaGUCAAAuasasa |
| GB00138 | 90 | AACCAACAGCAT AGTCAAATAAA | 329 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACAACCAA CAGCAUAGUCAAAUAAAuusUsu |
| GB00139 | 90 | AACCAACAGCAT AGTCAAATAAA | 43 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACAACCAA CAGCAUGUCAAuaaauusUsu |
| GB00140 | 90 | AACCAACAGCAT AGTCAAATAAA | 330 | gsusUcuguCUUuUGGUcaggacAACcgucuag CUAUAAGuGCuGCagggugugAGAAacuccu AuuGCUGgacgaugucucuuacgagGCAUUAG CACAACCAACAGCAUAGUCAAAuAAA uusUsu |
| GB00141 | 90 | AACCAACAGCAT AGTCAAATAAA | 331 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACaACCAAc aGCAuaGUCAAuaaauusUsu |

TABLE 1-continued

Exemplary Cas12b gRNAs targeting human ANGPTL3 gene

| gRNA ID | Proto- Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| GB00142 | 90 | AACCAACAGCAT AGTCAAATAAA | 332 | gsusUcuguCUUuUGGUcaggacAACcgucuag CUAUAAGuGCuGCagggugugAGAAacuccu AuuGCUGgacgaugucucuuacgagGCAUUAG CACAACCAACAGCAUAGUCAAAUAAA uususu |
| GB00143 | 90 | AACCAACAGCAT AGTCAAATAAA | 333 | gsusUcuguCUUuUGGUcaggacAACcgucuag CUAUAAGuGCuGCagggugugAGAAacuccu AuuGCUGgacgaugucucuuacgagGCAUUAG CACAACCAACAGCAUAGUCAAAuaaauu susu |
| GB00144 | 90 | AACCAACAGCAT AGTCAAATAAA | 334 | gsusUcuguCUUuUGGUcaggacAACcgucuag CUAUAAGuGCuGCagggugugAGAAacuccu AuuGCUGgacgaugucucuuacgagGCAUUAG CACaACCAAcaGCuaGUCAAAuaaauusus u |
| GB00145 | 91 | AGGTAGTCCATG GACATTAATTC | 44 | gsusUCUGUCUUUUGGUCAGGACAACC GUCUAGCUAUAAGUGCUGCAGGGGUGU GAGAAACUCCUAUUGCUGGACGAUGU CUCUUACGAGGCAUUAGCACAGGUAG UCCAUGGACAUUAaususc |
| GB00146 | 91 | AGGTAGTCCATG GACATTAATTC | 372 | gsusUCUGUCUUUUGGUCAGGACAACC GUCUAGCUAUAAGUGCUGCAGGGGUGU GAGAAACUCCUAUUGCUGGACGAUGU CUCUUACGAGGCAUUAGCACaGGuAGu cCAuggACAUuAaususc |
| GB00147 | 91 | AGGTAGTCCATG GACATTAATTC | 373 | gsusUCUGUCUUUUGGUCAGGACAACC GUCUAGCUAUAAGUGCUGCAGGGGUGU GAGAAACUCCUAUUGCUGGACGAUGU CUCUUACGAGGCAUUAGCACAGGUAG ucCAUggACAUUAaususc |
| GB00148 | 91 | AGGTAGTCCATG GACATTAATTC | 374 | gsusUCuGUCUUUUGGUcAGGAcAACcgU CuaGCUAUAAGUGCUGcaGGGugUGAGA AACUCCuaUUGcugGAcGAugUCuCUuacG AGGCAUUAGCACAGGUAGUCCAUGGA CAUUAaususc |
| GB00149 | 91 | AGGTAGTCCATG GACATTAATTC | 375 | gsusUCuGUCUUUUGGUcAGGAcAACcgU CuaGCUAuAaGuGCUGcaGgGugugGAGAAA CUCCuaUuGcugGAcGAugUCuCUuacGagG cAUuAGcACAGGUAGUCCAUGGACAUU Aaususc |
| GB00150 | 91 | AGGTAGTCCATG GACATTAATTC | 376 | gsusUcuguCUUuUGGUcaggacAACcgucuag CUAUAAGuGCuGCagggugugAGAAacuccu AuuGCUGgacgaugucucuuacgagGCAUUAG CACAGGUAGUCCAUGGACAUUAaususc |
| GB00151 | 91 | AGGTAGTCCATG GACATTAATTC | 377 | gsusUcuguCUUuUGGUcaggacAACcgucuag CUAUAAGUGCUGCagggugugAGAAacucc uAuuGCUGgacgaugucucuuacgagGCAUUAG CACAGGUAGUCCAUGGACAUUAaususc |
| GB00152 | 91 | AGGTAGTCCATG GACATTAATTC | 378 | gsusUCUGUCUUUUGGUCAGGACAACcg ucuagCUAUAAGuGCuGCagggugugAGAAa cuccuAuuGCUGgacgaugucucuuacgagGCAU UAGCACAGGUAGUCCAUGGACAUUAa ususc |
| GB00153 | 91 | AGGTAGTCCATG GACATTAATTC | 379 | gsusUcuguCUUuUGGUcaggacAACcgucuag CUAUAAGuGCuGCAGGGGUGUGAGAAA CUCCUAuuGCUGgacgaugucucuuacgagGC AUUAGCACAGGUAGUCCAUGGACAUU Aaususc |

TABLE 1-continued

<u>Exemplary Cas12b gRNAs targeting human ANGPTL3 gene</u>

| gRNA ID | Proto-Spacer SEQ ID NO: | Exemplary ANGPTL3 Protospacer (5'-3') | gRNA SEQ ID NO: | gRNA (5'-3') with Modified Exemplary Spacer |
|---------|---------|---------|---------|---------|
| GB00154 | 91 | AGGTAGTCCATG GACATTAATTC | 380 | gsusUCUGUCUUUUGGUCAGGACAACC GUCUAGCUAUAAGUGCUGCAGGGUGU GAGAAACUCCUAUUGCUGGACGAUGU CUCUUACGAGGCAUUAGCACaGGUAG ucCAUggACAUUAaususc |
| GB00155 | 91 | AGGTAGTCCATG GACATTAATTC | 381 | gsusUcuguCUUuUGGUcaggacAACcgucuag CUAUAAGuGCuGCagggugugAGAAacuccu AuuGCUGgacgaugucucuuacgagGCAUUAG CACaGGUAGucCAUggACAUUAaususc |
| GB00156 | 91 | AGGTAGTCCATG GACATTAATTC | 382 | gsusUcuguCUUuUGGUcaggacAACcgucuag CUAUAAGuGCuGCagggugugAGAAacuccu AuuGCUGgacgaugucucuuacgagGCAUUAG CACaGGuAGucCAuggACAUuAaususc |
| GB00157 | 91 | AGGTAGTCCATG GACATTAATTC | 383 | gsusUcuguCUUuUGGUcaggacAACcgucuag CuAUAAGuGCuGCagggugugAGAAacuccu AuuGCUGgacgaugucucuuacgagGcAUUAGC ACaGGuAGucCAuggACAUuAaususc |
| GB00158 | 91 | AGGTAGTCCATG GACATTAATTC | 45 | gsusUcuguCUUuUGGUcaggacAACcgucuag CUAUAAGuCuGCagggugugAGAAacuccuA uuGCUGgacgaugucucuuacgagGCAUUAGC ACAGGUAGUCCAUGGACAUUAAUUCu ususu |
| GB00159 | 91 | AGGTAGTCCATG GACATTAATTC | 341 | gsusUcuguCUUuUGGUcaggacAACcgucuag CUAUAAGuGCuGCagggugugAGAAacuccu AuuGCUGgacgaugucucuuacgagGCAUUAG CACAGGUAGUCCAUGGACAUUAauucuu susu |
| GB00160 | 91 | AGGTAGTCCATG GACATTAATTC | 342 | gsusUcuguCUUuUGGUcaggacAACcgucuag CUAUAAGuGCuGCagggugugAGAAacuccu AuuGCUGgacgaugucucuuacgagGCAUUAG CACaGGUAGucCAUggACAUUAauucuusus u |
| GB00161 | 90 | AACCAACAGCAT AGTCAAATAAA | 358 | gsusuCUGUCUUUUGGUCAGGACAACCG UCUAGCUAUAAGUGCUGCAGGGUGUG AGAAACUCCUAUUGCUGGACGAUGUC UCUUACGAGGCAUUAGCACAACCAAC AGCAUAGUCAAAuasasa |
| GB00162 | 90 | AACCAACAGCAT AGTCAAATAAA | 359 | gsusuCuGUCUUUUGGUcAGGAcAACcgU CuaGCUAUAAGUGCUGcaGGGugUGAGA AACUCCuaUUGcugGAcGAugUCuCUuacG AGGCAUUAGCACAACCAACAGCAUAG UCAAAuasasa |
| GB00163 | 90 | AACCAACAGCAT AGTCAAATAAA | 360 | gsusuCuGUCUUUUGGUcAGGAcAACcgU CuaGCuAuAaGuGCUGcaGgGugugAGAAA CUCCuaUuGcugGAcGAugUCuCUuacGagG cAUuAGcACAACCAACAGCAUAGUCAA Auasasa |
| GB00164 | 90 | AACCAACAGCAT AGTCAAATAAA | 361 | gsusuCUGUCUUUUGGUCAGGACAACCG UCUAGCUAUAAGUGCUGCAGGGUGUG AGAAACUCCUAUUGCUGGACGAUGUC UCUUACGAGGCAUUAGCACAACCAAC AGCAuAGUcAAAuasasa |
| GB00165 | 90 | AACCAACAGCAT AGTCAAATAAA | 362 | gsusuCuGUCUUUUGGUcAGGAcAACcgU CuaGCUAUAAGUGCUGcaGGGugUGAGA AACUCCuaUUGcugGAcGAugUCuCUuacG AGGCAUUAGCACAACCAACAGCAuAG UcAAAuasasa |

TABLE 1-continued

<u>Exemplary Cas12b gRNAs targeting human ANGPTL3 gene</u>

| gRNA ID | Proto-Spacer SEQ ID NO: | Exemplary ANGPTL3 Protospacer (5'-3') | gRNA SEQ ID NO: | gRNA (5'-3') with Modified Exemplary Spacer |
|---------|---------|---------|---------|---------|
| GB00166 | 90 | AACCAACAGCAT AGTCAAATAAA | 363 | gsususCuGUCUUUUGGUcAGGAcAACcgU CuaGCuAuAaGuGCUGcaGgGuguGAGAAA CUCCuaUuGcugGAcGAugUCuCUuacGagG cAUuAGcACAACCAACAGCAuAGUcAA Auasasa |
| GB00167 | 90 | AACCAACAGCAT AGTCAAATAAA | 364 | gsususcuguCUUuUGGUcaggacAACcgucuagC UAUAAGuGCUgCagggugugAGAAacuccuA uuGCUGgacgaugucucuuacgagGCAUUAGC ACAACCAACAGCAUAGUCAAAuasasa |
| GB00168 | 90 | AACCAACAGCAT AGTCAAATAAA | 365 | gsususcuguCUUuUGGUcaggacAACcgucuagC UAUAAGUGCUGCagggugugAGAAacuccu AuuGCUGgacgaugucucuuacgagGCAUUAG CACAACCAACAGCAUAGUCAAAuasasa |
| GB00169 | 90 | AACCAACAGCAT AGTCAAATAAA | 366 | gsususCUGUCUUUUGGUCAGGACAACcgu cuagCUAUAAGuGCuGCagggugugAGAAac uccuAuuGCUGgacgaugucucuuacgagGCAUU AGCACAACCAACAGCAUAGUCAAAuas asa |
| GB00170 | 90 | AACCAACAGCAT AGTCAAATAAA | 367 | gsususcuguCUUuUGGUcaggacAACcgucuagC UAUAAGuGCuGCAGGGUGUGAGAAAC UCCUAuuGCUGgacgaugucucuuacgagGCA UUAGCACAACCAACAGCAUAGUCAAA uasasa |
| GB00171 | 90 | AACCAACAGCAT AGTCAAATAAA | 368 | gsususCUGUCUUUUGGUCAGGACAACCG UCUAGCUAUAAGUGCUGCAGGGUGUG AGAAACUCCUAUUGCUGGACGAUGUC UCUUACGAGGCAUUAGCACaACCAAca GCAuaGUCAAAuasasa |
| GB00172 | 90 | AACCAACAGCAT AGTCAAATAAA | 369 | gsususcuguCUUuUGGUcaggacAACcgucuagC UAUAAGuGCuGCagggugugAGAAacuccuA uuGCUGgacgaugucucuuacgagGCAUUAGC ACaACCAAcaGCAuaGUCAAAuasasa |
| GB00173 | 90 | AACCAACAGCAT AGTCAAATAAA | 370 | gsususCUGUCUUUUGGUCAGGACAACCG UCUAGCUAUAAGUGCUGCAGGGUGUG AGAAACUCCUAUUGCUGGACGAUGUC UCUUACGAGGCAUUAGCACaACcAAca GcAuaGUCAAAuasasa |
| GB00174 | 90 | AACCAACAGCAT AGTCAAATAAA | 371 | gsususcuguCUUuUGGUcaggacAACcgucuagC uAUAAGuGCuGCagggugugAGAAacuccuA uuGCUGgacgaugucucuuacgagGcAUUAGCA CaACcAAcaGcAuaGUCAAAuasasa |
| GB00175 | 90 | AACCAACAGCAT AGTCAAATAAA | 335 | gsususCUGUCUUUUGGUCAGGACAACCG UCUAGCUAUAAGUGCUGCAGGGUGUG AGAAACUCCUAUUGCUGGACGAUGUC UCUUACGAGGCAUUAGCACAACCAAC AGCAUAGUCAAAUAAAuususu |
| GB00176 | 90 | AACCAACAGCAT AGTCAAATAAA | 271 | gsususCUGUCUUUUGGUCAGGACAACCG UCUAGCUAUAAGUGCUGCAGGGUGUG AGAAACUCCUAUUGCUGGACGAUGUC UCUUACGAGGCAUUAGCACAACCAAC AGCAUGUCAAAuaaausususu |
| GB00177 | 90 | AACCAACAGCAT AGTCAAATAAA | 336 | gsususcuguCUUuUGGUcaggacAACcgucuagC UAUAAGuGCuGCagggugugAGAAacuccuA uuGCUGgacgaugucucuuacgagGCAUUAGC ACAACCAACAGCAUAGUCAAAuAAAuu susu |
| GB00178 | 90 | AACCAACAGCAT AGTCAAATAAA | 337 | gsususCUGUCUUUUGGUCAGGACAACCG UCUAGCUAUAAGUGCUGCAGGGUGUG AGAAACUCCUAUUGCUGGACGAUGUC UCUUACGAGGCAUUAGCACaACCAAca GCAuaGUCAAAuaaauususu |

TABLE 1-continued

| gRNA ID | Proto-Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| | | Exemplary Cas12b gRNAs targeting human ANGPTL3 gene | | |
| GB00179 | 90 | AACCAACAGCAT AGTCAAATAAA | 338 | gsusucuguCUUuUGGUcaggacAACcgucuagC UAUAAGuGCuGCagggugugAGAAacuccuA uuGCUGgacgaugucucuuacgagGCAUUAGC ACAACCAACAGCAUAGUCAAAUAAAu ususu |
| GB00180 | 90 | AACCAACAGCAT AGTCAAATAAA | 339 | gsusucuguCUUuUGGUcaggacAACcgucuagC UAUAAGuGCuGCagggugugAGAAacuccuA uuGCUGgacgaugucucuuacgagGCAUUAGC ACAACCAACAGCAUAGUCAAAuaaauusu su |
| GB00181 | 90 | AACCAACAGCAT AGTCAAATAAA | 340 | gsusucuguCUUuUGGUcaggacAACcgucuagC UAUAAGuGCuGCagggugugAGAAacuccuA uuGCUGgacgaugucucuuacgagGCAUUAGC ACaACCAAcaGCAuaGUCAAAuaaauususu |
| GB00182 | 91 | AGGTAGTCCATG GACATTAATTC | 384 | gsusuCUGUCUUUUGGUCAGGACAACCG UCUAGCUAUAAGUGCUGCAGGGUGUG AGAAACUCCUAUUGCUGGACGAUGUC UCUUACGAGGCAUUAGCACAGGUAGU CCAUGGACAUUAaususc |
| GB00183 | 91 | AGGTAGTCCATG GACATTAATTC | 385 | gsusuCUGUCUUUUGGUCAGGACAACCG UCUAGCUAUAAGUGCUGCAGGGUGUG AGAAACUCCUAUUGCUGGACGAUGUC UCUUACGAGGCAUUAGCACaGGuAGuc CAuggACAUuAaususc |
| GB00184 | 91 | AGGTAGTCCATG GACATTAATTC | 386 | gsusuCUGUCUUUUGGUCAGGACAACCG UCUAGCUAUAAGUGCUGCAGGGUGUG AGAAACUCCUAUUGCUGGACGAUGUC UCUUACGAGGCAUUAGCACAGGUAGu cCAUggACAUUAaususc |
| GB00185 | 91 | AGGTAGTCCATG GACATTAATTC | 387 | gsusuCuGUCUUUUGGUcAGGAcAACcgU CuaGCUAUAAGUGCUGcaGGGugUGAGA AACUCCuaUUGcugGAcGAugUCuCUuacG AGGCAUUAGCACAGGUAGUCCAUGGA CAUUAaususc |
| GB00186 | 91 | AGGTAGTCCATG GACATTAATTC | 388 | gsusuCuGUCUUUUGGUcAGGAcAACcgU CuaGCUAuAaGuGCUGcaGgGugUGAGAAA CUCCuaUuGcugGAcGAugUCuCUuacGagG cAUuAGcACAGGUAGUCCAUGGACAUU Aaususc |
| GB00187 | 91 | AGGTAGTCCATG GACATTAATTC | 389 | gsusucuguCUUuUGGUcaggacAACcgucuagC UAUAAGuGCuGCagggugugAGAAacuccuA uuGCUGgacgaugucucuuacgagGCAUUAGC ACAGGUAGUCCAUGGACAUUAaususc |
| GB00188 | 91 | AGGTAGTCCATG GACATTAATTC | 390 | gsusucuguCUUuUGGUcaggacAACcgucuagC UAUAAGuGCUGCagggugugAGAAacuccu AuuGCUGgacgaugucucuuacgagGCAUUAG CACAGGUAGUCCAUGGACAUUAaususc |
| GB00189 | 91 | AGGTAGTCCATG GACATTAATTC | 391 | gsusuCUGUCUUUUGGUCAGGACAACcgu cuagCUAUAAGuGCuGCagggugugAGAAac uccuAuuGCUGgacgaugucucuuacgagGCAUU AGCACAGGUAGUCCAUGGACAUUAaus usc |
| GB00190 | 91 | AGGTAGTCCATG GACATTAATTC | 392 | gsusucuguCUUuUGGUcaggacAACcgucuagC UAUAAGuGCuGCAGGGUGUGAGAAAC UCCUAuuGCUGgacgaugucucuuacgagGCA UUAGCACAGGUAGUCCAUGGACAUUA aususc |

TABLE 1-continued

Exemplary Cas12b gRNAs targeting human ANGPTL3 gene

| gRNA ID | Proto-Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| GB00191 | 91 | AGGTAGTCCATG GACATTAATTC | 393 | gsusuCUGUCUUUUGGUCAGGACAACCG UCUAGCUAUAAGUGCUGCAGGGUGUG AGAAACUCCUAUUGCUGGACGAUGUC UCUUACGAGGCAUUAGCACaGGUAGuc CAUggACAUUAausus |
| GB00192 | 91 | AGGTAGTCCATG GACATTAATTC | 394 | gsusucuguCUUuUGGUcaggacAACcgucuagC UAUAAGuGCUgCagggugugAGAAacuccuA uuGCUGgacgaugucucuuacgagGCAUUAGC ACaGGUAGucCAUggACAUUAausus |
| GB00193 | 91 | AGGTAGTCCATG GACATTAATTC | 395 | gsusucuguCUUuUGGUcaggacAACcgucuagC UAUAAGuGCUgCagggugugAGAAacuccuA uuGCUGgacgaugucucuuacgagGCAUUAGC ACaGGuAGucCAuggACAUuAausus |
| GB00194 | 91 | AGGTAGTCCATG GACATTAATTC | 396 | gsusucuguCUUuUGGUcaggacAACcgucuagC uAUAAGuGCUgCagggugugAGAAacuccuA uuGCUGgacgaugucucuuacgagGcAUUAGCA CaGGuAGucCAuggACAUuAausus |
| GB00195 | 91 | AGGTAGTCCATG GACATTAATTC | 397 | gsusucuguCUUuUGGUcaggacAACcgucuagC UAUAAGuCuGCagggugugAGAAacuccuAu uGCUGgacgaugucucuuacgagGCAUUAGCA CAGGUAGUCCAUGGACAUUAAUUCuus usu |
| GB00196 | 91 | AGGTAGTCCATG GACATTAATTC | 343 | gsusucuguCUUuUGGUcaggacAACcgucuagC UAUAAGuGCUgCagggugugAGAAacuccuA uuGCUGgacgaugucucuuacgagGCAUUAGC ACAGGUAGUCCAUGGACAUUAauucuus usu |
| GB00197 | 91 | AGGTAGTCCATG GACATTAATTC | 344 | gsusucuguCUUuUGGUcaggacAACcgucuagC UAUAAGuGCUgCagggugugAGAAacuccuA uuGCUGgacgaugucucuuacgagGCAUUAGC ACaGGUAGucCAUggACAUUAauucuususu |
| GB00198 | 90 | AACCAACAGCAT AGTCAAATAAA | 46 | gsususCuGUCUUUUGGUcAGGAcXACcgU CuaGCUAUAAGUGCUGcaGGGugUGAGA AACUCCuaUUGcugGAcGAugUCuCUuacG AGGCAUUAGCACAACCAACAGCAUAG UCAAAusasasa |
| GB00199 | 90 | AACCAACAGCAT AGTCAAATAAA | 47 | gsususCuGUCUUUUGGUcAGGAcAXCcgU CuaGCUAUAAGUGCUGcaGGGugUGAGA AACUCCuaUUGcugGAcGAugUCuCUuacG AGGCAUUAGCACAACCAACAGCAUAG UCAAAusasasa |
| GB00200 | 90 | AACCAACAGCAT AGTCAAATAAA | 48 | gsususCuGUCUUUUGGUcAGGAcAACcgU CuaGCUXUAAGUGCUGcaGGGugUGAGA AACUCCuaUUGcugGAcGAugUCuCUuacG AGGCAUUAGCACAACCAACAGCAUAG UCAAAusasasa |
| GB00201 | 90 | AACCAACAGCAT AGTCAAATAAA | 49 | gsususCuGUCUUUUGGUcAGGAcAACcgU CuaGCUAUXAGUGCUGcaGGGugUGAGA AACUCCuaUUGcugGAcGAugUCuCUuacG AGGCAUUAGCACAACCAACAGCAUAG UCAAAusasasa |
| GB00202 | 90 | AACCAACAGCAT AGTCAAATAAA | 50 | gsususCuGUCUUUUGGUcAGGAcAACcgU CuaGCUAUAXGUGCUGcaGGGugUGAGA AACUCCuaUUGcugGAcGAugUCuCUuacG AGGCAUUAGCACAACCAACAGCAUAG UCAAAusasasa |
| GB00203 | 90 | AACCAACAGCAT AGTCAAATAAA | 51 | gsususCuGUCUUUUGGUcAGGAcAACcgU CuaGCUAUAAGUGCUGcaGGGugUGXGA AACUCCuaUUGcugGAcGAugUCuCUuacG AGGCAUUAGCACAACCAACAGCAUAG UCAAAusasasa |

TABLE 1-continued

Exemplary Cas12b gRNAs targeting human ANGPTL3 gene

| gRNA ID | Proto-Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| GB00204 | 90 | AACCAACAGCAT AGTCAAATAAA | 52 | gsususCuGUCUUUUGGUcAGGAcAACcgU CuaGCUAUAAGUGCUGcaGGGugUGAGX AACUCCuaUUGcugGAcGAugUCuCUuacG AGGCAUUAGCACAACCAACAGCAUAG UCAAAusasasa |
| GB00205 | 90 | AACCAACAGCAT AGTCAAATAAA | 53 | gsususCuGUCUUUUGGUcAGGAcAACcgU CuaGCUAUAAGUGCUGcaGGGugUGAGA XACUCCuaUUGcugGAcGAugUCuCUuacG AGGCAUUAGCACAACCAACAGCAUAG UCAAAusasasa |
| GB00206 | 90 | AACCAACAGCAT AGTCAAATAAA | 54 | gsususCuGUCUUUUGGUcAGGAcAACcgU CuaGCUAUAAGUGCUGcaGGGugUGAGA AXCUCCuaUUGcugGAcGAugUCuCUuacG AGGCAUUAGCACAACCAACAGCAUAG UCAAAusasasa |
| GB00207 | 90 | AACCAACAGCAT AGTCAAATAAA | 55 | gsususCuGUCUUUUGGUcAGGAcAACcgU CuaGCUAUAAGUGCUGcaGGGugUGAGA AACUCCuaUUGcugGXcGAugUCuCUuacG AGGCAUUAGCACAACCAACAGCAUAG UCAAAusasasa |
| GB00208 | 90 | AACCAACAGCAT AGTCAAATAAA | 56 | gsususCuGUCUUUUGGUcAGGAcAACcgU CuaGCUAUAAGUGCUGcaGGGugUGAGA AACUCCuaUUGcugGAcGXugUCuCUuacG AGGCAUUAGCACAACCAACAGCAUAG UCAAAusasasa |
| GB00209 | 90 | AACCAACAGCAT AGTCAAATAAA | 57 | gsususCuGUCUUUUGGUcAGGAcAACcgU CuxGCUAUAAGUGCUGcaGGGugUGAGA AACUCCuaUUGcugGAcGAugUCuCUuacG AGGCAUUAGCACAACCAACAGCAUAG UCAAAusasasa |
| GB00210 | 90 | AACCAACAGCAT AGTCAAATAAA | 58 | gsususCuGUCUUUUGGUcAGGAcAACcgU CuaGCUAUAAGUGCUGcxGGGugUGAGA AACUCCuaUUGcugGAcGAugUCuCUuacG AGGCAUUAGCACAACCAACAGCAUAG UCAAAusasasa |
| GB00211 | 90 | AACCAACAGCAT AGTCAAATAAA | 59 | gsususCuGUCUUUUGGUcAGGAcAACcgU CuaGCUAUAAGUGCUGcaGGGugUGAGA AACUCCuxUUGcugGAcGAugUCuCUuacG AGGCAUUAGCACAACCAACAGCAUAG UCAAAusasasa |
| GB00212 | 90 | AACCAACAGCAT AGTCAAATAAA | 197 | gsususCuGUCUUUUGGUcAGGAcAACcgU CuaGCUAUAAGUGCUGcaGGGugUGAGA AACUCCuaUUGcugGAcGAugUCuCUuacG AGGCAUUAGCACAACCAACAGCAUAG UCAAAusasasa |
| GB00213 | 90 | AACCAACAGCAT AGTCAAATAAA | 197 | gsususCuGUCUUUUGGUcAGGAcAACcgU CuaGCUAUAAGUGCUGcaGGGugUGAGA AACUCCuaUUGcugGAcGAugUCuCUuacG AGGCAUUAGCACAACCAACAGCAUAG UCAAAusasasa |
| GB00214 | 90 | AACCAACAGCAT AGTCAAATAAA | 197 | gsususCuGUCUUUUGGUcAGGAcAACcgU CuaGCUAUAAGUGCUGcaGGGugUGAGA AACUCCuaUUGcugGAcGAugUCuCUuacG AGGCAUUAGCACAACCAACAGCAUAG UCAAAusasasa |
| GB00215 | 90 | AACCAACAGCAT AGTCAAATAAA | 197 | gsususCuGUCUUUUGGUcAGGAcAACcgU CuaGCUAUAAGUGCUGcaGGGugUGAGA AACUCCuaUUGcugGAcGAugUCuCUuacG AGGCAUUAGCACAACCAACAGCAUAG UCAAAusasasa |

TABLE 1-continued

Exemplary Cas12b gRNAs targeting human ANGPTL3 gene

| gRNA ID | Proto-Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| GB00216 | 90 | AACCAACAGCAT AGTCAAATAAA | 197 | gsususCuGUCUUUUGGUcAGGAcAACcgU CuaGCUAUAAGUGCUGcaGGGugUGAGA AACUCCuaUUGcugGAcGAugUCuCUuacG AGGCAUUAGCACAACCAACAGCAUAG UCAAAusasasa |
| GB00217 | 90 | AACCAACAGCAT AGTCAAATAAA | 60 | gsususCuGUCUUUUGGUcAGGAcXACcgU CuaGCUAUAAGUGCUGcaGGGugUGAGA XACUCCuaUUGcugGAcGAugUCuCUuacG AGGCAUUAGCACAACCAACAGCAUAG UCAAAusasasa |
| GB00218 | 90 | AACCAACAGCAT AGTCAAATAAA | 61 | gsususCuGUCUUUUGGUcAGGAcAXCcgU CuxGCUAUAAGUGCUGcxGGGugUGAG AAACUCCuaUUGcugGAcGAugUCuCUuac GAGGCAUUAGCACAACCAACAGCAUA GUCAAAusasasa |
| GB00219 | 90 | AACCAACAGCAT AGTCAAATAAA | 62 | gsususCuGUCUUUUGGUcAGGAcAACcgU CuaGCUXUAAGUGCUGcaGGGugUGAGA AACUCCuxUUGcugGAcGAugUCuCUuacG AGGCAUUAGCACAACCAACAGCAUAG UCAAAusasasa |
| GB00220 | 90 | AACCAACAGCAT AGTCAAATAAA | 49 | gsususCuGUCUUUUGGUcAGGAcAACcgU CuaGCUAUXAGUGCUGcaGGGugUGAGA AACUCCuaUUGcugGAcGAugUCuCUuacG AGGCAUUAGCACAACCAACAGCAUAG UCAAAusasasa |
| GB00221 | 90 | AACCAACAGCAT AGTCAAATAAA | 63 | gsususCuGUCUUUUGGUcAGGAcAACcgU CuaGCUAUAXGUGCUGcaGGGugUGAGA AACUCCuaUUGcugGXcGAugUCuCUuacG AGGCAUUAGCACAACCAACAGCAUAG UCAAAusasasa |
| GB00222 | 90 | AACCAACAGCAT AGTCAAATAAA | 51 | gsususCuGUCUUUUGGUcAGGAcAACcgU CuaGCUAUAAGUGCUGcaGGGugUGXGA AACUCCuaUUGcugGAcGAugUCuCUuacG AGGCAUUAGCACAACCAACAGCAUAG UCAAAusasasa |
| GB00223 | 90 | AACCAACAGCAT AGTCAAATAAA | 64 | gsususCuGUCUUUUGGUcAGGAcAACcgU CuxGCUAUAAGUGCUGcaGGGugUGAGX AACUCCuaUUGcugGAcGAugUCuCUuacG AGGCAUUAGCACAACCAACAGCAUAG UCAAAusasasa |
| GB00224 | 90 | AACCAACAGCAT AGTCAAATAAA | 65 | gsususCuGUCUUUUGGUcAGGAcAACcgU CuxGCUAUAAGUGCUGcxGGGugUGAG AXACUCCuaUUGcugGAcGAugUCuCUuac GAGGCAUUAGCACAACCAACAGCAUA GUCAAAusasasa |
| GB00225 | 90 | AACCAACAGCAT AGTCAAATAAA | 66 | gsususCuGUCUUUUGGUcAGGAcAXCcgU CuaGCUAUAAGUGCUGcaGGGugUGAGA AXCUCCuaUUGcugGAcGAugUCuCUuacG AGGCAUUAGCACAACCAACAGCAUAG UCAAAusasasa |
| GB00226 | 90 | AACCAACAGCAT AGTCAAATAAA | 67 | gsususCuGUCUUUUGGUcAGGAcAACcgU CuaGCUAUAAGUGCUGcaGGGugUGAGA AACUCCuaUUGcugGXcGAugUCuCUuxcG AGGCAUUAGCACAACCAACAGCAUAG UCAAAusasasa |
| GB00227 | 90 | AACCAACAGCAT AGTCAAATAAA | 68 | gsususCuGUCUUUUGGUcAGGAcAACcgU CuxGCUAUAAGUGCUGcxGGGugUGAG AAACUCCuxUUGcugGAcGAugUCuCUuxc GAGGCAUUAGCACAACCAACAGCAUA GUCAAAusasasa |

TABLE 1-continued

<u>Exemplary Cas12b gRNAs targeting human ANGPTL3 gene</u>

| gRNA ID | Proto-Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| GB00228 | 90 | AACCAACAGCAT AGTCAAATAAA | 69 | gsususCuGUCUUUUGGUcAGGAcAACcgU CuaGCUAUAAGUGCUGcaGGGugUGAGA AACUCCuaUUGcugGAcGAugUCuCUuxcG AGGCAUUAGCAC<u>AACCAACAGCAUAG UCAAA</u>usasasa |
| GB00229 | 90 | AACCAACAGCAT AGTCAAATAAA | 70 | gsususCuGUCUUUUGGUcAGGAcAACcgU CuaGCUAUAAGUGCUGcaGGGugUGAGA AACUCCuaUUGcugGAcGAugUCuCUuacG XGGCAUUAGCAC<u>AACCAACAGCAUAG UCAAA</u>usasasa |
| GB00230 | 90 | AACCAACAGCAT AGTCAAATAAA | 298 | gsususCuGUCUUUUGGUcAGGAcAACcgU CuaGCUAUAAGUGCUGcaGGGugUGAGA AACUCCuaUUGcugGAcGAugUCuCUuacG AGGCAUUAGCAC<u>AACCAACAGCAUAG UCAAA</u>uasasa |
| GB00231 | 90 | AACCAACAGCAT AGTCAAATAAA | 298 | gsususCuGUCUUUUGGUcAGGAcAACcgU CuaGCUAUAAGUGCUGcaGGGugUGAGA AACUCCuaUUGcugGAcGAugUCuCUuacG AGGCAUUAGCAC<u>AACCAACAGCAUAG UCAAA</u>uasasa |
| GB00232 | 90 | AACCAACAGCAT AGTCAAATAAA | 298 | gsususCuGUCUUUUGGUcAGGAcAACcgU CuaGCUAUAAGUGCUGcaGGGugUGAGA AACUCCuaUUGcugGAcGAugUCuCUuacG AGGCAUUAGCAC<u>AACCAACAGCAUAG UCAAA</u>uasasa |
| GB00233 | 90 | AACCAACAGCAT AGTCAAATAAA | 298 | gsususCuGUCUUUUGGUcAGGAcAACcgU CuaGCUAUAAGUGCUGcaGGGugUGAGA AACUCCuaUUGcugGAcGAugUCuCUuacG AGGCAUUAGCAC<u>AACCAACAGCAUAG UCAAA</u>uasasa |
| GB00234 | 90 | AACCAACAGCAT AGTCAAATAAA | 71 | gsususCuGUCUUUUGGUcAGGAcXACcgU CuaGCUAUAAGUGCUGcaGGGugUGAGA XACUCCuaUUGcugGAcGAugUCuCUuacG AGGCAUUAGCAC<u>AACCAACAGCAUAG UCAAA</u>uasasa |
| GB00235 | 90 | AACCAACAGCAT AGTCAAATAAA | 72 | gsususCuGUCUUUUGGUcAGGAcAXCcgU CuxGCUAUAAGUGCUGcxGGGugUGAG AAACUCCuaUUGcugGAcGAugUCuCUuac GAGGCAUUAGCAC<u>AACCAACAGCAUA GUCAAA</u>uasasa |
| GB00236 | 90 | AACCAACAGCAT AGTCAAATAAA | 73 | gsususCuGUCUUUUGGUcAGGAcAACcgU CuaGCUXUAAGUGCUGcaGGGugUGAGA AACUCCuxUUGcugGAcGAugUCuCUuacG AGGCAUUAGCAC<u>AACCAACAGCAUAG UCAAA</u>uasasa |
| GB00237 | 90 | AACCAACAGCAT AGTCAAATAAA | 74 | gsususCuGUCUUUUGGUcAGGAcAACcgU CuaGCUAUXAGUGCUGcaGGGugUGAGA AACUCCuaUUGcugGAcGAugUCuCUuacG AGGCAUUAGCAC<u>AACCAACAGCAUAG UCAAA</u>uasasa |
| GB00238 | 90 | AACCAACAGCAT AGTCAAATAAA | 75 | gsususCuGUCUUUUGGUcAGGAcAACcgU CuaGCUAUAXGUGCUGcaGGGugUGAGA AACUCCuaUUGcugGXcGAugUCuCUuacG AGGCAUUAGCAC<u>AACCAACAGCAUAG UCAAA</u>uasasa |
| GB00239 | 90 | AACCAACAGCAT AGTCAAATAAA | 76 | gsususCuGUCUUUUGGUcAGGAcAACcgU CuaGCUAUAAGUGCUGcaGGGugUGXGA AACUCCuaUUGcugGAcGAugUCuCUuacG AGGCAUUAGCAC<u>AACCAACAGCAUAG UCAAA</u>uasasa |

TABLE 1-continued

| | | | | |
|---|---|---|---|---|
| | | Exemplary Cas12b gRNAs targeting human ANGPTL3 gene | | |
| gRNA ID | Proto-Spacer SEQ ID NO: | Exemplary ANGPTL3 Protospacer (5'-3') | gRNA SEQ ID NO: | gRNA (5'-3') with Modified Exemplary Spacer |
| GB00240 | 90 | AACCAACAGCAT AGTCAAATAAA | 77 | gsususCuGUCUUUUGGUcAGGAcAACcgU CuxGCUAUAAGUGCUGcaGGGugUGAGX AACUCCuaUUGcugGAcGAugUCUcUuacG AGGCAUUAGCACAACCAACAGCAUAG UCAAAuasasa |
| GB00241 | 90 | AACCAACAGCAT AGTCAAATAAA | 78 | gsususCuGUCUUUUGGUcAGGAcAACcgU CuxGCUAUAAGUGCUGcxGGGugUGAG AXACUCCuaUUGcugGAcGAugUCUcUuac GAGGCAUUAGCACAACCAACAGCAUA GUCAAAuasasa |
| GB00242 | 90 | AACCAACAGCAT AGTCAAATAAA | 79 | gsususCuGUCUUUUGGUcAGGAcAXCcgU CuaGCUAUAAGUGCUGcaGGGugUGAGA AXCUCCuaUUGcugGAcGAugUCUcUuacG AGGCAUUAGCACAACCAACAGCAUAG UCAAAuasasa |
| GB00243 | 90 | AACCAACAGCAT AGTCAAATAAA | 80 | gsususCuGUCUUUUGGUcAGGAcAACcgU CuaGCUAUAAGUGCUGcaGGGugUGAGA AACUCCuaUUGcugGXcGAugUCUcUuxcG AGGCAUUAGCACAACCAACAGCAUAG UCAAAuasasa |
| GB00244 | 90 | AACCAACAGCAT AGTCAAATAAA | 81 | gsususCuGUCUUUUGGUcAGGAcAACcgU CuxGCUAUAAGUGCUGcxGGGugUGAG AAACUCCuxUUGcugGAcGAugUCUcUuxc GAGGCAUUAGCACAACCAACAGCAUA GUCAAAuasasa |
| GB00245 | 90 | AACCAACAGCAT AGTCAAATAAA | 82 | gsususCuGUCUUUUGGUcAGGAcAACcgU CuaGCUAUAAGUGCUGcaGGGugUGAGA AACUCCuaUUGcugGAcGAugUCUcUuxcG AGGCAUUAGCACAACCAACAGCAUAG UCAAAuasasa |
| GB00246 | 90 | AACCAACAGCAT AGTCAAATAAA | 83 | gsususCuGUCUUUUGGUcAGGAcAACcgU CuaGCUAUAAGUGCUGcaGGGugUGAGA AACUCCuaUUGcugGAcGAugUCUcUuacG XGGCAUUAGCACAACCAACAGCAUAG UCAAAuasasa |
| GB00247 | 90 | AACCAACAGCAT AGTCAAATAAA | 84 | gsususCUGUCUUUUGGUCAGGACXXCC GUCUXGCUXUXXGUGCUGCXGGGUGU GXGXXXCUCCUXUUGCUGGXCGXUGU CUCUUXCGXGGCXUUXGCXCXXCCXX CXGCXUXGUCXXXusXsXsX |
| GB00248 | 90 | AACCAACAGCAT AGTCAAATAAA | 85 | gsususCUGUCUUUUGGUCAGGACXXCC GUCUAGCUAUXXGUGCUGCAGGGUGU GXGXXACUCCUAUUGCUGGACGAUGU CUCUUXCGAGGCAUUAGCACAACCAA CAGCAUAGUCAAAusasasa |
| GB00249 | 90 | AACCAACAGCAT AGTCAAATAAA | 399 | gsususCUGUCUUUUGGUCAGGACXXCC GUCUAGCUAUXXGUGCUGCAGGGGUGU GXGXxACUCCUAUUGCUGGACGAUGU CUCUUxCGAGGCAUUAGCACAACCAA CAGCAUAGUCAAAusasasa |
| GB00250 | 90 | AACCAACAGCAT AGTCAAATAAA | 86 | gsususCUGUCUUUUGGUCxGGxCxxCCG UCUxGCUxUxxGUGCUGCxGGGUGUGx GxxxCUCCUxUUGCUGGxCGxUGUCUCU UxCGxGGCxUUxGCxCxxCCxxCxGCxUxG UCxxxusxsxsx |
| GB00251 | 90 | AACCAACAGCAT AGTCAAATAAA | 398 | gsususCuGUCUUUUGGUcAGGAcXXccgU CuXGCUXUXXGUGCUGcXGGGugUGXG XXXCUCCuXUUGcugGXcGXugUCUcUuX cGXGGCXUUXGCXCXXCCXXCXGCXU XGUCXXXusXsXsX |

TABLE 1-continued

Exemplary Cas12b gRNAs targeting human ANGPTL3 gene

| gRNA ID | Proto- Spacer SEQ ID NO: | Exemplary ANGPTL3 Protospacer (5'-3') | gRNA SEQ ID NO: | gRNA (5'-3') with Modified Exemplary Spacer |
|---|---|---|---|---|
| GB00252 | 90 | AACCAACAGCAT AGTCAAATAAA | 87 | gsususCuGUCUUUUGGUcAGGAcAACcgU CuxGCUAUAAGUGCUGcxGGGugUGAG AAACUCCuxUUGcugGAcGAugUCuCUuxc GAGGCAUUAGCAC<u>AACCAACAGCAUA GUCAAA</u>usxsxsx |
| GB00253 | 90 | AACCAACAGCAT AGTCAAATAAA | 88 | gsususCuGUCUUUUGGUcXGGAcAACcgU CuaGCUAUAAGUGCUGcxGGGugUGAGA AACUCCuaUUGcugGAcGAugUCuCUuacG AGGCAUUAGCAC<u>AACCAACAGCAUAG UCAAA</u>usxsxsx |
| GB00254 | 90 | AACCAACAGCAT AGTCAAATAAA | 89 | gsususCuGUCUUUUGGUcAGGAcAACcgU CuaGCUAUAAGUGCUGcaGGGugUGAGA AACUCCuaUUGcugGAcGAugUCuCUuacG AGGCAUUAGCAC<u>AACCAACAGCAUAG UCAAA</u>usxsxsx |

Letters indicate:
For Protospacer-A: 2'-deoxyadenosine, C: 2'-deoxycytidine, G: 2'-deoxyguanosine and T: thymidine or 2'-deoxythymidine
For sgRNA/gRNA-A: Adensine, C: Cytidine; G: Guanosine, U: Uridine; T: thymidine; X: nebularine (Purine riboside) a: 2'-O-methyladenosine (2'-OMe-A); c: 2'-O-methylcytidine (2'-OMe-C); g: 2'-O-methylguanosine (2'-OMe-G); u: 2'-O-methyluridine (2'-OMe-U); x: 2'-O-methylnebularine; dX: 2'-deoxynebularine and s: phosphorothioate (PS) linkage
Underlined positions in the gRNA: ANGPTL3 RNA spacer sequence analogous to the protospacer (modified and adapted from the exemplary protospacer in the third column of Table 1)

Target Genes

It is contemplated that the chemically modified guide RNAs described herein target a polynucleotide sequence of a particular gene of interest. To edit a target gene, the compositions disclosed herein comprising a single gRNA and, e.g., a Cas12b protein, wherein the single gRNA comprises a spacer sequence and a scaffold sequence, wherein the spacer sequence hybridizes with a target polynucleotide sequence in a target gene and the scaffold sequence binds, e.g., a Cas12b protein, contact a target gene polynucleotide. The single gRNA therefore directs, e.g., a Cas12b protein to the target polynucleotide sequence to result in a modification in the target gene. In some embodiments, the target gene is selected from a gene encoding PCSK9, APOC3 and ANGPTL3. In some embodiments, the target polynucleotide sequence is in a PCSK9 gene. In some embodiments, the target polynucleotide sequence is in a ANTPLT3 gene.

In some embodiments, the disclosure provides genome/base-editing systems, compositions and methods for editing a polynucleotide encoding an Apolipoprotein C3 (APOC3) protein and variants thereof. In some embodiments, provided herein are genome/base-editing systems, compositions and methods for editing a polynucleotide encoding Proprotein convertase subtilisin/kexin type 9 (PCSK9) and variants thereof. In some embodiments, provided herein are genome/base-editing systems, compositions and methods for editing a polynucleotide encoding Angiopoietin-like 3 (ANGPTL3) and variants thereof.

For example, where editing of a gene target is desired (e.g., a liver cell), the gRNA in a ribonucleoprotein (RNP) complex of the gRNA and a Cas12b protein in a cell facilitate binding to the target gene with the composition disclosed herein to elicit Cas12b-mediated gene editing. In some embodiments, the binding of, e.g., a Cas12b-gRNA complex to its target polynucleotide sequence in the target gene is directed by a single guide RNA disclosed herein, e.g., a single guide RNA comprising (i) a spacer sequence and (ii) a scaffold sequence, wherein the spacer sequence hybridizes with a targeted complementary polynucleotide sequence in a target gene. Thus, by designing the guide RNA sequence for any gene of interest that binds to a Cas12b protein can guide the gRNA-protein complex to the desired target polynucleotide sequence in the target gene (e.g., target gene encoding PCSK9, APOC3 and ANGPTL3) to elicit Cas12b-mediated gene editing. In some embodiments, the guide RNA sequence is co-delivered or -transfected with, e.g., a Cas12b protein in a cell where editing is desired.

In some embodiments, a target gene comprising more than one mutation described herein are contemplated. For example, a target gene encoding a variant protein can be produced using the methods described herein that includes 1, 2, 3, 4, 5, 6, 7, 8, 9, 10, or more mutations. To make multiple mutations in the target gene, a plurality of guide RNA sequences can be used, each guide RNA sequence targeting one target polynucleotide sequence in the target gene. For example, a Cas12b protein is capable of editing each and every target polynucleotide sequence dictated by the guide RNA sequence. For instance, 1, 2, 3, 4, 5, 6, 7, 8, 9, 10, or more guide RNA sequences can be used in a gene editing reaction. In some embodiments, the guide RNA sequences as used (e.g., gRNA). In some embodiments, DNA molecule encoding the guide RNA sequences can also be used.

In some embodiments, simultaneous modifications of more than one target genes (e.g. more than one target gene in the LDL-mediated cholesterol clearance pathway) are also contemplated herein. For example, in some embodiments, a modification may be simultaneously introduced into PCSK9 and APOC3 gene. In some embodiments, a modification may be simultaneously introduced into PCSK9 and ANGPTL3 gene. In some embodiments, a modification may be simultaneously introduced into APOC3 and ANGPTL3 gene. In some embodiments, a modification may be simultaneously introduced into PCSK9. APOC3 and/or ANGPTL3 gene. To simultaneously introduce modifications into more than one target genes, multiple guide nucleotide sequences are used.

To edit a gene encoding the PCSK9 protein, the gene is contacted with the composition described herein. In some embodiments, a target polynucleotide sequence in a target gene is hybridized with the designed spacer complementary single guide RNA of the Cas12b protein-gRNA RNP complex disclosed herein and, e.g., a Cas12b protein or a nucleic acid sequence encoding, e.g., a Cas12b mRNA, wherein the mRNA translate to protein in the cell and the protein thus produced first forming RNP complex with single guide RNA to effect gRNA-directed Cas12b protein-mediated modification to the target gene (e.g., target gene encoding PCSK9, APOC3 and ANGPTL3). In some embodiments, the target polynucleotide sequence is the gene locus in the genomic DNA of a cell. In some embodiments, the cell is a cultured cell. In some embodiments, the cell is in vivo. In some embodiments, the cell is in vitro. In some embodiments, the cell is ex vivo.

In some embodiments, the cell is from a mammal. In some embodiments, the mammal is a human. In some embodiments, the mammal is a rodent. In some embodiments, the rodent is a mouse. In some embodiments, the rodent is a rat. As would be understood be those skilled in the art, a target polynucleotide sequence may be a DNA molecule comprising a coding strand and a complementary strand, e.g., the PCSK9 gene locus in a genome. As such, the target polynucleotide sequence may also include coding regions (e.g., exons) and non-coding regions (e.g., introns or splicing sites). In some embodiments, the target polynucleotide sequence is located in the coding region (e.g., an exon) of the target gene (e.g., the PCSK9 gene locus). As such, the modification in the coding region may result in an amino acid change in the protein encoded by the target gene, i.e., a mutation. In some embodiments, the mutation is a loss of function mutation. In some embodiments, the loss-of-function mutation is a naturally occurring loss-of-function mutation. In some embodiments, the target polynucleotide sequence is located in a non-coding region of the target gene, e.g., in an intron or a splicing site.

In some embodiments, a target polynucleotide sequence is located in a splicing site and the editing of such sequence causes alternative splicing of the mRNA of a target gene. In some embodiments, the alternative splicing leads to leading to loss-of-function mutants. In some embodiments, the alternative splicing leads to the introduction of a premature stop codon in a mRNA encoded by the target gene, resulting in truncated and unstable proteins. In some embodiments, mutants that are defective in folding are produced. A loss-of-function variant generated by a gene that is modified using the compositions and methods disclosed herein, may have reduced activity compared to a wild-type protein encoded by an unmodified target gene. Activity refers to any known biological activity of the wild-type protein in the art.

In some embodiments, the activity of a loss-of-function variant may be reduced by at least 20%, at least 30%, at least 40%, at least 50%, at least 60%, at least 70%, at least 80%, at least 90%, at least 99%, or more. In some embodiments, the loss-of-function variant has no more than 50%, no more than 40%, no more than 30%, no more than 20%, no more than 10%, no more than 5%, no more than 1% or less activity compared to a wild-type protein.

In some embodiments, cellular activity of a protein encoded by a target gene may be reduced by reducing the level of properly folded and active protein. Introducing destabilizing mutations into the wild-type protein may cause misfolding or deactivation of the protein. A variant generated by modifying a target gene using the compositions and methods disclosed herein comprises one or more destabilizing mutations may have reduced activity compared to the wild-type protein encoded by an unmodified target gene. For example, the activity of a variant comprising one or more destabilizing mutations may be reduced by at least about 20%, at least about 30%, at least about 40%, at least about 50%, at least about 60%, at least about 70%, at least about 80%, at least about 90%, at least about 95%, at least about 99%, or more.

In some embodiments, the methods and composition disclosed herein reduces or abolishes expression and/or function of protein encoded by a target gene. For example, the methods and composition disclosed herein reduces expression and/or function of protein encoded by the target gene by at least 3-fold, at least 4-fold, at least 5-fold, at least 6-fold, at least 7-fold, at least 8-fold, at least 9-fold, or at least 10-fold relative to a control.

In some embodiments, the methods and composition disclosed herein reduces or abolishes expression and/or function of the protein encoded by a target gene by at least 2-fold relative to a control. For example, the methods and composition disclosed herein reduces or abolishes expression and/or function of the protein encoded by a target gene by at least 3-fold, at least 4-fold, at least 5-fold, at least 6-fold, at least 7-fold, at least 8-fold, at least 9-fold, or at least 10-fold relative to a control.

Some aspects of the present disclosure provide strategies of editing target gene to reduce the amount of full-length, functional protein being produced. In some embodiments, stop codons may be introduced into the coding sequence of target gene upstream of the normal stop codon (referred to as a "premature stop codon"). Premature stop codons cause premature translation termination, in turn resulting in truncated and nonfunctional proteins and induces rapid degradation of the mRNA via the non-sense mediated mRNA decay pathway. See, e.g., Baker et al., Current Opinion in Cell Biology 16 (3): 293-299, 2004; Chang et al, Annual Review of Biochemistry 76:51-74, 2007; and Behm-Ansmant et al, Genes & Development 20 (4): 391-398, 2006, each of which is incorporated herein by reference.

The methods and compositions described herein may be used to convert several amino acid codons to a stop codon (e.g., TAA, TAG, or TGA). Thus, it is envisioned that, for amino acid codons containing a C base, the C base may be converted to T. For example, a CAG (Gin/Q) codon may be changed to a TAG (amber) codon via the deamination of the first C on the coding strand. For sense codons that contain a guanine (G) base, a C base is present on the complementary strand; and the G base may be converted to an adenosine (A) via the deamination of the C on the complementary strand. For example, a TGG (Trp/W) codon may be converted to a TAG (amber) codon via the deamination of the second C on the complementary strand. In some embodiments, two C to T changes are required to convert a codon to a nonsense codon. For example, a CGG (R) codon is converted to a TAG (amber) codon via the deamination of the first C on the coding strand and the deamination of the second C on the complementary strand.

In some embodiments, the introduction of stop codons may be efficacious in generating truncations when the target polynucleotide sequence is located in a flexible loop. In some embodiments, two codons adjacent to each other may both be converted to stop codons, resulting in two stop codons adjacent to each other (also referred to as "tandem stop codons"). "Adjacent" means there are no more than 5 amino acids between the two stop codons. For example, the two stop codons may be immediately adjacent to each other (0 amino acids in between) or have 1, 2, 3, 4, or 5 amino acids in between.

Some aspects of the present disclosure provide strategies of reducing cellular activity of the protein encoded by a target gene via preventing maturation and production of mRNA encoded by the target gene. In some embodiments, such strategies involve alterations of splicing sites in the target gene. Altered splicing site may lead to altered splicing and maturation of the mRNA. For example, in some embodiments, an altered splicing site may lead to the skipping of an exon, in turn leading to a truncated protein product or an altered reading frame. In some embodiments, an altered splicing site may lead to translation of an intron sequence and premature translation termination when an in frame stop codon is encountered by the translating ribosome in the intron. In some embodiments, a start codon is edited and protein translation initiates at the next ATG codon, which may not be in the correct coding frame. The splicing sites typically comprises an intron donor site, a Lariat branch point, and an intron acceptor site. The mechanism of splicing is familiar to those skilled in the art.

Proprotein Convertase Subtilisin-Kexin Type 9
(PCSK9)

In some embodiments, the target gene for modification using the compositions and methods disclosed herein is gene encoding PCSK9. Proprotein convertase subtilisin-kexin type 9 (PCSK9), also known as neural apoptosis-regulated convertase 1 ("NARC-I"), is a proteinase K-like subtilase identified as the 9th member of the secretory subtilase family. "Proprotein convertase subtilisin/kexin type 9 (PCSK9)" refers to an enzyme encoded by the PCSK9 gene. PCSK9 binds to the receptor for low-density lipoprotein (LDL) particles. In the liver, the LDL receptor removes LDL particles from the blood through the endocytosis pathway. When PCSK9 binds to the LDL receptor, the receptor is channeled towards the lysosomal pathway and broken down by proteolytic enzymes, limiting the number of times that a given LDL receptor is able to uptake LDL particles from the blood. Thus, blocking PCSK9 activity may lead to more LDL receptors being recycled and present on the surface of the liver cells, and will remove more LDL cholesterol from the blood.

Therefore, blocking PCSK9 can lower blood cholesterol levels. PCSK9 orthologs are found across many species. PCSK9 is inactive when first synthesized, a pre-pro enzyme, because a section of the peptide chain blocks its activity; proprotein convertases remove that section to activate the enzyme. Pro-PCSK9 is a secreted, globular, serine protease capable of proteolytic auto-processing of its N-terminal pro-domain into a potent endogenous inhibitor of PCSK9, which blocks its catalytic site. PCSK9's role in cholesterol homeostasis has been exploited medically. Drugs that block PCSK9 can lower the blood level of low-density lipoprotein cholesterol (LDL-C). The first two PCSK9 inhibitors, alirocumab and evolocumab, were approved by the U.S. Food and Drug Administration in 2015 for lowering cholesterol where statins and other drugs were insufficient.

The human gene for PCSK9 localizes to human chromosome 1p33-p34.3. PCSK9 is expressed in cells capable of proliferation and differentiation including, for example, hepatocytes, kidney mesenchymal cells, intestinal ileum, and colon epithelia as well as embryonic brain telencephalon neurons. See, e.g., Seidah et al., 2003 PNAS 100:928-933, which is incorporated herein by reference.

Original synthesis of PCSK9 is in the form of an inactive enzyme precursor, or zymogen, of 72-kDa, which undergoes autocatalytic, intramolecular processing in the endoplasmic reticulum ("ER") to activate its functionality. This internal processing event has been reported to occur at the SSVFAQ↓SIP motif (SEQ ID NO: 103), and has been reported as a requirement of exit from the ER. "↓" indicates cleavage site. See, Benjannet et al., 2004 J. Biol. Chem. 279:48865-48875, and Seidah et al, 2003 PNAS 100:928-933, each of which are incorporated herein by reference. The cleaved protein is then secreted. The cleaved peptide remains associated with the activated and secreted enzyme.

The gene sequence for human PCSK9 is ~22-kb long with 12 exons encoding a 692 amino acid protein. The protein sequence of human PCSK9 can be found, for example, at Deposit No. NP_777596.2, which sequence is incorporated herein in its entirety. Human, mouse and rat PCSK9 nucleic acid sequences have been deposited; see, e.g., GenBank Accession Nos.: AX127530 (also AX207686), AX207688, and AX207690, respectively, each of which sequence is incorporated herein in its entirety. The gene sequence of *Macaca fascicularis* can be found publicly, for example, NCBI Gene ID: 102142788, which sequence is incorporated herein in their entirety. *Macaca fascicularis* proprotein convertase subtilisin/kexin type 9 isoform X2 sequence can be found publicly, for example, at NCBI Reference Sequence: XP_005543317.1, which sequence is incorporated herein in its entirety.

The translated protein contains a signal peptide in the NH2-terminus, and in cells and tissues an about 74 kDa zymogen (precursor) form of the full-length protein is found in the endoplasmic reticulum. During initial processing in the cell, the about 14 kDa prodomain peptide is autocatalytically cleaved to yield a mature about 60 kDa protein containing the catalytic domain and a C-terminal domain often referred to as the cysteine-histidine rich domain (CHRD). This about 60 kDa form of PCSK9 is secreted from liver cells. The secreted form of PCSK9 appears to be the physiologically active species, although an intracellular functional role of the about 60 kDa form has not been ruled out.

Numerous PCSK9 variants are disclosed and/or claimed in several patent publications including, but not limited to the following: PCT Publication Nos. WO2001031007, WO2001057081, WO2002014358, WO2001098468, WO2002102993, WO2002102994, WO2002046383, WO2002090526, WO2001077137, and WO2001034768; US Publication Nos. US 2004/0009553 and US 2003/0119038, and European Publication Nos. EP 1 440 981, EP 1 067 182, and EP 1 471 152, each of which are incorporated herein by reference.

Several mutant forms of PCSK9 are well characterized, including S 127R, N157K, F216L, R218S, and D374Y, with S 127R, F216L, and D374Y being linked to autosomal dominant hypercholesterolemia (ADH). Benjannet et al. (J. Biol. Chem., 279(47): 48865-48875 (2004)) demonstrated that the S 127R and D374Y mutations result in a significant decrease in the level of pro-PCSK9 processed in the ER to form the active secreted zymogen. As a consequence, it is believed that wild-type PCSK9 increases the turnover rate of the LDL receptor causing inhibition of LDL clearance (Maxwell et al, PNAS, 102(6): 2069-2074 (2005); Benjannet et al, and Lalanne et al), while PCSK9 autosomal dominant mutations result in increased levels of LDLR, increased clearance of circulating LDL, and a corresponding decrease in plasma cholesterol levels. See, Rashid et al, PNAS, 102(15): 5374-5379 (2005); Abifadel et al, 2003 Nature Genetics 34:154-156; Timms et al, 2004 Hum. Genet. 114:349-353; and Leren, 2004 Clin. Genet. 65:419-422, each of which are incorporated herein by reference.

A later-published study on the S 127R mutation of Abifadel et al, reported that patients carrying such a mutation exhibited higher total cholesterol and apoB 100 in the plasma attributed to (1) an overproduction of apoB 100-containing lipoproteins, such as low-density lipoprotein ("LDL"), very low-density lipoprotein ("VLDL") and intermediate-density lipoprotein ("IDL"), and (2) an associated reduction in clearance or conversion of said lipoproteins. Together, the studies referenced above evidence the fact that PCSK9 plays a role in the regulation of LDL production. Expression or upregulation of PCSK9 is associated with increased plasma levels of LDL cholesterol, and inhibition or the lack of expression of PCSK9 is associated with low LDL cholesterol plasma levels. Significantly, lower levels of LDL cholesterol associated with sequence variations in PCSK9 have conferred protection against coronary heart disease; Cohen et al, 2006 N. Engl. J. Med. 354:1264-1272.

Lalanne et al. demonstrated that LDL catabolism was impaired and apolipoprotein B-containing lipoprotein synthesis was enhanced in two patients harboring S 127R mutations in PCSK9 (J. Lipid Research, 46:1312-1319 (2005)). Sun et al. also provided evidence that mutant forms of PCSK9 are also the cause of unusually severe dominant hypercholesterolaemia as a consequence of its effect of increasing apolipoprotein B secretion (Sun et al, Hum. Mol. Genet, 14(9): 1161-1169 (2005)). These results were consistent with earlier results which demonstrated adenovirus-mediated overexpression of PCSK9 in mice results in severe hypercholesteromia due to drastic decreases in the amount of LDL receptor Dubuc et al., Thromb. Vase. Biol., 24:1454-1459 (2004), in addition to results demonstrating mutant forms of PCSK9 also reduce the level of LDL receptor (Park et al., J. Biol. Chem., 279:50630-50638 (2004). The overexpression of PCSK9 in cell lines, including liver-derived cells, and in livers of mice in vivo, results in a pronounced reduction in LDLR protein levels and LDLR functional activity without changes in LDLR mRNA level (Maxwell et al., Proc. Nat. Amer. Set, 101:7100-7105 (2004); Benjannet S. et al, J. Bio. Chem. 279:48865-48875 (2004)).

Various therapeutic approaches to the inhibition of PSCK9 have been proposed, including: inhibition of PSCK9 synthesis by gene silencing agents, e.g., RNAi; inhibition of PCSK9 binding to LDLR by monoclonal antibodies, small peptides or adnectins; and inhibition of PCSK9 autocatalytic processing by small molecule inhibitors. These strategies have been described in Hedrick et al., Curr Opin Investig Drugs 2009; 10:938-46; Hooper et al, Expert Opin Biol Ther, 2013; 13:429-35; Rhainds et al, Clin Lipid, 2012; 7:621-40; Seidah et al; Expert Opin Ther Targets 2009; 13:19-28; and Seidah et al, Nat Rev Drug Discov 2012; 11:367-83, each of which are incorporated herein by reference.

In some embodiments, the loss of function mutation induced in PCSK9 e.g., G106R, L253F, A443T, R93C, etc. In some embodiments, the loss-of-function mutation is engineered (i.e., not naturally occurring), e.g., G24D, S47F, R46H, S 153N, H193Y, etc.

PCSK9 variants that can be useful in the present disclosure are loss-of-function variants that may boost LDL receptor-mediated clearance of LDL cholesterol, alone or in combination with other genes involved in the pathway, e.g., APOC3, LDL-R, or Idol. In some embodiments, the PCSK9 loss-of-function variants produced using the methods of the present disclosure express efficiently in a cell. In some embodiments, the PCKS9 loss-of-function variants produced using the methods of the present disclosure is activated and exported to engage the clathrin-coated pits from unmodified cells in a paracrine mechanism, thus competing with the wild-type PCSK9 protein. In some embodiments, the PCSK9 loss-of-function variant comprises mutations in residues in the LDL-R bonding region that make direct contact with the LDL-R protein. In some embodiments, the residues in the LDL-R bonding region that make direct contact with the LDL-R protein are selected from the group consisting of R194, R237, F379, S372, D374, D375, D378, R46, R237, and A443.

As described herein, a loss-of-function PCSK9 variant, may have reduced activity compared to a wild-type PCSK9 protein. PCSK9 activity refers to any known biological activity of the PCSK9 protein in the art. For example, in some embodiments, PCSK9 activity refers to its protease activity. In some embodiments, PCSK9 activity refers to its ability to be secreted through the cellular secretory pathway. In some embodiments, PCSK9 activity refers to its ability to act as a protein-binding adaptor in clathrin-coated vesicles. In some embodiments, PCSK9 activity refers to its ability to interact with LDL receptor. In some embodiments, PCSK9 activity refers to its ability to prevent LDL receptor recycling. These examples are not meant to be limiting.

In some embodiments, the activity of a loss-of-function PCSK9 variant may be reduced by at least 20%, at least 30%, at least 40%, at least 50%, at least 60%, at least 70%, at least 80%, at least 90%, at least 99%, or more. In some embodiments, the loss-of-function PCSK9 variant has no more than 50%, no more than 40%, no more than 30%, no more than 20%, no more than 10%, no more than 5%, no more than 1% or less activity compared to a wild-type PCSK9 protein. Non-limiting, exemplary assays for determining PCSK9 activity have been described in the art, e.g., in US Patent Application Publication US20120082680, which are incorporated herein by reference.

In some embodiments, cellular PCSK9 activity may be reduced by reducing the level of properly folded and active PCSK9 protein. Introducing destabilizing mutations into the wild-type PCSK9 protein may cause misfolding or deactivation of the protein. A PCSK9 variant comprising one or more destabilizing mutations described herein may have reduced activity compared to the wild-type PCSK9 protein. For example, the activity of a PCSK9 variant comprising one or more destabilizing mutations described herein may be reduced by at least about 20%, at least about 30%, at least about 40%, at least about 50%, at least about 60%, at least about 70%, at least about 80%, at least about 90%, at least about 95%, at least about 99%, or more.

In some embodiments, the methods and composition disclosed herein reduces or abolishes expression of protein encoded by a target gene and/or function thereof. For example, the methods and composition disclosed herein reduces expression and/or function of PCSK9 protein encoded by the PCSK9 gene by at least 3-fold, at least 4-fold, at least 5-fold, at least 6-fold, at least 7-fold, at least 8-fold, at least 9-fold, or at least 10-fold relative to a control. For example, the methods and composition disclosed herein reduces expression and/or function of APOC3 protein encoded by the APOC3 gene by at least 3-fold, at least 4-fold, at least 5-fold, at least 6-fold, at least 7-fold, at least 8-fold, at least 9-fold, or at least 10-fold relative to a control. For example, the methods and composition disclosed herein reduces expression and/or function of ANGPTL3 protein encoded by the ANGPTL3 gene by at least 3-fold, at least 4-fold, at least 5-fold, at least 6-fold, at least 7-fold, at least 8-fold, at least 9-fold, or at least 10-fold relative to a control.

In some embodiments, the loss of function PCSK9 variant produced using the methods described herein comprises a R46C mutation (CGT to TGT), mimicking the natural protective variant R46L. The PCSK9 R46L variant has been characterized to possess cholesterol-lowering effect and to reduce the risk of early-onset myocardial infraction. See, e.g., in Strom et al., Clinica Chimica Acta, Volume 411, Issues 3-4, 2, Pages 229-233, 2010; Saavedra et al., Arterioscler Thromb Vase Biol., 34(12): 2700-5, 2014; Cameron et al., Hum. Mol. Genet, 15 (9): 1551-1558, 2006; and Bonnefond et al., Diabetologia, Volume 58, Issue 9, pp 2051-2055, 2015, each of which is incorporated herein by reference.

In some embodiments, the loss-of-function PCSK9 variant produced using the method described herein comprises a L253F mutation (CTC to TTC). PCSK9 L253F variant has been shown to reduce plasma LDL-Cholesterol levels. See, e.g., in Kotowski et al., Am J Hum Genet, 78(3): 410-422, 2006; Zhao et al., Am J Hum Genet, 79 (3): 514-523, 2006; Huang et al., Circ Cardiovasc Genet, 2(4): 354-361, 2009; and Hampton et al., PNAS, vol 104, No. 37, 14604-14609, 2007, each of which are incorporated herein by reference.

In some embodiments, the loss-of-function PCSK9 variant produced using the method described herein comprises a A443T mutation (GCC to ACC). PCSK9 A443T mutant has been shown to be associated with reduced plasma LDL-Cholesterol levels. See, e.g., in Mayne et al., Lipids in Health and Disease, 2013-12:70, 2013; Allard et al., Hum Mutat, 26(5): 497, 2005; Huang et al, Circ Cardiovasc Genet, 2(4): 354-361, 2009; and Benjannet et al., Journal of Biological Chemistry, Vol. 281, No. 41, 2006, each of which are incorporated herein by reference.

In some embodiments, the loss-of-function PCSK9 variant produced using the method described herein comprises a R93C mutation (CGC to TGC). PCSK9 R93C variant has been shown to be associated with reduced plasma LDL-Cholesterol levels. See, e.g., in Mayne et al., Lipids in Health and Disease, 2013-12:70, 2013; Miyake et al., Atherosclerosis, 196(1): 29-36, 2008; and Tang et al., Nature Communications, 6, Article number: 10206, 2015, each of which are incorporated herein by reference.

Further, the present disclosure also contemplates the use of destabilizing mutations to counteract the effect of gain-of-function PCSK9 variant. Gain-of-function PCSK9 variants (e.g., the gain-of-function variants have been described in the art and are found to be associated with hypercholesterolemia (e.g., in Peterson et al., J Lipid Res. 2008 June; 49(6): 1152-1156; Benjannet et al., J Biol Chem. 2012 Sep. 28; 287(40): 33745-55; Abifadel et al, Atherosclerosis. 2012 August; 223(2): 394-400; and Cameron et al, Hum. Mol. Genet. (1 May 2006) 15(9): 1551-1558, each of which is incorporated herein by reference). Introducing destabilizing mutations into these gain-of-function PCSK9 variants may cause misfolding and deactivation of these gain-of-function variants, thereby counteracting the hyper-activity caused by the gain-of-function mutation. Further, gain-of-function mutations in several other key factors in the LDL-R mediated cholesterol clearance pathway, e.g., LDL-R, APOB, or APOC, have also been described in the art. Thus, making destabilizing mutations in these factors to counteract the deleterious effect of the gain-of-function mutation using the compositions and methods described herein, is also within the scope of the present disclosure. As such, the present disclosure further provides mutations that cause misfolding of PCSK9 protein or structurally destabilization of PCSK9 protein.

The introduction of tandem stop codons may be especially efficacious in generating truncation and nonfunctional PCSK9 mutations. Non-limiting examples of tandem stop codons that may be introduced include: W10X-W11X, Q99X-Q101X, Q342X-Q344X, and Q554X-Q555X, wherein X indicates the stop codon. In some embodiments, a stop codon may be introduced after a structurally destabilizing mutation to effectively produce truncation PCSK9 proteins. Non-limiting examples of a structurally destabilizing mutation followed by a stop codon include: P530S/L-Q531X, P581S/L-R582X, and P618S/L-Q619X, wherein X indicates the stop codon.

Some aspects of the present disclosure provide strategies of reducing cellular PCSK9 activity via preventing PCSK9 mRNA maturation and production. In some embodiments, such strategies involve alterations of splicing sites in the PCSK9 gene. Altered splicing site may lead to altered splicing and maturation of the PCSK9 mRNA. For example, in some embodiments, an altered splicing site may lead to the skipping of an exon, in turn leading to a truncated protein product or an altered reading frame. In some embodiments, an altered splicing site may lead to translation of an intron sequence and premature translation termination when an in frame stop codon is encountered by the translating ribosome in the intron. In some embodiments, a start codon is edited and protein translation initiates at the next ATG codon, which may not be in the correct coding frame.

The splicing sites typically comprises an intron donor site, a Lariat branch point, and an intron acceptor site. The mechanism of splicing is familiar to those skilled in the art. As a non-limiting example, the intron donor site has a consensus sequence of GGGTRAGT, and the C bases paired with the G bases in the intron donor site consensus sequence may be targeted by the methods and compositions described herein, thereby altering the intron donor site. The Lariat branch point also has consensus sequences, e.g., YTRAC, wherein Y is a pyrimidine and R is a purine. The intron acceptor site has a consensus sequence of YNCAGG, wherein Y is a pyrimidine and N is any nucleotide. As described herein, gene sequence for human PCSK9 is-22-kb long and contains 12 exons and 11 introns. Each of the exon-intron junction may be altered to disrupt the processing and maturation of the PCSK9 mRNA.

Wild-type PCSK9 Gene (NG_009061.1), *Homo sapiens* proprotein convertase subtilisin/kexin type 9 (PCSK9), RefSeqGene (LRG_275) on chromosome 1:

(SEQ ID NO: 104)

GTCCGATGGGGCTCTGGTGGCGTGATCTGCGCGCCCCAGGCGTCAAGCACCCACAC

CCTAGAAGGTTTCCGCAGCGACGTCGAGGCGCTCATGGTTGCAGGCGGGCGCCGCC

GTTCAGTTCAGGGTCTGAGCCTGGAGGAGTGAGCCAGGCAGTGAGACTGGCTCGGG

-continued

```
CGGGCCGGGACGCGTCGTTGCAGCAGCGGCTCCCAGCTCCCAGCCAGGATTCCGCG

CGCCCCTTCACGCGCCCTGCTCCTGAACTTCAGCTCCTGCACAGTCCTCCCCACCGC

AAGGCTCAAGGCGCCGCCGGCGTGGACCGCGCACGGCCTCTAGGTCTCCTCGCCAG

GACAGCAACCTCTCCCCTGGCCCTCATGGGCACCGTCAGCTCCAGGCGGTCCTGGTG

GCCGCTGCCACTGCTGCTGCTGCTGCTGCTCCTGGGTCCCGCGGGCGCCCGTGC

GCAGGAGGACGAGGACGGCGACTACGAGGAGCTGGTGCTAGCCTTGCGTTCCGAG

GAGGACGGCCTGGCCGAAGCACCCGAGCACGGAACCACAGCCACCTTCCACCGCTG

CGCCAAGGTGCGGGTGTAGGGATGGGAGGCCGGGGCGAACCCGCAGCCGGGACGG

TGCGGTGCTGTTTCCTCTCGGGCCTCAGTTTCCCCCCATGTAAGAGAGGAAGTGGAG

TGCAGGTCGCCGAGGGCTCTTCGCTTGGCACGATCTTGGGGACTGCAGGCAAGGCG

GCGGGGGAGGACGGGTAGTGGGGAGCACGGTGGAGAGCGGGGACGGCCGGCTCTT

TGGGGACTTGCTGGGGCGTGCGGCTGCGCTATTCAGTGGGAAGGTTCGCGGGGTTG

GGAGACCCGGAGGCCGAGGAAGGGCGAGCAGAGCACTGCCAGGATATCCTGCCCA

GATTTCCCAGTTTCTGCCTCGCCGCGGCACAGGTGGGTGAAGGAGTGAATGCCTGG

AACGTACTGGGAACTGCACCAGGCACAGAGAAAGCGGGCTTGCCATTATAGTGGGT

TCCGATTTGGTTTGGAAAACATGGGCAGCGGAGGGTGGAGGGCCTGGAGAGAAGG

CCCTACCCGAGACAGGGGCGGGGTGGGAAGGACGGCAGATGCTGGGAGCACGAGG

CAATTTCTTTATGACACAGAACTCATGCTCTAGTATTCCATCTGTTTCAGCCGAAGA

AAAGAACCAGCTGAAGGGGCAGGGGAGAAGGGGCGGAGGTATTCTCGAGGCCCAT

TGGCGTCCTTTAGGACTCAGGCAGGGAAGGGCCCTTGGTGCTCTGGAGCCGGAGGT

GGTGCGCCTGGTACTGGGACCCCGGAGCTGAGCCCGGCGCCTCAGCCCACCTGGCT

GTCTGCCGACCGTGTGCGGGGCGAGTTTGCTCAACAACTCTGCCAGCTTCTGGCCCT

CAGGCTGTGGGAAGCTTCTTCCCGGGGCGAGACCACTAGCTTTTTCTAAGTATTACC

AGCCCAGGACTTGGCTGAGGTTCTGTGTCCCCCAGCTTGGAGTCAGATGTGGGGTTG

AATCTTGGCTTCCTCTCACTAGCTGTGGTGCTTGACAAGTCACTTATCCTTGAGCCTC

CATTGCCTAATCTTTAAAAGGGAGGTGACAATCGTCCCTACGGCTCAGTGGCAGCA

GATGGGGAGATGAAGGGAAAGTTCTGTTGACCATGAGTGAACTTACAATGCAAGCC

CCGGGGGGATCACTTGCAGTTTTGTCCCTGTCTGCAGTGTGACCTGTTGGTGACATT

GTCTTTGCTCCAAACCACAGCTCCTGGGGCAGAGGGGAAAATTCTGCCACTCACAG

CTGCCTGCCCACGCTTCTGTCTGAGTGTGCTGGGTGGCAGGATGGCAAGTCCTTACT

CAGCTCAGTATAGCCCTCTTCCTTGTTCCCTGAGCCTTTGACTTTCTCGAGGGATGTT

GTGGGGTTGTGGCCAGGATAAGAAAGGGCATTTCAAGTTACCACTGCTCCAAAACA

ACTGTTCTGGAAATAGTGAGTACCCCATCCTGAGAGGTGAGTAAGCAGAGGCTGTA

TGACCACCTGAACCAAGCCCTTGAGGATGTTTCTTCTCTGGTGGAAGTTTGGAACAG

GAGCCTCCTCAAGTTCATTTATTCATTCATTCAATGGTTATTTTGTGGGAATCGAATT

TAGAATGAAAATATTTTTTGGCAAGCAGAAAATAATTTTTAGACCAATCCTTTTCTT

TTAGTCATGAGAAACTGAGGCCCAGAGAGAGGAGGTCACCCCAGGTGCATTAGAAC

TGGGTTTCCAGAACTGACACTCCACTGCACAGAGTACTCTCCCAATTCATTCAATTT

TTATTTAGCGGAAGGCATTTTCAGATGGGTCTTTGAAGCATTAGTAGGAGTTCAGCG

ATGATGGTGTCATGAGAATTTTATTCTAGGATTAGGAGGTACCATGAACAAAGATA

CAGAGCTGGGAAAACCAGAGGTGGAAGATAAGGAGCACATGTCCACAGTTCTTTTT
```

-continued

```
CTTTTTTTTTTGAGATGGAGTTTCGCTCTTGTTGCCCAGGCTGGAGTGCAATGGTGCA

GTCTCAGCTCACTGCAACATCTGTCTCCCGGGTTCAAGTGGTTCTCCTGCCTCAGCC

TCCCAAGAAGCTGGGATTACAGGTACCTGCCACCACGCCCGGCTAATTTTTGTATTT

TTAGTAGAGAAGGGGTTTCACCACGTTGGCCAGGCTAGTCGCAAACTCCTGACCTC

CTCAGTGGATCCGAGGAGGTGATCCTCCCGCCTCAGCCTCCCAAAGTGCTCGAATTA

CAGGTGTGAGCCACCACGCCTGGCCTCCACAGTTCTTTATCCACCGTCTGAAATGTA

AAATGTTACGAAAACCAAAAGTTTTTTTTGTGATTTATTTGATGGTAGCACCTGACG

TGAACTGACATGAGATTATTTTTAATTTAGTTGTGTGAATATGCATATTCATATATTT

TGCTGCATAGATTACAGTATGCAGCTCCAGATTCTTCCAAGCAGACTCTGATTGCCC

ATTACTGCCTTTCTAAAATCCAAACAAGTTCTGAGGTTCAAAACCGTTTTGGCCCTA

AGGCTTTGGGTAAAGGGGGTGGACTCTGTTCTACTCTGACTGGAGTCCAAGATGCA

TATATACAGAGATATGGGTGATGGGGCTGCAAGGTAGGTTGAGGTAGGGGCCAAG

GAGGAGCATGGAGTTTGGACTTGATTCATGAGGCTGTGGGGAGCCAGTGAAGGTTC

TTAAGCAGGTATGTCTGCCTGAGAGCAGTTGGAGCAGACAAGAGCTAAAAACCAAA

CAAATCACCATAGATAGTGGCTGCTATAATTTGTTTGTCCCCTCCAAATCTCATGTG

GAAATTTGGTCCTCAGTGTTGGAAGTGGGGCCTAATGGGAGGTGTTTGGGTCATGG

GGGAGGAACCCCTGTGAAAGGCTTGGTGCCGTCCTTGTGATAATGAGTAAGTTCTC

CCGCTATGATTTCCCTTGAAGGCTGATTATTAAAAAGAGCTTGGCACCTCCCTCTCT

TCTCTCTTGCTTCTTCTCTTGCCATGTGATTGATCTCTGCACATGTAGGCTCCCCTTC

ACCTTCTGCCATCAGTGAAAGCAGCTTAAGGCCCTCACCAGAAGCAGATGCTGGTG

CCATGCTTCCTGGAGAGCTTGCAGAATCATGAGCTGAATAAATCCCTTTTCCTTGTA

AATTACTCACCTTCAGGTATTCCTTTATATAGCAACACAAAAGGACTAAGACAGTG

GCCTTGACTTTTCTCTCTCTTTAAGAAGTGTTGCCTTTGCTCACTTAGTCATCCCTTCT

GCCTGCATTTGTAGAGCATCTGGATGGGAGATTTATATAACCGTCACTCTTGACTTT

CCCAGCAGGCCTATGTCATAGGTACTGTGGTCTCTACAATACAGCAGAGGTATCTG

AGGCTCCGAGAGGTTGAGTGACTTGCTCATGGCTGCACAACCAGTAAATATTGGAG

CTGGAATTCAGGTCCACGGTTTCCTGGCTCCAAAGCCCATGATTTTTTCCCTCAATTT

ATTCTGACTGGGGCATGGGGGAGGGGGTGGCCTTTGGGCAGGGCCACCAGGAGCG

ACCAGGCCCGTAGAGAGCTGGGTGCAGGTACAGAGGAAAACCTGTTGTCGAGTGTG

GCCCGTAGTTCCCATTTTTGCCTGAATGGCACATTTGAAAGTGTTATATAACCATGT

GAATAATAATAGTTGGCCTATATGAGTTCTTTAATTTGCTTTTTGGTCCGCATTTGGT

AACTTCTTTATCATCTACTATACTCTGTTGTGTCTCTTTTGTTGTAATTTGTAAGTAG

GGGTGAGATAAAGTACACCTAGGGTTTGCTGGGTTTCTTCCATGTCATCATGTTCCT

CCTTGCATGGGGCCAGGATCCGTGGAGGTTGCCTGGCACCTACGTGGTGGTGCTGA

AGGAGGAGACCCACCTCTCGCAGTCAGAGCGCACTGCCCGCCGCCTGCAGGCCCAG

GCTGCCCGCCGGGGATACCTCACCAAGATCCTGCATGTCTTCCATGGCCTTCTTCCT

GGCTTCCTGGTGAAGATGAGTGGCGACCTGCTGGAGCTGGTGAGCCACCCTTTTTGG

GAATGGCACTTCCTGATAGGGCTGGGCCACTGCATATACACTGGGGACTGTGCTTA

GTAGGCCCATTGCTGAAAATCAGAAGGGGACAGCAAGTATGTATTGAGCACTTATC

GGGTACCAAGCACAGTAACTACTGGCTTTCTGTATAGAATTCCCTTTAAGCCTGGCC
```

-continued

```
ATGCCCCAGTGGTACGTCTATCTTCATTTGAAAGACGAGGAGACTGAAGTTCAGAG

GGGACCACACAGACAGCTAGGGGTAGAGCCTGGATCAAACCCATTGGTCTGCCTGC

CAGCCATTCTTGTGCCAATGCATCTGCTGCCTACGGAAACCTGTAGGGACAAGGCC

CTGGGATGTTCAGTGGAGCCTGAGTCATTTTATAAAAAAGCATGACTCTAGGGTCC

AAAATTCCTTTGAAGCTGTTGCTATCCAGAGTGAAGTCCCTTCTTTAGGACAGGGTG

GCCCTCCTCCCTCCTGGATGTCACATCTTCGGTGGAGGGGCAGAAAGGGGACTGGG

TATTCTCCTCACCCTGGCCCTAGTGCTTCAAATCTTAAAAAAACGTTTTTATTTGTGC

TTCTGCACCACCTTCTAGCCCACCTCGTTTCCTGGCCTCTAACTTGATGAGAGCGTGT

GTCATTTTCACACTGATTCTCCACATGGCAGGCGGTGCTTCTTAGCCTCCTGCAGAC

AGTGAGGCCCCACGGTCTTGTCCAAGGTCACACAGCGTGTAATGGGCAGGGTCAGA

GTCTGGAGTCTGGACCTGGGTCTCCTAGCTGCACTGCACTGCTGCCCCATGGGTTAA

TCAGCTCAGCATACCGTGGCTGAACAGCTACCTCATACCAAGGCCTGTGGCGCCAT

GACAGGGATTGACAGGGTCCCTGCCTTGGAAACCCGTAGTCTAAGTAGAGGAGACT

GACAAGTCAATGCCTTCCATCAGTCTGCTCAACACACGTTTACCAAGTGCCTACTGT

GTGCTGCAGAGGCGAAGATGACACAGCTCAGGCCTTTCCCTTGAGCTTACAGTTCA

GGAGGAGAGACTGACCAGTGACTGCCAGTACAGTTGACTATGGGACAATGTGCTCA

GCCTTGGGGAGAGACGAAGAAGGTACCCGTATAGCACCAGATGACAGGCACGAGC

CCCACAGGCCAGGGCAGCTGCTCAGAGGAGAGTAGGCCAAGCAGAAGGCAAACAG

AAGGCTGCAGGCATTTGCCATCGAGAGCTGGACTTCAAACTGGGCATCATACCAGC

CTGGGTTCGAGTCCTGCCCAGCCCCTTATTGGCTGTCTAACCCTGAGCAAATCCCTT

CACCTCTCTGAGCCTCATTCCTCTATCTGTAAACCAGTTATAATAATTGGAACATTC

ATTTAAGGACTAAATGAGGTCGTGAAGCATTCAGCAGATGCTAGGTACGGAAACTC

GCTGAAGTGGGGGCAGGTTAAGAAGCCTCTGGGGATACGAAGGCATCCAGGGACT

AGTTGTGGCAGGAGGCTGTTACCACTTAGGTCTGAAGGGTAAGGAGAGGGAATAGC

TTTCCCTCTGCCCAGTTGGAGCCGGTGGCATGGAGGAGAGGCTGCCTGTGGGGAAT

CACCCGAGGGTTCACCGCTGCCATGCGCAGGGAGTCAGGAGGTAGGGAGGGAGTG

GGGCAGATGCACACCATTTTTTTTTTTTTTTGAGACTCTGTTGCCCAGACTGGAGTGC

AGTGGTGCCATATCTGCACCTCTGCCTCCCGGGTTCAAGCTCACTGCAACCTCTGCC

TCCCGGGTTCAAGCGATTCTCCTGCCTCAGCCTCCCGAGTAGCTGGGACTACAGGTG

TGTGCCACCATGCCTGGCTAATTTTTGTATTTTTAATAGAGATGGGGTTTCACCATGT

TGGCCAGGCTGGTCTCGAACTCTCGACCTCAGGTGATCCCCCACCTCGGCCTCCCAA

AGTGCTGGGATTACAGGCGTGAGTCACCGCTCCCAGCTGCTGATGCACTCTTGTCCT

TCTAACTCCTGCTAGTGCCTCCCATTGGCTGAGCCCAACTGGAAGCTTTGCAAGGGA

GCTGGTGCTGCAGTTTGCACTGAGCAGGCTGGAGAAGGCTGGAGAATAGACTAGGG

GACAAACCGAATTGCCAGTGCTGTTATGTCATGATTTAGGCATGGAGTCCAGGGCC

TGAGCTTCACTCCATGTCCATCCTGCCCAGAGCCTTGGCACAGCCTGGCTCCCAGAC

AAGATGTCAAGTTCAGAATCCTTCCTAAAAGGAATCCTCTATGCCAGACCGTGTTGC

AGGGATATGGGAGTGCTGGGCTCCCAGCCTGATCAAGGAGCGAGAAAACTCAGGCT

CCTAGTCTGTCCTCCGGGGCACTAGCAGGGACAAGGTGGGAGGCTGCTGGGCTGGG

ATGTGGGGACAGGTTTGATCAGGTAAGGCCAGGCTGTGGCTGTGTTTGCTGCTGTCC

AAATGGCTTAAGCAGAGTCCCCCGGCCTCTCTGGCTTCTGCAGGCCTTGAAGTTGCC
```

-continued

```
CCATGTCGACTACATCGAGGAGGACTCCTCTGTCTTTGCCCAGAGCATCCCGTGGAA

CCTGGAGCGGATTACCCCTCCACGGTACCGGGCGGATGAATACCAGCCCCCCGGTA

AGACCCCCATCTGTGCCCTGCCCCACCCCATCTGAGCTGAATCCATTTGCTCTGCCC

TGGCCTGGCCTCCCTGCTGGTGGTTTCCACTTCTCGGGGGGCTTTGGGACTCAGCAC

CTCCACTGACCCCTTTTTTTCTGTCCCATCCCCATCCCCTGCAGCCCCCACTGCCTGC

CTTCCTGTTGCCCCACAAATGCAAAGTCTTGCCTTAAATGATCCTCTTTTCCTTCTT

TTCTCTTGTTTTCCTTTTCTCACCATTTGGAATGGCCCAGCAGGCTGCACTTACCTTG

GAAGGAGGGTTCATCTGATGGTGACTCTACCTAGGGCCCCCAGGCCTCTATAACTCC

CAGTGCCCTGCAGACTGGACCAGATCCTTTAATGGGATAGACACAACCCTGTCTGG

GATGCCTCTGCCTACCTTCCTGTTTTGCTGCTCCACCTGCCTCCAGCTCCGTTTGGCT

TCCTGGGGCTCCCTGCCTGGGCCACTTTGTGTCTTCCCTCTAGGCCTTTCTTTCCACT

GTTCCCTCTGCCTGGTGTGGCCTGGCTATGGAAGGGAGGGAGGAGGAGCGGCCATG

GAAAACGGTCTGCATTCTAGCAGGGACTTGCAGGTGGCAATTCAGTCGGGGAAGAC

TCTAGATGCACCTGGCCTGAGGAGAGAATGAAGGGTTCTAGTTGGACTGTGTTAAG

TTTGAGGTGCCCATGGTGTGAGGTCTGGAGCTCAGCGCAGAGATGATGCAATGTGG

TGGGTCCATGCAACATGGTGCCAGGACGCAGAGCTTGGGGTGAACTCAGCTTTCAC

CCCTTACCGGTTCTCGTGGGATCTTGGGAAGCCACTTTCTTCTATGAGCTTTGTCGTT

CTTGTCTGTAAAATGGGCACATAACCCTGTCCCTGTCCTTCTCACAGGTTGCTGTGA

GACTCCAATGAGTTGAAGGATGTGCAGATGCTTTTGGAAGTGAAAAGTTGGGGGGC

TACTGTGTGACTTTGCATACACCCAAACTGTGTGACCTTGCATATGTCTGAGTTGCT

GCCATTGCAACAGATCAGAGCTGGTGGGCTGGGTGTGGAGAAAGGGTTTGTGTGGG

GGACATCCTCTGGCAAGGGTGGCAGCAGCAGAAGTGAGGGGCCTGGTCGGTCATGT

GTGCTGACCCGGCCTGGGCAGCCTGTGGCCAGGGAGAGGACAGCTCCTCTGTAGGA

AGAGCCTGTTCCTTTCCAACCAGGTGAGACCTCTTCAGTGGAGCCCTGGAGCCCCCT

GTACTCCACATCAGTGCCTCAGGGACCTCCCGGAGCAGGCTAATATCAGAGACCAA

GAGGGACACTGGCAGAGGATCACAGAGACCCCAGTCCAGGCAGGGACTGAGAAGA

TCTTGCCCCCTAAGTTAGTTTCCTAGCACTGCTGTGACAAATTACCACCCCCTCGGTT

GGAACAAGTTGATTCTCTGCAGTCCTGGAGGCCAGAAGCCTGAATCAGTGTCGGCA

GGACCACTTTCTCCCGGGGGGGCTCCAGGGAGAAGCTTCTCTTGCCTCTTCCGTGTCC

CAACAGCGGCAGCACACCAATCCCAGCCTCTGTCTTCACACAGCCTTCTCTGTGTCT

CTCTCCTCTTCATTGTCTCATAAGGACACTTGTCATTGGATTTAGGGCCCACTGGATC

CTCCAGGATGATCTCATGTGGGGAACCTTAACCACATCTGCAAGGACCCTTTTTCCA

AATAAGGTCACAGCCACAGGTTGTGGGGGTTAGGATGTGAGTGTATCTCTTTGGCA

GCCACTGTTCCCTCCTCTCCCTTGGGCCAGAAGCAGACGTGGGGCCCTTTCTTCCCC

ATAGGATGCCCATGGATTGCCCCCCTTCCCGCTTCCCCCGAGTGTCTGTGGGAGGTG

GCAGGAATGGCAGGCAGGGGTGTGGAACCCCTTCTGGAGTCATATCAAGGGCTTGG

CTGGAGGAAGTCCTCCTGGAGCTGTTGGGCTGGCATGGGGCAGGCTGGCTGGGCCC

AGCAGCAGCTTCTTCATTCATGGGGAGGCCACAAGCATGGGCCCTAGAGCTGGCTG

CCGCCCTCAAACCCAGACCCTGCACTCTTAACTGTGTGACCTTGCATACGTCACTCA

CCCTCTCTGATCTTCAGGTTCCTCTGCAAAAGGGAGGTAATGATAACCCTCACTCTG
```

-continued

```
GGGGGCTGTTTGGAGGGTTAAATCAGTTATTGCTGTAGCATGCATTTCTCTGTCAGG

TATTGAGTGAGGTGCTGTGATTTTAGCCCTGCATTTTTCTTTTCTTACCATTCAATAA

TAACGTTTTGAGCACCCACTGTGCGCCAGGCACCATATTAGGTGCTGGGGATACAA

ATGTGAATGAAATGAATGTGGTCTCTTCCCCCAACAGTGTATCCAGAAGATTAATCC

ATTCCTTAAACAAATGCTACTTGACACAGATTAGTTCTGGATAGGCTGAGAGCTCTG

AAGGAGTGCAGGCAGCTGCGAGCCTGTGTATCCAGCAGAAGGATCAGGAAAGGAT

TCCTGGAGGAAGCGCTGTTCTAGCCAAGACCTACGGGGGCATTATTAACCAGGCAA

AGGGGACGGTGTCCAAGCAGTGGAATGAACGTGGATTGAAGCTGTGAGGCAGGAG

GGAGTGTGGCCTGTGCAGAAGGGACCGAGGCTGGTGAGACCAGGAGGGCCTGGGT

GGCCTCCAGGTCAGATGTGAAAGGAAGAACTTGGCCACAGTCTGAGCTTCTCAGGC

GTATGGCAGGGCTGCCTGGTGAGAGGGAATGAGCTCCCTGCTCTGGAGGTATGCAA

GCAGGACTGGGCTCTCACCTGCCAGAGGCCACAGAGCTTTCCAGAGGCTGGAAGAG

GCCACTCCAAGGCCTCTTTGCCCCTGAGAGTGGTGGCTCTTCTTGAGGCCACCTTGC

CACGCTGTCACAGGGAACTAGCAGCCCCTGCCTCACCCGGGGGTTTGGAAGATAGA

GGGAGGCCTAGGAAGGGCCCTGTGTCTCATCCGAGCTGGGCCCCTTTCCAGCCTCTC

ACTGGAAGGAAGCCCAAGGATGTTCCTGTGGGGGCTTTTACCAGGCCCACCTGCCC

TCTGCTGGCCATGCTTGCAGCCTCCTGACCCTGTCCCAGCAGGACAGTGGGCTGGTG

TGAGCGGGCAGGAACCGCCTGCACTTAGAAGGTGTGGGGCTGCCTCCCCGAGCTTC

CATCTGCCGCTGGGGCCACACCCCAGGCCCAGGGATGGGACCCCACAGTGGTCACA

TCATCTTGCAGCAGAACCCAGGTACAGCTCCTGGAGCAGATGGTGGTCCCAAGCAC

GGGTGGGACCAGAAAGGACTCTCACCTGGGCTAACTCAGCTGCAGCCTCAGTTCCC

TCCTCACACACGACGAGGAACATGGACTGGAAGCCTGCCCAGCAGGCCTTCTGCTC

GATGTGCGTTGTGTGGCTTACGTCCAGGGAGGGAAGCAGCCTCTGTGCTGTCTTCTA

GATAAGCCTGTATTCCCCGGGCTGTCTGCCAATGTATCCAGTTGTCCCGTCAGCCTG

GAAGCTCTGAGGGAAAACCTTGGGCTGCTTCCTGAGCACCTGTATCCCCTGCAGCC

AGCCCGGGGCCTCTGCTAGGAGCAGACTGAGCATGGCTTATGGGCCTGGCACCATC

TGGCCTCTGCCCACCTTGCTGGCCTTGTCTTGTGTCTGCCCCTTCGACATTCCATAGC

CCAGCTCAATATCTAGTGGTTCCTCTAGGGTGGCGAGCACTGTTTGGTCTCCAGATG

TCTTCAGGTCGGAGCTCACAGCGCTCTCAGCCACCCCTTCCCAGTGTAGCACCGGGC

ACATGGTAGATGCCTATTGATGAGTGAAAGCTCCTAACACACTCAGAGAGCAAGGA

CTCCGCCTCATCCCACAGCCTGGGAGGAGAGGCAGACTGCCAAGGACCTGCTCAGC

ATGCTACAGAAGAAACCAAAGTGCCCACGGGACTGATCAGTGGAGCTTCCTGCCGA

GACTGGAGGCCTTAGGGCAGGGTAGACAGTGTGTGTGCAGGCTGGGGACTCACAGT

TCGGACTGTGCCCAGACCTACTAGCATAGTGGGTGGGTGGGAGGATGCGGGACTGG

GGGCCGACCTTGCCTGAAATTCATGTGGGATCTCAGAGCAGCCACTGAATTGCTCTG

TAGGGGGCTAAATAGTGGCCCCCACAGATACACACACCCAGACAGAGCCTGTGAGC

CAGACCTTATTTGGAGAAAAGGTCTTTGTAGATGTAATTAAGCATCTCAAGATGGC

ATCATCTGGATTATGCGGTGGGCTGTAAGTCCTGTGATGTGTCTTTATGAGAGAAAG

GCAGAGGGAGATTTGACACACACAGGAGGGGCCACGTGGAGACAGAGGTGGAGAT

TGGAGAAATGTGGCCACAAGCCAGGGAACACCAGCAGCCACCAGAAGCCGGAAGA

CGTGAGGCAGGGTTCTTCCCAGAGCCTTCGCTGCTGAGTCTGGGAATTTGTGACCGA
```

-continued

```
AGCCATAAGAAGTGGGTACACGCCCTGAGCCTCCCACACTTGCTCACCTGTCCTGA

GATGAGAATCTCTACTCTGCAGCATATTTGGAGGATCACTGCGGGGGCCACAGAGG

TGCTGTTCAGATGGCACTTCAGAAGACTCAGGAGACCCTGGGGCAGGAGCAGTTTG

ACTGACAGCCCAGAGGGCTGCCCTCTGATTCCACCTGAGGCCCTGCTTTTCCTGGCT

GCAGGGGTTCCAGGGCCAGGCCATTTCCGCTGGCGCAGGACTCTGCTAGCAGCAAC

CTGCCTGAAGTCTTCCTTTGGCCTGGCTGAGAGTTTCTGAGACCTGCGCTGGAGCGG

AGGTGCTTCCTTCCTTGCTTCCTTTCTTCCTCTCTCCCTTCTCCATCCAGCAGGCTGG

ACCTGCCTGGCATCTGTGAGCTCTCCCTACTTTCTCCTATACCCTAACCTTTGTCCTG

CATGGGCGACTCCCCCAGTGAGTCTCTTGCAGCTTTTACCCCAGTGCCTGCTTCTTG

GAGAATCCAAACTGATCCAGTTAGGGATGATAAAGTGTAGGGTAGGCGCTCGGTGA

CTGTTTTCTCTGAGGTTGTGACTCGTGTGAGGCAGAAGCAGTCCCCGTGAGCCCTCC

TGGTATCTTGTGGAGTGGAGAACGCTTGGACCTGGAGCCAGGAGGCCCAGACATAC

ATCCTGTCCGAGCTGCAGCTTCCTGTCTCTAAAATGAGCCGGCCAGCGCAGGTGGCC

AGACATCACTGTTATTCTCCTTTGAGTCTTTAAATCTTGTTGTCTTTCTTGCAGACTC

GGTGAGCTGTGAAAGGCTATAATAGGGGCTTTATTTTACACTTTGATACTATTTTTT

GAACATTCATATTATTGTTAGATATTGATATTCATATGAAGGAGCAGGATGACTTGG

GTCCTTCTTGGCAGTAGCATTGCCAGCTGATGGCCTTGGACAGTTACCTGCCCTCTC

TAGGCCTCCCTTTCCTTGTCTATGAAATACATTATAGAATAGGATGTAGTGTGTGAG

GATTTTTTGGAGGTTAAACGAGTGAATATATTTAAGGCGCTTTCACCAGTGCCTGGG

ATGTGCTCTGTAGTTTCTGTGTGTTAACTATAAGGTTGACTTTATGCTCATTCCCTCC

TCTCCCACAAATGTCGCCTTGGAAAGACGGAGGCAGCCTGGTGGAGGTGTATCTCC

TAGACACCAGCATACAGAGTGACCACCGGGAAATCGAGGGCAGGGTCATGGTCAC

CGACTTCGAGAATGTGCCCGAGGAGGACGGGACCCGCTTCCACAGACAGGTAAGCA

CGGCCGTCTGATGGGAGGGCTGCCTCTGCCCATATCCCCATCCTGGAGGTGGGTGG

GGACTGCCACCCCAGAGCGTTGCAGCTGTACTCCTGGGTTGCACCCCCCCCAGCTGT

CACTGTCCCCTCCCTGCCATCAGTTGTGGGAAGGGCGTTCATCCATCCAGCCACCTG

CTGATTTGTTATAGGGTGGAGGGGGGGTCTTTCTCATGTGGTCCTTGTGTTCGTCGA

GCAGGCCAGCAAGTGTGACAGTCATGGCACCCACCTGGCAGGGGTGGTCAGCGGCC

GGGATGCCGGCGTGGCCAAGGGTGCCAGCATGCGCAGCCTGCGCGTGCTCAACTGC

CAAGGGAAGGGCACGGTTAGCGGCACCCTCATAGGTAAGTGATGGCCCCAGACGCT

GGTCTCTCTCCATCTGGACCTGGCCTGGGAGGTGGCTTGGGCTGGGCCCAGGGAGA

GCTAATGTCTCCTAACCAAGAATGCTGTGGCAGCCTCTGCCGCAGAGCCAGAGAAC

CAGAGTGCCAAGGCTGGCAGGGTTCCCAGTGGCCACGAGTGCAGATGAAGAAACC

CAGGCCCCAAGAGGGTCATGCAGGTAGCCCAGGGAGTTCAGCCTTGACCCTGGGTC

AATGACCTTTCCACAGTTCCACACTGCTCCCCTTTTAAAATCCGGTGATGTCTTTATG

TCTTTTGTTATGTTATCTTCAATGTGGAGGGACTCGAGGTGATCTAAGCAAACTTTTT

CTATCTTCTGCTTGCATACCTCTGAGACCAGGGGACTCACTCACTTGCATGACTGGG

CCCTGCAGGTCACACTGGCCAGGCAGATGTGGTGGAGGAACTGGCAGAGGACTTTT

TCTAGACTGTGACTACATTTAGTCCACCCAGCGGCCCCCCTATGAAGTCCAGTTGAG

AACTAGGACTCTGGGGGCCGGTGGACAGAGAAGAGGGAGGGTTCTCTCCCTTACTG
```

-continued

ACTTCCTTCTGTGGCCAGACATTGAGCAAGGCCTCTGTACAGCATGTCCTGGGGCTG

GCCTTGCCGTAGCTGCTAAATAGTTGACGAAACCAGTCCAGAGAGGGGAGGTGACT

GCCAGGGTCGCACAGCTCAAGCTGGGGAACTCGCTGGGAAAACTGTCAGCTCTGGG

CAGCAGCTTGACTTCCACTGTAAGCCCCAGCCCCCAGGGTCAAACACTGGCTCTGGT

GCTGGCAGAGGCAGCCCACTAGCCTGTTTCAAAGGCTGAGAAGGCCCAGGAGTCTG

CCCTGTGCTCCACCAGTTCTGCCCGAGACTTTCCTACAGAGTACAGGTTTTGATGTT

CAGTTTTAAAGGCAAGAATCAATAACCTTCTGCCCCATCAGGTGACCCCTTGTGCCT

GTCCCACCCCTTTATTGACTGACCTCGGCTCAGTCAGGTCAGTTCCTGAAGGTCAGT

GTGTGGAGGGGAGGCTGTTCTTTCCCAGAAAGGCCTTCCCCAGGCCTGGTGCTCTGG

CCTCTGGAGGACTTCCTGGAGAAGTCCCTTCTTTGGGGTCCCAGTCAGTGTATGGGA

AGCCCTTATTGCATGACCTGGCACGGGGCAGGGGCTCAACAGTCACTATTGCCTTCC

TTGCCACTGCCATTTCCTCCTCTGTAAGCAGGTGATTGTGTGTCCAGTCTGAGCACA

GAGATAAGCACACAGCAGGTGCTTAATAACTAGCAGCTGTAGGCTGGGCGCGGTGG

CTCATGCCTGTAATCCCAGCACTTTGGGAGGCCGAGGTGGGCAGATCACCTGAGGT

CAGGAGTTCGAGACCAGCCTGTTCAACATGGTGAAACCCCGTCTCTACTAAAAATA

CAAAAATTAGCCAGGCATGGTGGTGGGTGTCTGTATCCCAGCTACTTGGGAGGCTA

AGGCAGGAGAATCGCTTGAACCCAGGAGGTGGAGGTTGCAGTGAGCTGAGATCGT

GCCACTGCAATCCAGCCTGAGTGATAGAGCGAGATTCCATCTCAAAAATAAATAAG

TAAATAACTAGCAGCTGTAAATGTGGCTGTTGTTCTTCACCTCCACACTCAGTGCCA

CTCCACTCCCTCCCTCCGTGGTGTGAGGGGCCTCACTAGCTGTCTCCTAGGAGGAGC

ATGGCTGTGAGATTCCAGCTCCATCCTTGGCCACGGCTCCTGGAGACATCTTAGAGG

CCAGGATCCAGAAGGCTCCCACACCTCATTTGACAGGGGAGAAGCTGTCAGTTCCA

GGTCCCCTTGCACATCAGGGCCAGAGCTGCGTTAGGCCTCCAGTCTCCAGGCCACTG

GGCCAGAGCTCACAGGCTGGCAGAGGGTTAGAACTGTTACTGGTGGCTGGGTGCAG

TGGCTCACGCCTGTAATCTTAGCACTTTGGGAGGGCAAGGCGGGAGGATCATGAGG

TCAGGACATCGAGACCATCCTTGCTAACACGGTGAAGCCCCGTCTCTACTAAAACT

ACAAAAAATTAGCCGGGCGTGGTGGCAGGCGCCTGTAGTCCCAGCTACTCAGGAGG

CTGAGGCAGGAGAATGGCGTGAACCCGGGAGGCGGAGCTTGCAGTGAGCCGAGAT

TGCGCCACTGCACTCCAGCCTGGGCAATAGAGCGAGACTCCGTCTGGAAAGAAAAA

AAAAAAAAAGAGCTGTTACTGTTGACAGTAGCATGAGGTAGACCATGGCCTGCACC

AAAATGGGGGAGTGGAGTGCCACTGAGGCCAGAAGGAACCACACCCTCAAGGGTG

GGGAGTTATGGTATGGGGGGTCCTAGGCATGGAGTCTTTTAATTCTTTAGACAATCC

TGGGAGCAACTGTCCCTGTTTCACAGAGGGCGGGGCCACACAGCTGGTGAGTGGGC

AGCCAAGACTCTGTTCAAGTTTGTGTGGGTCCAACACTTGCGGCCACGGTGGAGGG

GCATCTGAGCCAGGCCTCAGAGAGTGGCGGGGGAAGTTGGGTGGGGAAGTGTGCC

CTTCTCATTCCTCTGAGGCTCATCCTCTTGGTGCCTCTCTTTCATGGAAAGGGATAAT

AAGGTTATTGTGAGGATCCCCTGAGTTCGTATATTCAGACGCTTAGACAGAGCCAG

GCACAGAGAAGGGCCCGGGGTTGGCTAGTTTGATTGCTGGTGTAATTGCTAATATCT

TCCAGTTTGTATTGGTCAAGGTTCTGCAGAGAAGCAGAACCAGTAGGATGTATATA

TTAAGAGTTTCAAGCTCATGTGACCGTGCGGGCTGGCAAGTCTGAAATCCGCAGGG

CAGGCCAGGCAGGCTGGCAATTCCTGCAGAATTTGATGTTGCAATACTGAGTCCTA

-continued

```
AGGCAGTCCTGGGGCAGAATTCCTTCTTCCCTGGGAGGCCTCAGTCTGTTCTCTTAA

GGCCTTCAACTGATTAAATGAGGCCTGCCCAAGTTATAGAGAGTAACCTGCCTTACT

CCGTCTTCTGATTTAAATGTTAGTCACATCTAAAAAATATTTTCGCAGCAGCATTTC

CACTGGCTTTTGACCAAACATCAGGCCACAAAGTTGATCCCCAAAATTAACCATCA

CTCTGTGCCTGTAAGGGAGGGGCTGGGAAAGGGGAGCAGGTCTCCCCAAGGGGTG

ACCTTGGCTTTGTTCCTCCCAGGCCTGGAGTTTATTCGGAAAAGCCAGCTGGTCCAG

CCTGTGGGGCCACTGGTGGTGCTGCTGCCCCTGGCGGGTGGGTACAGCCGCGTCCTC

AACGCCGCCTGCCAGCGCCTGGCGAGGGCTGGGGTCGTGCTGGTCACCGCTGCCGG

CAACTTCCGGGACGATGCCTGCCTCTACTCCCCAGCCTCAGCTCCCGAGGTAGGTGC

TGGGGCTGCTGCCCCAAGGCGCGGGTAGGGGGCGGAGGGCGGAGGGCGGAGGGAG

GGCGGGCGGGCAGGCGGGCTTCTTGTGGCACGTGGGCTTCTTGTGGCACGTTCCTG

GAGGCCGAACCCTTCTGGCTTTGGAAGGAGTCGTCAGAGACCCCCGCCATGCGGGA

GGCTGGGGAGGAAGGGGCTCGAAACCTCCATCATCGCAGAGTCTGAATAGCAGTGG

CCCCGCCATGCGCCCACGTAGCGGCGCCTACGTAGCCACGCCCCCACACCCCGTCC

TGGCCACTCTCCCTCCTGAAGGTCTTCTGGTACCCGCCCCCTCCCCATCTCCATCCCC

AGGCCCTGCGTCCTCTGCCCAATACTCTTTGGGCCTCCCTGTTGTCCAGCTCTCTCCG

CGGCTCCATGACTGACAACTTGAGCAAGGCTAATGTGAATGGGAGCGGTTGAGGGC

TCAGACCTCTCACCCGAGGAACATCCACAGAGTGTGCCGCATGCCCGGTGCAGTGT

GGCTGCGGGGACACAGACACGGAGCCTCGGCCCTGAGGAGCTGGGGGGCAGTGAC

CGTCCCTCCTCTGACCCACCACTCCTCCAGTGTCAGGACACTGCGGGTATCTAGGGG

AAGGAATCTTGTTCCACTTCAAGTCTGGAACTTCAAGTCTGTGTGTGTGCGTGCGCG

CGCGCGCGTTGGGGGTGGGGGTTGCAGAGCAGATGCGTACCTGACAGCGGTAACCT

AGGTCCCCCCTGGCCTATCAAGGCTTCCCTGGCGGCCGAATTTAAAGGCATCAAGC

AAACAAAGCCCAACACATCTCTGCCTTGTCCTCTCAGTTTCCCCCCGTGGCACTTAG

AACCACTTGATACACCGAATAGTTTCCTATCTCCCCCACTAGGATGTAAACTCCACA

GGGGCATTGGGAATGCTGCCTGGCTATGGTAGGGACAGAGGGGAGCACCAGGGCG

GGGCAGGGGTGCCAGAGTTCTGCCTGGGCAGTCAGATTTTCCTTAGGAGGGGACAT

TTGAGTGGGACCCAAACAGGTGTATAGCAGTTGTCCAGCCCAGCTGGCAAGGCCTG

AGTCTGCCTCTGCAACCCCTCTCTTGGGCTCCTTTCTCTGCCACCCACCTCCTCACCT

TTCCAGGTCATCACAGTTGGGGCCACCAATGCCCAAGACCAGCCGGTGACCCTGGG

GACTTTGGGGACCAACTTTGGCCGCTGTGTGGACCTCTTTGCCCCAGGGGAGGACAT

CATTGGTGCCTCCAGCGACTGCAGCACCTGCTTTGTGTCACAGAGTGGGACATCACA

GGCTGCTGCCCACGTGGCTGGTAAGTCACCACCCCACTGCCTCGGCCACCGTGATGC

TAACAGCCCCTTTGGCAGTCAGGGTCTGTGCCGGGACCTCCAGTGCCAGGCTCTGTG

CAGGGGGACCAGAGATGAAGTAGGCCTGATGGTGCCTTCAAGGACACTCAGTCTGA

TGAGGGAGGCGAGTGCACAGAGGAAACACGAGGTCAGGGCTGTATTAGAGGGAGC

CCAGAGGAGGCACCTGCCCAGCCCGAGGGTCAGAGAAGGCATCTTGGAGGAGGGA

CATTTGATCGGGAGCTTGATGGATGAATAGGAGTTCACCTGGCCGATAAGACAGCA

ACTACCAAGGCTTAGAGGTGTGAGAGGAGGCTGTCTTACCTCACTGAGTAAGGACT

GCAGGCGGCTTACCTTCGAGAAGAGAGCTTAGTGTCTGTGTGCACGTGTGTTTGTGT
```

-continued

```
GTATGTGTGTGCGTGTGTGCACTGGCAGGAGTCCCCTGCTGGGGCAGGAGGGCCGG

GCCATCACCATCTTTCACCATTCACCCCTGCACCAGGCATTGCAGCCATGATGCTGT

CTGCCGAGCCGGAGCTCACCCTGGCCGAGTTGAGGCAGAGACTGATCCACTTCTCT

GCCAAAGATGTCATCAATGAGGCCTGGTTCCCTGAGGACCAGCGGGTACTGACCCC

CAACCTGGTGGCCGCCCTGCCCCCCAGCACCCATGGGGCAGGTAAGCAGGATGGCA

GGGTGGGCAAGTCCAGGCTGGGGCTTGGGAGGTCTGTGTGACCTTGACAGTCTCTC

CCTTCTCCCTTGTCTGTGTAAGGAGGATGACGCCACCTTAAATAGGATTAAATGAGA

ATGGGGCTCTGAAAGGGCTGTGCAATATTTTCATAACGTGTTTTTATAGAGACAGTT

GAGTATGTTCTTTAAGCCCTCCTCTCTCCTACCATGAACTAAAGATTTCTGTGGAGG

TCCCCTCACTCCCAGCACCCCCTCCTCATCCCAGGCCCTTTTTGCAGGTTGGCAGCT

GTTTTGCAGGACTGTATGGTCAGCACACTCGGGGCCTACACGGATGGCCACAGCCG

TCGCCCGCTGCGCCCCAGATGAGGAGCTGCTGAGCTGCTCCAGTTTCTCCAGGAGTG

GGAAGCGGCGGGGCGAGCGCATGGAGGTGACTGTACCCCTCCTTCGTGTGTGTGTG

TGTGTGTGTGTGTGTGTGTGTGTGTGTGTGTGTGTGTCAGTGCTGGGCCCTCA

GGGACCCCCAGCAAGCCCCTCCATCCTCCAGACTCCAGCTCTTCTGTAAGCTTACAG

GGCTGGCCAGACCAGGAGTGGGGCACTCCTCACTTCACGCGGCTGGGGGCTGCTGG

AGAGAGCCACAGCGGGAAGGGTTTCCTAGAGGCTGCAGGACAGTGCTGGATGGATT

TTCAATGCTCACCTGGGTGTGAGCGTGCGGCAGGGCCGCGTGAGGGTCAGCGATCT

GCTACTCTGGACTCAGCCATCTCTAGGCCCCTCTCACTCAGGTGCTCCATGGTTCTG

GGAGCTGAGAAATCTCAAACCAGCAAAAAAGTGGAATTGATGTTGATGCTACAGGA

TAGTGCACAGATGCCATCTGGTTGCAGCATTTTGGTGGAAGGGCAGTGCCCAGCTA

GGAGAGTGAGGAGGGGCAGGCATTTCTGGCTTGAGGAGATGGGGTCTTAATGCTCG

TGTGAGAGGCAGAGTGGGTGGAGTGGAGCTGGCTGGATCCTTGCTTTGGCCTCCTG

GATTTCTCTCTATCTCCATTTTGAAACCACTCTGTGTTTGGAAGAACTTTTGAGTATT

CAGAGCTGCCCACTGGCAGAACAGTCTTCCTTGGGCAGGAGTGAGCTCCTTGTCCCC

AGAAGGCTGGGTCTGGCTGGCCCCTGGCAGGGACACTGATGAGGGTGCTTGAGTTG

ATCCTGTCTAGTCCCTTTCTGTGTTTTCAAAGCCCATTCTAAAGCAGATTCCCATTTC

CGTCTTTGACTCTAAGGCCCAAGGGGGCAAGCTGGTCTGCCGGGCCCACAACGCTT

TTGGGGGTGAGGGTGTCTACGCCATTGCCAGGTGCTGCCTGCTACCCCAGGCCAACT

GCAGCGTCCACACAGCTCCACCAGCTGAGGCCAGCATGGGGACCCGTGTCCACTGC

CACCAACAGGGCCACGTCCTCACAGGTAGGAGGCTGGGCTTGCCCTGGGGTGAGGA

GGGGTCTCTTTCTCCTTATGCACCCACTGCCCGCGAGGCTTGGTCCTCACAAGTGTG

ATCCATGAGACTCAAGCCTGACTTGCAGTTCCATACTCTGGTTCTGCCACTTCCATG

CCCTTTGAGCCTGGGCAGGTGACCTTACTTCTCCTCATCTCAGCTTCCTCCTCCATAA

GAGGGAAAAAGGTATTACCTGCCTCATTGTGTTGCAAGGAGATGGGCAGCATCTAG

GGCACTGGCCTGGAGTATCGCAGGTGCTTTGCCTAAGGTGGTGCAGTCCAGGAGAG

GCAGCTCCAGAGAGAGGCCCCCGGCTGGGGCTGAAAGGAGGGCAGACCTCGGTTT

GAATTTCACCCTGCCGCTCTATAGCTGTGTGACTTGGGCAAATTACTTAACATCTCT

GTATGAGGAAATGATGAGTGCTAAGCACTTAGCTTAGTGCCGGGACAATATAAATT

CTAGCTATCGTTACTATTGTTTTCATCACCCGTTGCTTTAAAATCCAGCCTCTGGTAT

AGGCAACTATTGACGGGCTACCCTGTGTCGAAAACATGCCCAGGCAGGTAGCAGGA
```

-continued

```
AGTCACAGATGGGGACCTCTTGGGGCATCAAGGGATGGTGCCCTGAGGCTGAGCTG

TTCTGGTTGGGTGGAGCATGAGAGGTCTGGGAAGACAGTGGGACTCCAGCCTGGAA

TAAGAGGCTCAGAGTTGATTCTCGTCTGAGCACGTCCAGGGGAACCACTGAGGGTT

TGGGAACAGGAGAGTGAGGGTGAGAACCTGGTTCTGGGCACAGCAGGCTGGCATG

TAGGATGGATGTTCAGGAAAGATGAGCATAGTCAGGTGGCTGGTGCCCTTGTCCAG

GGGAGAGGCTCCGTCAGGTTCAGGGGTCCTGGCTTGGAGGGAAGTCCGCCATGCTC

TAATCACGCTCCCCTTTGGAAGTGCTCAGCCGATGAGCTCACAGGCACATGTCAGTT

TGAAGTCATGGAATCTGACTCCATGAAGCGCACCTCAAAGAGCACCATTTTGCAGC

TAAGGGAACTGCAGGCTGGACATGCTGAGTGGCTGCCCCGAGCCCTTGCAGCTAGG

ACATAGAGAATGCTAGTAACCACAACCCTACCATGTTCAGAGCACATGCCAGGCTC

CATGCTGGGGCTTCGCACGTGTCATCTTCACAGTGTCCCTGTGAGTAGGTGTGGTTT

CTCTTTCCATCTTACAAATGAGTAAACAGAGCCTCAGTGTAGCTAAGTAACCACTAT

TTTAGGTTTCTTAGCCAATGGGTGTGTCTGACTCCTAAGCCCATGGAGGGCATTCTG

AGGTGGTTCAGACAGACCCCGGCTTACCCTTGAACTTCTGCCTGCTGGCTGCATAGG

GAGGGGCTGGGGGGAGTTTGAGCATCTCAGGCCATAGAGCCCCTGCCTCACTGTCT

CCATCTCTGGGTGGAAAGATGGTGTTTTCCCTGAGAAACTAAGGCTCAGAGAGGTT

GAATGGCTCTCCCAAGGTCACACAGCTGGTCAGCTGCAGAGTTGAGAACACAGGAG

TCCTGGTGCTCAGGCCAGCATCTCTTTTTTTCTTTGAGTTGTTTCTAGGTTTCCTAGC

TCTTGCCTCAGACCTTAAAGAGAGAGGGTCTGATGGGGATGGGCACTGGAGACGGA

GCATCCCAGCATTTCACATCTGAGCTGGCTTTCCTCTGCCCCAGGCTGCAGCTCCCA

CTGGGAGGTGGAGGACCTTGGCACCCACAAGCCGCCTGTGCTGAGGCCACGAGGTC

AGCCCAACCAGTGCGTGGGCCACAGGGAGGCCAGCATCCACGCTTCCTGCTGCCAT

GCCCCAGGTCTGGAATGCAAAGTCAAGGAGCATGGAATCCCGGCCCCTCAGGAGCA

GGTGAAGAGGCCCGTGAGGCCGGGTGGGTGGGGTGCTGCGTGTCTCTCCTGCACAG

CTTTTCTGTGTCAGTTTGTGCCACCACCATACCGCCATGCATCAGGGTGGCGGTTTG

CCAGGTAGATGCTGTGGGCAGCTTCCGCCATTGTGTGGACAGCATGTATATGTGTCT

CTGTGTGGCTGGGTCTGTTTTTGCTTTTGTCCAGATCAGTAAGGTTTGCTACCTGGGT

ACCCCACTCCACTTGGAGTAGAATGTGCATAAATATGGCATAAAGAAATGCAATAT

GCATGCATTTATTGATTGATCTATTTTTTTCTGAGATGGGGTCTTGCTGTGTTGCCCA

GGCTGGTCTCAAATTCCTGGGCTCAAGCAATCCTCTGGTCTCAGCCTCCCCAAGTGT

TGGGATTATAGGCATGAGCCGCTGCACCTGGCCTCTCTGATCTATTTAACAAACCTG

CTGGGAGGGTCTCAGGGTCAGGAGCAGCACTGGGCTCTGAGGACACAGAGCTCACT

CAGCCGTGACCCAGAGGGGGTGCCTGAGCTGCATGCTGAAGGTTGTTAGCATGACC

AGCAAGGCAAGAAAAGGCCCTGCCGAGATTAGCAAGGCATGTGCCAAGCCCTGGA

ATGTGACAGCCGGGCCTTCTAGAAACCTGAGTGTATAACTCTCCTTAAAAGCCAGT

AGGAGCTCCTCAAAAGGCAGCCCTAAGGAGTCCACTCTTAAATGAACTCAGAGTCA

GTTTTAAAATGCAAGTCTGTGTTGATTCTGGTCTGGATGGTGCATTCCTCGAGAGCA

AAAGACAGTCTTGGTCTTGGATCCACTTGCCCTGGGTACACTGAGGGCTGCTAGGTT

CCAGGTGCTCTTCCTGGCACTGGGGAGGGATACAGGCCCAAGAGACATGCTGTTCT

CCCTCCTGGAGCATCTATTTTAGTGGAGGAAGACAGAAAACAAACCATTAATATAG
```

-continued

```
AGTACTGAAAAGATGCGATGGAGAAAACTATAGCAAGGAAGGGAATGGGGTGGGA

GAGAGGTCAGGAGAGGTCTCGCTGACAAGGTGGACGAAACAGGCCATGAGGCAGA

GAACATGTTCCAGGCAAAGCAAAGGCCCCCAGGTGGGGATGTGCAGGGAGTACCA

GGAAACCAGAGAGGTGGGAATAGTTATGAGATGGGGGGTGCCTCAGAGGGGACAG

GGCCAAGTCAGGTGAGACCTGAGGGTCACAGTCAGCAGTGAGCTGGGGCCATGCA

GGGGTCTGGCCTCAGAGGAGTGTGGTCTGGCCTGGATCTGAACCTCTCACTGTGGCC

TAGCTGCTGAGCTGAGAAGAGATGACAAGGACCTTGGGCAGAAGCAGGGAGACTG

GAGGGAGGCGGTGGAGGGTCCAGGCGTTGGGGCGGGGCTCAGGCTGGAGTCTGAA

GGGAGCCTGCAGGCCTGGTGGGTGGATGTGGGTGGGAGAGGGGGAGGATGGCACC

AAGGCTCGGGCCCCTGGACAGATGGAGTTGCCATTAAGTGGGATGGGGCAGGCTAT

GGGGCCATCAGTTTCAGAGGGATGAGTTTGGCACTGGCATGGTAGGCATCTGTCTA

TCTCCACGGCCCTCAAACCAGGCATGAAGCAGGAGCTCACGTGTTTGGTCAGCCAT

GGTGCAGAACCGCCTGGGTGGGAGGTGCGGGGTGGGAGATACACGGTTGTGTCCCA

AATGGGCTCTGAGCCAGCGAGGGCCGTCTGCACTTTGGCCTCACAGAAGGATGTCG

GAGGGAGAAATGAAGTGTGGGTGGGGGTCCCGGGCCACGCTAGACATGTGCTTTCT

TTTCCTCGGGCTCTGGCAGGTGACCGTGGCCTGCGAGGAGGGCTGGACCCTGACTG

GCTGCAGTGCCCTCCCTGGGACCTCCCACGTCCTGGGGGCCTACGCCGTAGACAAC

ACGTGTGTAGTCAGGAGCCGGGACGTCAGCACTACAGGCAGCACCAGCGAAGGGG

CCGTGACAGCCGTTGCCATCTGCTGCCGGAGCCGGCACCTGGCGCAGGCCTCCCAG

GAGCTCCAGTGACAGCCCCATCCCAGGATGGGTGTCTGGGGAGGGTCAAGGGCTGG

GGCTGAGCTTTAAAATGGTTCCGACTTGTCCCTCTCTCAGCCCTCCATGGCCTGGCA

CGAGGGGATGGGGATGCTTCCGCCTTTCCGGGGCTGCTGGCCTGGCCCTTGAGTGG

GGCAGCCTCCTTGCCTGGAACTCACTCACTCTGGGTGCCTCCTCCCCAGGTGGAGGT

GCCAGGAAGCTCCCTCCCTCACTGTGGGGCATTTCACCATTCAAACAGGTCGAGCTG

TGCTCGGGTGCTGCCAGCTGCTCCCAATGTGCCGATGTCCGTGGGCAGAATGACTTT

TATTGAGCTCTTGTTCCGTGCCAGGCATTCAATCCTCAGGTCTCCACCAAGGAGGCA

GGATTCTTCCCATGGATAGGGGAGGGGGCGGTAGGGGCTGCAGGGACAAACATCGT

TGGGGGGTGAGTGTGAAAGGTGCTGATGGCCCTCATCTCCAGCTAACTGTGGAGAA

GCCCCTGGGGGCTCCCTGATTAATGGAGGCTTAGCTTTCTGGATGGCATCTAGCCAG

AGGCTGGAGACAGGTGCGCCCCTGGTGGTCACAGGCTGTGCCTTGGTTTCCTGAGC

CACCTTTACTCTGCTCTATGCCAGGCTGTGCTAGCAACACCCAAAGGTGGCCTGCGG

GGAGCCATCACCTAGGACTGACTCGGCAGTGTGCAGTGGTGCATGCACTGTCTCAG

CCAACCCGCTCCACTACCCGGCAGGGTACACATTCGCACCCCTACTTCACAGAGGA

AGAAACCTGGAACCAGAGGGGGCGTGCCTGCCAAGCTCACACAGCAGGAACTGAG

CCAGAAACGCAGATTGGGCTGGCTCTGAAGCCAAGCCTCTTCTTACTTCACCCGGCT

GGGCTCCTCATTTTTACGGGTAACAGTGAGGCTGGGAAGGGGAACACAGACCAGGA

AGCTCGGTGAGTGATGGCAGAACGATGCCTGCAGGCATGGAACTTTTTCCGTTATC

ACCCAGGCCTGATTCACTGGCCTGGCGGAGATGCTTCTAAGGCATGGTCGGGGGAG

AGGGCCAACAACTGTCCCTCCTTGAGCACCAGCCCCACCCAAGCAAGCAGACATTT

ATCTTTTGGGTCTGTCCTCTCTGTTGCCTTTTTACAGCCAACTTTTCTAGACCTGTTTT

GCTTTTGTAACTTGAAGATATTTATTCTGGGTTTTGTAGCATTTTTATTAATATGGTG
```

-continued

ACTTTTTAAAATAAAAACAAACAAACGTTGTCCTAAC

Human PCSK9 Amino Acid Sequence (NP_777596.2):

(SEQ ID NO: 105)

MGTVSSRRSWWPLPLLLLLLLLLGPAGARAQEDEDGDYEELVLALRSEEDGLAEAPEH

GTTATFHRCAKDPWRLPGTYVVVLKEETHLSQSERTARRLQAQAARRGYLTKILHVFH

GLLPGFLVKMSGDLLELALKLPHVDYIEEDSSVFAQSIPWNLERITPPRYRADEYQPPDG

GSLVEVYLLDTSIQSDHREIEGRVMVTDFENVPEEDGTRFHRQASKCDSHGTHLAGVVS

GRDAGVAKGASMRSLRVLNCQGKGTVSGTLIGLEFIRKSQLVQPVGPLVVLLPLAGGY

SRVLNAACQRLARAGVVLVTAAGNFRDDACLYSPASAPEVITVGATNAQDQPVTLGTL

GTNFGRCVDLFAPGEDIIGASSDCSTCFVSQSGTSQAAAHVAGIAAMMLSAEPELTLAE

LRQRLIHFSAKDVINEAWFPEDQRVLTPNLVAALPPSTHGAGWQLFCRTVWSAHSGPT

RMATAVARCAPDEELLSCSSFSRSGKRRGERMEAQGGKLVCRAHNAFGGEGVYAIAR

CCLLPQANCSVHTAPPAEASMGTRVHCHQQGHVLTGCSSHWEVEDLGTHKPPVLRPR

GQPNQCVGHREASIHASCCHAPGLECKVKEHGIPAPQEQVTVACEEGWTLTGCSALPG

TSHVLGAYAVDNTCVVRSRDVSTTGSTSEGAVTAVAICCRSRHLAQASQELQ

Apolipoprotein C3 (APOC3)

In some embodiments, the target gene for modification using the compositions and methods disclosed herein is gene encoding APOC3. The LDL-R mediated cholesterol clearance pathway involves multiple players. Non-limiting examples of protein factors involved in this pathway include: Apolipoprotein C3 (APOC3), LDL receptor (LDL-R), and Increased Degradation of LDL Receptor Protein (IDOL). These protein factors and their respective function are described in the art. Further, loss-of-function variants of these factors have been identified and characterized, and are determined to have cardio protective functions. See, e.g., Jorgensen et al., N Engl J Med 2014; 371:32-41 Jul. 3, 2014; Scholtzl et al, Hum. Mol. Genet. (1999) 8 (11): 2025-2030; De Castro-Oros et al., BMC Medical Genomics, 20147:17; and Gu et al., J Lipid Res. 2013, 54(12): 3345-57, each of which are incorporated herein by reference. Thus, some aspects of the present disclosure provide the generation of loss-of-function variants of APOC3 {e.g., A43T and R19X), LDL-R, and IDOL {e.g., R266X) using the methods and compositions disclosed herein.

"Apolipoprotein C-III (APOC3)" is a protein that in humans is encoded by the APOC3 gene. APOC3 is a component of very low density lipoproteins (VLDL). APOC3 inhibits lipoprotein lipase and hepatic lipase. It is also thought to inhibit hepatic uptake of triglyceride-rich particles. An increase in APOC3 levels induces the development of hypertriglyceridemia. Recent evidence suggests an intracellular role for APOC3 in promoting the assembly and secretion of triglyceride-rich VLDL particles from hepatic cells under lipid-rich conditions. However, two naturally occurring point mutations in human apoC3 coding sequence, A23T and K58E have been shown to abolish the intracellular assembly and secretion of triglyceride-rich VLDL particles from hepatic cells.

Loss-of-function mutations that may be made in APOC3 gene using the methods and compositions described herein are also provided. The strategies to generate loss-of-function mutation are similar to that used for PCSK9 (e.g., premature stop codons, destabilizing mutations, altering splicing, etc.).

The protein sequence of human APOC3 can be found, for example, at Deposit No. NP_000031.1, which reference is incorporated herein in its entirety. Human nucleic acid sequences can be found at e.g., GenBank Accession Nos.: NG_008949.1, which sequence is incorporated herein in its entirety. Mouse, rat and monkey APOC3 nucleic acid sequences have been deposited; see, e.g., Ensembl accession number ENSMUSG00000032081, ENSRNOG00000047503, and ENSMFAG00000001837 respectively, each of which sequences is incorporated herein in its entirety.

NG_008949.1:5000-8165 *Homo sapiens* apolipoprotein C3 (APOC3), RefSeqGene on chromosome 11:

(SEQ ID NO: 106)

CTGCTCAGTTCATCCCTAGAGGCAGCTGCTCCAGGTAATGCCCTCTGGGGAGGGGA

AAGAGGAGGGGAGGAGGATGAAGAGGGGCAAGAGGAGCTCCCTGCCCAGCCCAGC

CAGCAAGCCTGGAGAAGCACTTGCTAGAGCTAAGGAAGCCTCGGAGCTGGACGGG

TGCCCCCCACCCCTCATCATAACCTGAAGAACATGGAGGCCCGGGAGGGGTGTCAC

TTGCCCAAAGCTACACAGGGGGTGGGGCTGGAAGTGGCTCCAAGTGCAGGTTCCCC

CCTCATTCTTCAGGCTTAGGGCTGGAGGAAGCCTTAGACAGCCCAGTCCTACCCCAG

ACAGGGAAACTGAGGCCTGGAGAGGGCCAGAAATCACCCAAAGACACACAGCATG

```
TTGGCTGGACTGGACGGAGATCAGTCCAGACCGCAGGTGCCTTGATGTTCAGTCTG

GTGGGTTTTCTGCTCCATCCCACCCACCTCCCTTTGGGCCTCGATCCCTCGCCCCTCA

CCAGTCCCCCTTCTGAGAGCCCGTATTAGCAGGGAGCCGGCCCCTACTCCTTCTGGC

AGACCCAGCTAAGGTTCTACCTTAGGGGCCACGCCACCTCCCCAGGGAGGGGTCCA

GAGGCATGGGGACCTGGGGTGCCCCTCACAGGACACTTCCTTGCAGGAACAGAGGT

GCCATGCAGCCCCGGGTACTCCTTGTTGTTGCCCTCCTGGCGCTCCTGGCCTCTGCC

CGTAAGCACTTGGTGGGACTGGGCTGGGGGCAGGGTGGAGGCAACTTGGGGATCCC

AGTCCCAATGGGTGGTCAAGCAGGAGCCCAGGGCTCGTCCAGAGGCCGATCCACCC

CACTCAGCCCTGCTCTTTCCTCAGGAGCTTCAGAGGCCGAGGATGCCTCCCTTCTCA

GCTTCATGCAGGGTTACATGAAGCACGCCACCAAGACCGCCAAGGATGCACTGAGC

AGCGTGCAGGAGTCCCAGGTGGCCCAGCAGGCCAGGTACACCCGCTGGCCTCCCTC

CCCATCCCCCCTGCCAGCTGCCTCCATTCCCACCCGCCCCTGCCCTGGTGAGATCCC

AACAATGGAATGGAGGTGCTCCAGCCTCCCCTGGGCCTGTGCCTCTTCAGCCTCCTC

TTTCCTCACAGGGCCTTTGTCAGGCTGCTGCGGGAGAGATGACAGAGTTGAGACTG

CATTCCTCCCAGGTCCCTCCTTTCTCCCCGGAGCAGTCCTAGGGCGTGCCGTTTTAG

CCCTCATTTCCATTTTCCTTTCCTTTCCCTTTCTTTCTCTTTCTATTTCTTTCTTTCTTTC

TTTCTTTCTTTCTTTCTTTCTTTCTTTCTTTCTTTCTTTCTTTCTTTCTTTCCTTTCTTTCT

TTCCTTTCTTTCTTTCCTTTCTTTCTTTCTTTCCTTTCTTTCTCTTTCTTTCTTTCTTTCC

TTTTTCTTTCTTTCCCTCTCTTCCTTTCTCTCTTTCTTTCTTCTTCTTTTTTTTTTTTAATGG

AGTCTCCCTCTGTCACCTAGGCTGGAGTGCAGTGGTGCCATCTCGGCTCACTGCAAC

CTCCGTCTCCCGGGTTCAACCCATTCTCCTGCCTCAGCCTCCCAAGTAGCTGGGATT

ACAGGCACGCGCCACCACACCCAGCTAATTTTTGTATTTTTAGCAGAGATGGGGTTT

CACCATGTTGGCCAGGTTGGTCTTGAATTCCTGACCTCAGGGGATCCTCCTGCCTCG

GCCTCCCAAAGTGCTGGGATTACAGGCATGAGCCACTGCGCCTGGCCCCATTTTCCT

TTTCTGAAGGTCTGGCTAGAGCAGTGGTCCTCAGCCTTTTTGGCACCAGGGACCAGT

TTTGTGGTGGACAATTTTTCCATGGGCCAGCGGGGATGGTTTTGGGATGAAGCTGTT

CCACCTCAGATCATCAGGCATTAGATTCTCATAAGGAGCCCTCCACCTAGATCCCTG

GCATGTGCAGTTCACAATAGGGTTCACACTCCTATGAGAATGTAAGGCCACTTGATC

TGACAGGAGGCGGAGCTCAGGCGGTATTGCTCACTCACCCACCACTCACTTCGTGCT

GTGCAGCCCGGCTCCTAACAGTCCATGGACCAGTACCTATCTATGACTTGGGGGTTG

GGGACCCCTGGGCTAGGGGTTTGCCTTGGGAGGCCCCACCTGACCCAATTCAAGCC

CGTGAGTGCTTCTGCTTTGTTCTAAGACCTGGGGCCAGTGTGAGCAGAAGTGTGTCC

TTCCTCTCCCATCCTGCCCCTGCCCATCAGTACTCTCCTCTCCCCTACTCCCTTCTCC

ACCTCACCCTGACTGGCATTAGCTGGCATAGCAGAGGTGTTCATAAACATTCTTAGT

CCCCAGAACCGGCTTTGGGGTAGGTGTTATTTTCTCACTTTGCAGATGAGAAAATTG

AGGCTCAGAGCGATTAGGTGACCTGCCCCAGATCACACAACTAATCAATCCTCCAA

TGACTTTCCAAATGAGAGGCTGCCTCCCTCTGTCCTACCCTGCTCAGAGCCACCAGG

TTGTGCAACTCCAGGCGGTGCTGTTTGCACAGAAAACAATGACAGCCTTGACCTTTC

ACATCTCCCCACCCTGTCACTTTGTGCCTCAGGCCCAGGGGCATAAACATCTGAGGT

GACCTGGAGATGGCAGGGTTTGACTTGTGCTGGGGTTCCTGCAAGGATATCTCTTCT
```

141 142

-continued

```
CCCAGGGTGGCAGCTGTGGGGGATTCCTGCCTGAGGTCTCAGGGCTGTCGTCCAGT

GAAGTTGAGAGGGTGGTGTGGTCCTGACTGGTGTCGTCCAGTGGGGACATGGGTGT

GGGTCCCATGGTTGCCTACAGAGGAGTTCTCATGCCCTGCTCTGTTGCTTCCCCTGA

CTGATTTAGGGGCTGGGTGACCGATGGCTTCAGTTCCCTGAAAGACTACTGGAGCA

CCGTTAAGGACAAGTTCTCTGAGTTCTGGGATTTGGACCCTGAGGTCAGACCAACTT

CAGCCGTGGCTGCCTGAGACCTCAATACCCCAAGTCCACCTGCCTATCCATCCTGCG

AGCTCCTTGGGTCCTGCAATCTCCAGGGCTGCCCCTGTAGGTTGCTTAAAAGGGACA

GTATTCTCAGTGCTCTCCTACCCCACCTCATGCCTGGCCCCCCTCCAGGCATGCTGG

CCTCCCAATAAAGCTGGACAAGAAGCTGCTATGA

NP_000031.1 Human apolipoprotein C-III precursor:
                                          (SEQ ID NO: 107)
MQPRVLLVVALLALLASARASEAEDASLLSFMQGYMKHATKTAKDALSSVQESQVAQ

QARGWVTDGFSSLKDYWSTVKDKFSEFWDLDPEVRPTSAVAA
```

Angiopoietin-Like 3 (ANGPTL3)

In some embodiments, the target gene for modification using the compositions and methods disclosed herein is gene encoding ANGPTL3. ANGPTL3 has been associated with diseases and disorders such as, but not limited to, Arteriosclerosis, Atherosclerosis, Cardiovascular Diseases, Coronary heart disease, Diabetes, Diabetes Mellitus, Non-Insulin-Dependent Diabetes Mellitus, Fatty Liver, Hyperinsulinism, Hyperlipidemia, Hypertriglyceridemia, Hypobetalipoproteinemias, Inflammation, Insulin Resistance, Metabolic Diseases, Obesity, Malignant neoplasm of mouth, Lipid Metabolism Disorders, Lip and Oral Cavity Carcinoma, Dyslipidemias, Metabolic Syndrome X, Hypotriglyceridemia, Opitz trigonocephaly syndrome, Ischemic stroke, Hypertriglyceridemia result, Hypobetalipoproteinemia Familial 2, Familial hypobetalipoproteinemia, and Ischemic Cerebrovascular Accident. Editing the ANGPTL3 gene using any of the methods described herein may be used to treat, prevent and/or mitigate the symptoms of the diseases and disorders described herein.

The ANGPTL3 gene encodes the Angiopoietin-Like 3 protein, which is a determinant factor of high-density lipoprotein (HDL) level in human. It positively correlates with plasma triglyceride and HDL cholesterol. The activity of ANGPTL3 is expressed predominantly in the liver. ANGPTL3 is associated with Dyslipidemias. Dyslipidemias is a genetic disease characterized by elevated level of lipids in the blood that contributes to the development of clogged arteries (atherosclerosis). These lipids include plasma cholesterol, triglycerides, or high-density lipoprotein. Dyslipidemia increases the risk of heart attacks, stroke, or other circulatory concerns. Current management includes lifestyle changes such as exercise and dietary modifications as well as use of lipid-lowering drugs such as statins. Non-statin lipid-lowering drugs include bile acid sequestrants, cholesterol absorption inhibitors, drugs for homozygous familial hypercholesteremia, fibrates, nicotinic acid, omega-3 fatty acids and/or combination products. Treatment options usually depend on the specific lipid abnormality, although different lipid abnormalities often coexist. Treatment of children is more challenging as dietary changes may be difficult to implement and lipid-lowering therapies have not been proven effective.

ANGPTL3 is also known to cause hypobetalipoproteinemia. Hypobetalipoproteinemia is an inherited disease (auto-somal recessive) that affects between 1 in 1000 and 1 in 3000 people worldwide. Common symptoms of hypobetalipoproteinemia include plasma levels of LDL cholesterol or apolipoprotein B below the 5th percentile which impairs the body's ability to absorb and transport fats and can lead to retinal degeneration, neuropathy, coagulopathy, or abnormal buildup of fats in the liver called hepatic steatosis. In severely affected patients, hepatic steatosis may progress to chronic liver disease (cirrhosis), Current treatment of hypobetalipoproteinemia includes severe restriction of long-chain fatty acids to 15 grams per day to improve fat absorption. In infants with hypobetalipoproteinemia, brief supplementation with medium-chain triglycerides may be effective but amount must be closely monitored to avoid liver toxicity. Another option for treating hypobetalipoproteinemia is administration high doses of vitamin E to prevent neurologic complications. Alternatively, vitamin A (10,000-25,000 IU/d) supplementation may be effective if an elevated prothrombin time suggests vitamin K depletion.

In one example, the target tissue for the compositions and methods described herein is liver tissue. In one example, the gene is Angiopoietin-Like 3 (ANGPTL3) which may also be referred to as Angiopoietin 5, ANGPT5, ANG-5, Angiopoietin-Like Protein 3, Angiopoietin-5, FHBL2, and ANL3. ANGPTL3 has a cytogenetic location of 1p31.3 and the genomic coordinate are on Chromosome 1 on the forward strand at position 62,597,487-62,606,159.

Loss-of-function mutations that may be made in ANGPTL3 gene using the methods and compositions described herein are also provided. The strategies to generate loss-of-function mutation are similar to that used for PCSK9 (e.g., premature stop codons, destabilizing mutations, altering splicing, etc.).

The nucleotide sequence of human ANGPTL3 is provided, for example, in NG_028169.1, which is incorporated herein in its entirety. The protein sequence of human ANGPTL3 is provided, for example, AAD34156.1, which is incorporated herein in its entirety.

Mouse, rat and monkey ANGPTL3 nucleic acid sequences have been deposited; see, e.g., Ensembl accession number ENSMUSG00000028553, ENSRNOG00000008638, and ENSMFAG00000007083 respectively, each of which sequences are incorporated herein its entirety.

The polypeptide and coding nucleic acid sequences of PCSK9, APOC3 and ANGPTL3 and of other members of the family of human origin and those of a number of animals are publically available, e.g., from the NCBI website or ENSEMBL website. Examples include, but are not limited to the following sequences, each of which sequences are incorporated herein in their entireties;

NG_028169.1 Human angiopoietin like 3 (ANGPTL3), RefSeqGene
on chromosome 1:

(SEQ ID NO: 108)

AATGACAAACTGAAAAAATCTATTGTTTGTTATATATATAACAAAGAATTAGTATCC

ACAATATGTAAATAATTCCTAAAATTAGTCAGAAAGAGACAAACTTAAAAAGAGGG

TAACAAGGAGGGGAGCAAATTATGTACATAACCAGATGATTCGCAAAGACGGCAA

CAGAGATGGCCAGCAAAACAAACTAGATATATACTTGTCTATTAGATTTATCAACA

TTTTTTGCCTTTTTCATTAAAAGCATTTGTAAAAGGATATAGGAAAAGAGGAACTCT

CATATACTCCTGGCAGGGATGTAAATTGGTACAACCCTTTTGAAGGACAATCTGAC

AAAAGCAATCGTAAGTTACAAGTCAACATCTATGAATGTATATGAAAATATTTATA

TACATACATCACCACCATAAAAGCATTTTCTATACATACTGTTTATAATTAGAAAAT

TGGAAACAAATGATTAAAAGGGGGCTGATTAAATTAAGGTTCATCTATATAACAGG

ATTATGCAGCTATTAAAAAGGACGTGGTAACTCTATAGACATTCATAGGAAAATAA

ATTTTAAAATACTAAGATCCTGAATGATATATATATCATGAGCTATTATACATAACA

AGATCCCACTTGTGTTATAAAAAATTATGTTTAGTCATTCAAAGGGTCTGGTATGAT

AGACCCAAAATGTTAATAGAGTCGAGATTTTTATTTTTTATAGGTTTTTGAAATACC

TGAATTTTCACAATAAGTACTTTGCACATTAAAAATCTTAGCTGGGCATGGTGGCTC

ACGCTTGTAATCCCAGCACTCTGGGAGGCCAAGGTAGGCAGATCACCTGAGGTCAG

GAGTTCGAGACCAGTCTGGCCAACATGGTGAAACCCCGTCTCTACTAAAAATACAA

AAATTAGCCAGGCTTGGTTGGGGGTGCCTGTAATTCCAGATACTCGGGAAGCTGAG

ACAGGAGAATCGCTTGAACCCAGGAGGGGGAAGTTGCAGTGAGCTGAGATCACGA

CGCTGCACTCCAGCCTGGGCAACAAAGAGCAAAACTCCGTCTCAAAAATAAATAAA

GAAAAAATCTTTACATGTCCAAAGATACGGCTGTTCAACTAAAAAATATATATGTA

TAAAACTTAACATGTTAATAGTGAACACACAAAACAGTAAGATAGATAAAATTATT

CCTTCAAAGCTCACTTAACCTCTGGATCTACACTGTCCAAAAAGACGGTCTAATGAG

ACAATTGAGCACTTGATAGGTGAGTGGTTCTAACTGAGATATGTTCTCAGTATAAAA

CATACAATAGGATCTTCCTATACAACATTAATTAAAAAAACAAACTATTGTAGTTAAA

AAGGAAAAAATTAGAGATACTATGTAAAAAAGAGCCAAAATACCTTGTATTTTATT

TGAAAGACATATCTCCATAAGATTACACAACCTCGTGTAGGATAAAGGACTTTGCTT

TGCTTGGAATTTAAACAATTTAGGCTCTTAAATGTCCTAAAATTCTCTGTAGCTAAG

AAATTTTTATATTGGTTCCTAGGAACTAGGAATCCTTAAATTAGGCCCTACATTTGC

TTACAAGTTTATTTTCCTTGGCATAAAATTTTTTAGTTTTTACATTACTGGTTATATTT

GATCAGGGTTCTATTTAAATAGGCACAAGTTCAAGCAAAGATCAGATTCTGCTTTTA

GCAGTGTGTACTCAGACAGGAAGTATTAAAAGGCAGGCAGAAAATCCTTTATAAAA

TTACTACTTTCAATGCATTTTCCCACGTTGAAATGCTTCTGCAGTTTATAATTAGGCA

AATTACTTTAATTATAATCAATAATGCTGTTCAAATTACTATAAGAATTATACAGAT

ATTTATACCAAGAGACAATATACTAGAAACCAAGACTACGTGACCATTACCTCTAC

TCTGTCAGTGTTATTTGTGAGAAATTGCACAAATTTTGCAAAAAGTGTTAGTATCCT

ACTACAGTAGGATATAATATAGAAGGAAATAATTTCATAAAGCCTGTCTTTGGTACT

AGTGCTCAGTTACTTTCATTAACTAAAAAAGGGGCTACTCTTCAAATTCCCTTCTCT

-continued

```
AAAAAGAATGTACTATATCAAAAGGGGGTAAACACTACTACGTATACATTCTGCAC

TTAGAAATCCCTATATGTTGATTTTATCATTCTCTTATTCAATAAATATTGTTTCTAC

AATGTGTAAGGCATTACTGTACTAAAGCATTATAAGGAATATAAGTTAAAAACACA

TACAAATCTTGCCAATCAACAGCTTATAGTGTAATAGGGGAGAGAAGCTGGCCCAT

CTATATTCTCCCTCAACTAGCAAGTGGATGAAATATCAGGGTCAATAGTTATAAGCC

ACAAAAGCTGACAGCTTAATTAAGAGAAGTTTTGAAATATGTATTTCATGACCAAT

AATTACAACTGTAACTTTTCTATTTAAAGAAGGAGAAAATTTGAATTTCTTCTCTAG

CTCAACATACACTTCTATAATTCCATTACATGAACCAGAGTAAAGGGTAAGATGGA

AATGAAGAATATTTTCTTACCCTTTTGTGGTTCTATATTGGACACTTAAAAATCATA

CACAACCTAATCAAAGATGTAATTCTTTAAAAAGGTACGAGACCAAAATTCAGAA

AATCTAGACTATAACAAAATTTCTCAATTTACATTATCTTAATATGCAATTAATTTTC

ACCAGTAAAATACTATAGTATGGGTACAAATGCATTGATTAGTTCTAATTACAAAA

ATGGCTAATATATAATACTGTGTAGTGTTTATGATACATCAGATAATGTTCTAAGTG

CTCTGAAAATATAAACTTTTAATCTTTTATACGACCCTATAAAATAGGTGTTATTCTC

ACTGGAGAGATGAGAAAACAGGGGTTCAGAGATGTGAAGTAATTTGACCAAAGGT

CACAAAGCTGAAGAATATGAAATCCGGGATTCTGATTCAGGCAGTCTTATTCCAGA

ATCATGCTCTTAACCACTATGGAATACTGCCTCTACTGTAACTATTATACCCAAAAC

CCTTAATCCTAAGTCATCAAAAGGAAGAGCCTCTATTTTACACAATGAAGAGGCAT

TTCTAAGAATAGAAATTTAGGGACGAGCACAGTGGCTTACTCCTTTAATATCAGCAC

TTTGAGAGGCTGATATGGGAGGTTCACTTGAAGTCAGGAGTTCAAGGTCAGCTTGG

GCAACATAGTGAAACACAGTCTCTACAAAATATTTAAAAATTAGCTGGGTGTGGTG

GCATGCATCTATAGTCTCAGCTACTTGGGAGACAGAGGGAGGAGGCTTGCTCGAGC

CCAGGAGTTCGTGGCTATAGTGAGCTATGATCATGCCACTGCACTCCAGCCTGGAC

AACAGAGCAAGACCCTGTCTCTAAAAAAGAAAAGAAATTTGGAAATGGTTTATTTT

GTATTAACAATTTATAATTTACACTGAAATTTATTATGATAAAACTTTTCCCTGTGTT

AAAAAGCTATTAACTTTATGAAAAATTTCTTTTAGGTAAGGTTGATTATATATACCC

ACACACATACACAGGTTAAAAGTTAGTTTCATGTGACATAATAACTAGCATTTTGAG

CACTACCTGTTTGCCCAGCACTGTTCTAAGTGCTCTACATGTATTATTGTTAAATTAT

CATAACACTATGAATTATGTACTATAATTACCCCAGCTTTACAGATGAGGAGACTAA

TCCATGGGGAGGTTAAGTAACTTGTCCAAGGCCAGACAGCTAGAGCCGGCTTTTGG

ACCCACACCACAGTCTGACTCCAGCACCCATATTCTTAACAATTTCACCATATTAAT

ATGTCAAGATTAAGCAGTTTTAAAGGATGCTATTTTCTCACAAATTTCTTAATATGA

ACACTCAATAAGAATAATCACTAATATAAGCATTTAGTATTTTTTTAACACTAAGTT

GGAAGCATAGTGGAACATTTATTTTTAGAAATATTATTAATTGGCTGGGCTCACGCT

TGTAATCGGCTGGGCTCATGCCTGTAAATTTTGGGAGGCCAAGGTAAAAGAATTGC

TTGAGCCCAGTATTTCCAGACCAGCATGGGCAATACATTAAGACATCATCTTTAAAA

AAAAAATGTTATTAATCTCCTCTTTTTGTTAAATGTATATTATCAAAATTGTTACTAA

GCTAACAAACTTCAGAAAAACTTATGATGGGCAAGCTGCTTGTGACATTGAAGGTA

TTTAAGATTCAATTCTAGTTTGGTCCTAGATGACCACATATCCATTGTTCCTTCAACG

AGCACATGGTAAAGAGCCTAGAACACAGAGACACAGAACACAGTGGAGAAAAGGG
```

-continued

```
AGTGAAATGTCTTTAATGACACTTACTATATATGGGATTTTGTGACAATATACAAGG

ATGGTTAAGACATATAAGGTGATGCAAAAAAACATATTAACAATTATAGTGACAAA

AAATGAGGAGCATATAATTATACATTGATTTATACAGAGTACCAGAGGAACACAGC

ATTGAGAGCCGTAACACCACCTGAGGGAGTGGAGAAAGGCTTCAGAGAGAAAGTG

TTTTTTGGAATGGATCACTGTTTCCAAAAGAACTAAAGTACAGTTTGAGAAATGCAT

ACTTAATTCATTACTTTTTTCCCCTCAACTTTAATAATAAATTTACCCAACAAAAA

GTTTATTTTTGACTTGTAAATCTCTTAAAATCATAAAAAAGTAAAATTAGCTTTTAA

AAACAGGTAGTCACCATAGCATTGAATGTGTAGTTTATAATACAGCAAAGTTAAAT

ACAATTTCAAATTACCTATTAAGTTAGTTGCTCATTTCTTTGATTTCATTTAGCATTG

ATCTAACTCAATGTGGAAGAAGGTTACATTCGTGCAAGTTAACACGGCTTAATGATT

AACTATGTTCACCTACCAACCTTACCTTTTCTGGGCAAATATTGGTATATATAGAGT

TAAGAAGTCTAGGTCTGCTTCCAGAAGAAAACAGTTCCACGTTGCTTGAAATTGAA

AATCAAGATAAAAATGTTCACAATTAAGCTCCTTCTTTTTATTGTTCCTCTAGTTATT

TCCTCCAGAATTGATCAAGACAATTCATCATTTGATTCTCTATCTCCAGAGCCAAAA

TCAAGATTTGCTATGTTAGACGATGTAAAAATTTTAGCCAATGGCCTCCTTCAGTTG

GGACATGGTCTTAAAGACTTTGTCCATAAGACGAAGGGCCAAATTAATGACATATT

TCAAAAACTCAACATATTTGATCAGTCTTTTTATGATCTATCGCTGCAAACCAGTGA

AATCAAAGAAGAAGAAAAGGAACTGAGAAGAACTACATATAAACTACAAGTCAAA

AATGAAGAGGTAAAGAATATGTCACTTGAACTCAACTCAAAACTTGAAAGCCTCCT

AGAAGAAAAAATTCTACTTCAACAAAAAGTGAAATATTTAGAAGAGCAACTAACTA

ACTTAATTCAAAATCAACCTGAAACTCCAGAACACCCAGAAGTAACTTCACTTAAA

GTAAGTAGAAAATAAAGAGGGTTCATGTTTATGTTTTCAATGTGGATCTTTTAAAAA

AAATATTTCTAAGGCATGCCATTTGAAATACTTTGTTGCATTGTTGAAATACTTTTTT

TTCCAAGAAAAATAATCTCCAGAAAATAAAATTTCCTATTATAATTTCAAGTTAGTT

TTTTGTTTCCCTAATGTTATATATGAAACACTGAAAATTTGCATTTTATATGAAAAT

TACAAATCGGTTAAATTATACAATCTAGAACACTATGTCATTACACTATTGTAAATT

ACTGAAGGTAAGTAAAAAGTTAAAAAAAATTTAAAACTATTCTCCAGTGTTTAAAA

CAGATTAAATAATACAGTAAATGGAAAAGATTTATTCATATGAAAATATGCTGGGC

TTTTTCTTTTAATTGAAGTTCAGAAAATCAAATTTTAGAGATAGTACAATTTAAATA

AAATGTTAAGGACAAAAATATGTGCTATTTGAAAGAAGCATACAAGGGGAAGGAA

TTGCCAATATTCATTTTTCAAATCCATTATTAGTTTAAAAATTTAGATTATGATAGTG

TTACAGGAAATTAATAGAAAGAAAGAGGAAAGCAACTTATAACCAACCTACTCTC

TATATCCAGACTTTTGTAGAAAAACAAGATAATAGCATCAAAGACCTTCTCCAGAC

CGTGGAAGACCAATATAAACAATTAAACCAACAGCATAGTCAAATAAAAGAAATA

GAAAATCAGGTAAGTCAGTATTTTAATGGTATGTCCCATCTTTCACACAGGTCTGTA

AAAACACTGAATCCTAAAATTATTTACAAGCTTTAACTGGATCATGAGTAAAATTAT

CACATCAGCATAACTGTTAAAATTGCAGGCTCTGAAGCTAATAAACTACCTGCATTT

AAACCATGGCTCTAAAACTTTGTGTGACCTTGAATAAATTACTTCACCCCTTTATCT

CTCAGTTTCCTCACATATACTACAAAGATAATAACAGAACTTATAGGATTATTGTAA

GAAAAAAAATTAATTCATAGCAGCCAATGTCATCTTACTAAAATTCAAATTAGATC

ATGTTTCTCTTTGCTCAAAACCACACAATAGCTTTCCATTTCACTCATATTGGCTCTT
```

-continued

```
TAGACCAAGATTACCCAACCCTTCGTCATCTCACTGACTTCACCTCCTCTACTCTAGT

TATTCTGACCGCTTTACCAGTATTCAAACACATCAAACATACTGCCACCTCAAAGCC

TTTGCCCTTGTTGTTTCCTCTAACTGGAACGCTCTTCTGCCCTGGTATCTACGTGGCC

CACTCTCTGATTTCCCTTAGGGTCGTTATCAAACAAAAAATTCCCAATGAAGACTTA

CAAGGTCACTTAACCAAAAATCACAACCGCCTGGTCCCATCCCTGAAAACTTCTACT

TCCTTAGCTACTTTTCTCCTGCACACTCACCTTTATTTAACATAACATAAATTTTAGT

TATTTATCTCTTCTATTCCTGCACTAAAATGTAAGCTCTGTGAATACAGGGATTTTTT

CCATTATCTTCATATTTTCCATTATTTGTATATACTCCAGAATATAGAATACTGTATG

GCACACAGTAGGCATTTCTGTTGAATTAATAAATGTAATGTCATATTCACACAGAAG

CGTGTGCTATGATTATTATTACTTGGATTACTAGAAATAGTGTGCCTCATAATTAAA

GGTCAACATTCAACAATGTAATTAATCTACAATGTAAACATCTGGTGAAGTGACAG

AGGGAAGCACTTGTTTAGAAAAAAGCTATGTCAGAATCCATGTATTCTAATATGCA

GTACAATAGTTTAAAAATATTAATAATACTCTCAAACAGCTATTCAAGAGGATTCA

AAAAACATAATATAAACTCAGAGAAACTGGTAAACAAAATCATTTTCAAGAGATAT

AAAACAAATATTATTACCAATTTCCACTAAACAAACATAATGTTAGTAGTGCTGCTA

AAAGGTTTTTTATCAACTACTTTTGGTTTCCATACTTTCCTTCTTATGATGTTATTATT

CTAAATTCTTTTCAATTATATCTTTTACTATGATTAAATGAACCTGCTCCCCAAAGCA

AAATGTTACTATAGTAATATACATTGTGTCTAAAAATAAAAATGTGTGAAGAAACC

AAAACAATGAATTTCTGAGTTGGAAGAAGAGTTAGATCATTTAACTTTCTCATATTT

AAATTAAAAAAACAAAACTCTAAAAATTTAAGTAACTTTAAGATCACATAGTTACT

TAGTAGAAAAGAGTAATACCCAGCAAGCAAACTTTACAATAGATCCTTTTAAATAA

GGTCCTAGGAAATATCATTCATGCCAGCATCAAAAAACTAACACTAATAATGCAAG

ATATTATATATTCTGCTTTTCTTACTGTCAATGAGAAAAACTATCATTCAATAAATTG

CAAACCCAACACACTTAAATAAAAATAAAATGTTACTGCTAAACTAACGATAAACT

ACTGAATATATAGAAAGTAAGCAAACAAACTTGCCAACCTGCCAACATCTACAGAT

ATGTTTACAGGTCAAAAATTATCAAATTATCAAGAAAGCCTGGTTCAAATTATGTAT

TATGTCTTTATCACAGGTCTGAAGATCAGTAAGACCTAAAACTGAAAATTATTAAAC

TTAAAATCTGAACAGAATATCAAATATATTTTATTCATATAAATAAAAGAATACATT

ACAATATTCTAAGCAAAGCAGTCTCTACTTTTGGCCTTGCTCTGTTTTCCGACCAAT

GTCTGCTTTTTTGCCTTGCTTTATTTTTTTATCTTATTAAATAATGTCCCTGATTAAAT

ATTTTGAGAACAGGTAATCTGTACAATCTGAATAACACTGTTTATCTAAATATCAAA

CACCGTTATAACATTATGAACTGAAAGACAAACTGTACTTCTGACATCCTTACTCAG

ATTTCCCCTAATTGTATATTCAGTATCATTTTAAAAAACAGATTTATATTCTTTTATC

AGCTCAGAAGGACTAGTATTCAAGAACCCACAGAAATTTCTCTATCTTCCAAGCCA

AGAGCACCAAGAACTACTCCCTTTCTTCAGTTGAATGAAATAAGAAATGTAAAACA

TGATGGTAAGACACTTTGGTGGGTTTCCTTCTTGAAGCTATTATTATCAAATTCCCTA

TTCTTAGGACTTGTTCTAGACTAAAAGATAGTTAAGAGATATCCATCAAATACAATG

TATCAACCTAAACTGGATGCTGGGGTTCTTTTTACACCCTATAAAAGACATACCTAA

GACAATCAGAGAAATACAAATATGGACTTGATTATTAGATAATATAGAAGGTTTAT

TAATTTTCTTAGATGTGATCATGGTATTGCAGTTTTAAAGGAGAACAATCTCCTGTT
```

-continued

```
TAAGAGATACATGCTGAAATATTTACGGAGTTAAAGGTCACTGGACTCCAGACTGG

TGATAGAACAAGACTCTGTCTCTAAAAAATAATTAATTTTTTAAAAGAAAATAGTTT

GGTAAGATGATTCTTACATTCTTAAATAACACGCCATCTAAGAAAAATGCTTTAACA

TAAACATTACTGAAAAAATGCTACATTTGCCACAACTTCATAAAATGTCAAGTGAA

ATCTCAAGCTCCAAAGATATTATTCCTATTACTAAATCTGATGTAATAACATTTTATT

GATTCTAGGCATTCCTGCTGAATGTACCACCATTTATAACAGAGGTGAACATACAA

GTGGCATGTATGCCATCAGACCCAGCAACTCTCAAGTTTTTCATGTCTACTGTGATG

TTATATCAGGTAAAACCTGTCTAAGGAGAATAGACAGTAGTTAGTTCAACTTACTCA

TTACGTATTAGGAAGATTAACCTGGTTATCATTGTTTTATACATATATATATGAAAT

ATATATGAGTATTCGTATAAATATAATACTTTTACCTTGTTTATGTATTTACTCAATA

TTCTCCTTTTCCTCTAAAATAATCTGAAGTGACTATTATCAATAAGTTTACTATGCCA

AAATTCATTAATTGCCTTTCACTTAACTTTTGGGACCATAATAAATAATAAAATGTA

TTGCCATAACATTAATAAACTACCTTACAAAACCACCAATTAAAATCAAACAAACA

AAAAAGTGTTATTTACATCTGTCAACATAAATCTACTAAAAATACATGATTTCATTC

ATTATATTCAGGTAGTCCATGGACATTAATTCAACATCGAATAGATGGATCACAAA

ACTTCAATGAAACGTGGGAGAACTACAAATATGGTTTTGGGAGGCTTGATGGTAAG

GGGACTACATTCAATCATTCATTCACTTGCTAATCTACAAATATTTACTGAGAACCT

CTTATGGACCAGGTATTAGGAAAAGTAGTAACGAACGAGAAGCAGTCTCAGCCTTC

ATATAATTTATTATCAAACAATTACACATTTGTTAGTAAATTACACTTATTACAACT

GTTATTATTTGAATTATATTTATCACAATTACATGTCTGTTCTTAAATATACTTATCA

CAATTTAATTCCACGGCTTACAATGATCATAACTATAATTATTAAAGACAATTTTGA

TTAAATGTTATGTCATAAGTAGTAACTGTTACAAATAAGCTGTGAAAAGAACCACT

CCTAGCATTAGTCACTCTATTCTCTCATTAACGTTTTACATATCAATTAATTGGAAGT

TAAAAGGACCAGGAAACTCAGACATACAGTATACATTTTAAAATTTCAATTATTTA

AATATAATATATAGAATGTATGGCTTATAATGAATTAGTTAACTCAATGCAAATTAT

TCTATTTTGATTACAAATAGTAAAATAAGCAAGATAAAATAACAGATGTTTAAAAT

CCAAAAAGCACATACAAAAATCCATGAATGATGTCTAAGTACTCACTTATAAAGTA

GAAGACATTCATTATTATATCAAATTTTTAAATGCTCAGTACTATTTGACCATTTAA

AAATTTTGTATTCAAACTACCAGTGAAAGCCCTACCTAGAAGGTATACTCAGTGATA

AGTTTTGTAGCTCCAAATCTTCTAATAGTGAGTGTAACCCCAAAATAAAAGGCTGAC

AGGTAAGTCGAGAATACTCACTTAATTCTGGTAAGAAAGCAACCCATTTGTACTTGT

ATTTACCAGCAATCCTTAAAATGAAGCTTCCTACTAACTCAATAGCAATAAGACAAT

AGTGAATGTTTAATGAAACAGTATTTTATAAATACTTTAATAAAAAGGATTGTGAT

GAAGAACAATCTATTTATATTTGTTATTTGTTTTTAATTCCAATAAAAATAATTTTTA

AAATTACAGAAAAAAGTTATTAAGAACCATGCTTTTAAATTTAAAATGATTTTTTAA

ATTTATTCCTGTCTTTTTCTACAAAGAAAGCATACATTAAGCAAATACCAAAGGCCA

GGTTTACATTTGAAGAAAGTGACATTATTATTACTCAAGTCTCTAGGAATACTTAAC

ACATCTCTTGACTGTATATGGATGTTAATAAATAGCTGACAGTAAAGTTTATCCATA

TAAAGACTTGCAAATATTCCTCTACCAATGACGAGACTTTAAAATATCTATAATAAT

GTAACACATTTCACTGGTGAAACATGTCTTGTCATATGCATTATAGAAAGGATAATC

AGACTTTCAGTTATATTAATATTTTTAACATTTTTGTGCACATAGCTATCTTCAATAA
```

-continued

```
AATTGTTTTAAAAGGTATTATTTTAAGATACACTAAAATGATCAAGGGATTCAAGAC

TAAACAACTCAATTAGTTGCACCAATAAAAAACACTTAAAAAAACTGTCAGTGTCC

AACCTGTACTTAATAACTCACAGATTTTTAAAACTTTTCTTTTCAGGAGAATTTTGGT

TGGGCCTAGAGAAGATATACTCCATAGTGAAGCAATCTAATTATGTTTTACGAATTG

AGTTGGAAGACTGGAAAGACAACAAACATTATATTGAATATTCTTTTTACTTGGGA

AATCACGAAACCAACTATACGCTACATCTAGTTGCGATTACTGGCAATGTCCCCAAT

GCAATCCCGGAAAACAAAGATTTGGTGTTTTCTACTTGGGATCACAAAGCAAAAGG

ACACTTCAACTGTCCAGAGGGTTATTCAGGTATCTTTTTCTGATACCAATACTTTATT

TTCATATCTTCAAAGTATCTTCCCACATTATTAGCTATTATCTGCAATGACAACTTTT

AAAAATCCGAATCCCAAATAAGCGTTTTCTCTCTAGACGAAAACCTCTTAACTATAA

TGAAAGTGTTCATTCTAGTTCAATCAGGTATTTTACCTCTAATCTTCCTCAGATTTTC

TATTTTTTGGTAGTGTATAGATTATTTATACAGATTATTTAAAATTGGGACTTATACA

GATTATTTAAAACTGGGATACATGCATCTAAAACACTGTAATATTTATAAGAAAGG

AAGATAAACTTACGGGGAAATACAGTAACAGTAACTACATACGAGTCTGTACCCAT

TAAATTGCATATCTATCTCCTTTAGGAGGCTGGTGGTGGCATGATGAGTGTGGAGAA

AACAACCTAAATGGTAAATATAACAAACCAAGAGCAAAATCTAAGCCAGAGAGGA

GAAGAGGATTATCTTGGAAGTCTCAAAATGGAAGGTTATACTCTATAAAATCAACC

AAAATGTTGATCCATCCAACAGATTCAGAAAGCTTTGAATGAACTGAGGCAAATTT

AAAAGGCAATAATTTAAACATTAACCTCATTCCAAGTTAATGTGGTCTAATAATCTG

GTATTAAATCCTTAAGAGAAAGCTTGAGAAATAGATTTTTTTTATCTTAAAGTCACT

GTCTATTTAAGATTAAACATACAATCACATAACCTTAAAGAATACCGTTTACATTTC

TCAATCAAAATTCTTATAATACTATTTGTTTTAAATTTTGTGATGTGGGAATCAATTT

TAGATGGTCACAATCTAGATTATAATCAATAGGTGAACTTATTAAATAACTTTTCTA

AATAAAAAATTTAGAGACTTTTATTTTAAAAGGCATCATATGAGCTAATATCACAAC

TTTCCCAGTTTAAAAAACTAGTACTCTTGTTAAAACTCTAAACTTGACTAAATACAG

AGGACTGGTAATTGTACAGTTCTTAAATGTTGTAGTATTAATTTCAAAACTAAAAAT

CGTCAGCACAGAGTATGTGTAAAAATCTGTAATACAAATTTTTAAACTGATGCTTCA

TTTTGCTACAAAATAATTTGGAGTAAATGTTTGATATGATTTATTTATGAAACCTAA

TGAAGCAGAATTAAATACTGTATTAAAATAAGTTCGCTGTCTTTAAACAAATGGAG

ATGACTACTAAGTCACATTGACTTTAACATGAGGTATCACTATACCTTATTTGTTAA

AATATATACTGTATACATTTTATATATTTTAACACTTAATACTATGAAAACAAATAA

TTGTAAAGGAATCTTGTCAGATTACAGTAAGAATGAACATATTTGTGGCATCGAGTT

AAAGTTTATATTTCCCCTAAATATGCTGTGATTCTAATACATTCGTGTAGGTTTTCAA

GTAGAAATAAACCTCGTAACAAGTTACTGAACGTTTAAACAGCCTGACAAGCATGT

ATATATGTTTAAAATTCAATAAACAAAGACCCAGTCCCTAAATTATAGAAATTTAA

ATTATTCTTGCATGTTTATCGACATCACAACAGATCCCTAAATCCCTAAATCCCTAA

AGATTAGATACAAATTTTTTACCACAGTATCACTTGTCAGAATTTATTTTTAAATAT

GATTTTTTAAAACTGCCAGTAAGAAATTTTAAATTAAACCCATTTGTTAAAGGATAT

AGTGCCCAAGTTATATGGTGACCTACCTTTGTCAATACTTAGCATTATGTATTTCAA

ATTATCCAATATACATGTCATATATATTTTTATATGTCACATATATAAAAGATATGT
```

-continued

```
ATGATCTATGTGAATCCTAAGTAAATATTTTGTTCCAGAAAAGTACAAAATAATAA

AGGTAAAAATAATCTATAATTTTCAGGACCACAGACTAAGCTGTCGAAATTAACGC

TGATTTTTTTAGGGCCAGAATACCAAAATGGCTCCTCTCTTCCCCCAAAATTGGACA

ATTTCAAATGCAAAATAATTCATTATTTAATATATGAGTTGCTTCCTCTATTTGGTTT

CCTTAAAAAAAAAAAAAACTCTCATAGGACATGTTTCATTTTGTTCCTTTCAGGAGT

AGTAAATTAGACGTTTTCCCCATATAAAGCTTTTTTCTACCAGAAAGATACTTCTGG

TAGAAGAAGAGAAAGGAGCTCTTTATGGTTCACACGACTGTCTCCTGTCCTAACTAC

TTTGCTTAAAGTGCTCAAATTCCATCACTACTCACAGTTGTCTAATCTAAGTCTAATC

CCCTTTGATCTCTCAGACTACCTTCCCTTTTATCTCTCTACTACTTAATAATAAGAAT

ATCTTTTTTTCAAACTTGACCTTCATTTTGCTTTCACAATACTATACTCTCCATGGAT

TATCCCTTATCTGAATCCATCTTTATAACCCTATTCCTTTCTCATATTTAGTACTGTG

GGCCAATGGACAACCTTCAATCATCTTTTCTACACTGACCCTCAGACATTCTATCTG

CTCTCACGGACTCCTTTATTTACCATGAATAAAGTTCCAAAATCTACATATTCATCC

CAAGTCTCTTTCCAGTTCCCCTTCTTACATTGCCTATTTGCCATTTCTCCCTTCAATAC

CCTATACTTCACTCAAATTCAACATACCAAAAATAAAAGGCCAGGCACGGTGGCTC

ACACCTGTAATCCCAGGACTTTGGGAGGCTGAGGCAGGTGGATCACCTGAGGTCAG

GAGTCTGACCAGCCTGACCAATATGGTGAAACCCCGTCTCTACCTAAAATACAAAA

ATTAGCCAGGCGTGGTGGCATGTGCCTACAGTCCCAGCTACTCAAGAGGCTGAGAC

AGGAGAATCGCTTGAACCCAGGAGGCGGAGGTTGCAGTGAGCTGAGATCACACCA

ATGCACTGGGTGACAGAACAAGACTGACTCAAAAAAAAATAAATAACAAATTCCCC

AGCCCCTTACTGCTACTGCTATCCCTTTCTACCCACCTTTCCCTCCTTTATACTCTTTC

ACACCATCTTCCTCACTTCTTTATATCCATTAATATGACCAGCATGTTCCCAGTCACA

GAAGCCTGGAACCCGGAAGACATCTCTGGCTTTTCACTCAACTTTGTAAACTACCTC

TTTTGTATCATAAGCCACCAAGTTCAATACAATCTTCTCTTGAAACGTCTCTTAATCT

TATAAGCTTTCTTCCCCAAAGACTGTCTTTAACTTCAGTGCTAGATTATATAAGT
```

AAD34156.1 human angiopoietin-related protein 3:

(SEQ ID NO: 109)

```
MFTIKLLLFIVPLVISSRIDQDNSSFDSLSPEPKSRFAMLDDVKILANGLLQLGHGLKDFV

HKTKGQINDIFQKLNIFDQSFYDLSLQTSEIKEEEKELRRTTYKLQVKNEEVKNMSLELN

SKLESLLEEKILLQQKVKYLEEQLTNLIQNQPETPEHPEVTSLKTFVEKQDNSIKDLLQTV

EDQYKQLNQQHSQIKEIENQLRRTSIQEPTEISLSSKPRAPRTTPFLQLNEIRNVKHDGIPA

ECTTIYNRGEHTSGMYAIRPSNSQVFHVYCDVISGSPWTLIQHRIDGSQNFNETWENYK

YGFGRLDGEFWLGLEKIYSIVKQSNYVLRIELEDWKDNKHYIEYSFYLGNHETNYTLHL

VAITGNVPNAIPENKDLVFSTWDHKAKGHFNCPEGYSGGWWWHDECGENNLNGKYN

KPRAKSKPERRRGLSWKSQNGRLYSIKSTKMLIHPTDSESFE
```

ApoLipoprotein (a) (LPA)

In some embodiments, the target gene for modification using the compositions and methods disclosed herein is gene encoding lipoprotein a (LPA). LPA is a low-density lipoprotein variant. Genetic and epidemiologic studies have identified LPA as a risk factor for atherosclerosis and related diseases, such as coronary heart disease and stroke. LPA concentrations vary more than one thousand times between individuals: from <0.2 to >200 mg/dL. This range of concentrations is observed in all populations studied by scientists so far. The mean and median concentrations between different world populations show distinct particularities, the main being the two to threefold higher LPA plasma concentration of populations of African descent compared to Asian, Oceanic, or European populations. High LPA in blood correlates with coronary heart disease (CHD), cardiovascular disease (CVD), atherosclerosis, thrombosis, and stroke. Individuals without LPA or with very low LPA levels seem to be healthy. Thus, plasma LPA is not vital, at least under normal environmental conditions. Since apo (a)/LPA appeared rather recently in mammalian evolution-only oldworld monkeys and humans have been shown to harbor LPA-its function might not be vital, but just evolutionarily advantageous under certain environmental conditions, e.g., in case of exposure to certain infectious diseases.

An exemplary LPA amino acid sequence encoded by Human reference sequence NG_016147.1 is provided below:

```
>sp|P08519|APOA_HUMAN Apolipoprotein(a) OS =
Homo sapiens OX = 9606 GN = LPA PE = 1 SV = 1
                              (SEQ ID NO: 110)
MEHKEVVLLLLLFLKSAAPEQSHVVQDCYHGDGQSYRGTYSTTVTGRTCQ

AWSSMTPHQHNRTTENYPNAGLIMNYCRNPDAVAAPYCYTRDPGVRWEYC

NLTQCSDAEGTAVAPPTVTPVPSLEAPSEQAPTEQRPGVQECYHGNGQSY

RGTYSTTVTGRTCQAWSSMTPHSHSRTPEYYPNAGLIMNYCRNPDAVAAP

YCYTRDPGVRWEYCNLTQCSDAEGTAVAPPTVTPVPSLEAPSEQAPTEQR

PGVQECYHGNGQSYRGTYSTTVTGRTCQAWSSMTPHSHSRTPEYYPNAGL

IMNYCRNPDAVAAPYCYTRDPGVRWEYCNLTQCSDAEGTAVAPPTVTPVP

SLEAPSEQAPTEQRPGVQECYHGNGQSYRGTYSTTVTGRTCQAWSSMTPH

SHSRTPEYYPNAGLIMNYCRNPDAVAAPYCYTRDPGVRWEYCNLTQCSDA

EGTAVAPPTVTPVPSLEAPSEQAPTEQRPGVQECYHGNGQSYRGTYSTTV

TGRTCQAWSSMTPHSHSRTPEYYPNAGLIMNYCRNPDAVAAPYCYTRDPG

VRWEYCNLTQCSDAEGTAVAPPTVTPVPSLEAPSEQAPTEQRPGVQECYH

GNGQSYRGTYSTTVTGRTCQAWSSMTPHSHSRTPEYYPNAGLIMNYCRNP

DAVAAPYCYTRDPGVRWEYCNLTQCSDAEGTAVAPPTVTPVPSLEAPSEQ

APTEQRPGVQECYHGNGQSYRGTYSTTVTGRTCQAWSSMTPHSHSRTPEY

YPNAGLIMNYCRNPDAVAAPYCYTRDPGVRWEYCNLTQCSDAEGTAVAPP

TVTPVPSLEAPSEQAPTEQRPGVQECYHGNGQSYRGTYSTTVTGRTCQAW

SSMTPHSHSRTPEYYPNAGLIMNYCRNPDAVAAPYCYTRDPGVRWEYCNL

TQCSDAEGTAVAPPTVTPVPSLEAPSEQAPTEQRPGVQECYHGNGQSYRG

TYSTTVTGRTCQAWSSMTPHSHSRTPEYYPNAGLIMNYCRNPDAVAAPYC

YTRDPGVRWEYCNLTQCSDAEGTAVAPPTVTPVPSLEAPSEQAPTEQRPG

VQECYHGNGQSYRGTYSTTVTGRTCQAWSSMTPHSHSRTPEYYPNAGLIM

NYCRNPDAVAAPYCYTRDPGVRWEYCNLTQCSDAEGTAVAPPTVTPVPSL

EAPSEQAPTEQRPGVQECYHGNGQSYRGTYSTTVTGRTCQAWSSMTPHSH

SRTPEYYPNAGLIMNYCRNPDAVAAPYCYTRDPGVRWEYCNLTQCSDAEG

TAVAPPTVTPVPSLEAPSEQAPTEQRPGVQECYHGNGQSYRGTYSTTVTG

RTCQAWSSMTPHSHSRTPEYYPNAGLIMNYCRNPDAVAAPYCYTRDPGVR

WEYCNLTQCSDAEGTAVAPPTVTPVPSLEAPSEQAPTEQRPGVQECYHGN

GQSYRGTYSTTVTGRTCQAWSSMTPHSHSRTPEYYPNAGLIMNYCRNPDA

VAAPYCYTRDPGVRWEYCNLTQCSDAEGTAVAPPTVTPVPSLEAPSEQAP

TEQRPGVQECYHGNGQSYRGTYSTTVTGRTCQAWSSMTPHSHSRTPEYYP

NAGLIMNYCRNPDAVAAPYCYTRDPGVRWEYCNLTQCSDAEGTAVAPPTV

TPVPSLEAPSEQAPTEQRPGVQECYHGNGQSYRGTYSTTVTGRTCQAWSS

MTPHSHSRTPEYYPNAGLIMNYCRNPDAVAAPYCYTRDPGVRWEYCNLTQ
```

-continued

```
CSDAEGTAVAPPTVTPVPSLEAPSEQAPTEQRPGVQECYHGNGQSYRGTY

STTVTGRTCQAWSSMTPHSHSRTPEYYPNAGLIMNYCRNPDAVAAPYCYT

RDPGVRWEYCNLTQCSDAEGTAVAPPTVTPVPSLEAPSEQAPTEQRPGVQ

ECYHGNGQSYRGTYSTTVTGRTCQAWSSMTPHSHSRTPEYYPNAGLIMNY

CRNPDAVAAPYCYTRDPGVRWEYCNLTQCSDAEGTAVAPPTVTPVPSLEA

PSEQAPTEQRPGVQECYHGNGQSYRGTYSTTVTGRTCQAWSSMTPHSHSR

TPEYYPNAGLIMNYCRNPDAVAAPYCYTRDPGVRWEYCNLTQCSDAEGTA

VAPPTVTPVPSLEAPSEQAPTEQRPGVQECYHGNGQSYRGTYSTTVTGRT

CQAWSSMTPHSHSRTPEYYPNAGLIMNYCRNPDAVAAPYCYTRDPGVRWE

YCNLTQCSDAEGTAVAPPTVTPVPSLEAPSEQAPTEQRPGVQECYHGNGQ

SYRGTYSTTVTGRTCQAWSSMTPHSHSRTPEYYPNAGLIMNYCRNPDAVA

APYCYTRDPGVRWEYCNLTQCSDAEGTAVAPPTVTPVPSLEAPSEQAPTE

QRPGVQECYHGNGQSYRGTYSTTVTGRTCQAWSSMTPHSHSRTPEYYPNA

GLIMNYCRNPDAVAAPYCYTRDPGVRWEYCNLTQCSDAEGTAVAPPTVTP

VPSLEAPSEQAPTEQRPGVQECYHGNGQSYRGTYSTTVTGRTCQAWSSMT

PHSHSRTPEYYPNAGLIMNYCRNPDAVAAPYCYTRDPGVRWEYCNLTQCS

DAEGTAVAPPTVTPVPSLEAPSEQAPTEQRPGVQECYHGNGQSYRGTYST

TVTGRTCQAWSSMTPHSHSRTPEYYPNAGLIMNYCRNPDAVAAPYCYTRD

PGVRWEYCNLTQCSDAEGTAVAPPTVTPVPSLEAPSEQAPTEQRPGVQEC

YHGNGQSYRGTYSTTVTGRTCQAWSSMTPHSHSRTPEYYPNAGLIMNYCR

NPDAVAAPYCYTRDPGVRWEYCNLTQCSDAEGTAVAPPTVTPVPSLEAPS

EQAPTEQRPGVQECYHGNGQSYRGTYSTTVTGRTCQAWSSMTPHSHSRTP

EYYPNAGLIMNYCRNPDAVAAPYCYTRDPGVRWEYCNLTQCSDAEGTAVA

PPTVTPVPSLEAPSEQAPTEQRPGVQECYHGNGQSYRGTYSTTVTGRTCQ

AWSSMTPHSHSRTPEYYPNAGLIMNYCRNPDAVAAPYCYTRDPGVRWEYC

NLTQCSDAEGTAVAPPTVTPVPSLEAPSEQAPTEQRPGVQECYHGNGQSY

RGTYSTTVTGRTCQAWSSMTPHSHSRTPEYYPNAGLIMNYCRNPDAVAAP

YCYTRDPGVRWEYCNLTQCSDAEGTAVAPPTVTPVPSLEAPSEQAPTEQR

PGVQECYHGNGQSYRGTYSTTVTGRTCQAWSSMTPHSHSRTPEYYPNAGL

IMNYCRNPDAVAAPYCYTRDPGVRWEYCNLTQCSDAEGTAVAPPTVTPVP

SLEAPSEQAPTEQRPGVQECYHGNGQSYRGTYSTTVTGRTCQAWSSMTPH

SHSRTPEYYPNAGLIMNYCRNPDAVAAPYCYTRDPGVRWEYCNLTQCSDA

EGTAVAPPTVTPVPSLEAPSEQAPTEQRPGVQECYHGNGQSYRGTYSTTV

TGRTCQAWSSMTPHSHSRTPEYYPNAGLIMNYCRNPDPVAAPYCYTRDPS

VRWEYCNLTQCSDAEGTAVAPPTITPIPSLEAPSEQAPTEQRPGVQECYH

GNGQSYQGTYFITVTGRTCQAWSSMTPHSHSRTPAYYPNAGLIKNYCRNP

DPVAAPWCYTTDPSVRWEYCNLTRCSDAEWTAFVPPNVILAPSLEAFFEQ

ALTEETPGVQDCYYHYGQSYRGTYSTTVTGRTCQAWSSMTPHQHSRTPEN

YPNAGLTRNYCRNPDAEIRPWCYTMDPSVRWEYCNLTQCLVTESSVLATL

TVVPDPSTEASSEEAPTEQSPGVQDCYHGDGQSYRGSFSTTVTGRTCQSW

SSMTPHWHQRTTEYYPNGGLTRNYCRNPDAEISPWCYTMDPNVRWEYCNL
```

-continued

```
TQCPVTESSVLATSTAVSEQAPTEQSPTVQDCYHGDGQSYRGSFSTTVTG

RTCQSWSSMTPHWHQRTTEYYPNGGLTRNYCRNPDAEIRPWCYTMDPSVR

WEYCNLTQCPVMESTLLTTPTVVPVPSTELPSEEAPTENSTGVQDCYRGD

GQSYRGTLSTTITGRTCQSWSSMTPHWHRRIPLYYPNAGLTRNYCRNPDA

EIRPWCYTMDPSVRWEYCNLTRCPVTESSVLTTPTVAPVPSTEAPSEQAP

PEKSPVVQDCYHGDGRSYRGISSTTVTGRTCQSWSSMIPHWHQRTPENYP

NAGLTENYCRNPDSGKQPWCYTTDPCVRWEYCNLTQCSETESGVLETPTV

VPVPSMEAHSEAAPTEQTPVVRQCYHGNGQSYRGTFSTTVTGRTCQSWSS

MTPHRHQRTPENYPNDGLTMNYCRNPDADTGPWCFTMDPSIRWEYCNLTR

CSDTEGTVVAPPTVIQVPSLGPPSEQDCMFGNGKGYRGKKATTVTGTPCQ

EWAAQEPHRHSTFIPGTNKWAGLEKNYCRNPDGDINGPWCYTMNPRKLFD

YCDIPLCASSSFDCGKPQVEPKKCPGSIVGGCVAHPHSWPWQVSLRTRFG

KHFCGGTLISPEWVLTAAHCLKKSSRPSSYKVILGAHQEVNLESHVQEIE

VSRLFLEPTQADIALLKLSRPAVITDKVMPACLPSPDYMVTARTECYITG

WGETQGTFGTGLLKEAQLLVIENEVCNHYKYICAEHLARGTDSCQGDSGG

PLVCFEKDKYILQGVTSWGLGCARPNKPGVYARVSRFVTWIEGMMRNN
```

Cas Protein-gRNA Complexes

In another aspect, provided herein is a complex comprising the single guide RNA as provided herein in complex with the Cas protein, e.g., the Cas12b protein, wherein the complex comprises increased stability as compared to a complex with an unmodified single guide RNA and a Cas12b protein, wherein the stability is measured by half-life of the complex ex vivo or in vitro.

In some embodiments, the complex comprises increased stability as compared to a complex with an unmodified single guide RNA and a Cas12b protein. In some embodiments, the complex comprises increased stability by at least 5%, at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, at least 1000%, at least 2000%, at least 3000%, at least 4000%, at least 5000%, at least 6000%, at least 7000%, at least 8000%, at least 9000%, at least 10000%, at least 20000%, at least 30000%, at least 40000%, at least 50000%, at least 60000%, at least 70000%, at least 80000%, at least 90000%, or at least 100000% as compared to a complex with an unmodified single guide RNA and a Cas12b protein. In some embodiments, the complex comprises increased stability by at least 2 fold, at least 3 fold, at least 4 fold, at least 5 fold, at least 10 fold, at least 20 fold, at least 25 fold, at least 30 fold, at least 40 fold, at least 50 fold, at least 60 fold, at least 70 fold, at least 80 fold, at least 90 fold, at least 100 fold, at least 200 fold, at least 300 fold, at least 400 fold, at least 500 fold, at least 600 fold, at least 700 fold, at least 800 fold, at least 900 fold, at least 1000 fold, at least 2000 fold, at least 3000 fold, at least 4000 fold, at least 5000 fold, at least 6000 fold, at least 7000 fold, at least 8000 fold, at least 9000 fold, or at least 10000 fold as compared to a complex with an unmodified single guide RNA and a Cas12b protein.

In some embodiments, wherein the stability of the complex is measured by half-life of the complex. In some embodiments, wherein the stability of the complex is measured by half-life of the complex ex vivo. In some embodiments, wherein the stability of the complex is measured by half-life of the complex in vitro.

In some embodiments, the complex comprises increased half-life by at least 5%, at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, at least 1000%, at least 2000%, at least 3000%, at least 4000%, at least 5000%, at least 6000%, at least 7000%, at least 8000%, at least 9000%, at least 10000%, at least 20000%, at least 30000%, at least 40000%, at least 50000%, at least 60000%, at least 70000%, at least 80000%, at least 90000%, or at least 100000% as compared to a complex with an unmodified single guide RNA and a Cas12b protein wherein half-life of the complex is measured ex vivo. In some embodiments, the single guide RNA exhibits increased half-life of the complex by at least 2 fold, at least 3 fold, at least 4 fold, at least 5 fold, at least 10 fold, at least 20 fold, at least 25 fold, at least 30 fold, at least 40 fold, at least 50 fold, at least 60 fold, at least 70 fold, at least 80 fold, at least 90 fold, at least 100 fold, at least 200 fold, at least 300 fold, at least 400 fold, at least 500 fold, at least 600 fold, at least 700 fold, at least 800 fold, at least 900 fold, at least 1000 fold, at least 2000 fold, at least 3000 fold, at least 4000 fold, at least 5000 fold, at least 6000 fold, at least 7000 fold, at least 8000 fold, at least 9000 fold, or at least 10000 fold as compared to a complex with an unmodified single guide RNA and a Cas12b protein, wherein half-life of the complex is measured ex vivo.

In some embodiments, the complex comprises increased half-life when measured in vitro by at least 5%, at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, at least 1000%, at least 2000%, at least 3000%, at least 4000%, at least 5000%, at least 6000%, at least 7000%, at least 8000%, at least 9000%, at least 10000%, at least 20000%, at least 30000%, at least 40000%, at least 50000%, at least 60000%, at least 70000%, at least 80000%, at least 90000%, or at least 100000% as compared to a complex with an unmodified single guide RNA and a Cas12b protein, wherein half-life of the complex is measured in vitro. In some embodiments, the single guide RNA exhibits increased half-life of the complex by at least 2 fold, at least 3 fold, at least 4 fold, at least 5 fold, at least 10 fold, at least 20 fold, at least 25 fold, at least 30 fold, at least 40 fold, at least 50 fold, at least 60 fold, at least 70 fold, at least 80 fold, at least 90 fold, at least 100 fold, at least 200 fold, at least 300 fold, at least 400 fold, at least 500 fold, at least 600 fold, at least 700 fold, at least 800 fold, at least 900 fold, at least 1000 fold, at least 2000 fold, at least 3000 fold, at least 4000 fold, at least 5000 fold, at least 6000 fold, at least 7000 fold, at least 8000 fold, at least 9000 fold, or at least 10000 fold as compared to a complex with an unmodified single guide RNA and a Cas12b protein, wherein half-life of the complex is measured in vitro.

In another aspect, provided herein is a cell comprising the complex as provided herein. In some embodiments, the cell may be an in vitro cell. In some embodiments, the cell may be an ex vivo cell. In some embodiments, the cell may be an in vivo cell. In some embodiments, the cell may be an isolated cell.

Gene Modification Compositions

In another aspect, provided herein is a composition for gene modification comprising the single guide RNA as provided herein and a Cas12b protein or a nucleic acid sequence encoding the Cas12b protein. In some embodiments, the composition further comprises a vector that comprises the nucleic acid sequence encoding the Cas12b protein.

In some embodiments, the nucleic acid sequence may be a DNA, an RNA or mRNA, or a modified nucleic acid sequence. In some embodiments, the vector may be an expression vector. In some embodiments, the nucleic acid is operatively linked to a promoter of the vector. In some embodiments, the vector is a plasmid or a viral vector.

The term "vector," as used herein, refers to a nucleic acid molecule capable of transporting another nucleic acid to which it has been linked. In some examples, a vector is an expression vector that is capable of directing the expression of nucleic acids to which they are operatively linked. The term "operably linked," as used herein, means that the nucleotide sequence of interest is linked to regulatory sequence(s) in a manner that allows for expression of the nucleotide sequence. The term "regulatory sequence," as used herein, includes, but is not limited to promoters, enhancers and other expression control elements. Such regulatory sequences are well known in the art and are described, for example, in Goeddel; Gene Expression Technology: Methods in Enzymology 185, Academic Press, San Diego, CA (1990). Examples of expression vectors include, but are not limited to, plasmid vectors, viral vectors based on vaccinia virus, poliovirus, adenovirus, adeno-associated virus, SV40, herpes simplex virus, human immunodeficiency virus, retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors.

Lipid Nanoparticles (LNPs)

In another aspect, provided herein is a lipid nanoparticle (LNP) comprising the composition as provided herein.

As used herein, a "lipid nanoparticle (LNP) composition" or a "nanoparticle composition" is a composition comprising one or more described lipids. LNP compositions are typically sized on the order of micrometers or smaller and may include a lipid bilayer. Nanoparticle compositions encompass lipid nanoparticles (LNPs), liposomes (e.g., lipid vesicles), and lipoplexes. In some embodiments, a LNP refers to any particle that has a diameter of less than 1000 nm, 500 nm, 250 nm, 200 nm, 150 nm, 100 nm, 75 nm, 50 nm, or 25 nm. In some embodiments, a nanoparticle may range in size from 1-1000 nm, 1-500 nm, 1-250 nm, 25-200 nm, 25-100 nm, 35-75 nm, or 25-60 nm.

In some embodiments, an LNP may be made from cationic, anionic, or neutral lipids. In some embodiments, an LNP comprises neutral lipids, such as the fusogenic phospholipid 1,2-Dioleoyl-sn-glycero-3-phosphoethanolamine (DOPE) or the membrane component cholesterol, as helper lipids to enhance transfection activity and nanoparticle stability. In some embodiments, an LNP comprises hydrophobic lipids, hydrophilic lipids, or both hydrophobic and hydrophilic lipids. Any lipid or combination of lipids that are known in the art can be used to produce an LNP. Examples of lipids used to produce LNPs include, but are not limited to DOTMA (N[1-(2,3-dioleyloxy)propyl]-N,N,N-trimethyl-ammonium chloride), DOSPA (N,N-dimethyl-N-([2-sper-minecarboxamido]ethyl)-2,3-bis(dioleyloxy)-1-propani-minium pentahydrochloride), DOTAP (1,2-Dioleoyl-3-trimethylammonium propane), DMRIE (N-(2-hydroxyethyl)-N,N-dimethyl-2,3-bis(tetradecyloxy-1- propanaminiumbromide), DC-cholesterol (3β-[N—(N',N'-dimethylaminoethane)-carbamoyl]cholesterol), DOTAP-cholesterol, GAP-DMORIE-DPyPE, and GL67A-DOPE-DMPE (2-Bis(dimethylphosphino)ethane)-polyethylene glycol (PEG). Examples of cationic lipids include, but are not limited to, 98N12-5, C12-200, DLin-KC2-DMA (KC2), DLin-MC3-DMA (MC3), XTC, MD1, and 7C1. Examples of neutral lipids include, but are not limited to, DPSC, DPPC (Dipalmitoylphosphatidylcholine), POPC (1-palmitoyl-2-oleoyl-sn-glycero-3-phosphocholine), DOPE, and SM (sphingomyelin). Examples of PEG-modified lipids include, but are not limited to, PEG-DMG (Dimyristoyl glycerol), PEG-CerC14, and PEG-CerC20. In some embodiments, the lipids may be combined in any number of molar ratios to produce a LNP. In some embodiments, the polynucleotide may be combined with lipid(s) in a wide range of molar ratios to produce a LNP.

Modifications of Target Genes

In another aspect, provided herein is a method for modifying a target polynucleotide sequence of a gene in a cell, wherein the single guide RNA directs the Cas12b protein to effect a modification in the targeted polynucleotide sequence complementary to the spacer of the modified single guide RNA.

In some embodiments, the targeted polynucleotide sequence is in a target gene that encodes a protein of interest. In some embodiments, the modification reduces or abolishes expression of the protein of interest encoded by the target gene in the cell.

In some embodiments, the modification reduces expression of the protein of interest encoded by the target gene in the cell. In some embodiments, the modification reduces expression of the protein of interest encoded by the target gene in the cell by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 98%, at least 99%, at least 99.5%, at least 99.9%, or 100%. In some embodiments, the modification reduces expression of the protein of interest encoded by the target gene in the cell by at least 2 fold, at least 3 fold, at least 4 fold, at least 5 fold, at least 10 fold, at least 20 fold, at least 25 fold, at least 30 fold, at least 40 fold, at least 50 fold, at least 60 fold, at least 70 fold, at least 80 fold, at least 90 fold, at least 100 fold, at least 200 fold, at least 300 fold, at least 400 fold, at least 500 fold, at least 600 fold, at least 700 fold, at least 800 fold, at least 900 fold, at least 1000 fold, at least 2000 fold, at least 3000 fold, at least 4000 fold, at least 5000 fold, at least 6000 fold, at least 7000 fold, at least 8000 fold, at least 9000 fold, or at least 10000 fold. In some embodiments, the modification abolishes expression of the protein of interest encoded by the target gene in the cell.

In some embodiments, the targeted polynucleotide sequence is in a PCSK9 gene. In some embodiments, the modification reduces or abolishes expression of functional PCSK9 protein encoded by the PCSK9 gene in the cell.

In some embodiments, the modification reduces expression of functional PCSK9 protein encoded by the PCSK9 gene in the cell. In some embodiments, the modification reduces expression of functional PCSK9 protein encoded by the PCSK9 gene in the cell by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 98%, at least 99%, at least 99.5%, at least 99.9%, or 100%. In some embodiments, the modification reduces expression of functional PCSK9 protein encoded by the PCSK9 gene in the cell by at least 2 fold, at least 3 fold, at least 4 fold, at least 5 fold, at least 10 fold, at least 20 fold, at least 25 fold, at least 30 fold, at least 40 fold, at least 50 fold, at least 60 fold, at least 70 fold, at least 80 fold, at least 90 fold, at least 100 fold, at least 200 fold, at least 300 fold, at least 400 fold, at least 500 fold, at least 600 fold, at least 700 fold, at least 800 fold, at least 900 fold, at least 1000 fold, at least 2000 fold, at least 3000 fold, at least 4000 fold, at least 5000 fold, at least 6000 fold, at least 7000 fold, at least 8000 fold, at least 9000 fold, or at least 10000 fold. In some embodiments, the modification abolishes expression of functional PCSK9 protein encoded by the PCSK9 gene in the cell.

In some embodiments, the targeted polynucleotide sequence is in an ANGPTL3 gene. In some embodiments, the modification results in reducing or abolishing expression of functional ANGPTL3 protein encoded by the ANGPTL3 gene in the cell.

In some embodiments, the modification reduces expression of functional ANGPTL3 protein encoded by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 98%, at least 99%, at least 99.5%, at least 99.9%, or 100%. In some embodiments, the modification reduces expression of functional ANGPTL3 protein encoded by the ANGPTL3 gene in the cell by at least 2 fold, at least 3 fold, at least 4 fold, at least 5 fold, at least 10 fold, at least 20 fold, at least 25 fold, at least 30 fold, at least 40 fold, at least 50 fold, at least 60 fold, at least 70 fold, at least 80 fold, at least 90 fold, at least 100 fold, at least 200 fold, at least 300 fold, at least 400 fold, at least 500 fold, at least 600 fold, at least 700 fold, at least 800 fold, at least 900 fold, at least 1000 fold, at least 2000 fold, at least 3000 fold, at least 4000 fold, at least 5000 fold, at least 6000 fold, at least 7000 fold, at least 8000 fold, at least 9000 fold, or at least 10000 fold. In some embodiments, the modification abolishes expression of functional ANGPTL3 protein encoded by the ANGPTL3 gene in the cell.

In some embodiments, the modification to the gene caused by the chemically modified single guide RNA directed Cas12b protein-guide RNA effector complex is a double strand break, a non-sense mutation, a frameshift mutation, a splice site alteration, or an inversion.

The term "modification" or "modification of a target polynucleotide sequence," as used herein, refers to any change or alteration in the genome of a cell.

The term "double stranded break," as used herein, refers to a change in which both strands in the double helix are severed.

The term "non-sense mutation," as used herein, refers to a mutation in which a sense codon that corresponds to one of the amino acids specified by the genetic code is changed to a chain-terminating codon (e.g., stop codons UAA, UGA or UAG).

The term "frameshift mutation," as used herein, refers to a genetic mutation caused by a deletion or insertion of a number of nucleotides in a DNA sequence that is not divisible by three. In some embodiments, the insertion or deletion may change the reading frame due to the triplet nature of gene expression by codons, resulting in a completely different translation from the original. In some embodiments, a frameshift mutation may alter the first stop codon encountered in the sequence.

The term "splice site alteration," as used herein, refers to a genetic alteration in the DNA sequence that occurs at the boundary of an exon and an intron (splice site). In some embodiments, the mutation in the splice-donor and splice-acceptor sequences may disrupt RNA splicing resulting in the loss of exons or the inclusion of introns and an altered protein-coding sequence.

The term "inversion," as used herein, refers to a chromosome rearrangement in which a segment of a chromosome is reversed end to end. In some embodiments, an inversion occurs when a single chromosome undergoes breakage and rearrangement within itself. In some embodiments, an inversion is a pericentric inversions that include the centromere and a break point in each arm. In some embodiments, an inversion is a paracentric inversion in which both breaks occur in one arm of the chromosome and the centromere is not included. In some embodiments, an inversion does not involve a loss of genetic information, but simply rearranges the linear gene sequence. In some embodiments, an inversion does not cause any abnormalities in carriers as long as the rearrangement is balanced with no extra or missing DNA. In some embodiments, in individuals which are heterozygous for an inversion, there is an increased production of abnormal chromatids.

In some embodiments, the modification of a target polynucleotide sequence may include, but are not limited to, insertion, deletion and correction.

The term "insertion," as used herein, refers to an addition of one or more nucleotides in a DNA sequence. In some embodiments, an insertion can range from a small insertion of a few nucleotides to an insertion of large segments such as a cDNA or a gene.

The term "deletion," as used herein, refers to a loss or removal of one or more nucleotides in a DNA sequence or a loss or removal of the function of a gene. In some embodiments, a deletion can include, for example, a loss of a few nucleotides, an exon, an intron, a gene segment, or the entire sequence of a gene. In some embodiments, deletion of a gene refers to the elimination or reduction of the function or expression of a gene or its gene product.

For example, in some embodiments, a deletion may include a gene knock-in, knock-out or knock-down. The term "knock-in, as used herein, refers to an addition of a DNA sequence or fragment thereof into a genome. In some embodiments, the DNA sequence or fragment thereof to be knocked-in may include an entire gene or genes or regulatory sequences associated with a gene or any fragment thereof. For example, in some embodiments, a knock-in strategy may involve substitution of an existing sequence with the provided sequence, e.g., substitution of a mutant allele with a wild-type copy or vice versa.

The term "knock-out," as used herein, refers to the elimination of a gene or the expression of a gene. In some embodiments, a gene can be knocked out by a deletion or an addition of a nucleotide sequence that leads to a disruption of the reading frame, or by a replacement of a part of the gene with an irrelevant sequence. The term, "knock-down," as used herein, refers to reduction in the expression of a gene or its gene product. In some embodiments, as a result of a gene knockdown, the protein activity or function may be attenuated or the protein levels may be reduced or eliminated.

The term "correction," as used herein, refers to a change of one or more nucleotides of a genome in a cell by insertion, deletion or substitution. In some embodiments, a correction may result in a more favorable genotypic or phenotypic outcome in structure or function to the genomic site which was corrected. For example, in some embodiments, a correction may include the correction of a mutant or defective sequence to a wild-type sequence which restores structure or function to a gene or its gene product.

Pharmaceutical Compositions

In another aspect, provided herein is a pharmaceutical composition for gene modification comprising the single guide RNA as provided herein and the Cas12b protein or a nucleic acid sequence encoding the Cas12b protein, for example an mRNA. "Pharmaceutical composition" and its grammatical equivalents as used herein can refer to a mixture or solution comprising a therapeutically effective amount of an active pharmaceutical ingredient together with one or more pharmaceutically acceptable excipients, carriers, and/or a therapeutic agent to be administered to a subject, e.g., a human in need thereof.

Pharmaceutical compositions described herein comprises the chemically modified guide RNA and an mRNA encoding the Cas12b protein in combination with one or more pharmaceutically or physiologically acceptable carriers, diluents or excipients. Such compositions can comprise a suspension of lipid nanoparticle constituted from the chemically modified guide RNA and the mRNA and lipid nanoparticle excipients, buffers such as neutral buffered saline, phosphate buffered saline and the like; stabilizers such as albumin; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. The aforementioned pharmaceutical compositions comprising lipid nanoparticles, in some embodiments, can be suspended in a pharmaceutically acceptable buffer in the presence or in the absence of one or more, or a combination of lipid nanoparticle stabilizers in the suspension, or in the frozen and/or lyophilized form. The pharmaceutically acceptable buffers include, but not limited to, neutral buffered saline, phosphate buffered saline and the like, and neutral or near neutral TRIS buffer and the stabilizers include, but not limited to carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

The term "pharmaceutically acceptable" and its grammatical equivalents as used herein can refer to an attribute of a material which is useful in preparing a pharmaceutical composition that is generally safe, non-toxic, and neither biologically nor otherwise undesirable and is acceptable for veterinary as well as human pharmaceutical use. "Pharmaceutically acceptable" can refer a material, such as a carrier or diluent, which does not abrogate the biological activity or properties of the compound, and is relatively nontoxic, i.e., the material may be administered to a subject without causing undesirable biological effects or interacting in a deleterious manner with any of the components of the pharmaceutical composition in which it is contained. Thus, a pharmaceutically acceptable excipient, carrier, or diluent" refers to an excipient, carrier, or diluent that can be administered to a subject, together with an agent, and which does not destroy the requisite or desired pharmacological activity thereof and is nontoxic when administered in doses sufficient to deliver a therapeutic amount of the agent.

Pharmaceutical compositions can be formulated in a conventional manner using one or more pharmaceutically acceptable inactive ingredients that facilitate processing of the active compounds into preparations that can be used pharmaceutically. A proper formulation is dependent upon the route of administration chosen and a summary of pharmaceutical compositions can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference. In embodiments, the pharmaceutical composition facilitates administration of the compound to an organism.

The administration of compositions described herein can be carried out in any convenient manner, including by aerosol inhalation, injection, ingestion, transfusion, implantation or transplantation. Examples of routes of administration include parenteral, e.g., intravenous or intra-arterial, intradermal, subcutaneous, oral (e.g., inhalation), transdermal (topical), transmucosal, nasal, pulmonary, ocular, gastrointestinal, and rectal administration. Alternate routes of administration include intraperitoneal, intra-articular, intracardiac, intracistemal, intradermal, intralesional, intraocular, intrapleural, intrathecal, intrauterine, intraventricular, intracranial, intrathecal, and the like.

A pharmaceutical composition used in the therapeutic methods of the disclosure is formulated to be compatible with its intended route of administration.

Disease and Treatment

In another aspect, provided herein is a method for treating or preventing a condition in a subject in need thereof, the method comprising administering to the subject the complex as provided herein, the composition as provided herein, or the lipid nanoparticle as provided herein, wherein the single guide RNA directs the Cas12b protein to effect a modification in a target polynucleotide sequence in a cell of the subject, thereby treating or preventing the condition.

In some embodiments, the target polynucleotide sequence is in a PCSK9 gene. In some embodiments, the modification reduces expression of functional PCSK9 protein encoded by the PCSK9 gene in the subject. In some embodiments, the condition is atherosclerotic vascular disease. In some embodiments, the target polynucleotide sequence is in an ANGPTL3 gene. In some embodiments, the modification reduces expression of functional ANGPTL3 protein encoded by the ANGPTL3 gene in the subject. In some embodiments, the condition is an atherosclerotic vascular disease, hypertriglyceridemia, or diabetes.

The terms "treat," "treating", and "treatment," and the like are used herein to generally mean obtaining a desired pharmacological and/or physiological effect. The effect may be prophylactic in terms of preventing or partially preventing a disease, symptom or condition thereof and/or may be therapeutic in terms of a partial or complete cure of a disease, condition, symptom or adverse effect attributed to the disease. Treating" may refer to administration of the pharmaceutical compositions described herein to a subject after the onset, or suspected onset, of a disease or condition. "Treating" includes the concepts of "alleviating," which refers to lessening the frequency of occurrence or recurrence, or the severity, of any symptoms or other ill effects related to a disease or condition and/or the side effects associated with the disease or condition. The term "treating" also encompasses the concept of "managing" which refers to reducing the severity of a particular disease or disorder in a patient or delaying its recurrence, e.g., lengthening the period of remission in a patient who had suffered from the disease. It is appreciated that, although not precluded, treating a disorder or condition does not require that the disorder, condition, or symptoms associated therewith be completely eliminated. The term "treatment" as used herein covers any treatment of a disease in a mammal, particularly, a human, and includes: (a) preventing the disease from occurring in a subject which may be predisposed to the disease but has not yet been diagnosed as having it; (b) inhibiting the disease, i.e., arresting its development; or (c) relieving the disease, i.e., mitigating or ameliorating the disease and/or its symptoms or conditions. The disclosure is directed towards treating a patient's suffering from cancer. The term "prophylaxis" is used herein to refer to a measure or measures taken for the prevention or partial prevention of a disease or condition.

As used herein, the terms "prevent," "preventing," "prevention," and the like, refer to reducing the probability of developing a disease or condition in a subject, who does not have, but is at risk of or susceptible to developing a disease or condition. The prevention may also be partial, such that the occurrence of pathology of a condition in a subject is less than that which would have occurred without the present disclosure. The term "ameliorate" as used herein can refer to decrease, suppress, attenuate, diminish, arrest, or stabilize the development or progression of a disease.

By "treating or preventing a condition" is meant ameliorating any of the conditions or signs or symptoms associated with the disorder before or after it has occurred. For example, as compared with an equivalent untreated control, alleviating a symptom of a disorder may involve reduction or degree of prevention at least 3%, 5%, 10%, 20%, 40%, 50%, 60%, 80%, 90%, 95%, 98%, 99%, 99.5%, 99.9%, or 100% as measured by any standard technique. In some embodiments, alleviating a symptom of a disorder may involve reduction or degree of prevention by at least 2 fold, at least 3 fold, at least 4 fold, at least 5 fold, at least 10 fold, at least 20 fold, at least 25 fold, at least 30 fold, at least 40 fold, at least 50 fold, at least 60 fold, at least 70 fold, at least 80 fold, at least 90 fold, at least 100 fold, at least 200 fold, at least 300 fold, at least 400 fold, at least 500 fold, at least 600 fold, at least 700 fold, at least 800 fold, at least 900 fold, at least 1000 fold, at least 2000 fold, at least 3000 fold, at least 4000 fold, at least 5000 fold, at least 6000 fold, at least 7000 fold, at least 8000 fold, at least 9000 fold, or at least 10000 fold as compared with an equivalent untreated control.

A patient who is being treated for a condition, a disease or a disorder is one who a medical practitioner has diagnosed as having such a condition. Diagnosis may be by any suitable means. Diagnosis and monitoring may involve, for example, detecting the presence of diseased, dying or dead cells in a biological sample (e.g., tissue biopsy, blood test, or urine test), detecting the presence of plaques, detecting the level of a surrogate marker in a biological sample, or detecting symptoms associated with a condition. A patient in whom the development of a condition is being prevented may or may not have received such a diagnosis. One in the art will understand that these patients may have been subjected to the same standard tests as described above or may have been identified, without examination, as one at high risk due to the presence of one or more risk factors (e.g., family history or genetic predisposition).

A "subject" or "subject in need thereof", refers to an individual who has a disease, a symptom of the disease, or a predisposition toward the disease, with the purpose to cure, heal, alleviate, relieve, alter, remedy, ameliorate, improve, or affect the disease, the symptom of the disease, or the predisposition toward the disease. In some embodiments, the subject has hypercholesterolemia. In some embodiments, the subject has atherosclerotic vascular disease. In some embodiments, the subject has hypertriglyceridemia. In some embodiments, the subject has diabetes. In some embodiments, the subject is a mammal. In some embodiments, the subject is a non-human primate. In some embodiments, the subject is human. Alleviating a disease includes delaying the development or progression of the disease, or reducing disease severity. Alleviating the disease does not necessarily require curative results.

"Subjects" and "patients" encompasses mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like.

As used therein, "delaying" the development of a disease means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset.

As used herein "onset" or "occurrence" of a disease includes initial onset and/or recurrence. Conventional methods, known to those of ordinary skill in the art of medicine, can be used to administer the isolated polypeptide or pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir.

"Administering" and its grammatical equivalents as used herein can refer to providing one or more pharmaceutical compositions described herein to a subject or a patient. By way of example and without limitation, "administering" can be performed by intravenous (i.v.) injection, sub-cutaneous (s.c.) injection, intradermal (i.d.) injection, intraperitoneal (i.p.) injection, intramuscular (i.m.) injection, intravascular injection, infusion (inf.), oral routes (p.o.), topical (top.) administration, or rectal (p.r.) administration. One or more such routes can be employed. Parenteral administration can be, for example, by bolus injection or by gradual perfusion over time.

The therapeutic methods of the disclosure may be carried out on subjects displaying pathology resulting from a disease or a condition, subjects suspected of displaying pathology resulting from a disease or a condition, and subjects at risk of displaying pathology resulting from a disease or a condition. For example, subjects that have a genetic predisposition to a disease or a condition can be treated prophylactically. Subjects exhibiting symptoms associated with a condition, a disease or a disorder may be treated to decrease the symptoms or to slow down or prevent further progression of the symptoms. The physical changes associated with the increasing severity of a disease or a condition are shown herein to be progressive. Thus, in embodiments of the disclosure, subjects exhibiting mild signs of the pathology associated with a condition or a disease may be treated to improve the symptoms and/or prevent further progression of the symptoms.

In some embodiments, the subject exhibits an elevated blood LDL cholesterol level, a reduced blood HDL cholesterol level, and/or a reduced blood triglycerides level as compared to before the administration.

In some embodiments, after the administration, the subject exhibits a reduced blood low-density lipoprotein (LDL) cholesterol level by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 98%, at least 99%, at least 99.5%, at least 99.9%, or 100% as compared to before the administration. In some embodiments, after the administration, the subject exhibits a reduced blood low-density lipoprotein (LDL) cholesterol level by at least 2 fold, at least 3 fold, at least 4 fold, at least 5 fold, at least 10 fold, at least 20 fold, at least 25 fold, at least 30 fold, at least 40 fold, at least 50 fold, at least 60 fold, at least 70 fold, at least 80 fold, at least 90 fold, at least 100 fold, at least 200 fold, at least 300 fold, at least 400 fold, at least 500 fold, at least 600 fold, at least 700 fold, at least 800 fold, at least 900 fold, at least 1000 fold, at least 2000 fold, at least 3000 fold, at least 4000 fold, at least 5000 fold, at least 6000 fold, at least 7000 fold, at least 8000 fold, at least 9000 fold, or at least 10000 fold as compared to before the administration.

In some embodiments, after the administration, the subject exhibits a reduced blood triglycerides level by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 98%, at least 99%, at least 99.5%, at least 99.9%, or 100% as compared to before the administration. In some embodiments, after the administration, the subject exhibits a reduced blood triglycerides level by at least 2 fold, at least 3 fold, at least 4 fold, at least 5 fold, at least 10 fold, at least 20 fold, at least 25 fold, at least 30 fold, at least 40 fold, at least 50 fold, at least 60 fold, at least 70 fold, at least 80 fold, at least 90 fold, at least 100 fold, at least 200 fold, at least 300 fold, at least 400 fold, at least 500 fold, at least 600 fold, at least 700 fold, at least 800 fold, at least 900 fold, at least 1000 fold, at least 2000 fold, at least 3000 fold, at least 4000 fold, at least 5000 fold, at least 6000 fold, at least 7000 fold, at least 8000 fold, at least 9000 fold, or at least 10000 fold as compared to before the administration.

The term "low-density lipoprotein (LDL)," as used herein, refers to a microscopic blob made up of an outer rim of lipoprotein and a cholesterol center. In some embodiments, LDL has a highly hydrophobic core composed of a polyunsaturated fatty acid known as linoleate and hundreds to thousands esterified and unesterified cholesterol molecules. In some embodiments, the core of LDL also carries triglycerides and other fats and is surrounded by a shell of phospholipids and unesterified cholesterol.

The term "high-density lipoprotein (HDL)," as used herein, refers to the smallest lipoprotein particles. In embodiments, plasma enzyme lecithin-cholesterol acyltransferase (LCAT) converts the free cholesterol into cholesteryl, which is then sequestered into the core of the lipoprotein particle, eventually causing the newly synthesized HDL to assume a spherical shape. In embodiments, HDL particles increase in size as they circulate through the bloodstream and incorporate more cholesterol and phospholipid molecules from cells and other lipoproteins.

The term "cholesterol," as used herein, refers to a lipid with a unique structure composed of four linked hydrocarbon rings forming the bulky steroid structure. The term "triglyceride," as used herein, refers to a tri-ester composed of a glycerol bound to three fatty acid molecules. In some embodiments, the fatty acids are saturated or unsaturated fatty acids.

In some embodiments, the condition is an atherosclerotic vascular disease, hypertriglyceridemia, or diabetes.

The term "atherosclerosis" or "atherosclerotic vascular disease," as used herein, refers to a disease in which the inside of an artery narrows due to the buildup of plaque. In some embodiments, it may result in coronary artery disease, stroke, peripheral artery disease, or kidney problems.

The term "hypertriglyceridemia," as used herein, refers to high (hyper-) blood levels (-emia) of triglycerides, the most abundant fatty molecule in most organisms. In some embodiments, elevated levels of triglycerides are associated with atherosclerosis, even in the absence of hypercholesterolemia (high cholesterol levels), and predispose to cardiovascular disease. In some embodiments, very high triglyceride levels increase the risk of acute pancreatitis. In some embodiments, hypertriglyceridemia is associated with overeating, obesity, diabetes mellitus and insulin resistance, excess alcohol consumption, kidney failure, nephrotic syndrome, genetic predisposition (e.g., familial combined hyperlipidemia, i.e., Type II hyperlipidemia), lipoprotein lipase deficiency, lysosomal acid lipase deficiency, cholesteryl ester storage disease, certain medications (e.g., isotretinoin, hydrochlorothiazide diuretics, beta blockers, protease inhibitors), hypothyroidism (underactive thyroid), systemic lupus erythematosus and associated autoimmune responses, glycogen storage disease type 1, propofol, or HIV medications.

The term "diabetes," as used herein, refers to a group of metabolic disorders characterized by a high blood sugar level over a prolonged period of time. In some embodiments, diabetes is type 1 diabetes that results from the pancreas's failure to produce enough insulin due to loss of beta cells. In some embodiments, diabetes is type 2 diabetes characterized by insulin resistance, a condition in which cells fail to respond to insulin properly. In some embodiments, diabetes is gestational diabetes that occurs when pregnant women without a previous history of diabetes develop high blood sugar levels.

As used herein, the term "effective amount" can be an amount sufficient to effect beneficial or desired results, such as beneficial or desired clinical results. An effective amount is also an amount that produces a prophylactic effect, e.g., an amount that delays, reduces, or eliminates the appearance of a pathological or undesired condition. An effective amount can be administered in one or more administrations. In terms of treatment, an "effective amount" of a composition of the disclosure is an amount that is sufficient to palliate, ameliorate, stabilize, reverse or slow the progression of a disease or a condition, e.g., an atherosclerotic vascular disease, hyper-triglyceridemia, or diabetes. An "effective amount" may be of any of the compositions of the disclosure used alone or in conjunction with one or more agents used to treat a condition. An "effective amount" of a therapeutic agent within the meaning of the present disclosure will be determined by a patient's attending physician or veterinarian. Such amounts are readily ascertained by one of ordinary skill in the art and will a therapeutic effect when administered in accordance with the present disclosure. Factors which influence what a therapeutically effective amount will be include, the specific activity of the therapeutic agent being used, the type of disorder, time elapsed since the initiation of the disorder, and the age, physical condition, existence of other disease states, and nutritional status of the individual being treated. Additionally, other medication the patient may be receiving will affect the determination of the therapeutically effective amount of the therapeutic agent to administer.

The phrase "therapeutically effective amounts" used herein refers to the amount of agent needed to treat, ameliorate, or prevent a targeted disease or condition. An effective initial method to determine a "therapeutically effective amount" may be by carrying out cell culture assays (for example, using neuronal cells) or using animal models (for example, mice, rats, rabbits, dogs or pigs). A dose may be formulated in animal models to achieve a concentration range that includes the IC50 (i.e., the concentration of the composition which achieves a half-maximal inhibition of symptoms) as determined in cell culture. Such information can be used to more accurately determine useful doses in humans. In addition to determining the appropriate concentration range for a composition provided herein to be therapeutically effective, animal models may also yield other relevant information such as preferable routes of administration that will give maximum effectiveness. Adjusting the dose to achieve maximal efficacy in humans based on the methods described above and other methods is well within the capabilities of the ordinarily skilled artisan. A "patient" as used in herein refers to the subject who is receiving treatment by administration of the composition of interest.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Adjustment and manipulation of established dosages (e.g., frequency and duration) are well within the ability of those skilled in the art. The treatment, such as those disclosed herein, can be administered to the subject on a daily, twice daily, biweekly, monthly or any applicable basis that is therapeutically effective. In embodiments, the treatment is only on an as-needed basis, e.g., upon appearance of signs or symptoms of a condition or a disease, e.g., an atherosclerotic vascular disease, hypertriglyceridemia, or diabetes.

The compositions described herein, may be administered to a subject in need thereof, in a therapeutically effective amount, to treat conditions related to high circulating cholesterol levels. Conditions related to high circulating cholesterol level that may be treated using the compositions and methods described herein include, without limitation: hyper-cholesterolemia, elevated total cholesterol levels, elevated low-density lipoprotein (LDL) levels, elevated blood LDL-cholesterol levels, reduced blood high-density lipoprotein cholesterol level, liver steatosis, coronary heart disease, vascular disease, ischemia, stroke, peripheral vascular disease, thrombosis, type 2 diabetes, hypertriglyceridemia, high elevated blood pressure, atherosclerosis, obesity, Alzheimer's disease, neurodegeneration, and combinations thereof. The compositions and methods disclosed herein are effective in reducing the circulating cholesterol level in the subject, thus treating the conditions. The compositions and methods disclosed herein are effective in reducing blood LDL cholesterol level, and/or a reducing blood triglycerides level as compared to before the administration.

Toxicity and therapeutic efficacy of the compositions of the disclosure can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects (the ratio LD50/ED50) is the therapeutic index. Agents that exhibit high therapeutic indices are preferred. The dosage of agents lies preferably within a range of circulating concentrations that include the ED50 with little or no toxicity. While agents that exhibit toxic side effects may be used, care should be taken to design a delivery system that targets such agents to the site of affected tissue in order to minimize potential damage to uninfected cells and, thereby, reduce side effects.

The skilled artisan will appreciate that certain factors may influence the dosage and frequency of administration required to effectively treat a subject, including but not limited to the severity of the disease or disorder, previous treatments, the general characteristics of the subject including health, sex, weight and/or age of the subject, and other diseases present. Moreover, treatment of a subject with a therapeutically effective amount of the compositions can include a single treatment or, preferably, can include a series of treatments. It will also be appreciated that the effective dosage of the composition of the disclosure used for treatment may increase or decrease over the course of a particular treatment. Changes in dosage may result and become apparent from the results of diagnostic assays as described herein. The therapeutically effective dosage will generally be dependent on the patient's status at the time of administration. The precise amount can be determined by routine experimentation but may ultimately lie with the judgment of the clinician, for example, by monitoring the patient for signs of disease and adjusting the treatment accordingly.

Frequency of administration may be determined and adjusted over the course of therapy, and is generally, but not necessarily, based on treatment and/or suppression and/or amelioration and/or delay of a disease. Alternatively, sustained continuous release formulations of a polypeptide or a polynucleotide may be appropriate. Various formulations and devices for achieving sustained release are known in the art. In some embodiments, dosage is daily, every other day, every three days, every four days, every five days, or every six days. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays.

The methods and compositions of the disclosure described herein including embodiments thereof can be administered with one or more additional therapeutic regimens or agents or treatments, which can be co-administered to the mammal. By "co-administering" is meant administering one or more additional therapeutic regimens or agents or treatments and the composition of the disclosure sufficiently close in time to enhance the effect of one or more additional therapeutic agents, or vice versa. In this regard, the composition of the disclosure described herein can be administered simultaneously with one or more additional therapeutic regimens or agents or treatments, at a different time, or on an entirely different therapeutic schedule (e.g., the first treatment can be daily, while the additional treatment is weekly). For example, in embodiments, the secondary therapeutic regimens or agents or treatments are administered simultaneously, prior to, or subsequent to the composition of the disclosure.

Kits

One aspect of the disclosure relates to kits including the compositions comprising a single guide RNA as provided herein, the complex as provided herein, the composition as provided herein, or the lipid nanoparticle as provided herein for treating or preventing a condition. The kits can further include one or more additional therapeutic regimens or agents for treating or preventing a condition.

Also disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include the composition of the disclosure, and optionally in addition with therapeutic regimens or agents disclosed herein. Such kits optionally include an identifying description or label or instructions relating to its use in the methods described herein.

A kit typically includes labels listing contents and/or instructions for use, and package inserts with instructions for use. A set of instructions will also typically be included.

In embodiments, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

EXAMPLE

These examples that follow are provided for illustrative purposes only and not to limit the scope of the claims provided herein.

In Vitro Analysis of Cas12b

Plasmids encoding Cas12b orthologs derived from *Bacillus hisashii* (BbCas12b) and *Bacillus* sp. V3-13 (BvCas12b) (Addgene #236181, 122446) were transfected in HEK293 at a 1:1 ratio with guides cloned to target ANGPTL3 (Addgene #122447, 122448). The protospacers are detailed in Table 2. Guide RNAs were screened for on-target activity using one or more techniques: 1) sanger sequencing, to identify evidence of insertions or deletions; 2) CEL I enzymatic mutation detection assay (surveyor nuclease assay), according to manufacturer's instructions (IDT).

Figure 15:
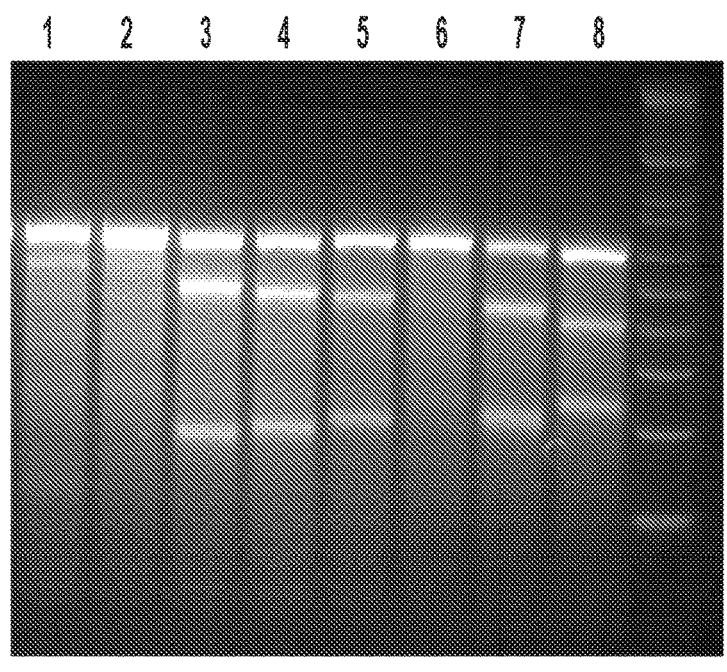
FIG. 15 shows the results from a CEL I enzymatic mutation detection assay (surveyor nuclease assay). HEK293 cells were transfected 1:1 with a plasmid encoding Cas12b and a plasmid encoding the gRNA depicted. The genomic DNA was harvested and PCR amplified at the target region. After performing the Surveyor nuclease assay per manufacturer's instructions, the PCR amplicons were separated and visualized on an agarose gel. Editing of target sites is identified by cleavage bands below the top amplicon band.
Figure 16:
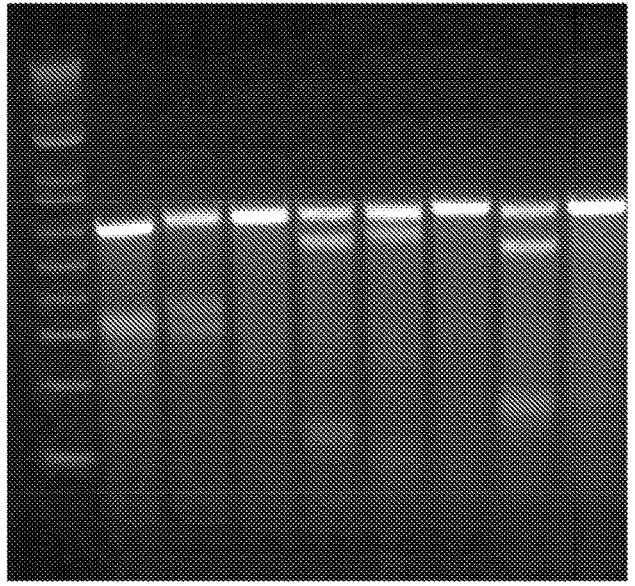
FIG. 16 shows the results from a CEL I enzymatic mutation detection assay (surveyor nuclease assay). HEK293 cells were transfected 1:1 with a plasmid encoding Cas12b and a plasmid encoding the gRNA depicted. The genomic DNA was harvested and PCR amplified at the target region. After performing the Surveyor nuclease assay per manufacturer's instructions, the PCR amplicons were separated and visualized on an agarose gel. Editing of target sites is identified by cleavage bands below the top amplicon band.
Figure 17:
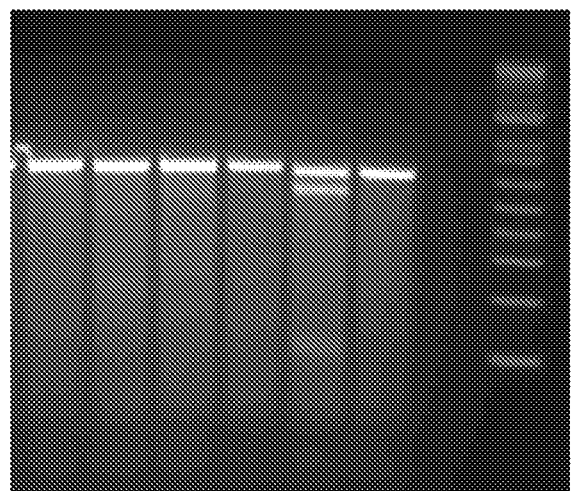
FIG. 17 shows the results from a CEL I enzymatic mutation detection assay (surveyor nuclease assay). HEK293 cells were transfected 1:1 with a plasmid encoding Cas12b and a plasmid encoding the gRNA depicted. The genomic DNA was harvested and PCR amplified at the target region. After performing the Surveyor nuclease assay per manufacturer's instructions, the PCR amplicons were separated and visualized on an agarose gel. Editing of target sites is identified by cleavage bands below the top amplicon band.

Several sites were identified to have significant on-target editing efficiency. By sanger sequencing, notable examples include hANG_CasA2b3 hANG_CasA2b5T hANG_Cas12b_7 hANG_Cas12b_14 hANG_Cas12b_33 hANG_Cas12b_34C hANG_Cas12b_42 hANG_Cas12b_64 hANG_Cas12b_82 hANG_Cas12b_84 hANG_Cas12b_87 hANG_Cas12b_88 hANG_Cas12b95 and hANG_Cas12b_117 (FIGS. 1-14). By surveyor nuclease assay, notable examples include hANG_CasT2b_1 hANG_CasC2b_3 hANG_Cas12b_4 hANG_Cas12b_5 hANG_Cas12b_7 hANG_Cas12b_8C hANG_Cas12b_10 hANG_Cas12b_11 hANG_Cas12b_131 hANG_Cas12b_14 hANG_Cas12b_16 and hANG_Cas12b_28 (FIGS. 15-17).

TABLE 2

Plasmid guides used for in vitro analysis

| Guide | Target | SEQ ID NO: | Protospacer (5'-3') | Editor Screened |
|---|---|---|---|---|
| hANG_Cas12b_1 | hANGPTL3 | 112 | AAAATCAAGATAAAAATGTTCAC | BvCas12b |
| hANG_Cas12b_2 | hcANGPTL3 | 113 | AGCTCCTTCTTTTTATTGTTCCT | BvCas12b |
| hANG_Cas12b_3 | hANGPTL3 | 114 | CCTCCAGAATTGATCAAGACAAT | BvCas12b |
| hANG_Cas12b_4 | hANGPTL3 | 115 | ATCAAGACAATTCATCATTTGAT | BvCas12b |
| hANG_Cas12b_5 | hANGPTL3 | 116 | ATCATTTGATTCTCTATCTCCAG | BvCas12b |
| hANG_Cas12b_6 | hANGPTL3 | 117 | GATTCTCTATCTCCAGAGCCAAA | BvCas12b |
| hANG_Cas12b_7 | hANGPTL3 | 118 | TCTATCTCCAGAGCCAAAATCAA | BvCas12b |
| hANG_Cas12b_8 | hcANGPTL3 | 119 | GCTATGTTAGACGATGTAAAAAT | BvCas12b |
| hANG_Cas12b_10 | hcANGPTL3 | 120 | ATGACATATTTCAAAAACTCAAC | BhCas12b |
| hANG_Cas12b_11 | hcANGPTL3 | 92 | CAAAAACTCAACATATTTGATCA | BhCas12b |

TABLE 2-continued

Plasmid guides used for in vitro analysis

| Guide | Target | SEQ ID NO: | Protospacer (5'-3') | Editor Screened |
|-------|--------|------------|---------------------|-----------------|
| hANG_Cas12b_12 | hcANGPTL3 | 122 | GATCAGTCTTTTTATGATCTATC | BhCas12b |
| hANG_Cas12b_13 | hcANGPTL3 | 93 | TACTTCAACAAAAAGTGAAATAT | BhCas12b |
| hANG_Cas12b_14 | hcANGPTL3 | 94 | AGAAGAGCAACTAACTAACTTAA | BhCas12b, BvCas12b |
| hANG_Cas12b_15 | hANGPTL3 | 125 | AAAATCAACCTGAAACTCCAGAA | BhCas12b |
| hANG_Cas12b_16 | hcANGPTL3 | 95 | TGGAGGAAATAACTAGAGGAACA | BhCas12b |
| hANG_Cas12b_17 | hANGPTL3 | 127 | TCTTGATCAATTCTGGAGGAAAT | BhCas12b |
| hANG_Cas12b_22 | hANGPTL3 | 128 | ATTTGGCCCTTCGTCTTATGGAC | BhCas12b |
| hANG_Cas12b_23 | hANGPTL3 | 129 | CACTGGTTTGCAGCGATAGATCA | BhCas12b |
| hANG_Cas12b_24 | hcANGPTL3 | 130 | TTGACTTGTAGTTTATATGTAGT | BhCas12b |
| hANG_Cas12b_25 | hcANGPTL3 | 131 | TTTACCTCTTCATTTTTGACTTG | BhCas12b |
| hANG_Cas12b_26 | hcANGPTL3 | 132 | TTTCTTCTAGGAGGCTTTCAAGT | BhCas12b |
| hANG_Cas12b_27 | hcANGPTL3 | 133 | CACTTTTTGTTGAAGTAGAATTT | BhCas12b |
| hANG_Cas12b_28 | hcANGPTL3 | 134 | AGTTAGTTAGTTGCTCTTCTAAA | BhCas12b |
| hANG_Cas12b_29 | hcANGPTL3 | 135 | TGAATTAAGTTAGTTAGTTGCTC | BhCas12b |
| hANG_Cas12b_31 | hANGPTL3 | 136 | TTTTATCAGCTCAGAAGGACTAG | BhCas12b |
| hANG_Cas12b_33 | hcANGPTL3 | 96 | AAGAACCCACAGAAATTTCTCTA | BhCas12b |
| hANG_Cas12b_34 | hcANGPTL3 | 138 | CTCTATCTTCCAAGCCAAGAGCA | BhCas12b, BvCas12b |
| hANG_Cas12b_35 | hANGPTL3 | 139 | CTGTGGGTTCTTGAATACTAGTC | BvCas12b |
| hANG_Cas12b_36 | hANGPTL3 | 140 | AACTGAAGAAAGGGAGTAGTTCT | BhCas12b, BvCas12b |
| hANG_Cas12b_37 | hANGPTL3 | 141 | CATTCAACTGAAGAAAGGGAGTA | BhCas12b |
| hANG_Cas12b_38 | hANGPTL3 | 142 | CTTATTTCATTCAACTGAAGAAA | BhCas12b |
| hANG_Cas12b_41 | hANGPTL3 | 143 | TTATCTTGATTTTCAATTTCAAG | BhCas12b |
| hANG_Cas12b_42 | hcANGPTL3 | 90 | AACCAACAGCATAGTCAAATAAA | BhCas12b |
| hANG_Cas12b_43 | hcANGPTL3 | 145 | TCTATTTCTTTTATTTGACTATG | BhCas12b |
| hANG_Cas12b_45 | hANGPTL3 | 146 | GACTATGCTGTTGGTTTAATTGT | BhCas12b, BvCas12b |
| hANG_Cas12b_46 | hANGPTL3 | 147 | TTTATATTGGTCTTCCACGGTCT | BhCas12b, BvCas12b |
| hANG_Cas12b_47 | hANGPTL3 | 148 | GTCTTCCACGGTCTGGAGAAGGT | BhCas12b, BvCas12b |
| hANG_Cas12b_48 | hANGPTL3 | 149 | TCTTGTTTTTCTACAAAAGTCTG | BhCas12b |
| hANG_Cas12b_49 | hcANGPTL3 | 150 | TATTGATTCTAGGCATTCCTGCT | BhCas12b |
| hANG_Cas12b_54 | hANGPTL3 | 151 | TAGGCATTCCTGCTGAATGTACC | BhCas12b |
| hANG_Cas12b_55 | hANGPTL3 | 152 | CTGCTGAATGTACCACCATTTAT | BhCas12b |
| hANG_Cas12b_56 | hANGPTL3 | 153 | ATAACAGAGGTGAACATACAAGT | BhCas12b |
| hANG_Cas12b_57 | hcANGPTL3 | 154 | AGCAGGAATGCCTAGAATCAATA | BhCas12b, BvCas12b |

TABLE 2-continued

Plasmid guides used for in vitro analysis

| Guide | Target | SEQ ID NO: | Protospacer (5'-3') | Editor Screened |
|---|---|---|---|---|
| hANG_Cas12b_58 | hcANGPTL3 | 155 | CATTCATTATATTCAGGTAGTCC | BhCas12b |
| hANG_Cas12b_59 | hcANGPTL3 | 156 | ATTATATTCAGGTAGTCCATGGA | BhCas12b |
| hANG_Cas12b_63 | hcANGPTL3 | 157 | TATTCAGGTAGTCCATGGACATT | BvCas12b |
| hANG_Cas12b_64 | hcANGPTL3 | 91 | AGGTAGTCCATGGACATTAATTC | BhCas12b, BvCas12b |
| hANG_Cas12b_65 | hcANGPTL3 | 159 | ATTCAACATCGAATAGATGGATC | BhCas12b, BvCas12b |
| hANG_Cas12b_69 | hcANGPTL3 | 160 | AACATCGAATAGATGGATCACAA | BhCas12b, BvCas12b |
| hANG_Cas12b_70 | hANGPTL3 | 161 | AATGTAGTCCCCTTACCATCAAG | BhCas12b |
| hANG_Cas12b_71 | hcANGPTL3 | 162 | GTAGTTCTCCCACGTTTCATTGA | BvCas12b |
| hANG_Cas12b_72 | hcANGPTL3 | 163 | AAGTTTTGTGATCCATCTATTCG | BhCas12b, BvCas12b |
| hANG_Cas12b_73 | hcANGPTL3 | 164 | GATGTTGAATTAATGTCCATGGA | BvCas12b |
| hANG_Cas12b_74 | hcANGPTL3 | 165 | ATGTCCATGGACTACCTGAATAT | BvCas12b |
| hANG_Cas12b_78 | hcANGPTL3 | 166 | AGTTGGAAGACTGGAAAGACAAC | BhCas12b |
| hANG_Cas12b_79 | hcANGPTL3 | 167 | TATTGAATATTCTTTTTACTTGG | BhCas12b |
| hANG_Cas12b_80 | hcANGPTL3 | 168 | AATATTCTTTTTACTTGGGAAAT | BhCas12b |
| hANG_Cas12b_81 | hcANGPTL3 | 169 | TTTTTACTTGGGAAATCACGAAA | BhCas12b |
| hANG_Cas12b_82 | hcANGPTL3 | 97 | CTGGCAATGTCCCCAATGCAATC | BhCas12b, BvCas12b |
| hANG_Cas12b_84 | hcANGPTL3 | 98 | CATTGGGGACATTGCCAGTAATC | BhCas12b, BvCas12b |
| hANG_Cas12b_85 | hANGPTL3 | 172 | GGGACATTGCCAGTAATCGCAAC | BhCas12b |
| hANG_Cas12b_86 | hANGPTL3 | 173 | CCAGTAATCGCAACTAGATGTAG | BvCas12b |
| hANG_Cas12b_87 | hcANGPTL3 | 99 | CCCAAGTAAAAAGAATATTCAAT | BhCas12b, BvCas12b |
| hANG_Cas12b_88 | hcANGPTL3 | 100 | AATATAATGTTTGTTGTCTTTCC | BhCas12b, BvCas12b |
| hANG_Cas12b_89 | hANGPTL3 | 176 | GTAAAACATAATTAGATTGCTTC | BhCas12b, BvCas12b |
| hANG_Cas12b_89 | hANGPTL3 | 176 | GTAAAACATAATTAGATTGCTTC | BvCas12b |
| hANG_Cas12b_90 | hcANGPTL3 | 177 | GATTGCTTCACTATGGAGTATAT | BhCas12b, BvCas12b |
| hANG_Cas12b_91 | hcANGPTL3 | 178 | CTTCACTATGGAGTATATCTTCT | BhCas12b |
| hANG_Cas12b_93 | hANGPTL3 | 179 | TCTTGGAAGTCTCAAAATGGAAG | BhCas12b |
| hANG_Cas12b_95 | hcANGPTL3 | 180 | GCCTCAGTTCATTCAAAGCTTTC | BhCas12b |
| hANG_Cas12b_99 | hANGPTL3 | 181 | TGAGACTTCCAAGATAATCCTCT | BhCas12b |
| hANG_Cas12b_101 | hcANGPTL3 | 182 | ACCATTTAGGTTGTTTTCTCCAC | BhCas12b |
| hANG_Cas12b_104 | hcANGPTL3 | 183 | ATTGTTCCTCTAGTTATTTCCTC | BvCas12b |
| hANG_Cas12b_105 | hcANGPTL3 | 184 | TTGTTCCTCTAGTTATTTCCTCC | BvCas12b |
| hANG_Cas12b_111 | hANGPTL3 | 185 | TCCATAAGACGAAGGGCCAAATT | BvCas12b |

TABLE 2-continued

| | | | | |
|---|---|---|---|---|
| | | Plasmid guides used for in vitro analysis | | |
| Guide | Target | SEQ ID NO: | Protospacer (5'-3') | Editor Screened |
| hANG_Cas12b_114 | hANGPTL3 | 186 | TATGATCTATCGCTGCAAACCAG | BhCas12b |
| hANG_Cas12b_115 | hANGPTL3 | 187 | ATGATCTATCGCTGCAAACCAGT | BvCas12b |
| hANG_Cas12b_117 | hcANGPTL3 | 101 | GAAGAGCAACTAACTAACTTAAT | BhCas12b |
| hANG_Cas12b_130 | hcANGPTL3 | 189 | GAGTTGAGTTCAAGTGACATATT | BhCas12b |

Synthesis of Guide RNAs (sgRNA or gRNA)

With high on-target editing efficiency in HEK293 cells, the hANG_Cas12b_42 protospacer, 5'-AACCAACAGCAT-AGTCAAATAAA-3' (SEQ ID NO: 90), was used for further sequence optimization. A structure-based approach was used to: 1) identify bases where 2'-O-methyl could be added to offer stability to the gRNA, while not causing steric hindrance with either the protein or gRNA; 2) introduce changes to the gRNA sequence to improve stability and/or improve nuclease activity (FIG. 18). The designed guide sequences are described in Table 1.

Primary hepatocytes were transfected with Cas12b mRNA and gRNA as described in detailed methods. Table 3 shows the results of Cas12b nuclease mediated in vitro gene editing in human primary hepatocytes. Many gRNA sequences showed editing efficiency that is equivalent or similar to a gRNA considered having minimal modifications, GB0001. These include GB0002, GB0004, GB0006, GB0007, GB0008, and GB0009. It is contemplated that these chemically-modified gRNAs offer improved stability and/or half-life as compared to an unmodified gRNA having the same nucleotide sequence, with little to no loss of editing efficiency.

TABLE 3

| | Cas12b nuclease mediated in vitro gene editing in human primary hepatocytes | | | |
|---|---|---|---|---|
| | | | Editing % | |
| gRNA | Cell Type | 2500 ng/mL | 500 ng/mL | 100 ng/mL |
| GB0001 | Human PH | ND | 47.74 | 15.30 |
| GB0002 | Human PH | 62.23 | 51.14 | 21.06 |
| GB0003 | Human PH | 55.66 | 35.58 | 11.15 |
| GB0004 | Human PH | 60.21 | 34.68 | 12.16 |
| GB0005 | Human PH | ND | 51.15 | 8.54 |
| GB0006 | Human PH | 55.54 | 20.38 | 5.34 |
| GB0007 | Human PH | 59.60 | 46.97 | 15.64 |
| GB0008 | Human PH | 59.05 | 38.78 | 18.87 |
| GB0009 | Human PH | 58.16 | 24.30 | 8.05 |
| GB0010 | Human PH | 37.30 | 19.84 | 6.79 |
| GB0011 | Human PH | 39.84 | 12.02 | 3.35 |
| GB0012 | Human PH | 2.00 | 10.97 | 5.25 |
| GB0013 | Human PH | 43.59 | 11.68 | 2.87 |
| GB0014 | Human PH | 38.54 | 19.01 | 5.98 |
| GB0015 | Human PH | 52.80 | 25.72 | 12.98 |
| GB0016 | Human PH | 40.09 | 24.97 | 3.58 |
| GB0017 | Human PH | 34.16 | 14.40 | 6.94 |
| GB0018 | Human PH | 37.00 | 12.10 | 2.39 |
| GB0019 | Human PH | 40.03 | 13.29 | 6.36 |
| GB0020 | Human PH | 38.45 | 0.09 | 0.11 |
| GB0021 | Human PH | 0.05 | 0.09 | 0.06 |

Detailed Methods gRNA synthesis: The guide RNA GB0001 to GB0021 set forth in Table 1 were synthesized under solid phase oligo-nucleotide synthesis and deprotection conditions using controlled pore glass support and commercially available phosphoramidite monomers and oligonucleotide synthesis reagents (see, e.g., Methods in Molecular Biology, 1993, 20, 81-114; ACS Chem. Biol. 2015, 10, 1181-1187, of which entire contents are incorporated herein by reference). The deprotected guide RANs were purified by HPLC and the integrity of each guide RNA was confirmed by mass spectrometric analysis. The observed mass of each guide RNA was conformed to calculated mass.

mRNA synthesis: mRNA for Cas12b was produced by methods well known in the art. One of such methods used herein was in vitro transcription (IVT) using T7 polymerase or additional RNA polymerase variants. Typically, IVT of mRNA uses a linearized DNA template that comprises a T7 polymerase promoter, mRNA coding sequence (CDS), 3' and 5' untranslated regions (UTRs), poly A tail, and additional replication and transcription regulatory elements. Prior to IVT, the DNA template was in the form of a plasmid, PCR product, or additional double-stranded DNA construct. A typical IVT reaction includes T7 polymerase, DNA template, RNase inhibitor, cap analog, inorganic pyrophosphatase, and naturally occurring ribonucleotides (rNTPs) such as GTP, ATP, CTP, UTP, or substitutions of natural rNTPs with modified rNTPs such as pseudouridine, N1-methylpseudouridine, 5-methyl cytidine, 5-methoxyuridine, N6-methyl adenosine, and N4-acetylcytidine. The cap analog was a dinucleotide or trinucleotide cap structure with the first initiating nucleotide containing standard 2'-hydroxyl group, 2'-O-methyl group, or additional 2' chemical modification. Cap analog also was added after the IVT reaction using a vaccinia capping enzyme. After IVT, in some cases DNase was added to the transcription mixture to remove DNA template; alternatively, residual DNA was removed by ion exchange column chromatography. Purification and concentration of mRNA were performed with ion exchange chromatography, affinity chromatography, precipitation, ion-pairing reverse-phase chromatography, enzymatic reactions, size exclusion chromatography, and/or tangential flow filtration. Similar IVT and purification process were used to produce mRNA encoding Cas12b. The DNA template, reaction conditions, and purification parameters were optimized for the specific gene of interest, i.e., ANGPTL3. In some examples, capped and polyadenylated mRNA were obtained from commercially sources (TnLink, for e.g.).

Primary Hepatocyte Cell Culture Conditions: Primary human liver hepatocytes (PHH) were cultured per the manufacturer's protocol. In accordance therewith, the cells were thawed and resuspended in hepatocyte thawing medium followed by centrifugation at 100 g for 10 min at 4° C. The supernatant was discarded, and the pelleted cells resuspended in hepatocyte plating medium. Each vial contained approximately 5 million cells that were used for plating one 24-well plate. Plated cells were allowed to settle and adhere for 4-6 h in a tissue culture incubator at 37° C. under 5% $CO_2$ atmosphere. After incubation, cells were checked for monolayer formation. The incubating media was then replaced with fresh hepatocyte maintenance media (complete INVITROGRO medium obtained from BioIVT, the cell line provider). The cells thus became ready for transfection.

Cloning Guide Plasmids: Plasmids were generated by annealing a DNA oligonucleotide containing the desired protospacer sequence. After expansion of the plasmid in bacteria, plasmids were purified and sequence confirmed.

Transfection of HEK293 cells: Cells were transfected using Mirus Transit-2020 transfection reagent per manufacturer's instructions. A plasmid encoding Cas12b and a plasmid containing the gRNA sequence were transfected at a 1:1 ratio. Cells were allowed to proliferate for 48-72 hours, and gDNA was isolated using the Qiagen DNEasy Blood & Tissue kit per manufacturer's instructions.

Transfection of Primary Cells: MessengerMAX from Thermo Fisher was used for transfection. Solution A: desired amount of guide RNA is mixed with 1:1 wt ratio of mRNA in OptiMEM. Solution B: MessengerMAX in OptiMEM. After mixing solutions A and B, the mixture was incubated at room temperature for 20 min. 60 μL of the incubated solution was added dropwise to each cell wells. The cells were then allowed to remain at 37° C. for 3 days. Cells were harvested and prepared for genomic DNA extraction using a Thermo Kingfisher extraction instrument. Extracted genomic DNA was processed by PCR to analyze for gene editing. Amplified PCR product was then subjected to next generation sequencing (NGS) on an Illumina MiSeq.

Next Generation Sequencing: Next generation sequencing, or deep sequencing, was performed on the region of interest to determine the extent of gene editing. Samples were prepare using the Nextera XT DNA library preparation kit (Illumina) according to the manufacturer's protocol. Briefly, two rounds of PCR were performed first to amplify the region of interest and second to add DNA sequences required for deep sequencing and sample identification to the initial product. The final amplicon was sequenced on the Illumina MiSeq instrument according to the manufacturer's protocol.

Bioinformatic Analysis: Paired-end reads were analyzed with the CRISPResso2 pipeline (nature.com/articles/s41587-019-0032-3). Briefly, low-quality reads were filtered out, adapter sequences were trimmed from the reads, and the paired-end reads were merged and aligned to the amplicon sequence. The editing percentage was calculated as the number of reads supporting an insertion or a deletion, over the total number of aligned reads. For Cas12b, the editing percentage was calculated as the number of reads supporting an insertion or a deletion, over the total number of aligned reads.

All patents and publications mentioned in this specification are herein incorporated by reference to the same extent as if each independent patent and publication was specifically and individually indicated to be incorporated by reference.

OTHER EMBODIMENTS

From the foregoing description, it will be apparent that variations and modifications may be made to the disclosure described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment, any portion of the embodiment, or in combination with any other embodiments or any portion thereof.

As is set forth herein, it will be appreciated that the disclosure comprises specific embodiments and examples of chemically modified guide polynucleotides (e.g., guide RNAs, single guide RNAs, crRNAs, tracrRNAs, etc.) including compositions that comprise such guide polynucleotides, designs and modifications thereto; and specific examples and embodiments describing the synthesis, manufacture, use, and efficacy of the foregoing individually and in combination including as pharmaceutical compositions for treating disease and for in vivo and in vitro delivery of active agents to mammalian cells under described conditions.

While specific examples and numerous embodiments have been provided to illustrate aspects and combinations of aspects of the foregoing, it should be appreciated and understood that any aspect, or combination thereof, of an exemplary or disclosed embodiment may be excluded therefrom to constitute another embodiment without limitation and that it is contemplated that any such embodiment can constitute a separate and independent claim. Similarly, it should be appreciated and understood that any aspect or combination of aspects of one or more embodiments may also be included or combined with any aspect or combination of aspects of one or more embodiments and that it is contemplated herein that all such combinations thereof fall within the scope of this disclosure and can be presented as separate and independent claims without limitation. Accordingly, it should be appreciated that any feature presented in one claim may be included in another claim; any feature presented in one claim may be removed from the claim to constitute a claim without that feature; and any feature presented in one claim may be combined with any feature in another claim, each of which is contemplated herein. The following enumerated clauses are further illustrative examples of aspects and combination of aspects of the foregoing embodiments and examples:

1. A chemically modified single guide RNA for a Cas12b protein that comprises (i) a spacer sequence and (ii) a tracr sequence that serves as a binding scaffold for the Cas12b protein, wherein the spacer sequence is complementary to a polynucleotide sequence of a gene of interest and wherein the single guide RNA comprises one or more chemical modifications.

2. The chemically modified single guide RNA of clause 1, wherein one or more of the chemical modifications is in the spacer sequence.

3. The chemically modified single guide RNA of clause 1, wherein one or more of the chemical modifications is in the tracr sequence.

4. The chemically modified single guide RNA of clause 3, wherein one or more of the chemical modifications is in a stem loop structure of the tracr sequence.

5. The chemically modified single guide RNA of clause 1, wherein the chemical modifications are in the spacer and tracr sequences.

6. The chemically modified single guide RNA of any one of clauses 1-5, wherein the single guide RNA comprises one or more unmodified nucleotides.

7. The chemically modified single guide RNA of clause 6, wherein one or more of the unmodified nucleotides comprises a 2'-hydroxyl that is in a region of the tracr sequence that serves as a binding scaffold for the Cas12b protein and is in close proximity to the Cas12b protein when the Cas12b protein is bound to the tracr sequence.

8. The chemically modified single guide RNA of clause 6, wherein one or more of the unmodified nucleotides comprises a 2'-hydroxyl that binds with the Cas12b protein when the Cas12b protein is bound to the tracr sequence.

9. The chemically modified single guide RNA of clause 6, wherein one or more of the unmodified nucleotides comprises a 2'-hydroxyl that is in close proximity with a unmodified nucleotide in the single guide RNA.

10. The chemically modified single guide RNA of clause 6, wherein the one or more unmodified nucleotides is at one or more nucleotide positions selected from positions 4, 6-15, 17-20, 22-24, 27, 28, 31-43, 46-48, 51-61, 64-66, 70, 71, 73, 74, 77, 78, 80, 81, and 85-116 as numbered in SEQ ID NO: 1 or a corresponding position or combination of corresponding positions thereof.

11. The chemically modified single guide RNA of clause 6, wherein the one or more unmodified nucleotides is at one or more nucleotide positions selected from positions 4, 6-15, 17-20, 22-24, 27, 28, 31, 32, 34, 36, 38, 40-43, 46, 48, 52-61, 64, 66, 70, 71, 73, 74, 77, 78, 80, 81, 85, 88, 90, 91, 93, 94 and 96-116 as numbered in SEQ ID NO: 1 or a corresponding position or combination of corresponding positions thereof.

12. The chemically modified single guide RNA of clause 6, wherein the one or more unmodified nucleotides is at one or more nucleotide positions selected from positions 8-10, 12-15, 22-24, 32-38, 40, 41, 43, 44, 53-56, 63, 66-69 and 88-116 as numbered in SEQ ID NO: 1 or a corresponding position or combination of corresponding positions thereof.

13. The chemically modified single guide RNA of clause 6, wherein the one or more unmodified nucleotides is at one or more nucleotide positions selected from positions 8-10, 12-15, 22-24, 32-44, 53-56, 63, 66-69 and 88-116 as numbered in SEQ ID NO: 1 or a corresponding position or combination of corresponding positions thereof.

14. The chemically modified single guide RNA of any one of clauses 1-9, wherein the one or more chemical modifications is at one or more nucleotide positions selected from positions 1-3, 5, 16, 21, 25, 29, 30, 44, 45, 49, 50, 62, 63, 67-69, 72, 75, 76, 79, 82-84 and 117-120 as numbered in SEQ ID NO: 1 or a corresponding position or combination of corresponding positions thereof.

15. The chemically modified single guide RNA of any one of clauses 1-9, wherein the one or more chemical modifications is at one or more nucleotide positions selected from positions 1, 2, 3, 5, 16, 21, 25, 29, 30, 33, 35, 37, 39, 44, 45, 47, 49-51, 62, 63, 65, 67-69, 72, 75, 76, 79, 82-84, 86, 87, 89, 92, 95 and 117-120 as numbered in SEQ ID NO: 1 or a corresponding position or combination of corresponding positions thereof.

16. The chemically modified single guide RNA of any one of clauses 1-9, wherein the one or more chemical modifications is at one or more nucleotide positions selected from positions 1-7, 11, 16-21, 25-31, 45-52, 57-62, 64, 65, 70-87 and 117-120 as numbered in SEQ ID NO: 1 or a corresponding position or combination of corresponding positions thereof.

17. The chemically modified single guide RNA of any one of clauses 1-9, wherein the one or more chemical modification is at one or more nucleotide positions selected from positions 1-7, 11, 16-21, 25-31, 39, 42, 45-52, 57-62, 64, 65, 70-87, and 117-120 as numbered in SEQ ID NO: 1 or a corresponding position or combination of corresponding positions thereof.

18. The chemically modified single guide RNA of any one of clauses 1-17 wherein one or more of the chemical modifications comprises a 2'-OMe modification.

19. The chemically modified single guide RNA of any one of clauses 1-17 wherein one or more of the chemical modifications comprises a nebularine.

20. The chemically modified single guide RNA of any one of clauses 1-17, wherein one or more of the chemical modifications comprises a deoxynebularine.

21. The chemically modified single guide RNA of any one of clauses 1-17, wherein one or more of the chemical modifications comprises a 2'-O-methylnebularine.

22. The chemically modified single guide RNA of any one of clauses 1-17, wherein one or more of the chemical modifications comprises a phosphorothioate linkage.

23. The chemically modified single guide RNA of any one of clauses 1-17, wherein the single guide RNA comprises a phosphorothioate linkage at a 5' end or at a 3' end.

24. The chemically modified single guide RNA of clause 23, wherein the single guide RNA comprises two and no more than two contiguous phosphorothioate linkages at the 5' end.

25. The chemically modified single guide RNA of clause 23, wherein the single guide RNA comprises two and no more than two contiguous phosphorothioate linkages at the 3' end.

26. The chemically modified single guide RNA of clause 23, wherein the single guide RNA comprises two and no more than two contiguous phosphorothioate linkages at the 5' end and 3' end.

27. The chemically modified single guide RNA of clause 23, wherein the single guide RNA comprises three phosphorothioate linkages at the 3' end.

28. The chemically modified single guide RNA of clause 23, wherein the single guide RNA comprises three phosphorothioate linkages at the 5' end.

29. The chemically modified single guide RNA of clause 23, wherein the single guide RNA comprises three and no more than three contiguous phosphorothioate linkages at the 5' end and 3' end.

30. The chemically modified single guide RNA of clause 23, wherein the single guide RNA comprises three phosphorothioate linkages at the 5' end and two phosphorothioate linkages at the 3' end.

31. The chemically modified single guide RNA of clause 23, wherein the single guide RNA comprises two phosphorothioate linkages at the 5' end and three phosphorothioate linkages at the 3' end.

32. The chemically modified single guide RNA of clause 27, wherein the single guide RNA comprises the 5'-NsNsN-3', 5'-NsNsNsS-3', 5'-nsnsnsn-3', or 5'-nsnsn-3' at the 3' end, wherein N independently is an unmodified nucleotide adenosine, cytidine, guanosine or uridine; and n is a modified nucleotide adenosine, cytidine, guanosine or uridine, wherein the modification of the nucleotide is a 2'-H, 2'-OMe or nucleobase modification; and each s is a phosphorothioate linkage.

33. The chemically modified single guide RNA of clause 27, wherein the single guide RNA comprises the sequence 5'-UsUsU-3', 5'-UsUsUsU-3', 5'-usususu-3', or 5'-ususu-3' at the 3' end, wherein U is an unmodified uridine; and u is a modified uridine, wherein the modification of the uridine is a 2'-H, 2'-OMe or nucleobase modification; and each s is a phosphorothioate linkage.

34. The chemically modified single guide RNA of any one of clauses 1-33, wherein each one of the last four nucleotides at the 3'end of the single guide RNA comprises a 2'-OMe modification.

35. The chemically modified single guide RNA of any one of clauses 1-34, wherein the target polynucleotide sequence is in an ANGPTL3, PCSK9, APOC3, or Lp(a) gene.

36. The chemically modified single guide RNA of any one of clauses 1-34, wherein the target polynucleotide sequence is in an ANTPLT3 gene.

37. The chemically modified single guide RNA of any one of clauses 1-36, wherein the single guide RNA binds the Cas12b protein with increased binding affinity as compared to an unmodified single guide RNA.

38. The chemically modified single guide RNA of any one of clauses 1-37, wherein the tracr sequence comprises between 90 to 100 nucleotides.

39. The chemically modified single guide RNA of any one of clauses 1-37, wherein the tracr sequence comprises between 95 to 105 nucleotides.

40. The chemically modified single guide RNA of any one of clauses 1-37, wherein the tracr sequence comprises 97 nucleotides.

41. The chemically modified single guide RNA of any one of clauses 1-40, wherein the spacer sequence comprises between 20-30 nucleotides.

42. The chemically modified single guide RNA of any one of clauses 1-40, wherein the spacer sequence comprises between 20-25 nucleotides.

43. The chemically modified single guide RNA of any one of clauses 1-40, wherein the spacer sequence comprises 23 or 24 nucleotides.

44. A chemically modified single guide RNA for Cas12b protein that comprises (i) a spacer sequence having a length of 23 nucleotides and (ii) a tracr sequence having a length of 97 nucleotides, wherein the spacer sequence is complementary to a polynucleotide sequence of a gene of interest, wherein the tracr sequence serves as binding scaffold for the Cas12b protein, and wherein the single guide RNA comprises a chemical modification.

45. A chemically modified single guide RNA comprising a sequence selected from any one of SEQ ID NOs: 2-89, wherein the single guide RNA comprises one or more chemical modifications.

46. A chemically modified single guide RNA comprising a sequence of SEQ ID NO: 2, wherein the guide RNA comprises chemical modifications of the guide RNA of GB0002, GB0003, GB0007 or GB0008 of Table 1.

47. A chemically modified single guide RNA comprising a gRNA sequence of Table 1 wherein a, u, g, and c indicate 2'-OMe modified adenine, uridine, guanine, and cytidine, wherein s indicates a phosphorothioate linkage, wherein X indicates a nebularine, wherein x indicates a 2'-O-methylnebularine and wherein dX indicates a 2'-deoxynebularine.

48. A ribonucleoprotein complex comprising the chemically modified single guide RNA of any one of clauses 1-47 in complex with the Cas12b protein, wherein the complex comprises increased stability as compared to a complex with an unmodified single guide RNA and a Cas12b protein, wherein the stability is measured by half-life of the complex ex vivo or in vitro.

49. A cell comprising the ribonucleoprotein complex of clause 48.

50. A composition for gene modification comprising the chemically modified single guide RNA of any one of clauses 1-47 and a Cas12b protein or a nucleic acid sequence encoding the Cas12b protein.

51. The composition of clause 50 further comprising a vector that comprises the nucleic acid sequence encoding the Cas12b protein.

52. The composition of clause 50 or 51 further comprising a pharmaceutically acceptable carrier.

53. A lipid nanoparticle comprising the composition of any one of clauses 50-52.

54. A method for modifying a target polynucleotide sequence in a cell comprising introducing into the cell the ribonucleoprotein complex of clause 48, the composition of any one of clauses 50-52, or the lipid nanoparticle of clause 53, wherein the single guide RNA directs the Cas12b protein to effect a modification in the target polynucleotide sequence in the cell.

55. The method of clause 54, wherein the target polynucleotide sequence is in an ANGPTL3, PCSK9, APOC3, or Lp(a) gene.

56. The method of clause 54, wherein the target polynucleotide sequence is in an ANGPTL3 gene.

57. The method of any one of clauses 54-56, wherein the modification results in less off-target effect in the cell as compared to an unmodified single guide RNA.

58. The method of any one of clauses 54-57, wherein the single guide RNA exhibits increased stability in the cell compared to an unmodified single guide RNA, wherein the stability is measured by half-life of the single guide RNA in the cell.

59. The method of any one of clauses 54-58, wherein the modification is a double stranded break, a non-sense mutation, a frameshift mutation, a splice site alteration, or an inversion.

60. The method of any one of clauses 54-58, wherein the modification reduces or abolishes expression of functional PCSK9 protein encoded by the PCSK9 gene in the cell.

61. The method of any one of clauses 54-58, wherein the modification reduces or abolishes expression of functional ANGPTL3 protein encoded by the ANGPTL3 gene in the cell.

62. A method for treating or preventing a condition in a subject in need thereof, the method comprising administering to the subject the ribonucleoprotein complex of clause 48, the composition of any one of clauses 50-52, or the lipid nanoparticle of clause 53, wherein the single guide RNA directs the Cas12b protein to effect a modification in a target polynucleotide sequence in a cell of the subject, thereby treating or preventing the condition.

63. The method of clause 62, wherein the target polynucleotide sequence is in an ANGPTL3, PCSK9, APOC3, or Lp(a) gene.

64. The method of clause 62, wherein the target poly-nucleotide sequence is in an ANGPTL3 gene and wherein the chemically modified single guide RNA comprises a gRNA from Table 1.

65. The method of clause 62, wherein the modification reduces expression of functional PCSK9 protein encoded by the PCSK9 gene in the subject.

66. The method of clause 62, wherein the modification reduces expression of functional ANGPTL3 protein encoded by the ANGPTL3 gene in the subject.

67. The method of clause 63 or 65 wherein the condition is atherosclerotic vascular disease.

68. The method of clause 64 or 66 wherein the condition is an atherosclerotic vascular disease, hypertriglyceri-demia, or diabetes.

69. A Cas12b gene editing system that comprises:
(a) a single guide RNA comprising a spacer that is 20-30 nucleotides in length and complimentary to a DNA sequence of an ANGPTL3 gene; and
(b) a Cas 12b nuclease protein or a nucleic acid expressing a Cas 12b nuclease protein, wherein the single guide RNA and the Cas12b protein form a ribonucleoprotein complex that is capable of medi-ating in vitro ANGPTL3 gene editing in human primary hepatocytes at or above the editing percent-ages set forth in Table 3.

It will also be appreciated from reviewing the present disclosure, that it is contemplated that the one or more aspects or features presented in one of or a group of related clauses may also be included in other clauses or in combi-nation with the one or more aspects or features in other clauses.

---

What is claimed is:

1. A chemically modified single guide RNA for a Cas12b protein, comprising:

(i) a spacer sequence complimentary to a polynucleotide sequence located on a strand of a human ANGPTL3 gene, and wherein the spacer sequence is designed to hybridize to the polynucleotide sequence located on the human ANGPTL3 gene, and (ii) a scaffold sequence that serves as a binding scaffold for the Cas12b protein, wherein the spacer sequence comprises about 10 to about 40 nucleotides in length, wherein the scaffold sequence has a nucleotide base sequence, wherein the nucleotide base sequence has at least 90% identity to positions 1 to 97 of SEQ ID NO: 1, wherein the scaffold sequence comprises a plurality of different chemical modifications, wherein the plurality of different chemical modifications are at two or more nucleotide positions selected from positions 1-7, 11, 16-21, 25-31, 39, 42, 45-52, 57-62, 64, 65, and 70-87 as numbered in SEQ ID NO: 1 or a corresponding position or combination of corresponding positions thereof, and wherein the one or more chemical modifications comprise a 2'-O-methyladenosine, a 2'-O-methylcytidine, a 2'-O-methylguanosine, a 2'-O-methyluridine, a nebularine, a 2'-O-methylnebularine, or a phosphorothioate linkage.

2. The chemically modified single guide RNA of claim 1, wherein the plurality of different chemical modifications are at one or more nucleotide positions selected from positions 1-7, 11, 16-21, 25-31, 45-52, 57-62, 64, 65, and 70-87 as numbered in SEQ ID NO: 1 or a corresponding position or combination of corresponding positions thereof.

3. The chemically modified single guide RNA of claim 1, wherein the plurality of different chemical modifications are at two or more nucleotide positions selected from positions 1-3, 5, 16, 21, 25-26, 29, 30, 33, 35, 37, 39, 44, 45, 47, 49-51, 62, 63, 65, 67-69, 72, 75, 76, 79, 82-84, 86, 87, 89, 92, and 95 as numbered in SEQ ID NO: 1 or a corresponding position or combination of corresponding positions thereof.

4. The chemically modified single guide RNA of claim 1, wherein the plurality of different chemical modifications are at two or more nucleotide positions selected from positions 1-3, 5, 16, 21, 25-26, 29, 30, 44, 45, 49, 50, 62, 63, 67-69, 72, 75, 76, 79, and 82-84 as numbered in SEQ ID NO: 1 or a corresponding position or combination of corresponding positions thereof.

5. The chemically modified single guide RNA of claim 1, wherein the plurality of different chemical modifications are at two or more nucleotide positions selected from positions 16, 21, 25, 29, 30, 44, 45, 49, 50, 62, 63, 67-69, 72, 75, 76, 79, and 82-84 as numbered in SEQ ID NO: 1 or a corresponding position or combination of corresponding positions thereof.

6. The chemically modified single guide RNA of claim 1, wherein the scaffold sequence comprises the plurality of different chemical modifications
   (i) at positions 1-7, 11, 16-21, 25-31, 39, 42, 45-52, 57-62, 64, 65, and 70-87,
   (ii) at positions 1-7, 11, 16-21, 25-31, 45-52, 57-62, 64, 65, and 70-87,
   (iii) at positions 1-3, 5, 16, 21, 25-26, 29, 30, 44, 45, 49, 50, 62, 63, 67-69, 72, 75, 76, 79, and 82-84, or
   (iv) at positions 1-3, 5, 16, 21, 25-26, 29, 30, 44, 45, 49, 50, 62, 63, 67-69, 72, 75, 76, 79, and 82-84,
   as numbered in SEQ ID NO: 1 or a corresponding position or combination of corresponding positions thereof.

7. The chemically modified single guide RNA of claim 1, wherein the chemically modified single guide RNA comprises one or more unmodified nucleotides.

8. The chemically modified single guide RNA of claim 7, wherein the one or more unmodified nucleotides are at one or more nucleotide positions selected from positions 4, 6-15, 17-20, 22-24, 27, 28, 31-43, 46-48, 51-61, 64-66, 70, 71, 73, 74, 77, 78, 80, 81, and 85-116 as numbered in SEQ ID NO: 1 or a corresponding position or combination of corresponding positions thereof.

9. The chemically modified single guide RNA of claim 7, wherein the one or more unmodified nucleotides comprise a 2'-hydroxyl group,
   wherein the 2'-hydroxyl group is in a region of the scaffold sequence that serves as a binding scaffold for the Cas12b protein, and/or
   wherein the 2'-hydroxyl group is in close proximity to the Cas12b protein when the Cas12b protein is bound to the scaffold sequence.

10. The chemically modified single guide RNA of claim 1, wherein the one or more chemical modifications comprise the phosphorothioate linkage, and wherein the chemically modified single guide RNA comprises two and no more than two contiguous phosphorothioate linkages at the 5' end and/or at the 3' end of the chemically modified single guide RNA.

11. The chemically modified single guide RNA of claim 1, wherein the chemically modified single guide RNA comprises the phosphorothioate linkage, and wherein the chemically modified single guide RNA comprises three and no more than three contiguous phosphorothioate linkages at the 5' end and/or the 3' end of the chemically modified single guide RNA.

12. The chemically modified single guide RNA of claim 1, wherein the chemically modified single guide RNA comprises a sequence of 5'-NsNsN-3', 5'-NsNsNsN-3', 5'-nsnsnsn-3', or 5'-nsnsn-3' at the 3' end of the chemically modified single guide RNA, wherein N independently is an unmodified nucleotide adenosine, cytidine, guanosine or uridine; and n independently is a modified nucleotide adenosine, cytidine, guanosine or uridine, wherein the modification of the nucleotide is a 2'-H, 2'-OMe or nucleobase modification; and each s is a phosphorothioate linkage.

13. The chemically modified single guide RNA of claim 1, wherein the chemically modified single guide RNA comprises a sequence of 5'-UsUsU-3', 5'-UsUsUsU-3', 5'-usususu-3', or 5'-ususu-3' at the 3' end of the chemically modified single guide RNA, wherein U is an unmodified uridine; and u is a modified uridine, wherein the modification of the uridine is a 2'-H, 2'-OMe or nucleobase modification; and each s is a phosphorothioate linkage.

14. The chemically modified single guide RNA of claim 1, wherein each one of the last four nucleotides at the 3' end of the chemically modified single guide RNA comprises a 2'-OMe modification.

15. The chemically modified single guide RNA of claim 1, wherein the human ANGPTL3 gene comprises a sequence of SEQ ID NO: 108.

16. The chemically modified single guide RNA of claim 1, wherein the human ANGPTL3 gene comprises a protospacer sequence of any one of SEQ ID NOs: 90-101.

17. The chemically modified single guide RNA of claim 1, wherein the chemically modified single guide RNA comprises a sequence with at least 90% 18 identity to a sequence selected from any one of SEQ ID NOs: 2-89.

18. The chemically modified single guide RNA of claim 1, wherein the chemically modified single guide RNA comprises a nucleotide sequence of gsususCuGUC-UUIUUGGUcAGGAcAACcgUCuaGC-UAUAAGUGCUGcaGGGugUGA GAAACUCC-uaUUGcugGAcGAugUCuCUuacGAGGCAUUAG-CACAACCAACAGC AUAGUCAAAusasasa, wherein uppercase A, U, G, and C represent unmodified adenosine, uridine, guanosine and cytidine respectively, lowercase a, u, g, and c represent 2'-O-methyl modified adenosine, uridine, guanosine and cytidine respectively, and the lowercase s represents a phosphorothioate linkage.

19. The chemically modified single guide RNA of claim 1, wherein the chemically modified single guide RNA is about 90 to about 135 nucleotides in length.

20. The chemically modified single guide RNA of claim 1, wherein the chemically modified single guide RNA comprises a nucleotide sequence of gsususCuGUC-UUUUGGUcAGGAcAACcgUCuaGC-uAuAaGuGCUGcaGgGuguGAGA AACUCC-uaUuGcugGAcGAugUCuCUuacGagGcAUuAGcACA-ACCAACAGCAUAG UCAAAusasasa, wherein uppercase A, U, G, and C represent unmodified adenosine, uridine, guanosine and cytidine respectively, lowercase a, u, g, and c represent 2'-O-methyl modified adenosine, uridine, guanosine and cytidine respectively, and the lowercase s represents a phosphorothioate linkage.

21. The chemically modified single guide RNA of claim 1, wherein the chemically modified single guide RNA comprises a nucleotide sequence of gsususcuguCUUuUG-GUcaggacAACcgucuagCUAUAAGuGCuGCagggu-gugAGAAacuc cuAuuGCUGgacgaugucucuuacgagG-CAUUAGCACAACCAACAGCAUAGUCAAAusa sasa, wherein uppercase A, U, G, and C represent unmodified adenosine, uridine, guanosine and cytidine respectively, lowercase a, u, g, and c represent 2'-O-methyl modified adenosine, uridine, guanosine and cytidine respectively, and the lowercase s represents a phosphorothioate linkage.

22. The chemically modified single guide RNA of claim 1, wherein the chemically modified single guide RNA comprises a nucleotide sequence of gsususcuguCUUuUG-GUcaggacAACcgucuagCUAUAAGUGCUGCagggu-gugAGAAacu ccuAuuGCUGgacgaugucucuuacgagG-CAUUAGCACAACCAACAGCAUAGUCAAAus asasa, wherein uppercase A, U, G, and C represent unmodified adenosine, uridine, guanosine and cytidine respectively, lowercase a, u, g, and c represent 2'-O-methyl modified adenosine, uridine, guanosine and cytidine respectively, and the lowercase s represents a phosphorothioate linkage.

23. The chemically modified single guide RNA of claim 1, wherein the chemically modified single guide RNA comprises a nucleotide sequence of gsususCuGUC-UUUUGGUcAGGAcAACcgUCuaGC-UAUAAGUGCUGcaGGGugUGA GAAACUCC-uaUUGcugGAcGAugUCuCUuacGAGGCAUUAGCAC-AACCAACAGC AuAGUcAAAusasasa, wherein uppercase A, U, G, and C represent unmodified adenosine, uridine, guanosine and cytidine respectively, lowercase a, u, g, and c represent 2'-O-methyl modified adenosine, uridine, guanosine and cytidine respectively, and the lowercase s represents a phosphorothioate linkage.

24. The chemically modified single guide RNA of claim 1, wherein the chemically modified single guide RNA comprises a nucleotide sequence of gsususCuGUC-UUUUGGUcAGGAcAACcgUCuaGC-uAuAaGuGCUGcaGgGuguGAGA AACUCC-uaUuGcugGAcGAugUCuCUuacGagGcAUuAGcACA-ACCAACAGCAuAGU cAAAusasasa, wherein uppercase A, U, G, and C represent unmodified adenosine, uridine, guanosine and cytidine respectively, lowercase a, u, g, and c represent 2'-O-methyl modified adenosine, uridine, guanosine and cytidine respectively, and the lowercase s represents a phosphorothioate linkage.

25. The chemically modified single guide RNA of claim 1, wherein the chemically modified single guide RNA comprises a nucleotide sequence of gsususCUGUC-UUUUGGUCAGGACAACcgucuagC-UAUAAGuGCuGCagggugugAGA Aacucc-uAuuGCUGgacgaugucucuuacgagGCAUUAGCACAAC-CAACAGCAUAGUCA AAusasasa, wherein uppercase A, U, G, and C represent unmodified adenosine, uridine, guanosine and cytidine respectively, lowercase a, u, g, and c represent 2'-O-methyl modified adenosine, uridine, guanosine and cytidine respectively, and the lowercase s represents a phosphorothioate linkage.

26. The chemically modified single guide RNA of claim 1, wherein the chemically modified single guide RNA comprises a nucleotide sequence of gsususcuguCUUuUG-GUcaggacAACcgucuagCUAUAAGuGCuGCAGGGU-GUGAGAA ACUCCUAuuGCUGgacgaugucucuuacgagG-CAUUAGCACAACCAACAGCAUAGUC AAAusasasa, wherein uppercase A, U, G, and C represent unmodified adenosine, uridine, guanosine and cytidine respectively, lowercase a, u, g, and c represent 2'-O-methyl modified adenosine, uridine, guanosine and cytidine respectively, and the lowercase s represents a phosphorothioate linkage.

27. The chemically modified single guide RNA of claim 1, wherein the chemically modified single guide RNA comprises a nucleotide sequence of gsususcuguCUUuUG-GUcaggacAACcgucuagCUAUAAGuGCuGCagggu-gugAGAAacuc cuAuuGCUGgacgaugucucuuacgagG-CAUUAGCACaACCAAcaGCAuaGUCAAAusasas a, wherein uppercase A, U, G, and C represent unmodified adenosine, uridine, guanosine and cytidine respectively, lowercase a, u, g, and c represent 2'-O-methyl modified adenosine, uridine, guanosine and cytidine respectively, and the lowercase s represents a phosphorothioate linkage.

* * * * *